US010647994B2

(12) United States Patent
Narva et al.

(10) Patent No.: US 10,647,994 B2
(45) Date of Patent: May 12, 2020

(54) RAS OPPOSITE (ROP) AND RELATED NUCLEIC ACID MOLECULES THAT CONFER RESISTANCE TO COLEOPTERAN AND/OR HEMIPTERAN PESTS

(71) Applicants: Dow AgroSciences LLC, Indianapolis, IN (US); Fraunhofer-Gesellschaft zur Förderung der angewandten Forschung E. V., München (DE)

(72) Inventors: Kenneth E. Narva, Zionsville, IN (US); Huarong Li, Zionsville, IN (US); Chaoxian Geng, Zionsville, IN (US); Kanika Arora, Indianapolis, IN (US); Balaji Veeramani, Indianapolis, IN (US); Premchand Gandra, Indianapolis, IN (US); Sarah Worden, Indianapolis, IN (US); Andreas Vilcinskas, Giessen (DE); Eileen Knorr, Giessen (DE); Elane Fishilevich, Indianapolis, IN (US); Murugesan Rangasamy, Zionsville, IN (US); Meghan Frey, Greenwood, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 802 days.

(21) Appl. No.: 14/577,811

(22) Filed: Dec. 19, 2014

(65) Prior Publication Data

US 2015/0176025 A1 Jun. 25, 2015

Related U.S. Application Data

(60) Provisional application No. 61/919,322, filed on Dec. 20, 2013.

(51) Int. Cl.
*C12N 15/82* (2006.01)
*C12N 15/113* (2010.01)

(52) U.S. Cl.
CPC ........ *C12N 15/8286* (2013.01); *C12N 15/113* (2013.01); *C12N 15/8218* (2013.01); *C12N 2310/14* (2013.01); *C12N 2310/531* (2013.01); *Y02A 40/162* (2018.01)

(58) Field of Classification Search
CPC ................................................. C12N 15/8286
USPC ......................................................... 800/279
See application file for complete search history.

(56) References Cited

U.S. PATENT DOCUMENTS

2012/0164205 A1* 6/2012 Baum ................... A01N 63/02
424/409

FOREIGN PATENT DOCUMENTS

| | | | |
|---|---|---|---|
| CN | 1330140 | A | 1/2002 |
| EP | 2330107 | A2 | 6/2011 |
| JP | 2012-517475 | A | 8/2012 |
| WO | 2012/092544 | A2 | 7/2012 |
| WO | 2012/092573 | A2 | 7/2012 |
| WO | 2012/092596 | A2 | 7/2012 |

OTHER PUBLICATIONS

Thomas et al. 2001, The Plant Journal 25(4):417-425.*
Colliver et al. Plant Molecular Biology 35:509-522.*
Yibrah et al. 1993 Hereditas 118:273-280.*
Salzberg et al: "The *Drosophila* Ras2 and ROP gene pair: a dual homology with a yeast Ras-like gene and a suppressor of its loss-of-function phenotype". Development, 1993, vol. 17, pp. 1309-1319.
Harrison, S. D., et al., "Mutations in the *Drosophila* Rop gene suggest a function in general secretion and synaptic transmission," Neuron, Cell Press, Sep. 1, 1994, pp. 555-566, vol. 13, No. 3.
Bolognesi et al, 'Characterizing the Mechanism of Action of Double-Stranded RNA Activity against Western Corn Rootworm (*Diabrotica virgifera virgifera* LeConte)', pp. e47534, PLOS One, vol. 7, 2012.
Database EMBL [Online] Aug. 28, 2007 (Aug. 28, 2007), "ST040002A 1OH10 Normalized and subtracted western corn rootworm female head cDNA library Diabrotica virgifera virgifera cDNA clone ST040002A 1OH10 5', mRNA sequence.", retrieved from EBI accession No. EM EST:EW775191 Database accession No. EW775191.
GenBank:NM_214669. 1, "Strongylocentrotus purpuratus syntaxin binding protein 1 (sec1), mRNA," NCBI Reference Sequence: NM_214669.1, dated Aug. 25, 2012.
EMBL:CV748534. 1, dated Feb. 27, 2011.
EMBL:GT346238. 1, dated Jun. 28, 2012.
Database DDBJ/EMBL/Genbank [online], Accession No. EW774226, <http://www.ncbi.nlm.nih.gov/nucest/EW774226> Aug. 23, 2007 uploaded, [retrieved on Nov. 5, 2018], Robertson, H. et al., Definition: ST020039A10H07 Normalized and subtracted western corn rootworm female head cDNA library Diabrotica virgifera virgifera cDNA clone ST020039AI 0H07 5-, mRNA sequence.
Database DDBJ/EMBL/GenBank [online], Accession No. EW772552, <http://www.ncbi.nlm.nih.gov/nucest/EW772552> Aug. 23, 2007 uploaded, [retrieved on Nov. 5, 2018], Robertson, H. et al., Definition: ST020017B10E03 Normalized and subtracted western corn rootworm female head cDNA library Diabrotica virgifera virgifera cDNA clone ST020017B10E03 5-, mRNA sequence.
Okamura et al., "The long and short of inverted repeat genes in animals: MicroRNAs, mirtrons and hairpin RNAs," Cell Cycle, Sep. 15, 2008, pp. 2840-2845, vol. 7, Issue 18.

(Continued)

*Primary Examiner* — Li Zheng
(74) *Attorney, Agent, or Firm* — Magleby Cataxinos & Greenwood

(57) ABSTRACT

This disclosure concerns nucleic acid molecules and methods of use thereof for control of coleopteran and/or hemipteran pests through RNA interference-mediated inhibition of target coding and transcribed non-coding sequences in coleopteran and/or hemipteran pests. The disclosure also concerns methods for making that express nucleic acid molecules useful for the control of coleopteran and/or hemipteran pests, and the plant cells and plants obtained thereby.

25 Claims, 1 Drawing Sheet

Specification includes a Sequence Listing.

(56) References Cited

OTHER PUBLICATIONS

Qu et al., "Artificial MicroRNA-Mediated Virus Resistance in Plants," Journal of Virology, Jun. 2007, pp. 6690-6699, vol. 81, No. 12.

First Office Action and Search Report in Chinese application No. 201480075840.2, dated Jun. 2, 2017, 9 pages.

Baum et al., "Control of coleopteran insect pests through RNA interference," Nature Biotechnoly, Nov. 2007, pp. 1322-1326, vol. 25, No. 11.

Third Office Action and Search Report in Chinese application No. 01480075840.2, dated Aug. 23, 2018, 10 pages.

Abdurakhmonov et al., "RNA Interference for Functional Genomics and Improvement of Cotton (*Gossypium* sp.)," Frontiers in Plant Science, Feb. 2016, vol. 7, Article 202, 17 pages.

Kola et al., "Key enzymes and proteins of crop insects as candidate for RNAi based gene silencing," Frontiers in Physiology, Apr. 2015, vol. 6, Article 119, 15 pages.

Nandety et al., "Emerging strategies for RNA interference (RNAi) applications in insects," Bioengineered, Jan./Feb. 2015, pp. 8-19, vol. 6, Issue 1.

Mao et al., Feeding-Based RNA Intereference of a Gap Gene Is Lethal to the Pea Aphid, *Acyrthosiphon pisum,* PLoS ONE, Nov. 2012, vol. 7, Issue 11, 7 pages.

Kupferschmidt, "A Lethal Dose of RNA," Science, Aug. 16, 2013, pp. 732-733, vol. 341.

Notice of Reasons for Rejection in Japanese application No. 2016-541168, dated Nov. 13, 2018, 20 pages.

International Search Report and Written Opinion in International application No. PCT/US2014/071628, dated Mar. 31, 2015, 19 pages.

International Preliminary Report on Patentability in International application No. PCT/US2014/071628, dated Jun. 30, 2016, 11 pages.

* cited by examiner

SEQUENCE LISTING

```
<160> NUMBER OF SEQ ID NOS: 134

<210> SEQ ID NO 1
<211> LENGTH: 4816
<212> TYPE: DNA
<213> ORGANISM: Diabrotica virgifera

<400> SEQUENCE: 1

cggatttcac ggattctgcg cgtttgagac ctttcattca tctttttgtt attgttgcgg     60

aggtcaattt tttatatcgg aagacaattt tatccaaatt tttgaaaaat ctccaattct    120

gtcactgaat taggacttaa gtggaacacc atggcgttaa agaaccaagt tggtcaaaaa    180

atcatgaatg aagtcatcaa gcacaagccc accaagaaga atgggccaac tccaggacag    240

caagcccatg ggtagaatg gaggatcctt gtggtggacc agcttgccat gaggatggtt    300

tcagcatgct gtaaaatgca tgatatatca gcagaaggca ttacattggt tgaagatatt    360

atgaagaaaa gggaaccgct tggtaccatg gaagctgtgt acttgataac accttcagaa    420

aagtcagttc atgctcttat gaatgacttt gaaccaccaa gacagatgta cagaggggca    480

cacgtgtttt ttacagaagc gtgtccagac caattattta gtaccttgtg ccaccacccc    540

gtagcaaagt ttattaaaac cctaaaagaa atcaacatag cattcattcc gactgagtca    600

caggtgttct cattggattc accagacacg ttccagtgta gctacgatcc atcattttcc    660

gctgctagaa acgccaacat ggaaagaatg gcagaacaaa ttgcgacact ctgtgcgact    720

ctaggggaat acccacacgt cagatataga actgattggg aaagaaatgt tgagctggct    780

caactaattc agcagaaatt ggacgcctat aaagccgacg aacctaccat gggagagggg    840

ccggaaaagg cgagatcaca attaattatc ctcgaccgag gtttcgactg tgtatctccc    900
```

-continued

```
cttcttcacg aacttacttt ccaagcaatg gcctatgact tactacccat agaaaatgat    960
gtatataagt acgaagcatc ggctggtgtt atgaaagaag tccttctaga cgaaaacgac   1020
gagctttggg tcgatctacg ccaccaacac atcgcggtgg tgtctcagag cgtcaccaag   1080
aatctgaaga aattcaccga ctccaaacgc atgacccaga gcgacaagca gtcgatgaag   1140
gatctctcaa ccatgatcaa aaagatgccg caatatcaga aagaattgtc caagtatgct   1200
acgcatcttc atctcgctga agactgcatg aaggcctatc aggggtatat agacaagttg   1260
tgtaaagttg agcaggattt ggcaatggga actgatgccg aaggcgagaa aatcaaggat   1320
cacatgcgca acatcgtccc catcttgcta gatcccaaaa tcaccaatga atacgataag   1380
atgcgtatta tagcattgta cgccatgacg aaaaacggca tcacagatga aaatctctcc   1440
aaattggcta cccatgccca aatcaaggac aaacagacca tcgccaacct tcagttactt   1500
ggagtcaacg ttattaatga tggaggacca agaaaaaaac aatatacagt accgcgcaaa   1560
gaaagaatta cagaacaaac gtaccaaatg tcaagatgga cacctatcat taaggatata   1620
atggaggatt gcatagacga caaactggat cagaaacact acccgtattt gagcggacga   1680
gcacagtcta cgggatacca tgcagcgccc tctagtgccc gttatggcca gtggcacaaa   1740
gacagaggtc aacaagccgt gaagaacgtt cctcgactgc tcgtcttcgt cgtgggtgga   1800
atcagttttt cagagatcag gtgcgcctac gaagtgacca acgcgcagaa gaactgggaa   1860
gtcatcatcg gctcgtcgca catactcact cccgaggact tcctaagcaa tctggcaacg   1920
ttggccggct agaatcagat gaaaaaggtt acttttaatg tacccgagta aacagtttcg   1980
cagtcgtagt ttaaaataat gtaatgagtc tttttaatcc caatttaaac atatttatat   2040
agaatgactt tcgatcagta tcgaaccgtt ttctttgtta cgagagttaa agctgttcaa   2100
attatcttga aatttgtgca gaattgtcat acattaaatt gttgcgcttc tgaaattgtt   2160
gtgcaataaa agaaaatgtc taaggtgctc aaaactcaaa gccttcgatg agtttatgat   2220
tataaattga gaataaaaag actcattgag cttaaaaagt attatttcct accctttttt   2280
tgtatttttc caatagcaga gtttttttatt caatttttgc ggttattggg atattatcgc   2340
tttatttaca aaattgtgta aaaggtataa aaatgacgtt tttgaggagt cttcctgtaa   2400
aattaatttc aatagtcaga gatttaccaa aaaaatattt ttttttgttt agattttagt   2460
ttcttaacat attataaaat acatcgtttt ttttgtttta tttactgtta aagcttctat   2520
attgtcttct tgaactgctg tggcgacccc atcattgaaa acacttccaa gaacaagaac   2580
acatttggct ttttgttgta attatctttt tgggaagata tatttgagga aacagctttg   2640
taattttggg tcacactagt ttttcgtttt tcattctacc catttttttgg ttgattgttg   2700
gccacactgt tctgtgtttt cggcatgaag gcatacaaac aaaaaatgtt ccaggtgtaa   2760
ctttctctgg tttttgaaaa cgtatataag ttttctttca atagtatgaa ctatcattca   2820
taaatataca tatttttgct atcagagcat accaaatgaa gtagttctgt atttatttca   2880
aacaagtaca tttagtttat ttgttcagtt atatgtttcc atttctagta gtcttctggt   2940
atctgtggct ggattttagt gtgtcaactc cagttttata acctaaccaa acctcaccta   3000
atgcaaccta acctcacata acctcaaata atataacaaa atctctcgta gactaaccta   3060
ataatgcatt ggtgtggtat gaacgattcg gaatttgttt taattaaaga aatttttcaa   3120
aaattatgta tatttatgca aaaatcttca ttttttcttg tttacactgc tattgatatt   3180
gtattcgttg actagtctgc gtccagttgc acaaacgaca cccctaaagc tacttaacag   3240
taagacgatg cttttaaatg ctttttgtgt gactggtaca tatattataa attaagctta   3300
```

```
gcgagtaatt aagaatctta tctttaaata tccagttgta catcttacat agtgtacctc   3360

ttagaatagg aaaatgtatt tttcaactgt acctaaccaa acgcgtatag caaaaggtgt   3420

agaacgtgac aaagaatagc ataaagaagg acctgagctt gttttagtta ttcttccttc   3480

aaaattagat aatccttaaa ttaaactaga tatgtgtgct aaaaaatcat ctctggcggt   3540

acagccaata gaaaagaagc tgaggaaggt ctcagatcac cgtgatcaat tatttaagca   3600

gaataatgga aaactggtcg tgagccatct aaatcttctc tatgctatag tttaaacgta   3660

ctacacctat tttcaaatca cagctttgta ttcatgctag ctaactttgt atcatatcct   3720

cagtagttta tcgtgaccta ttttttatat atctactaaa agacaccgat agtttttcca   3780

aaaaaaaaaa cttctatttg atagaaaaat aaaaatttat cgtttacaaa ttatggtaaa   3840

attatttagt tgttattatt cagcatttac aacggtacaa cgctttcttt cagtgcagaa   3900

cgagtatcaa aatcataata cgagcaaaac ttaacggagc cccaacatat accaaccttg   3960

aataacacaa aatacaacaa tttcttagat ctggggaaaa tcgtcgaaga tttgacaatt   4020

tcggccaatc agagcgccat attgtagtca cgtgacctaa aattttccta gattccagta   4080

aactggacta ttacaggagc gataaagcat taatagcgtt atttgtgttg gctatcccga   4140

agtttgattt tttatagtag tcacgatgtt tttggtcgat gaaagacttt agacaatgat   4200

tttatattcc ctactactcg ttttgccact gaatgaagca ttttccacat tcctgttcgt   4260

tttctaggaa tataagtgta aaattgactg acaaattaca tgttttcgtt actatcatcg   4320

atacatcatt ttcgtagagg gctggatcat gcgtgggtga ttaaaataca gttgttgtac   4380

gtttcttttc gtcaccctag tcaataaagt ccttatttat gtgctagtgt ttctattatc   4440

gttggtttac agcggtgtgt acatgacaag ggcgatttaa acggatctgc gggtaaatac   4500

catagacata ttatcgatag accaagctag gaatatgcca ctcaatgcat cggggtgtaa   4560

cgccaatatc aagtacggtg gtctagctat ctttgtctgt cgtgcgagtg tgagcgtatc   4620

taccaagagg tgggagtaat ggaacgacac agacacagag gcagcggcca tcatatgcta   4680

gagagagaaa gctaagcgcc ggtagagaga gatagataga ccaccgaccc gaactgctcc   4740

gcgttacgct atttttcgga cctggcctaa tctattgtgt tattatatct atggttcaac   4800

tccagtttaa ccaatg                                                   4816

<210> SEQ ID NO 2
<211> LENGTH: 593
<212> TYPE: PRT
<213> ORGANISM: Diabrotica virgifera

<400> SEQUENCE: 2

Met Ala Leu Lys Asn Gln Val Gly Gln Lys Ile Met Asn Glu Val Ile
1               5                   10                  15

Lys His Lys Pro Thr Lys Lys Asn Gly Pro Thr Pro Gly Gln Gln Ala
            20                  25                  30

His Gly Val Glu Trp Arg Ile Leu Val Val Asp Gln Leu Ala Met Arg
        35                  40                  45

Met Val Ser Ala Cys Cys Lys Met His Asp Ile Ser Ala Glu Gly Ile
    50                  55                  60

Thr Leu Val Glu Asp Ile Met Lys Lys Arg Glu Pro Leu Gly Thr Met
65                  70                  75                  80

Glu Ala Val Tyr Leu Ile Thr Pro Ser Glu Lys Ser Val His Ala Leu
                85                  90                  95
```

-continued

```
Met Asn Asp Phe Glu Pro Pro Arg Gln Met Tyr Arg Gly Ala His Val
            100                 105                 110

Phe Phe Thr Glu Ala Cys Pro Asp Gln Leu Phe Ser Thr Leu Cys His
        115                 120                 125

His Pro Val Ala Lys Phe Ile Lys Thr Leu Lys Glu Ile Asn Ile Ala
    130                 135                 140

Phe Ile Pro Thr Glu Ser Gln Val Phe Ser Leu Asp Ser Pro Asp Thr
145                 150                 155                 160

Phe Gln Cys Ser Tyr Asp Pro Ser Phe Ser Ala Ala Arg Asn Ala Asn
                165                 170                 175

Met Glu Arg Met Ala Glu Gln Ile Ala Thr Leu Cys Ala Thr Leu Gly
            180                 185                 190

Glu Tyr Pro His Val Arg Tyr Arg Thr Asp Trp Glu Arg Asn Val Glu
        195                 200                 205

Leu Ala Gln Leu Ile Gln Gln Lys Leu Asp Ala Tyr Lys Ala Asp Glu
    210                 215                 220

Pro Thr Met Gly Glu Gly Pro Glu Lys Ala Arg Ser Gln Leu Ile Ile
225                 230                 235                 240

Leu Asp Arg Gly Phe Asp Cys Val Ser Pro Leu Leu His Glu Leu Thr
                245                 250                 255

Phe Gln Ala Met Ala Tyr Asp Leu Leu Pro Ile Glu Asn Asp Val Tyr
            260                 265                 270

Lys Tyr Glu Ala Ser Ala Gly Val Met Lys Glu Val Leu Leu Asp Glu
        275                 280                 285

Asn Asp Glu Leu Trp Val Asp Leu Arg His Gln His Ile Ala Val Val
    290                 295                 300

Ser Gln Ser Val Thr Lys Asn Leu Lys Lys Phe Thr Asp Ser Lys Arg
305                 310                 315                 320

Met Thr Gln Ser Asp Lys Gln Ser Met Lys Asp Leu Ser Thr Met Ile
                325                 330                 335

Lys Lys Met Pro Gln Tyr Gln Lys Glu Leu Ser Lys Tyr Ala Thr His
            340                 345                 350

Leu His Leu Ala Glu Asp Cys Met Lys Ala Tyr Gln Gly Tyr Ile Asp
        355                 360                 365

Lys Leu Cys Lys Val Glu Gln Asp Leu Ala Met Gly Thr Asp Ala Glu
    370                 375                 380

Gly Glu Lys Ile Lys Asp His Met Arg Asn Ile Val Pro Ile Leu Leu
385                 390                 395                 400

Asp Pro Lys Ile Thr Asn Glu Tyr Asp Lys Met Arg Ile Ile Ala Leu
                405                 410                 415

Tyr Ala Met Thr Lys Asn Gly Ile Thr Asp Glu Asn Leu Ser Lys Leu
            420                 425                 430

Ala Thr His Ala Gln Ile Lys Asp Lys Gln Thr Ile Ala Asn Leu Gln
        435                 440                 445

Leu Leu Gly Val Asn Val Ile Asn Asp Gly Gly Pro Arg Lys Lys Gln
    450                 455                 460

Tyr Thr Val Pro Arg Lys Glu Arg Ile Thr Glu Gln Thr Tyr Gln Met
465                 470                 475                 480

Ser Arg Trp Thr Pro Ile Ile Lys Asp Ile Met Glu Asp Cys Ile Asp
                485                 490                 495

Asp Lys Leu Asp Gln Lys His Tyr Pro Tyr Leu Ser Gly Arg Ala Gln
            500                 505                 510

Ser Thr Gly Tyr His Ala Ala Pro Ser Ser Ala Arg Tyr Gly Gln Trp
```

-continued

```
        515                 520                 525

His Lys Asp Arg Gly Gln Gln Ala Val Lys Asn Val Pro Arg Leu Leu
    530                 535                 540

Val Phe Val Val Gly Gly Ile Ser Phe Ser Glu Ile Arg Cys Ala Tyr
545                 550                 555                 560

Glu Val Thr Asn Ala Gln Lys Asn Trp Glu Val Ile Ile Gly Ser Ser
                565                 570                 575

His Ile Leu Thr Pro Glu Asp Phe Leu Ser Asn Leu Ala Thr Leu Ala
            580                 585                 590

Gly


<210> SEQ ID NO 3
<211> LENGTH: 392
<212> TYPE: DNA
<213> ORGANISM: Diabrotica virgifera

<400> SEQUENCE: 3

accatggcgt taaagaacca agttggtcaa aaaatcatga atgaagtcat caagcacaag      60

cccaccaaga agaatgggcc aactccagga cagcaagccc atggggtaga atggaggatc     120

cttgtggtgg accagcttgc catgaggatg gtttcagcat gctgtaaaat gcatgatata     180

tcagcagaag gcattacatt ggttgaagat attatgaaga aaagggaacc gcttggtacc     240

atggaagctg tgtacttgat aacaccttca gaaaagtcag ttcatgctct tatgaatgac     300

tttgaaccac caagacagat gtacagaggg gcacacgtgt tttttacaga agcgtgtcca     360

gaccaattat ttagtacctt gtgccaccac cc                                  392


<210> SEQ ID NO 4
<211> LENGTH: 627
<212> TYPE: DNA
<213> ORGANISM: Diabrotica virgifera

<400> SEQUENCE: 4

ctcgaccgag gtttcgactg tgtatctccc cttcttcacg aacttacttt ccaagcaatg      60

gcctatgact tactacccat agaaaatgat gtatataagt acgaagcatc ggctggtgtt     120

atgaaagaag tccttctaga cgaaaacgac gagctttggg tcgatctacg ccaccaacac     180

atcgcggtgg tgtctcagag cgtcaccaag aatctgaaga aattcaccga ctccaaacgc     240

atgacccaga gcgacaagca gtcgatgaag gatctctcaa ccatgatcaa aaagatgccg     300

caatatcaga aagaattgtc caagtatgct acgcatcttc atctcgctga agactgcatg     360

aaggcctatc aggggtatat agacaagttg tgtaaagttg agcaggattt ggcaatggga     420

actgatgccg aaggcgagaa aatcaaggat cacatgcgca acatcgtccc catcttgcta     480

gatcccaaaa tcaccaatga atacgataag atgcgtatta tagcattgta cgccatgacg     540

aaaaacggca tcacagatga aaatctctcc aaattggcta cccatgccca aatcaaggac     600

aaacagacca tcgccaacct tcagtta                                       627


<210> SEQ ID NO 5
<211> LENGTH: 24
<212> TYPE: DNA
<213> ORGANISM: Artificial Sequence
<220> FEATURE:
<223> OTHER INFORMATION: T7 phage promoter Oligonucleotide

<400> SEQUENCE: 5

ttaatacgac tcactatagg gaga                                            24
```

<210> SEQ ID NO 6
<211> LENGTH: 503
<212> TYPE: DNA
<213> ORGANISM: Artificial Sequence
<220> FEATURE:
<223> OTHER INFORMATION: Portion of YFP coding region

<400> SEQUENCE: 6
caccatgggc tccagcggcg ccctgctgtt ccacggcaag atcccctacg tggtggagat 60
ggagggcaat gtggatggcc acaccttcag catccgcggc aagggctacg gcgatgccag 120
cgtgggcaag gtggatgccc agttcatctg caccaccggc gatgtgcccg tgccctggag 180
caccctggtg accaccctga cctacggcgc ccagtgcttc gccaagtacg gccccgagct 240
gaaggatttc tacaagagct gcatgcccga tggctacgtg caggagcgca ccatcacctt 300
cgagggcgat ggcaatttca agacccgcgc cgaggtgacc ttcgagaatg gcagcgtgta 360
caatcgcgtg aagctgaatg gccagggctt caagaaggat ggccacgtgc tgggcaagaa 420
tctggagttc aatttcaccc cccactgcct gtacatctgg ggcgatcagg ccaatcacgg 480
cctgaagagc gccttcaaga tct 503

<210> SEQ ID NO 7
<211> LENGTH: 46
<212> TYPE: DNA
<213> ORGANISM: Artificial Sequence
<220> FEATURE:
<223> OTHER INFORMATION: PCR Primer Oligonucleotide

<400> SEQUENCE: 7
ttaatacgac tcactatagg gagaaccatg gcgttaaaga accaag 46

<210> SEQ ID NO 8
<211> LENGTH: 44
<212> TYPE: DNA
<213> ORGANISM: Artificial Sequence
<220> FEATURE:
<223> OTHER INFORMATION: PCR Primer Oligonucleotide

<400> SEQUENCE: 8
ttaatacgac tcactatagg gagagggtgg tggcacaagg tact 44

<210> SEQ ID NO 9
<211> LENGTH: 42
<212> TYPE: DNA
<213> ORGANISM: Artificial Sequence
<220> FEATURE:
<223> OTHER INFORMATION: PCR Primer Oligonucleotide

<400> SEQUENCE: 9
ttaatacgac tcactatagg gagactcgac cgaggtttcg ac 42

<210> SEQ ID NO 10
<211> LENGTH: 46
<212> TYPE: DNA
<213> ORGANISM: Artificial Sequence
<220> FEATURE:
<223> OTHER INFORMATION: PCR Primer Oligonucleotide

<400> SEQUENCE: 10
ttaatacgac tcactatagg gagataactg aaggttggcg atggtc 46

<210> SEQ ID NO 11

<211> LENGTH: 47
<212> TYPE: DNA
<213> ORGANISM: Artificial Sequence
<220> FEATURE:
<223> OTHER INFORMATION: PCR Primer Oligonucleotide

<400> SEQUENCE: 11
ttaatacgac tcactatagg gagacaccat gggctccagc ggcgccc 47

<210> SEQ ID NO 12
<211> LENGTH: 47
<212> TYPE: DNA
<213> ORGANISM: Artificial Sequence
<220> FEATURE:
<223> OTHER INFORMATION: PCR Primer Oligonucleotide

<400> SEQUENCE: 12
ttaatacgac tcactatagg gagaagatct tgaaggcgct cttcagg 47

<210> SEQ ID NO 13
<211> LENGTH: 645
<212> TYPE: DNA
<213> ORGANISM: Artificial Sequence
<220> FEATURE:
<223> OTHER INFORMATION: ROP hairpin forming sequence

<400> SEQUENCE: 13
tcagcatgct gtaaaatgca tgatatatca gcagaaggca ttacattggt tgaagatatt 60
atgaagaaaa gggaaccgct tggtaccatg gaagctgtgt acttgataac accttcagaa 120
aagtcagttc atgctcttat gaatgacttt gaaccaccaa gacagatgta cagaggggca 180
cacgtgtttt ttacagaagc gtgtccagac gactagtacc ggttgggaaa ggtatgtttc 240
tgcttctacc tttgatatat atataataat tatcactaat tagtagtaat atagtatttc 300
aagtattttt ttcaaaataa aagaatgtag tatatagcta ttgcttttct gtagtttata 360
agtgtgtata ttttaattta taacttttct aatatatgac caaaacatgg tgatgtgcag 420
gttgatccgc ggttagtctg gacacgcttc tgtaaaaaac acgtgtgccc ctctgtacat 480
ctgtcttggt ggttcaaagt cattcataag agcatgaact gacttttctg aaggtgttat 540
caagtacaca gcttccatgg taccaagcgg ttcccttttc ttcataatat cttcaaccaa 600
tgtaatgcct tctgctgata tatcatgcat tttacagcat gctga 645

<210> SEQ ID NO 14
<211> LENGTH: 607
<212> TYPE: DNA
<213> ORGANISM: Artificial Sequence
<220> FEATURE:
<223> OTHER INFORMATION: ROP hairpin forming sequence

<400> SEQUENCE: 14
caagtatgct acgcatcttc atctcgctga agactgcatg aaggcctatc aggggtatat 60
agacaagttg tgtaaagttg agcaggattt ggcaatggga actgatgccg aaggcgagaa 120
aatcaaggat cacatgcgca acatcgtccc catcttgcta gatcccaaaa tcaccaatga 180
atacgataag agactagtac cggttgggaa aggtatgttt ctgcttctac ctttgatata 240
tatataataa ttatcactaa ttagtagtaa tatagtattt caagtatttt tttcaaaata 300
aaagaatgta gtatatagct attgcttttc tgtagtttat aagtgtgtat attttaattt 360
ataacttttc taatatatga ccaaaacatg gtgatgtgca ggttgatccg cggttatctt 420
atcgtattca ttggtgattt tgggatctag caagatgggg acgatgttgc gcatgtgatc 480

-continued cttgatttc tcgccttcgg catcagttcc cattgccaaa tcctgctcaa ctttacacaa 540
cttgtctata tacccctgat aggccttcat gcagtcttca gcgagatgaa gatgcgtagc 600
atacttg 607

<210> SEQ ID NO 15
<211> LENGTH: 471
<212> TYPE: DNA
<213> ORGANISM: Artificial Sequence
<220> FEATURE:
<223> OTHER INFORMATION: YFP hairpin forming sequence

<400> SEQUENCE: 15
atgtcatctg gagcacttct ctttcatggg aagattcctt acgttgtgga gatggaaggg 60
aatgttgatg gccacacctt tagcatacgt gggaaaggct acggagatgc ctcagtggga 120
aaggactagt accggttggg aaaggtatgt ttctgcttct acctttgata tatatataat 180
aattatcact aattagtagt aatatagtat ttcaagtatt tttttcaaaa taaaagaatg 240
tagtatatag ctattgcttt tctgtagttt ataagtgtgt atattttaat ttataacttt 300
tctaatatat gaccaaaaca tggtgatgtg caggttgatc cgcggttact ttcccactga 360
ggcatctccg tagcctttcc cacgtatgct aaaggtgtgg ccatcaacat tcccttccat 420
ctccacaacg taaggaatct tcccatgaaa gagaagtgct ccagatgaca t 471

<210> SEQ ID NO 16
<211> LENGTH: 225
<212> TYPE: DNA
<213> ORGANISM: Solanum tuberosum

<400> SEQUENCE: 16
gactagtacc ggttgggaaa ggtatgtttc tgcttctacc tttgatatat atataataat 60
tatcactaat tagtagtaat atagtatttc aagtattttt ttcaaaataa aagaatgtag 120
tatatagcta ttgcttttct gtagtttata agtgtgtata ttttaattta taacttttct 180
aatatatgac caaaacatgg tgatgtgcag gttgatccgc ggtta 225

<210> SEQ ID NO 17
<211> LENGTH: 702
<212> TYPE: DNA
<213> ORGANISM: Artificial Sequence
<220> FEATURE:
<223> OTHER INFORMATION: Plant-optimized sequence encoding YFP

<400> SEQUENCE: 17
atgtcatctg gagcacttct ctttcatggg aagattcctt acgttgtgga gatggaaggg 60
aatgttgatg gccacacctt tagcatacgt gggaaaggct acggagatgc ctcagtggga 120
aaggttgatg cacagttcat ctgcacaact ggtgatgttc ctgtgccttg gagcacactt 180
gtcaccactc tcacctatgg agcacagtgc tttgccaagt atggtccaga gttgaaggac 240
ttctacaagt cctgtatgcc agatggctat gtgcaagagc gcacaatcac ctttgaagga 300
gatggcaact tcaagactag ggctgaagtc acctttgaga atgggtctgt ctacaatagg 360
gtcaaactca atggtcaagg cttcaagaaa gatggtcatg tgttgggaaa gaacttggag 420
ttcaacttca ctccccactg cctctacatc tggggtgacc aagccaacca cggtctcaag 480
tcagccttca agatctgtca tgagattact ggcagcaaag gcgacttcat agtggctgac 540
cacacccaga tgaacactcc cattggtgga ggtccagttc atgttccaga gtatcatcac 600

-continued atgtcttacc atgtgaaact ttccaaagat gtgacagacc acagagacaa catgtccttg 660
aaagaaactg tcagagctgt tgactgtcgc aagacctacc tt 702

<210> SEQ ID NO 18
<211> LENGTH: 218
<212> TYPE: DNA
<213> ORGANISM: Diabrotica virgifera

<400> SEQUENCE: 18
tagctctgat gacagagccc atcgagtttc aagccaaaca gttgcataaa gctatcagcg 60
gattgggaac tgatgaaagt acaatmgtmg aaattttaag tgtmcacaac aacgatgaga 120
ttataagaat ttcccaggcc tatgaaggat tgtaccaacg mtcattggaa tctgatatca 180
aaggagatac ctcaggaaca ttaaaaaaga attattag 218

<210> SEQ ID NO 19
<211> LENGTH: 424
<212> TYPE: DNA
<213> ORGANISM: Diabrotica virgifera
<220> FEATURE:
<221> NAME/KEY: misc_feature
<222> LOCATION: (393)..(393)
<223> OTHER INFORMATION: n is a, c, g, or t
<220> FEATURE:
<221> NAME/KEY: misc_feature
<222> LOCATION: (394)..(394)
<223> OTHER INFORMATION: n is a, c, g, or t
<220> FEATURE:
<221> NAME/KEY: misc_feature
<222> LOCATION: (395)..(395)
<223> OTHER INFORMATION: n is a, c, g, or t

<400> SEQUENCE: 19
ttgttacaag ctggagaact tctctttgct ggaaccgaag agtcagtatt taatgctgta 60
ttctgtcaaa gaaataaacc acaattgaat ttgatattcg acaaatatga agaaattgtt 120
gggcatccca ttgaaaaagc cattgaaaac gagttttcag gaaatgctaa acaagccatg 180
ttacacctta tccagagcgt aagagatcaa gttgcatatt tggtaaccag gctgcatgat 240
tcaatggcag gcgtcggtac tgacgataga actttaatca gaattgttgt ttcgagatct 300
gaaatcgatc tagaggaaat caaacaatgc tatgaagaaa tctacagtaa aaccttggct 360
gataggatag cggatgacac atctggcgac tannnaaaag ccttattagc cgttgttggt 420
taag 424

<210> SEQ ID NO 20
<211> LENGTH: 397
<212> TYPE: DNA
<213> ORGANISM: Diabrotica virgifera

<400> SEQUENCE: 20
agatgttggc tgcatctaga gaattacaca agttcttcca tgattgcaag gatgtactga 60
gcagaatagt ggaaaaacag gtatccatgt ctgatgaatt gggaagggac gcaggagctg 120
tcaatgccct tcaacgcaaa caccagaact tcctccaaga cctacaaaca ctccaatcga 180
acgtccaaca aatccaagaa gaatcagcta aacttcaagc tagctatgcc ggtgatagag 240
ctaaagaaat caccaacagg gagcaggaag tggtagcagc ctgggcagcc ttgcagatcg 300
cttgcgatca gagacacgga aaattgagcg atactggtga tctattcaaa ttctttaact 360
tggtacgaac gttgatgcag tggatggacg aatggac 397

<210> SEQ ID NO 21
<211> LENGTH: 490
<212> TYPE: DNA
<213> ORGANISM: Diabrotica virgifera

<400> SEQUENCE: 21
gcagatgaac accagcgaga aaccaagaga tgttagtggt gttgaattgt tgatgaacaa 60
ccatcagaca ctcaaggctg agatcgaagc cagagaagac aactttacgg cttgtatttc 120
tttaggaaag gaattgttga gccgtaatca ctatgctagt gctgatatta aggataaatt 180
ggtcgcgttg acgaatcaaa ggaatgctgt actacagagg tgggaagaaa gatgggagaa 240
cttgcaactc atcctcgagg tataccaatt cgccagagat gcggccgtcg ccgaagcatg 300
gttgatcgca caagaacctt acttgatgag ccaagaacta ggacacacca ttgacgacgt 360
tgaaaacttg ataaagaaac acgaagcgtt cgaaaaatcg gcagcggcgc aagaagagag 420
attcagtgct ttggagagac tgacgacgtt cgaattgaga gaaataaaga ggaaacaaga 480
agctgcccag 490

<210> SEQ ID NO 22
<211> LENGTH: 330
<212> TYPE: DNA
<213> ORGANISM: Diabrotica virgifera

<400> SEQUENCE: 22
agtgaaatgt tagcaaatat aacatccaag tttcgtaatt gtacttgctc agttagaaaa 60
tattctgtag tttcactatc ttcaaccgaa aatagaataa atgtagaacc tcgcgaactt 120
gcctttcctc caaaatatca agaacctcga caagtttggt tggagagttt agatacgata 180
gacgacaaaa aattgggtat tcttgagctg catcctgatg tttttgctac taatccaaga 240
atagatatta tacatcaaaa tgttagatgg caaagtttat atagatatgt aagctatgct 300
catacaaagt caagatttga agtgagaggt 330

<210> SEQ ID NO 23
<211> LENGTH: 320
<212> TYPE: DNA
<213> ORGANISM: Diabrotica virgifera

<400> SEQUENCE: 23
caaagtcaag atttgaagtg agaggtggag gtcgaaaacc gtggccgcaa aagggattgg 60
gacgtgctcg acatggttca attagaagtc cactttggag aggtggagga gttgttcatg 120
gaccaaaatc tccaacccct catttttaca tgattccatt ctacacccgt ttgctgggtt 180
tgactagcgc actttcagta aaatttgccc aagatgactt gcacgttgtg gatagtctag 240
atctgccaac tgacgaacaa agttatatag aagagctggt caaaagccgc ttttgggggt 300
ccttcttgtt ttatttgtag 320

<210> SEQ ID NO 24
<211> LENGTH: 46
<212> TYPE: DNA
<213> ORGANISM: Artificial Sequence
<220> FEATURE:
<223> OTHER INFORMATION: PCR Primer Oligonucleotide

<400> SEQUENCE: 24
ttaatacgac tcactatagg gagagctcca acagtggttc cttatc 46

<210> SEQ ID NO 25

<211> LENGTH: 29
<212> TYPE: DNA
<213> ORGANISM: Artificial Sequence
<220> FEATURE:
<223> OTHER INFORMATION: PCR Primer Oligonucleotide

<400> SEQUENCE: 25
ctaataattc ttttttaatg ttcctgagg 29

<210> SEQ ID NO 26
<211> LENGTH: 22
<212> TYPE: DNA
<213> ORGANISM: Artificial Sequence
<220> FEATURE:
<223> OTHER INFORMATION: PCR Primer Oligonucleotide

<400> SEQUENCE: 26
gctccaacag tggttcctta tc 22

<210> SEQ ID NO 27
<211> LENGTH: 53
<212> TYPE: DNA
<213> ORGANISM: Artificial Sequence
<220> FEATURE:
<223> OTHER INFORMATION: PCR Primer Oligonucleotide

<400> SEQUENCE: 27
ttaatacgac tcactatagg gagactaata attctttttt aatgttcctg agg 53

<210> SEQ ID NO 28
<211> LENGTH: 48
<212> TYPE: DNA
<213> ORGANISM: Artificial Sequence
<220> FEATURE:
<223> OTHER INFORMATION: PCR Primer Oligonucleotide

<400> SEQUENCE: 28
ttaatacgac tcactatagg gagattgtta caagctggag aacttctc 48

<210> SEQ ID NO 29
<211> LENGTH: 24
<212> TYPE: DNA
<213> ORGANISM: Artificial Sequence
<220> FEATURE:
<223> OTHER INFORMATION: PCR Primer Oligonucleotide

<400> SEQUENCE: 29
cttaaccaac aacggctaat aagg 24

<210> SEQ ID NO 30
<211> LENGTH: 24
<212> TYPE: DNA
<213> ORGANISM: Artificial Sequence
<220> FEATURE:
<223> OTHER INFORMATION: PCR Primer Oligonucleotide

<400> SEQUENCE: 30
ttgttacaag ctggagaact tctc 24

<210> SEQ ID NO 31
<211> LENGTH: 48
<212> TYPE: DNA
<213> ORGANISM: Artificial Sequence
<220> FEATURE:
<223> OTHER INFORMATION: PCR Primer Oligonucleotide

<400> SEQUENCE: 31
ttaatacgac tcactatagg gagacttaac caacaacggc taataagg 48

<210> SEQ ID NO 32
<211> LENGTH: 47
<212> TYPE: DNA
<213> ORGANISM: Artificial Sequence
<220> FEATURE:
<223> OTHER INFORMATION: PCR Primer Oligonucleotide

<400> SEQUENCE: 32
ttaatacgac tcactatagg gagaagatgt tggctgcatc tagagaa 47

<210> SEQ ID NO 33
<211> LENGTH: 22
<212> TYPE: DNA
<213> ORGANISM: Artificial Sequence
<220> FEATURE:
<223> OTHER INFORMATION: PCR Primer Oligonucleotide

<400> SEQUENCE: 33
gtccattcgt ccatccactg ca 22

<210> SEQ ID NO 34
<211> LENGTH: 23
<212> TYPE: DNA
<213> ORGANISM: Artificial Sequence
<220> FEATURE:
<223> OTHER INFORMATION: PCR Primer Oligonucleotide

<400> SEQUENCE: 34
agatgttggc tgcatctaga gaa 23

<210> SEQ ID NO 35
<211> LENGTH: 46
<212> TYPE: DNA
<213> ORGANISM: Artificial Sequence
<220> FEATURE:
<223> OTHER INFORMATION: PCR Primer Oligonucleotide

<400> SEQUENCE: 35
ttaatacgac tcactatagg gagagtccat tcgtccatcc actgca 46

<210> SEQ ID NO 36
<211> LENGTH: 46
<212> TYPE: DNA
<213> ORGANISM: Artificial Sequence
<220> FEATURE:
<223> OTHER INFORMATION: PCR Primer Oligonucleotide

<400> SEQUENCE: 36
ttaatacgac tcactatagg gagagcagat gaacaccagc gagaaa 46

<210> SEQ ID NO 37
<211> LENGTH: 22
<212> TYPE: DNA
<213> ORGANISM: Artificial Sequence
<220> FEATURE:
<223> OTHER INFORMATION: PCR Primer Oligonucleotide

<400> SEQUENCE: 37
ctgggcagct tcttgtttcc tc 22

<210> SEQ ID NO 38
<211> LENGTH: 22
<212> TYPE: DNA

<213> ORGANISM: Artificial Sequence
<220> FEATURE:
<223> OTHER INFORMATION: PCR Primer Oligonucleotide

<400> SEQUENCE: 38
gcagatgaac accagcgaga aa 22

<210> SEQ ID NO 39
<211> LENGTH: 46
<212> TYPE: DNA
<213> ORGANISM: Artificial Sequence
<220> FEATURE:
<223> OTHER INFORMATION: PCR Primer Oligonucleotide

<400> SEQUENCE: 39
ttaatacgac tcactatagg gagactgggc agcttcttgt ttcctc 46

<210> SEQ ID NO 40
<211> LENGTH: 51
<212> TYPE: DNA
<213> ORGANISM: Artificial Sequence
<220> FEATURE:
<223> OTHER INFORMATION: PCR Primer Oligonucleotide

<400> SEQUENCE: 40
ttaatacgac tcactatagg gagaagtgaa atgttagcaa atataacatc c 51

<210> SEQ ID NO 41
<211> LENGTH: 26
<212> TYPE: DNA
<213> ORGANISM: Artificial Sequence
<220> FEATURE:
<223> OTHER INFORMATION: PCR Primer Oligonucleotide

<400> SEQUENCE: 41
acctctcact tcaaatcttg actttg 26

<210> SEQ ID NO 42
<211> LENGTH: 27
<212> TYPE: DNA
<213> ORGANISM: Artificial Sequence
<220> FEATURE:
<223> OTHER INFORMATION: PCR Primer Oligonucleotide

<400> SEQUENCE: 42
agtgaaatgt tagcaaatat aacatcc 27

<210> SEQ ID NO 43
<211> LENGTH: 50
<212> TYPE: DNA
<213> ORGANISM: Artificial Sequence
<220> FEATURE:
<223> OTHER INFORMATION: PCR Primer Oligonucleotide

<400> SEQUENCE: 43
ttaatacgac tcactatagg gagaacctct cacttcaaat cttgactttg 50

<210> SEQ ID NO 44
<211> LENGTH: 50
<212> TYPE: DNA
<213> ORGANISM: Artificial Sequence
<220> FEATURE:
<223> OTHER INFORMATION: PCR Primer Oligonucleotide

<400> SEQUENCE: 44
ttaatacgac tcactatagg gagacaaagt caagatttga agtgagaggt 50

<210> SEQ ID NO 45
<211> LENGTH: 25
<212> TYPE: DNA
<213> ORGANISM: Artificial Sequence
<220> FEATURE:
<223> OTHER INFORMATION: PCR Primer Oligonucleotide

<400> SEQUENCE: 45
ctacaaataa aacaagaagg acccc 25

<210> SEQ ID NO 46
<211> LENGTH: 26
<212> TYPE: DNA
<213> ORGANISM: Artificial Sequence
<220> FEATURE:
<223> OTHER INFORMATION: PCR Primer Oligonucleotide

<400> SEQUENCE: 46
caaagtcaag atttgaagtg agaggt 26

<210> SEQ ID NO 47
<211> LENGTH: 49
<212> TYPE: DNA
<213> ORGANISM: Artificial Sequence
<220> FEATURE:
<223> OTHER INFORMATION: PCR Primer Oligonucleotide

<400> SEQUENCE: 47
ttaatacgac tcactatagg gagactacaa ataaaacaag aaggacccc 49

<210> SEQ ID NO 48
<211> LENGTH: 1150
<212> TYPE: DNA
<213> ORGANISM: Zea mays

<400> SEQUENCE: 48
caacggggca gcactgcact gcactgcaac tgcgaatttc cgtcagcttg gagcggtcca 60
agcgccctgc gaagcaaact acgccgatgg cttcggcggc ggcgtgggag ggtccgacgg 120
ccgcggagct gaagacagcg ggggcggagg tgattcccgg cggcgtgcga gtgaaggggt 180
gggtcatcca gtcccacaaa ggccctatcc tcaacgccgc ctctctgcaa cgctttgaag 240
atgaacttca aacaacacat ttacctgaga tggtttttgg agagagtttc ttgtcacttc 300
aacatacaca aactggcatc aaatttcatt ttaatgcgct tgatgcactc aaggcatgga 360
agaaagaggc actgccacct gttgaggttc ctgctgcagc aaaatggaag ttcagaagta 420
agccttctga ccaggttata cttgactacg actatacatt tacgacacca tattgtggga 480
gtgatgctgt ggttgtgaac tctggcactc cacaaacaag tttagatgga tgcggcactt 540
tgtgttggga ggatactaat gatcggattg acattgttgc cctttcagca aaagaaccca 600
ttcttttcta cgacgaggtt atcttgtatg aagatgagtt agctgacaat ggtatctcat 660
ttcttactgt gcgagtgagg gtaatgccaa ctggttggtt tctgcttttg cgtttttggc 720
ttagagttga tggtgtactg atgaggttga gagacactcg gttacattgc ctgtttggaa 780
acggcgacgg agccaagcca gtggtacttc gtgagtgctg ctggagggaa gcaacatttg 840
ctactttgtc tgcgaaagga tatccttcgg actctgcagc gtacgcggac ccgaacctta 900
ttgcccataa gcttcctatt gtgacgcaga agacccaaaa gctgaaaaat cctacctgac 960
tgacacaaag gcgccctacc gcgtgtacat catgactgtc ctgtcctatc gttgcctttt 1020
gtgtttgcca catgttgtgg atgtacgttt ctatgacgaa acaccatagt ccatttcgcc 1080
tgggccgaac agagatagct gattgtcatg tcacgtttga attagaccat tccttagccc 1140
tttttccccc 1150

<210> SEQ ID NO 49
<211> LENGTH: 22
<212> TYPE: DNA
<213> ORGANISM: Artificial Sequence
<220> FEATURE:
<223> OTHER INFORMATION: T20NV Oligonucleotide
<220> FEATURE:
<221> NAME/KEY: misc_feature
<222> LOCATION: (22)..(22)
<223> OTHER INFORMATION: n is a, c, g, or t

<400> SEQUENCE: 49
tttttttttt tttttttttt vn 22

<210> SEQ ID NO 50
<211> LENGTH: 20
<212> TYPE: DNA
<213> ORGANISM: Artificial Sequence
<220> FEATURE:
<223> OTHER INFORMATION: P5U76S (F) PCR Primer Oligonucleotide

<400> SEQUENCE: 50
ttgtgatgtt ggtggcgtat 20

<210> SEQ ID NO 51
<211> LENGTH: 24
<212> TYPE: DNA
<213> ORGANISM: Artificial Sequence
<220> FEATURE:
<223> OTHER INFORMATION: P5U76A (R) PCR Primer Oligonucleotide

<400> SEQUENCE: 51
tgttaaataa aaccccaaag atcg 24

<210> SEQ ID NO 52
<211> LENGTH: 21
<212> TYPE: DNA
<213> ORGANISM: Artificial Sequence
<220> FEATURE:
<223> OTHER INFORMATION: TIPmxF PCR Primer Oligonucleotide

<400> SEQUENCE: 52
tgagggtaat gccaactggt t 21

<210> SEQ ID NO 53
<211> LENGTH: 24
<212> TYPE: DNA
<213> ORGANISM: Artificial Sequence
<220> FEATURE:
<223> OTHER INFORMATION: TIPmxR PCR Primer Oligonucleotide

<400> SEQUENCE: 53
gcaatgtaac cgagtgtctc tcaa 24

<210> SEQ ID NO 54
<211> LENGTH: 32
<212> TYPE: DNA
<213> ORGANISM: Artificial Sequence
<220> FEATURE:
<223> OTHER INFORMATION: ProbeHXTIP Probe Oligonucleotide

<400> SEQUENCE: 54
tttttggctt agagttgatg gtgtactgat ga 32

<210> SEQ ID NO 55
<211> LENGTH: 151
<212> TYPE: DNA
<213> ORGANISM: Artificial Sequence
<220> FEATURE:
<223> OTHER INFORMATION: Portion of SpecR coding region

<400> SEQUENCE: 55
gaccgtaagg cttgatgaaa caacgcggcg agctttgatc aacgaccttt tggaaacttc 60
ggcttcccct ggagagagcg agattctccg cgctgtagaa gtcaccattg ttgtgcacga 120
cgacatcatt ccgtggcgtt atccagctaa g 151

<210> SEQ ID NO 56
<211> LENGTH: 69
<212> TYPE: DNA
<213> ORGANISM: Artificial Sequence
<220> FEATURE:
<223> OTHER INFORMATION: Portion of AAD1 coding region

<400> SEQUENCE: 56
tgttcggttc cctctaccaa gcacagaacc gtcgcttcag caacacctca gtcaaggtga 60
tggatgttg 69

<210> SEQ ID NO 57
<211> LENGTH: 4233
<212> TYPE: DNA
<213> ORGANISM: Zea mays

<400> SEQUENCE: 57
agcctggtgt ttccggagga gacagacatg atccctgccg ttgctgatcc gacgacgctg 60
gacggcgggg gcgcgcgcag gccgttgctc ccggagacgg accctcgggg gcgtgctgcc 120
gccggcgccg agcagaagcg gccgccggct acgccgaccg ttctcaccgc cgtcgtctcc 180
gccgtgctcc tgctcgtcct cgtggcggtc acagtcctcg cgtcgcagca cgtcgacggg 240
caggctgggg gcgttcccgc gggcgaagat gccgtcgtcg tcgaggtggc cgcctcccgt 300
ggcgtggctg agggcgtgtc ggagaagtcc acggccccgc tcctcggctc cggcgcgctc 360
caggacttct cctggaccaa cgcgatgctg gcgtggcagc gcacggcgtt ccacttccag 420
ccccccaaga actggatgaa cggttagttg gacccgtcgc catcggtgac gacgcgcgga 480
tcgttttttt cttttttcct ctcgttctgg ctctaacttg gttccgcgtt tctgtcacgg 540
acgcctcgtg cacatggcga tacccgatcc gccggccgcg tatatctatc tacctcgacc 600
ggcttctcca gatccgaacg gtaagttgtt ggctccgata cgatcgatca catgtgagct 660
cggcatgctg cttttctgcg cgtgcatgcg gctcctagca ttccacgtcc acgggtcgtg 720
acatcaatgc acgatataat cgtatcggta cagagatatt gtcccatcag ctgctagctt 780
tcgcgtattg atgtcgtgac attttgcacg caggtccgct gtatcacaag ggctggtacc 840
acctcttcta ccagtggaac ccggactccg cggtatgggg caacatcacc tggggccacg 900
ccgtctcgcg cgacctcctc cactggctgc acctaccgct ggccatggtg cccgatcacc 960
cgtacgacgc caacggcgtc tggtccgggt cggcgacgcg cctgcccgac ggccggatcg 1020
tcatgctcta cacgggctcc acggcggagt cgtcggcgca ggtgcagaac ctcgcggagc 1080
cggccgacgc gtccgacccg ctgctgcggg agtgggtcaa gtcggacgcc aacccggtgc 1140

-continued

```
tggtgccgcc gccgggcatc gggccgacgg acttccgcga cccgacgacg gcgtgtcgga   1200
cgccggccgg caacgacacg gcgtggcggg tcgccatcgg gtccaaggac cgggaccacg   1260
cggggctggc gctggtgtac cggacggagg acttcgtgcg gtacgacccg gcgccggcgc   1320
tgatgcacgc cgtgccgggc accggcatgt gggagtgcgt ggacttctac ccggtggccg   1380
cgggatcagg cgccgcggcg ggcagcgggg acgggctgga gacgtccgcg gcgccgggac   1440
ccggggtgaa gcacgtgctc aaggctagcc tcgacgacga caagcacgac tactacgcga   1500
tcggcaccta cgacccggcg acggacacct ggacccccga cagcgcggag gacgacgtcg   1560
ggatcggcct ccggtacgac tatggcaagt actacgcgtc gaagaccttc tacgaccccg   1620
tccttcgccg gcgggtgctc tgggggtggg tcggcgagac cgacagcgag cgcgcggaca   1680
tcctcaaggg ctgggcatcc gtgcaggtac gtctcagggt ttgaggctag catggcttca   1740
atcttgctgg catcgaatca ttaatgggca gatattataa cttgataatc tgggttggtt   1800
gtgtgtggtg gggatggtga cacacgcgcg gtaataatgt agctaagctg gttaaggatg   1860
agtaatgggg ttgcgtataa acgacagctc tgctaccatt acttctgaca cccgattgaa   1920
ggagacaaca gtaggggtag ccggtagggt tcgtcgactt gccttttctt ttttcctttg   1980
ttttgttgtg gatcgtccaa cacaaggaaa ataggatcat ccaacaaaca tggaagtaat   2040
cccgtaaaac atttctcaag gaaccatcta gctagacgag cgtggcatga tccatgcatg   2100
cacaaacact agataggtct ctgcagctgt gatgttcctt tacatatacc accgtccaaa   2160
ctgaatccgg tctgaaaatt gttcaagcag agaggccccg atcctcacac ctgtacacgt   2220
ccctgtacgc gccgtcgtgg tctcccgtga tcctgccccg tcccctccac gcggccacgc   2280
ctgctgcagc gctctgtaca agcgtgcacc acgtgagaat ttccgtctac tcgagcctag   2340
tagttagacg ggaaaacgag aggaagcgca cggtccaagc acaacacttt gcgcgggccc   2400
gtgacttgtc tccggttggc tgagggcgcg cgacagagat gtatggcgcc gcggcgtgtc   2460
ttgtgtcttg tcttgcctat acaccgtagt cagagactgt gtcaaagccg tccaacgaca   2520
atgagctagg aaacgggttg gagagctggg ttcttgcctt gcctcctgtg atgtctttgc   2580
cttgcatagg gggcgcagta tgtagctttg cgttttactt cacgccaaag gatactgctg   2640
atcgtgaatt attattatta tatatatatc gaatatcgat ttcgtcgctc tcgtggggtt   2700
ttattttcca gactcaaact tttcaaaagg cctgtgtttt agttcttttc ttccaattga   2760
gtaggcaagg cgtgtgagtg tgaccaacgc atgcatggat atcgtggtag actggtagag   2820
ctgtcgttac cagcgcgatg cttgtatatg tttgcagtat tttcaaatga atgtctcagc   2880
tagcgtacag ttgaccaagt cgacgtggag ggcgcacaac agacctctga cattattcac   2940
ttttttttta ccatgccgtg cacgtgcagt caatccccag gacggtcctc ctggacacga   3000
agacgggcag caacctgctc cagtggccgg tggtggaggt ggagaacctc cggatgagcg   3060
gcaagagctt cgacggcgtc gcgctggacc gcggatccgt cgtgcccctc gacgtcggca   3120
aggcgacgca ggtgacgccg cacgcagcct gctgcagcga acgaactcgc gcgttgccgg   3180
cccgcggcca gctgacttag tttctctggc tgatcgaccg tgtgcctgcg tgcgtgcagt   3240
tggacatcga ggctgtgttc gaggtggacg cgtcggacgc ggcgggcgtc acggaggccg   3300
acgtgacgtt caactgcagc accagcgcag gcgcggcggg ccggggcctg ctcggcccgt   3360
tcggccttct cgtgctggcg gacgacgact tgtccgagca gaccgccgtg tacttctacc   3420
tgctcaaggg cacggacggc agcctccaaa ctttcttctg ccaagacgag ctcaggtatg   3480
tatgttatga cttatgacca tgcatgcatg cgcatttctt agctaggctg tgaagcttct   3540
```

-continued

```
tgttgagttg tttcacagat gcttaccgtc tgctttgttt cgtatttcga ctaggcatcc   3600

aaggcgaacg atctggttaa gagagtatac gggagcttgg tccctgtgct agatggggag   3660

aatctctcgg tcagaatact ggtaagtttt tacagcgcca gccatgcatg tgttggccag   3720

ccagctgctg gtactttgga cactcgttct tctcgcactg ctcattattg cttctgatct   3780

ggatgcacta caaattgaag gttgaccact ccatcgtgga gagctttgct caaggcggga   3840

ggacgtgcat cacgtcgcga gtgtacccca cacgagccat ctacgactcc gcccgcgtct   3900

tcctcttcaa caacgccaca catgctcacg tcaaagcaaa atccgtcaag atctggcagc   3960

tcaactccgc ctacatccgg ccatatccgg caacgacgac ttctctatga ctaaattaag   4020

tgacggacag ataggcgata ttgcatactt gcatcatgaa ctcatttgta caacagtgat   4080

tgtttaattt atttgctgcc ttccttatcc ttcttgtgaa actatatggt acacacatgt   4140

atcattaggt ctagtagtgt tgttgcaaag acacttagac accagaggtt ccaggagtat   4200

cagagataag gtataagagg gagcagggag cag                                4233
```

<210> SEQ ID NO 58
<211> LENGTH: 25
<212> TYPE: DNA
<213> ORGANISM: Artificial Sequence
<220> FEATURE:
<223> OTHER INFORMATION: ST-LS1- F PCR Primer Oligonucleotide

<400> SEQUENCE: 58

```
gtatgtttct gcttctacct ttgat                                           25
```

<210> SEQ ID NO 59
<211> LENGTH: 29
<212> TYPE: DNA
<213> ORGANISM: Artificial Sequence
<220> FEATURE:
<223> OTHER INFORMATION: ST-LS1- R PCR Primer Oligonucleotide

<400> SEQUENCE: 59

```
ccatgttttg gtcatatatt agaaaagtt                                       29
```

<210> SEQ ID NO 60
<211> LENGTH: 34
<212> TYPE: DNA
<213> ORGANISM: Artificial Sequence
<220> FEATURE:
<223> OTHER INFORMATION: ST-LS1-P Probe Oligonucleotide

<400> SEQUENCE: 60

```
agtaatatag tatttcaagt atttttttca aaat                                 34
```

<210> SEQ ID NO 61
<211> LENGTH: 20
<212> TYPE: DNA
<213> ORGANISM: Artificial Sequence
<220> FEATURE:
<223> OTHER INFORMATION: GAAD1-F PCR Primer Oligonucleotide

<400> SEQUENCE: 61

```
tgttcggttc cctctaccaa                                                 20
```

<210> SEQ ID NO 62
<211> LENGTH: 22
<212> TYPE: DNA
<213> ORGANISM: Artificial Sequence
<220> FEATURE:

<223> OTHER INFORMATION: GAAD1-R PCR Primer Oligonucleotide

<400> SEQUENCE: 62
caacatccat caccttgact ga 22

<210> SEQ ID NO 63
<211> LENGTH: 24
<212> TYPE: DNA
<213> ORGANISM: Artificial Sequence
<220> FEATURE:
<223> OTHER INFORMATION: GAAD1-P Probe Oligonucleotide

<400> SEQUENCE: 63
cacagaaccg tcgcttcagc aaca 24

<210> SEQ ID NO 64
<211> LENGTH: 18
<212> TYPE: DNA
<213> ORGANISM: Artificial Sequence
<220> FEATURE:
<223> OTHER INFORMATION: IVR1-F PCR Primer Oligonucleotide

<400> SEQUENCE: 64
tggcggacga cgacttgt 18

<210> SEQ ID NO 65
<211> LENGTH: 19
<212> TYPE: DNA
<213> ORGANISM: Artificial Sequence
<220> FEATURE:
<223> OTHER INFORMATION: IVR1-R PCR Primer Oligonucleotide

<400> SEQUENCE: 65
aaagtttgga ggctgccgt 19

<210> SEQ ID NO 66
<211> LENGTH: 26
<212> TYPE: DNA
<213> ORGANISM: Artificial Sequence
<220> FEATURE:
<223> OTHER INFORMATION: IVR1-P Probe Oligonucleotide

<400> SEQUENCE: 66
cgagcagacc gccgtgtact tctacc 26

<210> SEQ ID NO 67
<211> LENGTH: 19
<212> TYPE: DNA
<213> ORGANISM: Artificial Sequence
<220> FEATURE:
<223> OTHER INFORMATION: SPC1A PCR Primer Oligonucleotide

<400> SEQUENCE: 67
cttagctgga taacgccac 19

<210> SEQ ID NO 68
<211> LENGTH: 19
<212> TYPE: DNA
<213> ORGANISM: Artificial Sequence
<220> FEATURE:
<223> OTHER INFORMATION: SPC1S PCR Primer Oligonucleotide

<400> SEQUENCE: 68
gaccgtaagg cttgatgaa 19

<210> SEQ ID NO 69
<211> LENGTH: 21
<212> TYPE: DNA
<213> ORGANISM: Artificial Sequence
<220> FEATURE:
<223> OTHER INFORMATION: TQSPEC Probe Oligonucleotide

<400> SEQUENCE: 69
cgagattctc cgcgctgtag a 21

<210> SEQ ID NO 70
<211> LENGTH: 393
<212> TYPE: DNA
<213> ORGANISM: Diabrotica virgifera

<400> SEQUENCE: 70
catcgattgc ttgtcgcctt ggctcatgcg tttcgattcg gtgaatttct ttaagttctg 60
agttacttgt gtcgaaacga cggcgatatg ctgatgacgc aattccaccc acaattcgtc 120
gttttcgtcc agcagcacct ccttgtcgtt ggcattcggt gccggcacaa acttgtaaac 180
atcgttgacg atgggcaaca gatcgtaggc catcgcttgt agtgtcagct cgtgtagcag 240
cggcgtgaca cagtcaaagc ctcgatccaa aattaacagt tgagaacggg ccttttcggg 300
tccttcgccc attgttggct catccgcttt ataagcatcc aatttctgtt gaatcaattg 360
ggccaattca acatttcgat cccaatcgct tcg 393

<210> SEQ ID NO 71
<211> LENGTH: 240
<212> TYPE: DNA
<213> ORGANISM: Diabrotica virgifera

<400> SEQUENCE: 71
taaagcgtcg cgactcagtg gcgacgcaaa gttcaaatgc acggcgctgt agagctctgc 60
ggcgcagtcg gcgacgatgc gctcaatgtt cgcagctgtc ggttcgacaa agtagatcgc 120
agggacgtct gggatcgcgt cgcgctcggc gtcaatgagc atgtggagcg tcacgccctt 180
gcgccggagc tcgtggagct tgaggatcgg cgagatgatg tcgcggcaga acttgtcgta 240

<210> SEQ ID NO 72
<211> LENGTH: 287
<212> TYPE: DNA
<213> ORGANISM: Diabrotica virgifera

<400> SEQUENCE: 72
gcgcgactct ctatcgccga gcaggatgcc gtcaacgcac tcgtttacct cggcgtacgt 60
atcactcgtg gaccgaatga cagggacatc aagcgtaaga tcaagcaaaa gcccgctcag 120
gacgaagaat atgacctgtc gcgatataag ccgttgttgc gtacaatggt cgaggaacat 180
gtgtctggca aactcgacga aacactcttt ccctatgtga aggactctcc tctcgcagga 240
gcgtctgctt cccccaaggt ggccgccccg cccccaacga cctctct 287

<210> SEQ ID NO 73
<211> LENGTH: 216
<212> TYPE: DNA
<213> ORGANISM: Diabrotica virgifera

<400> SEQUENCE: 73
gttttctcgg agtcaatatc gtatcagatg gcaacagaaa gaagacatac accgtaccac 60
gaaaggagcg catcaccgaa cacacttatc aaatgtccag atggactccg gtcatcaaag 120
acataatgga agattgcatt gaagacaaac tggatgctcg acatttcccg ttcttggctg 180
gacgcgccca aagtactgcc tatcacgcac cgacaa 216

<210> SEQ ID NO 74
<211> LENGTH: 215
<212> TYPE: DNA
<213> ORGANISM: Diabrotica virgifera

<400> SEQUENCE: 74
tctccaggac gttcacaaat cctgacggat cgaagatctc cgttccgccg tatgatactc 60
ttttacctgt acgcttcgcc cattcctcca agttgccata ttcaacatat cctgcgcctc 120
ctacaacaaa cactgtcgac tctccgaacg ccatacgccg tggtcgccct tgcgcgcctg 180
cgcccgcacc ggaatagccc gcatttggat tgcgt 215

<210> SEQ ID NO 75
<211> LENGTH: 292
<212> TYPE: DNA
<213> ORGANISM: Diabrotica virgifera

<400> SEQUENCE: 75
cccggtactc ctcgtaatct cagcagcatc ggccttgtat ttgttgagct cggcatcgat 60
gtcctcggca acctctggga acggattcgc actgttcttt gcccaaaaga agtcttttgc 120
atcaaggtcg taccccttct tcttgccatc aggaccagct actgttacgc ggttaagctt 180
caacgtgagg cagtcggaaa cgagggactg ataggtccag ccatgagaga tcatgggtac 240
aaggtcaccg ttgcgatcga caagtaggag aagaggacgt tgtaggttag at 292

<210> SEQ ID NO 76
<211> LENGTH: 2105
<212> TYPE: DNA
<213> ORGANISM: Diabrotica virgifera

<400> SEQUENCE: 76 ttttttttt taaatttaaa taaatattta tttataaaaa taataatata tactataact 60
cctgacccaa taaagcaagc tgttgtagaa attgtttagc gttgttaaat gttgttgaac 120
cataagatat cctctttgcg ttacccgccg ttgtctttac tttcgcataa tcaactagat 180
tttgatattc aatataattt ccacctccaa caacaaaaac tatagcctct tggaatgccg 240
atcgatttct gggaatttca gttaatttca gttgttttgg atctaaataa aaatactcct 300
ccatttctga actattttta aattccatga gattatcaac tattttcgtt acgggaagat 360
tatgtctctt aattactaaa tttttaactc cttccattac aaagtttgaa ccttgtgata 420
ccaacttgga aaacatatta acagttttgg ttccggcacc ttcatattga ttccctatcc 480
cacttgccat tttagtatag ctcttccatc ttttgatata cagcagtggt gataaatcac 540
agccagcctc ggttaaggcg ttttcatatt tgtgtaaatc gtgatccgag atatgagggg 600
tacaaataaa atatattata aatagccgca atttatcttc aggtgtcccc gctgtaggat 660
ctgctaatat atccattagc agtttttcca ggccttgtgc tttgctcatt attttctcct 720
ctaattcaaa gaacgtgtct aattttctag atttaatgca gttaagcaaa gatgtagcta 780
cagaagtatg catgtcaatc aggcgtttct tttctaataa ttgtggcaag gaattgacag 840
ccgacgttat cttagctgta ttatcagaca ccatcgtcaa agcgatatca ttttcgttat 900
cgattcccat tgaacttttt agtttcttca cttccccctc tgacgatttg tactgttcta 960
actcctcctg aattgcctcg gccacggtgg gaaaaggaga acctttgtgt gtagaccaaa 1020
atttatcttt agaatccaac tcacaagatc gactcttggc tcttgctcct ccagttggca 1080
ccgactcttc aatagtaacg cggtttagag ccaaatctaa cagatcatga gcaagtgcct 1140
gataagtcca tgtgtgatgt agcgatgttg ccatatctac gtttctatct aaaataatca 1200
atagaggcct ctggaaatta aaattgccgg actgtgcgtc cgaaacaaac aaattgtttc 1260
tagtatcaaa aatattttct cgaagcttct tgtccagttt tttggctacc atttcggctg 1320
cgtttccttt aggacttcga attattggca cagttcctaa agttacaaag actgaaaaca 1380
agctgtccac tatgttgttc ataatagcct ccatttctga atcttttata tcacctttgt 1440
ttatactgta atatgacata atatcactgt tttggtgttt taggacaaat aaatcatctt 1500
ccaatgaaat gaagtttatg tattgatcat aaaccttatg aatatttgct acgctgtttg 1560
cagctattgc tgctgaagct agatcctcta atttatctct agatatcgga gaaataaaat 1620
ttaagtggta tatgtcatat gttcctcttt ggaaatcttg acttatccta tctaaattat 1680
cttctgtggc agcacaaaaa tatattgcag gaacctctgg tattggatct ctatccgaat 1740
gtaactgaac aaacaatgta acgccttgtt ctctcaattc tttcacagaa attaagggcg 1800
atataatgtc ttgccctatt ctgtcgtaaa ttaatacttt ccatacaggt tcagaggctg 1860
ataacttagt ctggggttga tttaaattta acatttgctt tatagcattg atttgtttct 1920
gtcttaaaga cgtcatagtt gaattaaagt ttctggaaaa agttaaaaca aattaattat 1980
atgtttaata tttaatatta aaatacgtgg acttagaaac ccattcgaaa tctgtgagct 2040
gtcaccgctc ttcttaatgt caatgacgtt ctgtttcgac ttgtggaagt cttgttttgt 2100
tttgg 2105

<210> SEQ ID NO 77
<211> LENGTH: 315
<212> TYPE: DNA
<213> ORGANISM: Diabrotica virgifera

<400> SEQUENCE: 77
ctgcacggta tagtggacga ttcggatgtt cgaaatcttt catcaacgct cgaacagact 60
cctccgacgg agtgatcaaa taaacggcat ccatggtcgg caagggttca cgtttttttgt 120 ggatgtcttc gaccaaagtt atgccctcgg cgctgatgtc atgcatttta cagcacgcgg 180
ataccatacg catagccagc ttatccacta caagaatacg ccattcaaca gttggcgctt 240
tgccagtagc tggcttcttc gtagctggac ccttgtagcg gatcaattaa ttcataattt 300
ttttgaccga cttgc 315

<210> SEQ ID NO 78
<211> LENGTH: 212
<212> TYPE: DNA
<213> ORGANISM: Diabrotica virgifera

<400> SEQUENCE: 78
cggagagacg aaatagaccg ccggtacgtc ttgcagtggt gggcgattcg aatgtagttg 60
tacatggagc gtcgcaccag catctcgcaa gtcttgcacg cggagaactg ttgcaagtac 120
atcctgagtt tgcgcatcga ggacgaggac cttccacaca agcggccctg tctgtactgg 180
cgtgctgcct cccgcttgcg cgcctgcttt cg 212

<210> SEQ ID NO 79
<211> LENGTH: 267
<212> TYPE: DNA

<213> ORGANISM: Diabrotica virgifera

<400> SEQUENCE: 79
cgccgccacc ggagagcgcc gcccggtgga gaaccaatct tgcgaggga gaggtggcac 60 gcgagtacga gagcgcggag agcgattatg tgagcaggca ccttgctttt gctgtgcaaa 120
aggtattgga agattacaaa cggaataact ccgacttccc taaaaaatca gaccgtggtc 180
gggctactct aatcatcacg gaccgggcct tcgacatgtt cgctcctttg cttcacgaat 240
tcacgtacca agcgatgtgc aatgacc 267

<210> SEQ ID NO 80
<211> LENGTH: 259
<212> TYPE: DNA
<213> ORGANISM: Diabrotica virgifera

<400> SEQUENCE: 80
gtgtaattaa ggactttgac ttccgacagc agtatgctgc ggcacacctg ttcttcatcg 60
aagccctacc tgaacaatta cttgagaagc tattttcgtc gtccgcagag ccatacttga 120
agggggtgaa agaactattc ctgaactact gggcaattga ggcacaagca ttcactctcc 180
gtaaccctgc catgtttttc agcatgtatg cgcctccaaa gacagagaat gagttccgtt 240
ctgctagaga caggctgga 259

<210> SEQ ID NO 81
<211> LENGTH: 317
<212> TYPE: DNA
<213> ORGANISM: Diabrotica virgifera

<400> SEQUENCE: 81
tgtcctcaac aagatgcttc ggagtctttc cctcggcagt taggcctgtc gcgcaacatt 60
gttcgacgtt tgcaacggta ggaagcttgt ccttctcaaa tatgctcatg cactgctccg 120
ccatattaag atgaagagag aacttttcgc gcatctcctg atattgcggt agatttgcga 180
gcatgtcctt catatcgttc aaacttgccg caccctctcc cttgaatcca gcattttctt 240
ctaagaactt gttgaagtct gccataagct tgtcgatcgc ctctcgcata tgcatgtgcc 300
gaacttcggt ccaaacg 317

<210> SEQ ID NO 82
<211> LENGTH: 867
<212> TYPE: DNA
<213> ORGANISM: Diabrotica virgifera

<400> SEQUENCE: 82
caaaactcgg caacccctgc ccgagctcga ttgtatatac tttctcacac cgaagaaaga 60
atcagtggag cagcttatac aggatttcaa atctgagaag aagcccactt acagatcagt 120
ccatatattt tggtcgacga gcatagctgc cgccccgaa ttaatggagt tgattggatc 180
ttgctccccc ctcttgactc gcatcaaatc gtttgtcgat ttcaatcttc actttcgagc 240
gtttgagagt cgagtgttcc atttggatct cccctggcg ttaaggcaac tgctgacaaa 300
aaatgtgaag ctagacgaga gtttactcag actgatcgcg gccagactcg ccacagtctg 360
tatcaccatg ggtgagacac ctagcatacg attcctcggc gacggaccac acgccgctct 420
caatcgtaag gttgcacagt acgttcaaga atactttgac agcgtcaaag tcaccggact 480
caatcgaagc aaatcagagc tgattataat cgaccgttcc atcgatgtat gcgtcatgct 540
agtgcatgag tatacttatc aagccctggc ttacgacgtc ctcgaaatac cgatctgtgt 600

```
gccacccggc caaaaactct tgtcaaacgg agaacagcga atggaagaca cgtattcttt    660

cgtcgatccg aagaagggga acaagatgtt tcttttgtct gaacaagacg agctgtatgt    720

tagatacagg cacaagcata ttgcctcagt aatcaccggc gtcaatgacg aactgaaaaa    780

attctcaaaa gacaacgctg ctgcgcagta caacaccaag ggggccacta aggcagaagg    840

tggtgtggat gtggctcagg ccattcg                                        867
```

<210> SEQ ID NO 83
<211> LENGTH: 944
<212> TYPE: DNA
<213> ORGANISM: Diabrotica virgifera

<400> SEQUENCE: 83

```
ccagctttga attcagcgcg gatgacgaat tctggcgaag ccatcaaggg gcactttatc     60

cggaggtggg cgcagacaca actagactag tcaacgaatt tcgtggtaaa cttgaattct    120

tgaatagcgg ctcagcgact gacactgtga gaaacgcgct ggagatggct ccgcacgtgc    180

tagcgcaaaa gaaggcactc gatatgcaca caataattgc tcaagcgttg tacgacgaat    240

tagagaaacg atcgattcct gaatactgtc atattgaaag cgacttgtta gacaatgtcg    300

cctcgtcgag gggggttaac tttcaggccg ttcgagatat gctagataaa ggttcacttg    360

aagataagca gcgtttgata tgctgcgtgt acaccgtgtg taaagatcaa gacgcaaaga    420

tcaatagtct ctgccacctt ctcaaagtaa atgtcgccga tcctactata atcccggcgt    480

taaaatttct gaggtaccaa gatagtctag ctctcagatc gacacaacct acttacgaca    540

gtctaaagat agagagtctt gtgtcgtcta aatcagcagc cggattaagc agtggtcaag    600

cagggggcac ttcgggtaac caaagtgctc cgaactttgg cgagtttggg aacaaagcga    660

aaggatggtt gtatcagtca ctcaagcaat tgatcaatct gaaacagaga ccaaagatcg    720

tcagtttggt tgaaggacta tctcaacaag gcaaaatcag tgagcagtac gacactctcg    780

accccttggg agttcctggg gatgttcggc aaaccagtgt gaatagtatt attcttttct    840

tgctgggtgg cgcgagttac atagaagccg aggctgctag cagatgggct actgacaatg    900

gcaaaaacct gattgttggg tctaccgctc ttctgagacc gtgc                     944
```

<210> SEQ ID NO 84
<211> LENGTH: 2274
<212> TYPE: DNA
<213> ORGANISM: Diabrotica virgifera

<400> SEQUENCE: 84

```
tgacccggca tcatagatgt tacgtagagg aaaaactgta atttgcatgt tcacgaatta     60

tatacgaaaa aatagattga aacaaataag gagaacttac gatcaatcgg atttgtaaaa    120

aaattatttc ataaaatatt aagaaataag tgaatttcgg gtcacgcttg acccagtctt    180

cgtactccga aggttaataa gataacgtat cacagtacaa aatagataga aatataacat    240

aactaaaaat atcgattatg gcataaatac cacatataca aagaaaacaa aatctttaat    300

ggcatcttgt ctttgagacc aaccaagaac attaataaag cttttatttc tcaatttagc    360

tggtattttt cgcataaaag attaaaagag cgtaggaatg taatattagt tttcaataat    420

ggaattcaaa aatgtcgtcc cattaatcaa cttggtagta cctattacaa attcaacatt    480

tgaatcttct tgcgtggata aaaatctcag agcagatatc tctgcaaatg tacatccacc    540

aataaagaat acaagaactg tttgtggtga atctgaattt attatagtgt taactgatct    600
```

```
ggtttcatct aaagttggac ctggtagtaa gcctaacaca tcctgcaatt gtttagttcc    660
tccagttctg gttacatgtt ccactaatct gatactcatc ggtgcgtata tactatgaac    720
gtaactaatg tctgtaggat taatttcgga agtgttttcc atggttaaac ttaatgcttt    780
tctcagaact gtgtattgtc tagtactaga ttgaagtttc aatagtccaa ctttttccaa    840
tttcgatatt gccagaaggg cctccaggcc gtaaacctgt actagatccc ttttatagct    900
ttccaaaatt ttgggcttta atccagaact tgcgatacat tgtaaacaca ttaaccttaa    960
cactttcacc attggtttgc tctgagcgat catttcttca atgtaagcac tgggtttgtc   1020
tacttctatg cagtttaaaa actcctgttc agcctgtaac gtatccaaaa aatcataccc   1080
atccgtgatt tccttaatac attccgcaat tgctgtatgt gttgccagtt gctttttctt   1140
tgccaaaatt tgaggaagtc tttgaacata aagcttcatc tcctggacag acttttcctg   1200
tgtattttcc atctgggcac taattgcttt agcctctttt gagagataac cgcctacagc   1260
attgaaattc ttgtcccgga tgtcagcaaa aattttgtca gttgaatcta gaatcagttg   1320
cttcttatct tctgataacg attctgtagt tctttcttca gtgcttaaaa aattatcgat   1380
tgggaaatag gcagttgaat tatttatacc gaaaatttca tcaatcaatc cttcataagt   1440
taactgtgta gctaaaggtg tgatcaaatc tacagaccta tcgattaata tgatttgatc   1500
aatacatgac tgttgattat ttttcatatc ttcactgtta ttcttttctc tttgcaatct   1560
aaccacaaga tcccaaactt gcttagctgc atttcctttg ccccaaactt taggaatagt   1620
tccatacatt ttttgaaggt atattatagc ttgtgctgtt tggtataaat acgtagggtc   1680
gttttcaatt gtgtactccc taaaaatact aaaaacctca gatatttcca ttgatactaa   1740
gtcagattca aatggaaaaa gctggcattt gaattcatca attaacatta cgcttccata   1800
gactccttta tgtttcaatc tttccatgca caataagctt ttctttggta caaaaaaacaa  1860
atggtattgc ttcttactgc cacttttcgt tttactgtca gcatgtacat tttgtgcaat   1920
gtagtccatc agatacaatt tgggccttga gatgaagata atatgatcga catcagtttc   1980
aggtaaaggc atatttcgaa gtgggaacat cttaggagcc tggtgctcct tgaggattgc   2040
atatttggct acaagtccaa ctggtccagc taagctgtta tcccaaacaa tgactttctt   2100
accaggacat tgttctaaaa ggtttatcag gtttgcccta gctgctgctt gaattaagga   2160
tatatctact tttccacttt gcatgtgagc catatttcac tttagccttt aacttaacta   2220
taactgatca aaagaggtgg atttaaatgt ttatatttta ttctgtcact gtcg         2274
```

<210> SEQ ID NO 85
<211> LENGTH: 575
<212> TYPE: DNA
<213> ORGANISM: Diabrotica virgifera

<400> SEQUENCE: 85

```
tgggtatcga ctccggctta gcctcttgga agccgcagtt tctaataact ctttgatcac     60
tggctcaaat cgactgagct catattgcgc tgatttggct cgctttttat agtagtttag    120
taactcttca ttcttatgta ttttgtggac atgtttgagc gagctcgcac caggcccatt    180
ctcctccgat ttggcgtcat tggacaagtc taaagaaccg aatgtatcaa ttatctgctc    240
aatctccagg gacatgcctg ctgcgcgaat cattttcttc ttatcttcag cttgtactcc    300
gtccatcatt gaaaaatata gcagcagcaa tctaaccttc tcggtcatta tcacaccact    360
tttgtcagaa acaagcttag caagctcctc cagaatcttc aacacctgaa cagacttgcc    420
gtgcttatct acccctgtcg ctagatcctg ctctaatacg ccagctctga aaatccctgt    480
```

```
ttgattgaga gtactaaagc agctctcaga catattgata tgattcatga acttctcgag    540

catttccgag tactgaggaa gagcccgaat ggcct                               575


<210> SEQ ID NO 86
<211> LENGTH: 276
<212> TYPE: DNA
<213> ORGANISM: Diabrotica virgifera

<400> SEQUENCE: 86

gaggattaag ttgaagtgac tgaatcagct gcgagcactt ggtcgtcaga tttgcgaatt     60

gcatgtcagt catgggcgtg acgaactgta agtcataagc catgtatttt cgtgaagcct    120

cgtcctgaag tattatggtc aggttctttt cagtcgcctc tacgaagtac acagcacaca    180

catcctcaac tgggctccgt tcagaggcta tatgcaacat tagagtaacg ccttgctggc    240

gaagttcgcc gactttcacc accggggcga tgatca                              276


<210> SEQ ID NO 87
<211> LENGTH: 260
<212> TYPE: DNA
<213> ORGANISM: Diabrotica virgifera

<400> SEQUENCE: 87

ggaagctgtt gaatctgtgg tcaatggttt gatttcgttc tgcgcagcga tgcaacttcg     60

gcccctgatc aagatcccta aaaatgaagc gtcgcccgcg cgactggttg gaacaagatt    120

agatgaagaa ttgcgaaaac tacaagtgcg ttttggcgat aaatttgttt ccttatccaa    180

ctcaggcaat aggagaccga tactagttct cactgatcga acactagact ttttcacgcc    240

cctatcccac agctccacat                                                260


<210> SEQ ID NO 88
<211> LENGTH: 1929
<212> TYPE: DNA
<213> ORGANISM: Diabrotica virgifera

<400> SEQUENCE: 88

ttgtaataga ttttaattct aaattaacag taaatatact tagtataatt taacaataaa     60

tatttaatta cacatctttg gatagtatat atataaagga atgtaaattt tattcaaaat    120

ggatatttct tatgtttctt gtatgtcttc taggacagtt tttagtagct tgttcgactt    180

cctccaaaaa gctcgtagag ttgtggatag tagtacctcc cagtagcaca ttaaaatttg    240

gatagtttct gtttatggaa tgcactgtta atgactcctc gtaagtagca ccacctacaa    300

taaaaacaat gatgtcttgt ggtctaccat tgcttccatg actgccaaga taaggataca    360

actgttcctt aagcctgccc ttaactagat cttccaatgt ttcatgtagg agtggtttgt    420

gttgggtgta aacgttgtcc actccactta agcctttgat aaacctttta gtgattttaa    480

cagcattttc tacattgaat aaatcgcttt gtctagcatg tgatcctgca tattctataa    540

tattaacaat attcctcagc aacttgtcag gcacatttct ctttttgagt aaatctacta    600

atcctgtaat gtcattattg ttgtgatttt ggtatcttaa ggcatacatc atcactaatt    660

tgacagcgtc agtatttcta attttatcgt tagtcaataa ttttttaata ctctgtaaat    720

gagcatagta atcgttattt tgcgaagata tttcttgttc gatttcagaa acatccaaca    780

aatgatactt gttcaccatt gagctcagtt ctccaacaac tgttacatgt ttagtgacat    840

taccagacag tttcttaaac tgtggatatg attctacaaa gtttttcatg tcggctatac    900
```

-continued

```
tttctatttt ctggtgactt ttagcttttg cctggaattg atccatcaac tgttttatat    960

ttgtaccgat ttcaccatag ttcataaata catttttggc gtaaaaagtg tcttgttcaa   1020

ctgataaaac cacttctgac agttcttttg caacacctgg cacattggac aaattaactc   1080

tgttgttgta tattgttaat aattcgtgca ccattgcttg ataagtccac tggtttagta   1140

aaggtgtgat aggatcatct ctacgatcta aaataagtaa taaagagcta ttgatctggt   1200

tgaaagcaaa cagcgaagat tccttattta taacctcgtc tattcttgag cccaaatctt   1260

tacaaacatt tgagtttgct tgatacctaa tcactggaca tttcttaaga gacagtaata   1320

cagaaataat gccttggacg cttatttgta aagcacttgg attccaactg agtgaagtca   1380

aagcagcgtt taaaccaagt gaaaacagat gtggattgac agccaaataa tccatgtaaa   1440

gctcttggac ttctttaacc acctcgtgtt cgtcatgctc ggcaagaatt ttgatatcag   1500

ctttagctat tatattacta aagtagacat agtaagcacc atacttaggg tttcgaagtt   1560

ctgcacatag agcactgata ttctgttgag tcggtctcag gaaggctaag cacttcaagt   1620

aacgaagacc tgtcgagttt gcgaagctgg gagagtctat tcgctctagt aaaaatacct   1680

ctttttgttg aatttctgat tgcccataga ccatactgat aacacttgtt gtgtctttgt   1740

ccattagcag cactttcatg cccggttcgc tctcgctggt cattttgact atataggcct   1800

taattgccga tatgacgttc attttggatg cttattaaaa ttgttttaca ctaaattaaa   1860

ctgtttacaa ttttgttgta ttaagttttc attttgcaag caaactgagc gaacttcaca   1920

gtggtcgat                                                            1929
```

<210> SEQ ID NO 89
<211> LENGTH: 2881
<212> TYPE: DNA
<213> ORGANISM: Diabrotica virgifera

<400> SEQUENCE: 89

```
tagcgcgctc atcactgtat gtacatacat tagtgcaata tctcaaaagt tatcaaatta     60

aggccacaac atagtaataa cattaagatg gttttatgtt atgtaatttt catgctatgc    120

aagagccatg caagacatat tatacaactg cgcatgccca catgctattt tcaagcaatt    180

cctgtgctag acaaaagatt agaatgtgtt ctattttcca tgcaagttgt tgtcaaaatt    240

cttgttgtca acatagcaaa attttttagt gtagaataaa actttttttct tgtaagttta    300

aatgttatct attttgtgta ataatttctg atttatattt gaatatattt aatgctggac    360

tgaaatttct aagcgaaata tctaaaatta atgattcaat atatttcttt tgttgccaac    420

aatgaaagta gtatctaaaa ttgcatagaa atagctttgg tgtaaacaaa ttaggctagg    480

taagatatat gccatgcagg acagacttgc atagcatgaa atttacatgt cctagatgta    540

cagctgcttt taaaatatca aagaaaaact ttgtattaaa tctatattaa aataggaagt    600

gtcatgtttg aaaaaattta aagagaagac ttcaaataac tataattcat ctaccgaaca    660

gatggagtta tcatgtgaat aaatcacaat attttttcaa aatccttaac gcactccctt    720

gtacacaata ccgatcacag acatatacaa ctttattgaa gtaagtaaat caactgttgg    780

tattcaatga aataatcata cagctaccca agcaaaccat ggctgatgag agagaccctg    840

tctgtgtaaa gtttagatgg gtgtacaata catagataaa ggggttgtca ctggccatgg    900

ttcatgccag gagctatagt cacgtgaaga tcatgcattt ttttctccgt ctcttcagta    960

gactaattat agtttatgat atgatacctt cttagagatt caaatagcta tggtgaaacc   1020

aaaatttcac aaaacaaatc atcatttggg ataatctaaa atgccttgca ttaaataatt   1080
```

```
cccagtaaca actctatcac ttaaaataac aatttgtgtc cctgttagag tttccagtaa   1140

attgcaggca gctatttcag cgtaagtgac tcctccaatc atatatataa gcaccatcct   1200

attctgaaga ggatatcctc tttcatttct taacgataga tgaccaaaca cttccaattt   1260

agttctaatc tcatctaaag gaattgaatt aagaatcatt ccagctattt gggttataag   1320

aggaatgtag ttgcctccaa atacataact ggtacatgta ggaaacttta gattcactgc   1380

agtaggatca ggtgggattt gttttaaatt tttagaattg atttggctat tacttgaact   1440

aaatattgga atcttcaatt ttccttgtat atttaaacta ttgcttgttt ctactgactc   1500

tggaataaaa cctatattca gtagattatg aaaagcaaaa ccatagctaa agccaaactg   1560

atgcaagaat tttagccaga atgttctaat ttcgctttca ctcattggct gatacagtat   1620

taacagacag aataaccgca atgttatgta tttgtcattt tctgtgttta aaacctcttc   1680

caaatagttt aagtttaagg ctctatcatt gtttcttact atattatgtt ccaccatctt   1740

ctgattttcg tatctatggc ctaagatgtt gattatactt tctgcagcct gtaaatggtt   1800

tgttataaac ttcttcttgg atttagttgc gtgtagttgt gtttgtacat attgtttaat   1860

ttcatctaat gccatttccc tggaactcat cttttctgtt tttaactctt ttgttaaatt   1920

acttaaaaca gataatactt ctgtaaaata tctattttta atgtcatagt aaatactatc   1980

aacattacta tctaaactaa agttaattga ttgtttttct ggtaaaggat tacatttcgt   2040

atcaaatttt tctagtttct cttccttttt ttcacaaatc cctgcactaa cgttgtatat   2100

ctcagccagt agggctgcat atgtacctgg agttaataat gcacttgtgt agtctatgtt   2160

tctatccatt attattaagg ctccaaaatc agattctagt ctatcagttt ctcctctgtc   2220

ttcgcagcat tgatcaaatt gagctagaac tgctttagaa tactcaccta gacataaaat   2280

aaaccttggt ttacctatta caaaattgag ttgccacaag cacttggaca aaacaggtag   2340

ataagttaag tttttatata caaagagaga actgtataga ttcggtattt cgagactcag   2400

taaacttgtg tccagatgta aaggcatcca ctggaagtga tgtattctta ttgtaccata   2460

aacacctaat gcttctagtt cattttcaaa tgcacaattg taacaaggta ctacaataat   2520

gtgaaattta ttctttactg gttgttcaat gttctcaatc tgtgatctga tctgatctac   2580

tacctgttta aatactattg tatcaaaata tatcatgtaa aatacaacat ttgatcctgc   2640

atatggattt acgggttcta atttaaatat tttctctatg ccatttcctt ttaaccatgt   2700

aacaccacat actctttcca gtggcctaat taatgatggt tctattatta aatacttcgg   2760

gtttgaaacc acgtttaata tcttggagag ttgtgctttg gatatttctt gtaaacctga   2820

caattttgtt gtaatatcca taatattatt atgtttgttg ctttttaaat ttgacaaaag   2880

t                                                                   2881
```

<210> SEQ ID NO 90
<211> LENGTH: 1042
<212> TYPE: DNA
<213> ORGANISM: Diabrotica virgifera

<400> SEQUENCE: 90

```
gaatacaatg tgttgctcta gcgaagatgg tggtcagctt ggtaccctga atttagtcac     60

ctcccttgcc ggcaaaactt ccgacgtcac ggccaacctg gtcaaggacg cctggaacga    120

gctgttgagt gacggcaaga aggtgcccag tcctaccaac aactgctgtg tggtcattct    180

agaccgatct gacgatccca tagtcccgtg tctcttgccc tggacatatt tgggcatgat    240
```

-continued

```
tcaagaatat cttaaactgg atcagtgcgg cattctaacc ttgaccgatg ggactcaagc    300

taatctatca tttagaagcg actctttttt tcgagagaac tacaataaaa atttcggtga    360

acttgcaaat ctactttcca agccgccagc tgagacaaaa gcagatttta ccactagcct    420

acacgagttt gaaacggcca agaaagactt gagcgaatac gaactacact caaaaatact    480

tcacgagata aaagatgtga ttgagaggga ccaaattttt gcggtttgga aagtcgagca    540

agatgtacta aaagcaacga caatcacgcg caacgacgcc gtcatattag gcattgacca    600

gctgactagt aatggcattg tgaaaacttc ggcgatacat agactgatca aactgatcaa    660

aatcaagtgc cggtatatac ttggagagga ttatccggat gcagcgtgga ttaactggac    720

gcctgacccc ctagatgctc ccttaatcca ggcattctac caaaacatga cttataaagt    780

cactcaccgc tttggtctac agaatagcga ttatagtcca ctcacccatc gaataatatc    840

taccttgctt aaaggtcagc tgcctccaaa gatgatcagc agcatgccac tgaacggagt    900

gtcgcccaag cacattgttg tactgattgt gggctcggcg tacgccgctg aggcaccaca    960

aaaaatgtgg accacgtctc aggtgggcgg tctccaccct cttttgatcg attagaattt   1020

ttgaacatgc gcttcgtgtg gg                                             1042
```

<210> SEQ ID NO 91
<211> LENGTH: 810
<212> TYPE: DNA
<213> ORGANISM: Diabrotica virgifera

<400> SEQUENCE: 91

```
ctttgacagc gtcaaagtca ccggactcaa tcgaagcaaa tcagagctga ttataatcga     60

ccgttccatc gatgtatgcg tcatgctagt gcatgagtat acttatcaag ccctggctta    120

cgacgtcctc gaaataccga tctgtgtgcc acccggccaa aaactcttgt caaacggaga    180

acagcgaatg gaagacacgt attctttcgt cgatccgaag aaggggaaca agatgtttct    240

tttgtctgaa caagacgagc tgtatgttag atacaggcac aagcatattg cctcagtaat    300

caccggcgtc aatgacgaac tgaaaaaatt ctcaaaagac aacgctgctg cgcagtacaa    360

caccaagggg gccactaagg cagaaggtgg tgtggatgtg gctcaggcca ttcgggctct    420

tcctcagtac tcggaaatgc tcgagaagtt catgaatcat atcaatatgt ctgagagctg    480

ctttagtact ctcaatcaaa cagggatttt cagagctggc gtattagagc aggatctagc    540

gacaggggta gataagcacg gcaagtctgt tcaggtgttg aagattctgg aggagcttgc    600

taagcttgtt tctgacaaaa gtggtgtgat aatgacagag aaggttagat tgctgctgct    660

atatttttca atgatggacg gagtacaagc tgaagataag aagaaaatga ttcgcgcagc    720

aggcatgtcc ctggagattg agcagataat tgatacattc ggttctttag acttgtccaa    780

tgacgccaaa tcggaggaga atgggcctgg                                     810
```

<210> SEQ ID NO 92
<211> LENGTH: 2866
<212> TYPE: DNA
<213> ORGANISM: Diabrotica virgifera

<400> SEQUENCE: 92

```
ctttattaaa atcttttaaa atattatttt tgaatttgaa attgtgcaag ttatgaacgt     60

agctctataa aagcacaaga atatttatca aaaaaaacag ccataggaaa acaaagaaga    120

aaaacttttc ttcatttaat atatttatca tatttatcta ccaaattcta gatggcacaa    180

tggaaaattt gtgttatgga ttatcacaaa gggggttaat gatggaaagt ccttgaaaat    240
```

```
tgtagtttca gcagtgattc atacgggtcg cactataccg tcacggattt cacggattct    300
gcgcgtttga gacctttcat tcatcttttt gttattgttg cggaggtcaa tttttatat     360
cggaagacaa ttttatccaa atttttgaaa aatctccaat tctgtcactg aattaggact    420
taagtggaac accatggcgt taaagaacca agttggtcaa aaaatcatga atgaagtcat    480
caagcacaag cccaccaaga agaatgggcc aactccagga cagcaagccc atggggtaga    540
atggaggatc cttgtggtgg accagcttgc catgaggatg gtttcagcat gctgtaaaat    600
gcatgatata tcagcagaag gcattacatt ggttgaagat attatgaaga aaagggaacc    660
gcttggtacc atggaagctg tgtacttgat aacaccttca gaaaagtcag ttcatgctct    720
tatgaatgac tttgaaccac caagacagat gtacagaggg gcacacgtgt tttttacaga    780
agcgtgtcca gaccaattat ttagtacctt gtgccaccac cccgtagcaa agtttattaa    840
aaccctaaaa gaaatcaaca tagcattcat tccgactgag tcacaggtgt tctcattgga    900
ttcaccagac acgttccagt gtagctacga tccatcattt tccgctgcta gaaacgccaa    960
catggaaaga atggcagaac aaattgcgac actctgtgcg actctagggg aatacccaca   1020
cgtcagatat agaactgatt gggaaagaaa tgttgagctg gctcaactaa ttcagcagaa   1080
attggacgcc tataaagccg acgaacctac catgggagag gggccggaaa aggcgagatc   1140
acaattaatt atcctcgacc gaggtttcga ctgtgtatct ccccttcttc acgaacttac   1200
tttccaagca atggcctatg acttactacc catagaaaat gatgtatata agtacgaagc   1260
atcggctggt gttatgaaag aagtccttct agacgaaaac gacgagcttt gggtcgatct   1320
acgccaccaa cacatcgcgg tggtgtctca gagcgtcacc aagaatctga agaaattcac   1380
cgactccaaa cgcatgaccc agagcgacaa gcagtcgatg aaggatctct caaccatgat   1440
caaaaagatg ccgcaatatc agaaagaatt gtccaagtat gctacgcatc ttcatctcgc   1500
tgaagactgc atgaaggcct atcaggggta tatagacaag ttgtgtaaag ttgagcagga   1560
tttggcaatg ggaactgatg ccgaaggcga gaaaatcaag gatcacatgc gcaacatcgt   1620
ccccatcttg ctagatccca aaatcaccaa tgaatacgat aagatgcgta ttatagcatt   1680
gtacgccatg acgaaaaacg gcatcacaga tgaaaatctc tccaaattgg ctacccatgc   1740
ccaaatcaag gacaaacaga ccatcgccaa ccttcagtta cttggagtca acgttattaa   1800
tgatggagga ccaagaaaaa aacaatatac agtaccgcgc aaagaaagaa ttacagaaca   1860
aacgtaccaa atgtcaagat ggacacctat cattaaggat ataatggagg attgcataga   1920
cgacaaactg gatcagaaac actacccgta tttgagcgga cgagcacagt ctacgggata   1980
ccatgcagcg ccctctagtg cccgttatgg ccagtggcac aaagacagag gtcaacaagc   2040
cgtgaagaac gttcctcgac tgctcgtctt cgtcgtgggt ggaatcagtt tttcagagat   2100
caggtgcgcc tacgaagtga ccaacgcgca gaagaactgg gaagtcatca tcggctcgtc   2160
gcacatactc actcccgagg acttcctaag caatctggca acgttggccg gctagaatca   2220
gatgaaaaag gttactttta atgtacccga gtaaacagtt tcgcagtcgt agtttaaaat   2280
aatgtaatga gtctttttaa tcccaattta aacatattta tatagaatga ctttcgatca   2340
gtatcgaacc gttttctttg ttacgagagt taaagctgtt caaattatct tgaaatttgt   2400
gcagaattgt catacattaa attgttgcgc ttctgaaatt gttgtgcaat aaaagaaaat   2460
gtctaaggtg ctcaaaactc aaagccttcg atgagtttat gattataaat tgagaataaa   2520
aagactcatt gagcttaaaa agtattattt cctacccttt ttttgtattt ttccaatagc   2580
```

-continued agagtttttt attcaatttt tgcggttatt gggatattat cgctttattt acaaaattgt 2640
gtaaaaggta taaaaatgac gtttttgagg agtcttcctg taaaattaat ttcaatagtc 2700
agagatttac caaaaaaata tttttttggg ttaagatttt agtttcttaa catattataa 2760
aatacatcgt tttttttgtt ttatttactg ttaaagcttc tatattgtct tcttgaactg 2820
ctgtggcgac cccatcattg aaaacacttc caagaacaag aacaca 2866

<210> SEQ ID NO 93
<211> LENGTH: 265
<212> TYPE: DNA
<213> ORGANISM: Diabrotica virgifera

<400> SEQUENCE: 93
atcaagatcc ctaagaatga agcgtcgccc gcgcgactgg ttggaacaag attagatgaa 60
gaattgcgaa aactacaagt gcgttttggc gataaatttg tttccttatc caactcaggc 120
aataggagac cgatactagt tctcactgat cgaacactag actttttcac gcccctatcc 180
cacagctcca catacgaggc tctactacac gattgcttcg gtataaaatt gaattggatt 240
caaataaatg aaagcaaata tgaac 265

<210> SEQ ID NO 94
<211> LENGTH: 258
<212> TYPE: DNA
<213> ORGANISM: Diabrotica virgifera

<400> SEQUENCE: 94
cagatttgcg aattgcatgt cagtcatggg cgtgacgaac tgtaagtcat aagccgtgta 60
ttttcgtgaa gccacgtcct gaagtattat ggtcaggttc ttttcagtcg cctctacgaa 120
gtacacagca cacacatcct caactgggct ccgttcagag gctatatgca acattagagt 180
aacgccttgc tggcgaagtt cgccgacttt caccaccggg gcgatgatca tttgcgaacg 240
gtcgtcatat atgagaat 258

<210> SEQ ID NO 95
<211> LENGTH: 423
<212> TYPE: DNA
<213> ORGANISM: Diabrotica virgifera

<400> SEQUENCE: 95
gccgaacgga tttcgctgaa gctgatgccg ccgaggcaga aaagaataac cttgggcttg 60
tccgttgtat tcgcgtttcg agctagattt gctaaatttt gatcgtctac gggcgaaacg 120
tctgaacttt cccagtccca atcaaattga gttgcgcgaa tgcgtcctcc gtgagaattg 180
ttttgagtag cgacgtagcc tccgaaatcg ggatcttgta gatatgggga tcgactccgg 240
cttagcctct tggaagccgc agtttctaat aactctttga tcactggctc aaatcgactg 300
agctcatatt gcgctgattt ggctcgcttt ttatagtagt ttagtaactc ttcattctta 360
tgtattttgt ggacatgttt gagcgagctc gcaccaggcc cattctcctc cgatttggcg 420
tca 423

<210> SEQ ID NO 96
<211> LENGTH: 209
<212> TYPE: DNA
<213> ORGANISM: Diabrotica virgifera

<400> SEQUENCE: 96
ctcctcatct tttgtttttg cgctgttcaa tgcccaatag gtatgctcct tctgcatccc 60

```
aagactaaaa agatcgggct ccgtgacgat gaagttgagg tattggtcgt aaacttgtgc    120

aatttgttcc gaggtgcctg cagcagctgt ttgcgcggca aagtcctcca gaaggggtcg    180

gggtatcgag gagaggaagt tgagatggg                                       209


<210> SEQ ID NO 97
<211> LENGTH: 4816
<212> TYPE: DNA
<213> ORGANISM: Diabrotica virgifera

<400> SEQUENCE: 97

cggatttcac ggattctgcg cgtttgagac ctttcattca tctttttgtt attgttgcgg     60

aggtcaattt tttatatcgg aagacaattt tatccaaatt tttgaaaaat ctccaattct    120

gtcactgaat taggacttaa gtggaacacc atggcgttaa agaaccaagt tggtcaaaaa    180

atcatgaatg aagtcatcaa gcacaagccc accaagaaga atgggccaac tccaggacag    240

caagcccatg gggtagaatg gaggatcctt gtggtggacc agcttgccat gaggatggtt    300

tcagcatgct gtaaaatgca tgatatatca gcagaaggca ttacattggt tgaagatatt    360

atgaagaaaa gggaaccgct tggtaccatg gaagctgtgt acttgataac accttcagaa    420

aagtcagttc atgctcttat gaatgacttt gaaccaccaa gacagatgta cagaggggca    480

cacgtgtttt ttacagaagc gtgtccagac caattattta gtaccttgtg ccaccacccc    540

gtagcaaagt ttattaaaac cctaaaagaa atcaacatag cattcattcc gactgagtca    600

caggtgttct cattggattc accagacacg ttccagtgta gctacgatcc atcattttcc    660

gctgctagaa acgccaacat ggaaagaatg gcagaacaaa ttgcgacact ctgtgcgact    720

ctaggggaat acccacacgt cagatataga actgattggg aaagaaatgt tgagctggct    780

caactaattc agcagaaatt ggacgcctat aaagccgacg aacctaccat gggagagggg    840

ccggaaaagg cgagatcaca attaattatc ctcgaccgag gtttcgactg tgtatctccc    900

cttcttcacg aacttacttt ccaagcaatg gcctatgact tactacccat agaaaatgat    960

gtatataagt acgaagcatc ggctggtgtt atgaaagaag tccttctaga cgaaaacgac   1020

gagctttggg tcgatctacg ccaccaacac atcgcggtgg tgtctcagag cgtcaccaag   1080

aatctgaaga aattcaccga ctccaaacgc atgacccaga gcgacaagca gtcgatgaag   1140

gatctctcaa ccatgatcaa aaagatgccg caatatcaga aagaattgtc caagtatgct   1200

acgcatcttc atctcgctga agactgcatg aaggcctatc aggggtatat agacaagttg   1260

tgtaaagttg agcaggattt ggcaatggga actgatgccg aaggcgagaa aatcaaggat   1320

cacatgcgca acatcgtccc catcttgcta gatcccaaaa tcaccaatga atacgataag   1380

atgcgtatta tagcattgta cgccatgacg aaaaacggca tcacagatga aaatctctcc   1440

aaattggcta cccatgccca aatcaaggac aaacagacca tcgccaacct tcagttactt   1500

ggagtcaacg ttattaatga tggaggacca agaaaaaaac aatatacagt accgcgcaaa   1560

gaaagaatta cagaacaaac gtaccaaatg tcaagatgga cacctatcat taaggatata   1620

atggaggatt gcatagacga caaactggat cagaaacact acccgtattt gagcggacga   1680

gcacagtcta cgggatacca tgcagcgccc tctagtgccc gttatggcca gtggcacaaa   1740

gacagaggtc aacaagccgt gaagaacgtt cctcgactgc tcgtcttcgt cgtgggtgga   1800

atcagttttt cagagatcag gtgcgcctac gaagtgacca acgcgcagaa gaactgggaa   1860

gtcatcatcg gctcgtcgca catactcact cccgaggact tcctaagcaa tctggcaacg   1920
```

```
ttggccggct agaatcagat gaaaaaggtt acttttaatg tacccgagta aacagtttcg   1980
cagtcgtagt ttaaaataat gtaatgagtc tttttaatcc caatttaaac atatttatat   2040
agaatgactt tcgatcagta tcgaaccgtt ttctttgtta cgagagttaa agctgttcaa   2100
attatcttga aatttgtgca gaattgtcat acattaaatt gttgcgcttc tgaaattgtt   2160
gtgcaataaa agaaaatgtc taaggtgctc aaaactcaaa gccttcgatg agtttatgat   2220
tataaattga gaataaaaag actcattgag cttaaaaagt attatttcct accctttttt   2280
tgtatttttc caatagcaga gtttttttatt caatttttgc ggttattggg atattatcgc   2340
tttatttaca aaattgtgta aaaggtataa aaatgacgtt tttgaggagt cttcctgtaa   2400
aattaatttc aatagtcaga gatttaccaa aaaaatattt ttttttgttt agattttagt   2460
ttcttaacat attataaaat acatcgtttt ttttgtttta tttactgtta aagcttctat   2520
attgtcttct tgaactgctg tggcgacccc atcattgaaa acacttccaa gaacaagaac   2580
acatttggct ttttgttgta attatctttt tgggaagata tatttgagga aacagctttg   2640
taattttggg tcacactagt ttttcgtttt tcattctacc catttttttgg ttgattgttg   2700
gccacactgt tctgtgtttt cggcatgaag gcatacaaac aaaaaatgtt ccaggtgtaa   2760
ctttctctgg tttttgaaaa cgtatataag ttttctttca atagtatgaa ctatcattca   2820
taaatataca tatttttgct atcagagcat accaaatgaa gtagttctgt atttatttca   2880
aacaagtaca tttagtttat ttgttcagtt atatgtttcc atttctagta gtcttctggt   2940
atctgtggct ggattttagt gtgtcaactc cagttttata acctaaccaa acctcaccta   3000
atgcaaccta acctcacata acctcaaata atataacaaa atctctcgta gactaaccta   3060
ataatgcatt ggtgtggtat gaacgattcg gaatttgttt taattaaaga aatttttcaa   3120
aaattatgta tatttatgca aaaatcttca tttttttcttg tttacactgc tattgatatt   3180
gtattcgttg actagtctgc gtccagttgc acaaacgaca cccctaaagc tacttaacag   3240
taagacgatg cttttaaatg ctttttgtgt gactggtaca tatattataa attaagctta   3300
gcgagtaatt aagaatctta tctttaaata tccagttgta catcttacat agtgtacctc   3360
ttagaatagg aaaatgtatt tttcaactgt acctaaccaa acgcgtatag caaaaggtgt   3420
agaacgtgac aaagaatagc ataaagaagg acctgagctt gttttagtta ttcttccttc   3480
aaaattagat aatccttaaa ttaaactaga tatgtgtgct aaaaaaatcat ctctggcggt   3540
acagccaata gaaaagaagc tgaggaaggt ctcagatcac cgtgatcaat tatttaagca   3600
gaataatgga aaactggtcg tgagccatct aaatcttctc tatgctatag tttaaacgta   3660
ctacacctat tttcaaatca cagctttgta ttcatgctag ctaactttgt atcatatcct   3720
cagtagttta tcgtgaccta ttttttatat atctactaaa agacaccgat agtttttcca   3780
aaaaaaaaaa cttctatttg atagaaaaat aaaaatttat cgtttacaaa ttatggtaaa   3840
attatttagt tgttattatt cagcatttac aacggtacaa cgctttcttt cagtgcagaa   3900
cgagtatcaa aatcataata cgagcaaaac ttaacggagc cccaacatat accaaccttg   3960
aataacacaa aatacaacaa tttcttagat ctggggaaaa tcgtcgaaga tttgacaatt   4020
tcggccaatc agagcgccat attgtagtca cgtgacctaa aattttccta gattccagta   4080
aactggacta ttacaggagc gataaagcat taatagcgtt atttgtgttg gctatcccga   4140
agtttgattt tttatagtag tcacgatgtt tttggtcgat gaaagacttt agacaatgat   4200
tttatattcc ctactactcg ttttgccact gaatgaagca ttttccacat tcctgttcgt   4260
tttctaggaa tataagtgta aaattgactg acaaattaca tgttttcgtt actatcatcg   4320
```

atacatcatt ttcgtagagg gctggatcat gcgtgggtga ttaaaataca gttgttgtac 4380
gtttcttttc gtcaccctag tcaataaagt ccttatttat gtgctagtgt ttctattatc 4440
gttggtttac agcggtgtgt acatgacaag ggcgatttaa acggatctgc gggtaaatac 4500
catagacata ttatcgatag accaagctag gaatatgcca ctcaatgcat cggggtgtaa 4560
cgccaatatc aagtacggtg gtctagctat ctttgtctgt cgtgcgagtg tgagcgtatc 4620
taccaagagg tgggagtaat ggaacgacac agacacagag gcagcggcca tcatatgcta 4680
gagagagaaa gctaagcgcc ggtagagaga gatagataga ccaccgaccc gaactgctcc 4740
gcgttacgct atttttcgga cctggcctaa tctattgtgt tattatatct atggttcaac 4800
tccagtttaa ccaatg 4816

<210> SEQ ID NO 98
<211> LENGTH: 2664
<212> TYPE: DNA
<213> ORGANISM: Diabrotica virgifera

<400> SEQUENCE: 98
ttttgttatt gttgcggagg tcaatttttt atatcggaag acaattttat ccaaattttt 60
gaaaaatctc caattctgtc actgaattag gacttaagtg gaacaccatg gcgttaaaga 120
accaagttgg tcaaaaaatc atgaatgaag tcatcaagca caagcccacc aagaagaatg 180
ggccaactcc aggacagcaa gcccatgggg tagaatggag gatccttgtg gtggaccagc 240
ttgccatgag gatggtttca gcatgctgta aaatgcatga tatatcagca gaaggcatta 300
cattggttga agatattatg aagaaaaggg aaccgcttgg taccatggaa gctgtgtact 360
tgataacacc ttcagaaaag tcagttcatg ctcttatgaa tgactttgaa ccaccaagac 420
agatgtacag aggggcacac gtgtttttta cagaagcgtg tccagaccaa ttatttagta 480
ccttgtgcca ccaccccgta gcaaagttta ttaaaaccct aaaagaaatc aacatagcat 540
tcattccgac tgagtcacag gtattgacaa ttgcttaaaa tcacctaaag gtatgcttgt 600
tgtttttcac gttcaaatac taacctacta actcagtctt tgtctgctct tgtatattcg 660
ccttttccta ctaacattat gaaaaatgta atatctgtgc gattttgttt aaatgtggtc 720
tgaattgttg ttttgtctaa cagtatgccc ggaggaactg ttcaatgagc tctgcaagtc 780
ttgtgcggcc agaaaaatta agactctcaa ggaaatcaac attgcgttct tgccgtatga 840
gtctcaggtg ttctcattgg attcaccaga cacgttccag tgtagctacg atccatcatt 900
ttccgctgct agaaacgcca acatggaaag aatggcagaa caaattgcga cactctgtgc 960
gactctaggg gaatacccac acgtcagata tagaactgat tgggaaagaa atgttgagct 1020
ggctcaacta attcagcaga aattggacgc ctataaagcc gacgaaccta ccatgggaga 1080
ggggccggaa aaggcgagat cacaattaat tatcctcgac cgaggtttcg actgtgtatc 1140
tccccttctt cacgaactta ctttccaagc aatggcctat gacttactac ccatagaaaa 1200
tgatgtatat aagtacgaag catcggctgg tgttatgaaa gaagtccttc tagacgaaaa 1260
cgacgagctt tgggtcgatc tacgccacca acacatcgcg gtggtgtctc agagcgtcac 1320
caagaatctg aagaaattca ccgactccaa acgcatgacc cagagcgaca agcagtcgat 1380
gaaggatctc tcaaccatga tcaaaaagat gccgcaatat cagaaagaat tgtccaagta 1440
tgctacgcat cttcatctcg ctgaagactg catgaaggcc tatcaggggt atatagacaa 1500
gttgtgtaaa gttgagcagg atttggcaat gggaactgat gccgaaggcg agaaaatcaa 1560

-continued ggatcacatg cgcaacatcg tccccatctt gctagatccc aaaatcacca atgaatacga 1620
taagatgcgt attatagcat tgtacgccat gacgaaaaac ggcatcacag atgaaaatct 1680
ctccaaattg gctacccatg cccaaatcaa ggacaaacag accatcgcca accttcagtt 1740
acttggagtc aacgttatta atgatggagg accaagaaaa aaacaatata cagtaccgcg 1800
caaagaaaga attacagaac aaacgtacca aatgtcaaga tggacaccta tcattaagga 1860
tataatggag gattgcatag acgacaaact ggatcagaaa cactacccgt atttgagcgg 1920
acgagcacag tctacgggat accatgcagc gccctctagt gcccgttatg gccagtggca 1980
caaagacaga ggtcaacaag ccgtgaagaa cgttcctcga ctgctcgtct tcgtcgtggg 2040
tggaatcagt ttttcagaga tcaggtgcgc ctacgaagtg accaacgcgc agaagaactg 2100
ggaagtcatc atcggctcgt cgcacatact cactcccgag gacttcctaa gcaatctggc 2160
aacgttggcc ggctagaatc agatgaaaaa ggttactttt aatgtacccg agtaaacagt 2220
ttcgcagtcg tagtttaaaa taatgtaatg agtcttttta atcccaattt aaacatattt 2280
atatagaatg actttcgatc agtatcgaac cgttttcttt gttacgagag ttaaagctgt 2340
tcaaattatc ttgaaatttg tgcagaattg tcatacatta aattgttgcg cttctgaaat 2400
tgttgtgcaa taaaagaaaa tgtctaaggt gctcaaaact caaagccttc gatgagttta 2460
tgattataaa ttgagaataa aaagactcat tgagcttaaa aagtattatt tcctaccctt 2520
tttttgtatt tttccaatag cagagttttt tattcaattt ttgcggttat tgggatatta 2580
tcgctttatt tacaaaattg tgtaaaaggt ataaaaatga cgtttttgag gagtcttcct 2640
gtaaaattaa tttcaatagt caga 2664

<210> SEQ ID NO 99
<211> LENGTH: 275
<212> TYPE: DNA
<213> ORGANISM: Diabrotica virgifera

<400> SEQUENCE: 99
ctcaaggttc atcgtttgtt atggaaggtg tgaagaattt agtggtgaaa cgacacaatc 60
ttcctgttac caaaattacc gaacaattga tggaatgccg gactggtggc gatatagacg 120
attatttgta tttggatccc aaattgttga aaggtggcga cattgtcccg aaaaatcgtg 180
ctccatttca ggatgcagtt gtgtttatgg ttggaggtgg taattacatt gaatatcaga 240
atttggtgga ctttataaag caaaaacaat catca 275

<210> SEQ ID NO 100
<211> LENGTH: 254
<212> TYPE: DNA
<213> ORGANISM: Diabrotica virgifera

<400> SEQUENCE: 100
atgctgaggg tgagaagata aaagatcata tgcgcaacat tgtgcccatt ctactagaag 60
cgtcgatctc caactacgat aaagttcgaa tcatcgccct ctacgtgatg atcaaaaacg 120
gaatatccga agagaatttg atgaaattgt tcacccacgc tcagatcggc ccgaaggaac 180
aggatatggt gcgaaatctt agttttctcg gagtcaatat cgtatcagat ggcaacagaa 240
agaagacata cacg 254

<210> SEQ ID NO 101
<211> LENGTH: 342
<212> TYPE: DNA
<213> ORGANISM: Diabrotica virgifera

<400> SEQUENCE: 101
cacaaaggat aaattttgga aaacacacaa aggaagtccg tttccaacgg ttgccgaggc 60
tattcaagaa gagctggaat cgtatcgcag ctcagaagat gagataaaga aattgaaaac 120
ttcgatggga attgacggcg aaacggagat agcctattcg atggtaaatg acaacacaga 180
gaaattaacg aatgcagtga actcgttgcc acagctgatg gaaaagaaac gactgatcga 240
catgcatacg aaaatagcga cgtccatttt gaattacatt aagtcgagac gtttggactc 300 gtttttgaa ctagaggaaa aaattatgtc gaaactggcg ct 342

<210> SEQ ID NO 102
<211> LENGTH: 2124
<212> TYPE: DNA
<213> ORGANISM: Diabrotica virgifera

<400> SEQUENCE: 102
tctacaactt gacgacagtg acagaataaa atataaacat ttaaatccac ctcttttgat 60
cagttatagt taagttaaag gctaaagtga aatatggctc acatgcaaag tggaaaagta 120
gatatatcct taattcaagc agcagctagg gcaaacctga taaacctttt agaacaatgt 180
cctggtaaga aagtcattgt ttgggataac agcttagctg gaccagttgg acttgtagcc 240
aaatatgcaa tcctcaagga gcaccaggct cctaagatgt tcccacttcg aaatatgcct 300
ttacctgaaa ctgatgtcga tcatattatc ttcatctcaa ggcccaaatt gtatctgatg 360
gactacattg cacaaaatgt acatgctgac agtaaaacga aaagtggcag taagaagcaa 420
taccatttgt tttttgtacc aaagaaaagc ttattgtgca tggaaagatt gaaacataaa 480
ggagtctatg gaagcgtaat gttaattgat gaattcaaat gccagctttt tccatttgaa 540
tctgacttag tatcaatgga aatatctgag gtttttaggg agtacacaat tgaaaacgac 600
cctacgtatt tataccaaac agcacaagct ataatatacc ttcaaaaaat gtatggaact 660
attcctaaag tttggggcaa aggaaatgca gctaagcaag tttgggatct tgtggttaga 720
ttgcaaagag aaaagaataa cagtgaagat atgaaaaata atcaacagtc atgtattgat 780
caaatcatat taatcgatag gtctgtagat ttgatcacac ctttagctac acagttaact 840
tatgaaggat tgattgatga aattttcggt ataaataatt caactgccta tttcccaatc 900
gataattttt taagcactga agaaagaact acagaatcgt tatcagaaga taagaagcaa 960
ctgattctag attcaactga caaaattttt gctgacatcc gggacaagaa tttcaatgct 1020
gtaggcggtt atctctcaaa agaggctaaa gcaattagtg cccagatgga aaatacacag 1080
gaaaagtctg tccaggagat gaagctttat gttcaaagac ttcctcaaat tttggcaaag 1140
aaaaagcaac tggcaacaca tacagcaatt gcggaatgta ttaaggaaat cacggatggg 1200
tatgattttt tggatacgtt acaggctgaa caggagtttt taaactgcat agaagtagac 1260
aaacccagtg cttacattga agaaatgatc gctcagagca aaccaatggt gaaagtgtta 1320
aggttaatgt gtttacaatg tatcgcaagt tctggattaa agcccaaaat tttggaaagc 1380
tataaaaggg atctagtaca ggtttacggc ctggaggccc ttctggcaat atcgaaattg 1440
gaaaaagttg gactattgaa acttcaatct agtactagac aatacacagt tctgagaaaa 1500
gcattaagtt taaccatgga aaacacttcc gaaattaatc ctacagacat tagttacgtt 1560
catagtatat acgcaccgat gagtatcaga ttagtggaac atgtaaccag aactggagga 1620
actaaacaat tgcaggatgt gttaggctta ctaccaggtc caactttaga tgaaaccaga 1680

-continued

```
tcagttaaca ctataataaa ttcagattca ccacaaacag ttcttgtatt ctttattggt   1740

ggatgtacat ttgcagaagt aactaacatt gtgcattact ttaacaaaaa ttactaattt   1800

cttcgtttca gatatctgct ctgagatttt tatccacgca agaagattca aatgttgaat   1860

ttgtaatagg tactaccaag ttgattaatg ggacgacatt tttgaattcc attattgaaa   1920

actaatatta cattcctacg ctcttttaat cttttatgcg aaaaatacca gctaaattga   1980

gaaataaaag ctttattaat gttcttggtt ggtctcaaag acaagatgcc attaaagatt   2040

ttattttctt tgtatatgtg gtatttatgc cataatcgat atttttagtt atgttatatt   2100

tctatctatt ttgtactgtg atac                                          2124
```

<210> SEQ ID NO 103
<211> LENGTH: 478
<212> TYPE: DNA
<213> ORGANISM: Diabrotica virgifera

<400> SEQUENCE: 103

```
aagacgagaa ggttttaagg gctatttgcg agcgattggt ctcagtgtgt gcgaccttgg     60

aagaataccc gtacgttcga tataaggctg accagcctcg tatggagcaa ctcgctcagc    120

tgtttcaagc caaaatgaac gagttcgtcg caaaaaatga tgcatttaca tacgcaacga    180

accgagggac gctcttcttt attgatcgtg gtcaggattt agttgcacca atgatgcatg    240

agagcacttt tcaggctatg atttacgact tgatcgacgt caacgaagag cagatcacat    300

atccagctga aacgaactca ggaacagtga tgaaaacagc gtttctaaat gaaaacgaca    360

agttttggat tgaatatcgt catacacata ttgcaaaggt tagcgaagag attggcaaac    420

gaatggcgca gttgtcgtca tcaaatgctg ggacgtcact cgggaaaggc aagtcaac      478
```

<210> SEQ ID NO 104
<211> LENGTH: 288
<212> TYPE: DNA
<213> ORGANISM: Diabrotica virgifera

<400> SEQUENCE: 104

```
gcttcctatg cagagcttcg tacaatttac gagttgcgtc aatccgaaaa acgagatatc     60

attctaggag cgacctcgtt catcaaaccg aaggcatttg tcgacgcact gtctgtgctt    120

catgaagcga atcccacctc aaaccctccg ccagttggtc gtggtgctga tgtgacgcct    180

ttaagcagtg cagagattca tgtactggtg gagaatcaaa ctaaaccagc gagttcaggg    240

actccctttg agaaaattgg tggcgaaggc tccaagacct cttccttc                 288
```

<210> SEQ ID NO 105
<211> LENGTH: 699
<212> TYPE: DNA
<213> ORGANISM: Diabrotica virgifera

<400> SEQUENCE: 105

```
ggcgcgatgg caaaggtcgt gtacgacatg atggcgcact tcaagcgcga gcaagaggtc     60

gctgggaatc cgatcggcgt cctcgatccc gagatcgaca cgctcgtgct cttggaccgg    120

actgtggacc tcgcgacgcc gatgtgtacg ccactgacgt acgaaggctt gttggacgag    180

atcctgagca tcacgcatgg cttcatcaca gtcgacgccg agctcattgc ggaagacagt    240

gagagcagtc ctagctctgg tcctagtggt ccgagtggca agaaagtgtc gatcccactc    300

aactcgaacg acaagctgta cgcggacgtg cgcgactacc acgtcgagcg cttgggcatg    360

acgctccagc agcaagcgca cgacatccgc gcgcgctacg acgagttccg gaagaaccgc    420
```

```
gacgcgtcga tcagcgagat ccgcgagttc gtcaagcgca ttccagggct caagcagaac    480

taccagtcgc tcatgcagca catcaacttg gctgagctca tcaagaaaac gacggacaac    540

aaggcgttcc gggacctcaa agtcgccgag cacgcgatgc tcatgggcga aacgatcttc    600

gagcagctcg aagagcgcat tggcttccag gacccgatcc tcagtgtctt gcgtcagctc    660

tgtctccagt cggtcacgag cggcggcatc aaatccaag                           699
```

```
<210> SEQ ID NO 106
<211> LENGTH: 270
<212> TYPE: DNA
<213> ORGANISM: Diabrotica virgifera

<400> SEQUENCE: 106

ttgtggcctg aaggcgcgtg gagatcgtcc cgcgtgtatc acctggcccc gaagattgct     60

gtataagccg gtgctagagt cttggcagca caatggacgt gatcgtagca gtgcggcagt    120

atctggagaa ggtcataaat gaccctcaga tcgatggcat gaaggctcta ctgctcgatg    180

cagacaccac gacggtgatc tcgatggtga tgtcgcagtc gcatattcta cagcgggaag    240

tctttttggt agagcaggtt gacgcgtccc                                     270
```

```
<210> SEQ ID NO 107
<211> LENGTH: 317
<212> TYPE: DNA
<213> ORGANISM: Diabrotica virgifera

<400> SEQUENCE: 107

gagcctgggt attaaaaaga gaaggaattt cgaattattt tgtagacgtt tttaagaaga     60

aacacacctg agactcatac ggcaagaacg caatgttgat ttccttgaga gtcttaattt    120

ttctggccgc acaagacttg cagagctcat tgaacagttc ctccgggcat actgttagac    180

aaaacaacaa ttcagaccac atttaaacaa aatcgcacag atattacatt tttcataatg    240

ttagtaggaa aaggcgaata tacaagagca gacaaagact gagttagtag gttagtattt    300

gaacgtgaaa aacaaca                                                   317
```

```
<210> SEQ ID NO 108
<211> LENGTH: 258
<212> TYPE: DNA
<213> ORGANISM: Diabrotica virgifera

<400> SEQUENCE: 108

cgcatggtcg cggagcagct cagcaacttg atccgcgagc acttgtcggc gcgcaatggc     60

gtctttagcg aaggcagcgt gtcgttccag cgcccagtgc tgatcatcat ggaccgcaac    120

gaagacctcg cgtcgagtct ccaccacccg tcgacgtacc aagcgctcgt tgacgacatg    180

ctcaagatcc agatgaaccg cgtgaaagtg acagtcaaga cgtccagtgg tgcgaatggc    240

agtgacggca atggcagc                                                  258
```

```
<210> SEQ ID NO 109
<211> LENGTH: 696
<212> TYPE: DNA
<213> ORGANISM: Diabrotica virgifera

<400> SEQUENCE: 109

cgccgccaca aacgaagacg agcatctttt cgccaccaaa tgtgtctttg tccgcatcag     60

gctttcctgg ttttggttgc actttcttgc ggagtgagat cgggcccctt ttcttgctgt    120
```

-continued

```
catctaaagc tgatgccgat ccgagaggcg gcgcaatgat atacggatag tcgtgttcat    180

tcaaagtgtt cttcagcgct tgcttcagga ctgacttaat atgtggttca tatctcgcat    240

tggaatactc aacttgttca gccttcaatg ctgctttctt gatgtcttcc gaagatagag    300

aactgttgcc gttctgcgtg taaagtgcag caccgccaac tgcaaccaga ttactcattg    360

cccagtcata cttctgtgat agatttgcag cctggataat tttctttttc tcgtggtcct    420

tcattgtgtc ttgcgtcaac gaaaatacca tagctactcg aaatttatcc gcctcggata    480

gcttcggatc tttgaacagg tcctcaagct gcttagtcag tattgcgtgc ttgattttct    540

tcccggattc gtcaacacca gtcgccatgg tttgctcaat gttagatgcc tcaaggaggc    600

ttgattttgt aaatataccc atagcatttc ctgcgagcca caggtgctga gaaagttttc    660

caagcatctc tctgtattcg ggcagctccc gtaatg                              696
```

```
<210> SEQ ID NO 110
<211> LENGTH: 1565
<212> TYPE: DNA
<213> ORGANISM: Diabrotica virgifera

<400> SEQUENCE: 110

cttcagcggt cagagctttt tgtggtcgta cttccagttg gcagctgacg atcgcccatc     60

gccgcgctcc agtccatacg catccgcgat ctctgcgaga tatgaggttg agttgtggat    120

gaatgtgccg cccaagatga tgcgttggcc ggagatagca agtttctgat tcaactcggc    180

caccttcgtg gcctcctcaa acgtgacacc accacagatg aacacaataa tgtcacgaac    240

cttcttgatg ccaggtgtgg tcgtaccgtt cacgatacca aactcgttgt cgagcaagtt    300

gcccttgaca atcagctcga ggtggcgaat gagaggtggc acatgctgtg cgtatacgtt    360

cggaacacct tgcacgcctt gtgtcatggc acgcatgaac ttcttgaggc cacgatcgcc    420

gtagagatcg ccagaccgca cgttcgcacc tccatacttg aggaacgtgt ccacaagtgc    480

cacacgctct gatggcaaac ccgaggcaga caacagatct ttcacaactt tgacttgcac    540

agagctgttg gcttcgtacc gcagcacgta caaaattgca agtcgcaact tgtttagcgg    600

cttgatctga gcattcttga gctttgacac aaggtctttg aagtgtgaat tgtgatcatc    660

accacaagct agctcctgct caagttgact gacgtccatg agcccatcta cttccaccag    720

acgtgccagc tcacccatga gcgtcacatg cttggacacg gcaactgact gcgagcggaa    780

tgctggataa ttgtccacga aacgctgcat gtcctcaata gacacgatat tttcgtgtgt    840

ttgtgtcttg gcctggtatt cgtcgaccat cttcttgact gccatgccca gatcaccgaa    900

gttggcgtac aagtgtttct cgaagaagct gtcagacgtg gtcgaaagca cgagctctgt    960

catgtcctta cgcactcctg gagcgttttt catgtcgaca cggttctcat ttagctctag   1020

cagttcatga accatggctt gatatgtcca ctgactcaag agcggggtca ctgggtcatc   1080

tcgacgatcg aggacgtaga gcaatggcat gacttccgga cgacggaaat caaataaacc   1140

gtcttgctca agctgcatgc gtgcggagac ctctcgcgca agcttttcag caatttcaga   1200

gcccttttga tatctgatag ttggacgctt cttcaatgcg agtagcactg acagcagccc   1260

ttcgacgctt cggttgaaaa ggtgtgtggc cttagctggc aaagctgcgc tagtattggt   1320

gacgactcct gcagtcgctg gtgtagatgc tgaagcaccg tgccccttaa tgctcatcgc   1380

gacagtgcca cgcaagttga aatgaaacaa cgtgtcgttc actgcgagga agtccgcgta   1440

gtattcctgg atttgatgaa tcacctcctt ctcgtccgct tcagcaagtc gctcgagcag   1500

ctcaactggt agaatattcg tgaagaagat gtggtattgg ccatacttgg gattcttgag   1560
```

ttcct 1565

<210> SEQ ID NO 111
<211> LENGTH: 340
<212> TYPE: DNA
<213> ORGANISM: Diabrotica virgifera

<400> SEQUENCE: 111
gcgaggaggc gcggcaaagg acaccaggaa gaaggccacc tcgctcaaga cccagaccag 60
ggtgcggtcg accaagggca aggacagaat cgacggtgac gcggaggacc tgggtcccag 120
ggtcatcgtg ttcgtcgctg gtggtatcac ccactctgaa atccgttccg cctaccagct 180
cttcgacaag agggaggtga tcatcggagg cacgtccatc ctgaccccac acaagttcac 240
ctcgtatttt cattggattc tcctgacact tttcaatgtt tttacgatcc gagctttgcc 300
gccgctcgaa atgccaatat ggaacgaatg gctgaacaaa 340

<210> SEQ ID NO 112
<211> LENGTH: 47
<212> TYPE: DNA
<213> ORGANISM: Artificial Sequence
<220> FEATURE:
<223> OTHER INFORMATION: ROPv3FT7 Primer Oligonucleotide

<400> SEQUENCE: 112
ttaatacgac tcactatagg gagacaagta tgctacgcat cttcatc 47

<210> SEQ ID NO 113
<211> LENGTH: 50
<212> TYPE: DNA
<213> ORGANISM: Artificial Sequence
<220> FEATURE:
<223> OTHER INFORMATION: ROPv3RT7 Primer Oligonucleotide

<400> SEQUENCE: 113
ttaatacgac tcactatagg gagatcttat cgtattcatt ggtgattttg 50

<210> SEQ ID NO 114
<211> LENGTH: 191
<212> TYPE: DNA
<213> ORGANISM: Diabrotica virgifera

<400> SEQUENCE: 114
caagtatgct acgcatcttc atctcgctga agactgcatg aaggcctatc aggggtatat 60
agacaagttg tgtaaagttg agcaggattt ggcaatggga actgatgccg aaggcgagaa 120
aatcaaggat cacatgcgca acatcgtccc catcttgcta gatcccaaaa tcaccaatga 180
atacgataag a 191

<210> SEQ ID NO 115
<211> LENGTH: 2238
<212> TYPE: DNA
<213> ORGANISM: Euschistus heros

<400> SEQUENCE: 115
tacctctcct ggctatattc aacaaagtta ctcaaacaat gagttatggt atctggagaa 60
gtgtaacaag tgcttaccgc aattgagtag tgttctgata caggagtgat agggttagac 120
cagaccagtt tgacacttga cacaaacgag tgaaaatggc gctgaaagct ctcgttggtc 180
aaaaaattat gaacgatgcg atcaggcaaa agaaaaaagg gaaagaggta gagtggagag 240

-continued

```
tccttgtcgt ggatcagcta gcgatgcgga tgatctctgc ttgctgtaaa atgcatgaaa    300

tttctgccga gggcttaacg attgttgaag acattaataa aaagagggag ccacttccat    360

caatggaagc tgtttatcta ataaccccga gtgaaaaatc cgtacatgcc ttgatgaacg    420

attttgcctc accgaatcgt atcatgtaca aagctgccca tgtctatttc acagaagtat    480

gtcaggagga actatttaac gagctgtgca aatcgtatgc atcgagaaag attaaaacgc    540

tgaaagagat caacattgct tttttgccat acgagagcca ggtgttttcc cttgatgctc    600

cagaaacatt ccagtgcttc tacaacccat cattggctaa cagccgactt gctaatatgg    660

agcgtattgc agaacagata gccacattgt gcgccacgct tggtgaatac ccatctgtca    720

gatataggag tgattttgat aaaaatgtag aattagctca gatagtgcag cagaaattgg    780

atgcctacaa agctgatgaa cctacaatgg gtgaagggcc tgaaaaatct cgttcccaat    840

tgttgatcct tgatcgaggt tttgatgcag tttctcctct tcttcacgaa ctcactcttc    900

aggcaatggc ctatgatctt cttccaattg agaatgatgt atataagtat gaagctactg    960

ctggagctcc ggagaaagaa gtattgttag atgaaaatga tgaattatgg gtagaactac   1020

gccatcagca tattgctgtt gtctcacaga atgtcacaaa gaacctgaag aaattcaccg   1080

agtctaagag aatgccacaa ggagacaaac agtcaatgag ggatctcagt caaatgatta   1140

aaaagatgcc acaatatcag aaagaactta gcaagtattc cactcattta caccttgcgg   1200

aagattgtat gaatgcttat cagggccatg ttgataagct ctgcaaggtt gagcaggatt   1260

tggcaatggg taccgacgct gaaggagaac gtataaagga ccacatgaga aatattgttc   1320

cgatactcct tgaccaatcc gtatctaatt atgacaaaat gaggatcatc cttctgtata   1380

cattgtcaaa gaatggtatt tctgaggaaa acttgaacaa actcgttcaa cacgctcaga   1440

tccagccaca cgagaagcag gccatcgtca acctaggaaa tcttggccta aatgttgttg   1500

ttgatggtac tcgtataaag aagccatacg taccccctcg taaagagcgt atcacagaac   1560

aaacttacca gatgtctcgt tggactcctg tcataaagga tcttatggag gactgtatag   1620

atgacaagct cgacctcaaa cacttcccct ttctcgccgg tagggctgcc tcttctggat   1680

atcatgctcc tgccagcgtg cgatatggac actggcacaa agataagggc cagcagaccg   1740

tgaagaatgt gcctcgaatc atcgtcttca tcatcggtgg tatgagcttc tcagagatcc   1800

gatgtgccta tgaagttacc aatgctgtca aaaattggga ggtgataatt ggttcttcac   1860

atatcctgac acctgaagac ttcctaagta acctcgccaa cttgagcaac tagagaatgg   1920

actgattgtt agtcagcgta gtcactctcg ttcttatttg gtacacactc aaatgtgata   1980

atgtaaaatt atgtagcttc atttaaactt aggaacggca cgctcttaaa agtttacttc   2040

tttgttatgt gtatcgtgta gagaaaaaca cattacttct ttcataaaat gtgtatatct   2100

actgaggcat actttaagga taggtatcct agatatcagt tattatttgt ttttatctgt   2160

gaaagattag aattactttt gtagttaaca gtttagcggt gttcattgca tgtaatatta   2220

tatatttaag tattgttt                                                 2238
```

```
<210> SEQ ID NO 116
<211> LENGTH: 585
<212> TYPE: PRT
<213> ORGANISM: Euschistus heros

<400> SEQUENCE: 116

Met Ala Leu Lys Ala Leu Val Gly Gln Lys Ile Met Asn Asp Ala Ile
1               5                   10                  15
```

-continued

```
Arg Gln Lys Lys Lys Gly Lys Glu Val Glu Trp Arg Val Leu Val Val
            20                  25                  30

Asp Gln Leu Ala Met Arg Met Ile Ser Ala Cys Cys Lys Met His Glu
        35                  40                  45

Ile Ser Ala Glu Gly Leu Thr Ile Val Glu Asp Ile Asn Lys Lys Arg
    50                  55                  60

Glu Pro Leu Pro Ser Met Glu Ala Val Tyr Leu Ile Thr Pro Ser Glu
65                  70                  75                  80

Lys Ser Val His Ala Leu Met Asn Asp Phe Ala Ser Pro Asn Arg Ile
                85                  90                  95

Met Tyr Lys Ala Ala His Val Tyr Phe Thr Glu Val Cys Gln Glu Glu
            100                 105                 110

Leu Phe Asn Glu Leu Cys Lys Ser Tyr Ala Ser Arg Lys Ile Lys Thr
        115                 120                 125

Leu Lys Glu Ile Asn Ile Ala Phe Leu Pro Tyr Glu Ser Gln Val Phe
    130                 135                 140

Ser Leu Asp Ala Pro Glu Thr Phe Gln Cys Phe Tyr Asn Pro Ser Leu
145                 150                 155                 160

Ala Asn Ser Arg Leu Ala Asn Met Glu Arg Ile Ala Glu Gln Ile Ala
                165                 170                 175

Thr Leu Cys Ala Thr Leu Gly Glu Tyr Pro Ser Val Arg Tyr Arg Ser
            180                 185                 190

Asp Phe Asp Lys Asn Val Glu Leu Ala Gln Ile Val Gln Gln Lys Leu
        195                 200                 205

Asp Ala Tyr Lys Ala Asp Glu Pro Thr Met Gly Glu Gly Pro Glu Lys
    210                 215                 220

Ser Arg Ser Gln Leu Leu Ile Leu Asp Arg Gly Phe Asp Ala Val Ser
225                 230                 235                 240

Pro Leu Leu His Glu Leu Thr Leu Gln Ala Met Ala Tyr Asp Leu Leu
                245                 250                 255

Pro Ile Glu Asn Asp Val Tyr Lys Tyr Glu Ala Thr Ala Gly Ala Pro
            260                 265                 270

Glu Lys Glu Val Leu Leu Asp Glu Asn Asp Glu Leu Trp Val Glu Leu
        275                 280                 285

Arg His Gln His Ile Ala Val Val Ser Gln Asn Val Thr Lys Asn Leu
    290                 295                 300

Lys Lys Phe Thr Glu Ser Lys Arg Met Pro Gln Gly Asp Lys Gln Ser
305                 310                 315                 320

Met Arg Asp Leu Ser Gln Met Ile Lys Lys Met Pro Gln Tyr Gln Lys
                325                 330                 335

Glu Leu Ser Lys Tyr Ser Thr His Leu His Leu Ala Glu Asp Cys Met
            340                 345                 350

Asn Ala Tyr Gln Gly His Val Asp Lys Leu Cys Lys Val Glu Gln Asp
        355                 360                 365

Leu Ala Met Gly Thr Asp Ala Glu Gly Glu Arg Ile Lys Asp His Met
    370                 375                 380

Arg Asn Ile Val Pro Ile Leu Leu Asp Gln Ser Val Ser Asn Tyr Asp
385                 390                 395                 400

Lys Met Arg Ile Ile Leu Leu Tyr Thr Leu Ser Lys Asn Gly Ile Ser
                405                 410                 415

Glu Glu Asn Leu Asn Lys Leu Val Gln His Ala Gln Ile Gln Pro His
            420                 425                  430

Glu Lys Gln Ala Ile Val Asn Leu Gly Asn Leu Gly Leu Asn Val Val
```

```
        435                 440                 445

Val Asp Gly Thr Arg Ile Lys Lys Pro Tyr Val Pro Pro Arg Lys Glu
    450                 455                 460

Arg Ile Thr Glu Gln Thr Tyr Gln Met Ser Arg Trp Thr Pro Val Ile
465                 470                 475                 480

Lys Asp Leu Met Glu Asp Cys Ile Asp Asp Lys Leu Asp Leu Lys His
                485                 490                 495

Phe Pro Phe Leu Ala Gly Arg Ala Ala Ser Ser Gly Tyr His Ala Pro
            500                 505                 510

Ala Ser Val Arg Tyr Gly His Trp His Lys Asp Lys Gly Gln Gln Thr
        515                 520                 525

Val Lys Asn Val Pro Arg Ile Ile Val Phe Ile Ile Gly Gly Met Ser
    530                 535                 540

Phe Ser Glu Ile Arg Cys Ala Tyr Glu Val Thr Asn Ala Val Lys Asn
545                 550                 555                 560

Trp Glu Val Ile Ile Gly Ser Ser His Ile Leu Thr Pro Glu Asp Phe
                565                 570                 575

Leu Ser Asn Leu Ala Asn Leu Ser Asn
            580                 585


<210> SEQ ID NO 117
<211> LENGTH: 50
<212> TYPE: DNA
<213> ORGANISM: Artificial Sequence
<220> FEATURE:
<223> OTHER INFORMATION: BSB_Rop-1-For PCR Primer Oligonucleotide

<400> SEQUENCE: 117

ttaatacgac tcactatagg gagagaagat tgtatgaatg cttatcaggg                50


<210> SEQ ID NO 118
<211> LENGTH: 45
<212> TYPE: DNA
<213> ORGANISM: Artificial Sequence
<220> FEATURE:
<223> OTHER INFORMATION: BSB_Rop-1-Rev PCR Primer Oligonucleotide

<400> SEQUENCE: 118

ttaatacgac tcactatagg gagacgctgg caggagcatg atatc                     45


<210> SEQ ID NO 119
<211> LENGTH: 499
<212> TYPE: DNA
<213> ORGANISM: Euschistus heros

<400> SEQUENCE: 119

gaagattgta tgaatgctta tcagggccat gttgataagc tctgcaaggt tgagcaggat      60

ttggcaatgg gtaccgacgc tgaaggagaa cgtataaagg accacatgag aaatattgtt     120

ccgatactcc ttgaccaatc cgtatctaat tatgacaaaa tgaggatcat ccttctgtat     180

acattgtcaa agaatggtat ttctgaggaa aacttgaaca aactcgttca acacgctcag     240

atccagccac acgagaagca ggccatcgtc aacctaggaa atcttggcct aaatgttgtt     300

gttgatggta ctcgtataaa gaagccatac gtaccccctc gtaaagagcg tatcacagaa     360

caaacttacc agatgtctcg ttggactcct gtcataaagg atcttatgga ggactgtata     420

gatgacaagc tcgacctcaa acacttcccc tttctcgccg gtagggctgc ctcttctgga     480

tatcatgctc ctgccagcg                                                  499
```

<210> SEQ ID NO 120
<211> LENGTH: 2550
<212> TYPE: DNA
<213> ORGANISM: Meligethes aeneus

<400> SEQUENCE: 120

```
tttgacattt aatgataatt gtgcagtggg tgctattaaa aattatattg tttaaatagg      60
tagttaaaat attataaaat attgttagag tgttcatcac aaattatatg caatatggcg     120
ttaaaaggac aagttgggca aaaaattatg aacgaggtaa taaagcataa accaaagaaa     180
aatggacccg ctcatggagt ggaatggaga gttttggttg tggatcaact tgccatgaga     240
atggtttcag cctgttgtaa aatgcacgat atttcagctg agggcatcac attggttgaa     300
gatataaaca agaaaagaga acccttaaac accatggaag caatatatct aataacacca     360
tctgaaaaat ctgttcactc actgatgaac gattttgaat cgccaagact tatgtacaaa     420
ggggcacatg tattttttac tgaagtctgt cccgaagaac tcttcaatga gttgtgtaaa     480
tcttgtgctg caaggaaaat taaaacgcta aaggaaatca acattgcctt cttgccctat     540
gaatcacagg tgttttcttt ggactgccca gaaacattcc aatgcagtta tgatcctgct     600
atggaagcag ccagaaatgc aaacatggag agaatggcag aacaaattgc tacattgtgt     660
gcaactctgg gagaataccc ttcagtaaga taccgaagtg attgggaacg caacgtggaa     720
ctagcgcaga tgattcagca aaagttggat gcctataaag cggatgagcc cacaatggga     780
gaggggcctg aaaaagcgag atcgcaactt ttgattcttg accgcggctt cgactgcgta     840
tcacccatgc tgcacgaact tacattccag gcaatggcct acgatttgct gccaatcgaa     900
aacgacgtgt acaaatatga agcttcagcg ggagtattta aggaagtgtt gctcgacgaa     960
aacgacgagt tatgggtaga attacgacat cagcatatcg ctgtagtgtc gcagagtgtg    1020
acgaaaaact tgaagaaatt taccgattca aaacgaatga cccaaagtga taaacaatca    1080
atgaaagatc tgtcacaaat gattaagaaa atgccccaat atcaaaagga gttatctaaa    1140
tatgctacac acttgcatct tgctgaagac tgcatgaaat cttaccaagg atatgttgac    1200
aaattatgta aagttgaaca agacctagca atgggtacag atgcagaagg agaaaaaatt    1260
aaagaccata tgcgtaacat cgtaccgatt ttacttgatc caaaaataac aaacgaatat    1320
gacaaaatga gaataattgc tctatatgca atgattaaaa atggcataac cgacgaaaat    1380
ttatcaaaac ttgctactca tgcccaaata aaagacaaac aaactattgc taatttgcaa    1440
ttcttgggag ttaatgttat caatgatggt gggaaccgga aaaaaccgta ttcggtgcca    1500
agaaaagagc gtattactga acaaacgtat caaatgtcta gatggacgcc tgtaattaag    1560
gatattatgg aagacgctat tgaagataaa ttagatcaaa aacactttcc atttttagct    1620
ggccgagcgc aaaccagtgc ttaccacgcc ccaacaagtg ctcgatatgg tcattggcat    1680
aaagacaagg cccagcagac agtgaaaaat gtgcccagaa taattgtctt cattgttgga    1740
ggcatgagtt tttcagaaat cagatgtgcg tatgaggtaa caaacgccca aaaaaattgg    1800
gaggtcatta ttggatcctc caacattttg actccccaaa gttttcttaa ggatttaaac    1860
actcttacag tctaggattc aggaaaaaaa gttactttta atatacctga taattaaaaa    1920
tgctttcgtc atgtgaattt gattgcttaa gataaatggt tagttttact ggaattttta    1980
attgtagttg acattttgag atatttgtac ctactaacgt taaaaatgtg cagacctaag    2040
caagatatta caatataatc ttggatgcta gtctatcttc cctttctaaa aataactttt    2100
atttttaata attataattc tggattgaaa aataaaatgt atgtaaagta cttaagggaa    2160
```

```
ctgattattt tttttatttt ttaagttgag cagtctcaca caaacaatac attactcgtg   2220

cgccagcgca cttcatagac ttctaaaaaa aacattgggt ataaaaaact gttctcaatt   2280

tactaacgga acatttaaat ttattttaag cccctaagct ttaattatta aaaattgtat   2340

aaatgttgtt agaaataaag taagttttca aaggcgttat ataaatgttt agcgtgttat   2400

ggcgtttaac accataattc aaaaatatca aatatttaaa gttatttatc acgtttttat   2460

tgttatttct tgttataagt agttttttag atacttaaac ttgtattgta ttcagtattt   2520

cttttcaata gttatacatg tattatattc                                    2550


<210> SEQ ID NO 121
<211> LENGTH: 586
<212> TYPE: PRT
<213> ORGANISM: Meligethes aeneus

<400> SEQUENCE: 121

Met Ala Leu Lys Gly Gln Val Gly Gln Lys Ile Met Asn Glu Val Ile
1               5                   10                  15

Lys His Lys Pro Lys Lys Asn Gly Pro Ala His Gly Val Glu Trp Arg
            20                  25                  30

Val Leu Val Val Asp Gln Leu Ala Met Arg Met Val Ser Ala Cys Cys
        35                  40                  45

Lys Met His Asp Ile Ser Ala Glu Gly Ile Thr Leu Val Glu Asp Ile
    50                  55                  60

Asn Lys Lys Arg Glu Pro Leu Asn Thr Met Glu Ala Ile Tyr Leu Ile
65                  70                  75                  80

Thr Pro Ser Glu Lys Ser Val His Ser Leu Met Asn Asp Phe Glu Ser
                85                  90                  95

Pro Arg Leu Met Tyr Lys Gly Ala His Val Phe Phe Thr Glu Val Cys
            100                 105                 110

Pro Glu Glu Leu Phe Asn Glu Leu Cys Lys Ser Cys Ala Ala Arg Lys
        115                 120                 125

Ile Lys Thr Leu Lys Glu Ile Asn Ile Ala Phe Leu Pro Tyr Glu Ser
    130                 135                 140

Gln Val Phe Ser Leu Asp Cys Pro Glu Thr Phe Gln Cys Ser Tyr Asp
145                 150                 155                 160

Pro Ala Met Glu Ala Ala Arg Asn Ala Asn Met Glu Arg Met Ala Glu
                165                 170                 175

Gln Ile Ala Thr Leu Cys Ala Thr Leu Gly Glu Tyr Pro Ser Val Arg
            180                 185                 190

Tyr Arg Ser Asp Trp Glu Arg Asn Val Glu Leu Ala Gln Met Ile Gln
        195                 200                 205

Gln Lys Leu Asp Ala Tyr Lys Ala Asp Glu Pro Thr Met Gly Glu Gly
    210                 215                 220

Pro Glu Lys Ala Arg Ser Gln Leu Leu Ile Leu Asp Arg Gly Phe Asp
225                 230                 235                 240

Cys Val Ser Pro Met Leu His Glu Leu Thr Phe Gln Ala Met Ala Tyr
                245                 250                 255

Asp Leu Leu Pro Ile Glu Asn Asp Val Tyr Lys Tyr Glu Ala Ser Ala
            260                 265                 270

Gly Val Phe Lys Glu Val Leu Leu Asp Glu Asn Asp Glu Leu Trp Val
        275                 280                 285

Glu Leu Arg His Gln His Ile Ala Val Val Ser Gln Ser Val Thr Lys
    290                 295                 300
```

-continued

```
Asn Leu Lys Lys Phe Thr Asp Ser Lys Arg Met Thr Gln Ser Asp Lys
305                 310                 315                 320

Gln Ser Met Lys Asp Leu Ser Gln Met Ile Lys Lys Met Pro Gln Tyr
                325                 330                 335

Gln Lys Glu Leu Ser Lys Tyr Ala Thr His Leu His Leu Ala Glu Asp
            340                 345                 350

Cys Met Lys Ser Tyr Gln Gly Tyr Val Asp Lys Leu Cys Lys Val Glu
        355                 360                 365

Gln Asp Leu Ala Met Gly Thr Asp Ala Glu Gly Glu Lys Ile Lys Asp
    370                 375                 380

His Met Arg Asn Ile Val Pro Ile Leu Leu Asp Pro Lys Ile Thr Asn
385                 390                 395                 400

Glu Tyr Asp Lys Met Arg Ile Ile Ala Leu Tyr Ala Met Ile Lys Asn
                405                 410                 415

Gly Ile Thr Asp Glu Asn Leu Ser Lys Leu Ala Thr His Ala Gln Ile
            420                 425                 430

Lys Asp Lys Gln Thr Ile Ala Asn Leu Gln Phe Leu Gly Val Asn Val
        435                 440                 445

Ile Asn Asp Gly Gly Asn Arg Lys Lys Pro Tyr Ser Val Pro Arg Lys
    450                 455                 460

Glu Arg Ile Thr Glu Gln Thr Tyr Gln Met Ser Arg Trp Thr Pro Val
465                 470                 475                 480

Ile Lys Asp Ile Met Glu Asp Ala Ile Glu Asp Lys Leu Asp Gln Lys
                485                 490                 495

His Phe Pro Phe Leu Ala Gly Arg Ala Gln Thr Ser Ala Tyr His Ala
            500                 505                 510

Pro Thr Ser Ala Arg Tyr Gly His Trp His Lys Asp Lys Ala Gln Gln
        515                 520                 525

Thr Val Lys Asn Val Pro Arg Ile Ile Val Phe Ile Val Gly Gly Met
    530                 535                 540

Ser Phe Ser Glu Ile Arg Cys Ala Tyr Glu Val Thr Asn Ala Gln Lys
545                 550                 555                 560

Asn Trp Glu Val Ile Ile Gly Ser Ser Asn Ile Leu Thr Pro Gln Ser
                565                 570                 575

Phe Leu Lys Asp Leu Asn Thr Leu Thr Val
            580                 585
```

<210> SEQ ID NO 122
<211> LENGTH: 2550
<212> TYPE: DNA
<213> ORGANISM: Meligethes aeneus

<400> SEQUENCE: 122

```
tttgacattt aatgataatt gtgcagtggg tgctattaaa aattatattg tttaaatagg      60

tagttaaaat attataaaat attgttagag tgttcatcac aaattatatg caatatggcg     120

ttaaaaggac aagttgggca aaaaattatg aacgaggtaa taaagcataa accaaagaaa     180

aatggacccg ctcatggagt ggaatggaga gttttggttg tggatcaact tgccatgaga     240

atggtttcag cctgttgtaa aatgcacgat atttcagctg agggcatcac attggttgaa     300

gatataaaca agaaaagaga acccttaaac accatggaag caatatatct aataacacca     360

tctgaaaaat ctgttcactc actgatgaac gattttgaat cgccaagact tatgtacaaa     420

ggggcacatg tattttttac tgaagcatgc cctgataatt tatttcaaaa attgtctcaa     480
```

-continued

```
catccagtag tgaaatatat taaaacttgt aaagaaatca acattgcatt tataccaaat    540
gaatcacagg tgttttcttt ggactgccca gaaacattcc aatgcagtta tgatcctgct    600
atggaagcag ccagaaatgc aaacatggag agaatggcag aacaaattgc tacattgtgt    660
gcaactctgg gagaataccc ttcagtaaga taccgaagtg attgggaacg caacgtggaa    720
ctagcgcaga tgattcagca aaagttggat gcctataaag cggatgagcc cacaatggga    780
gaggggcctg aaaaagcgag atcgcaactt ttgattcttg accgcggctt cgactgcgta    840
tcacccatgc tgcacgaact tacattccag gcaatggcct acgatttgct gccaatcgaa    900
aacgacgtgt acaaatatga agcttcagcg ggagtattta aggaagtgtt gctcgacgaa    960
aacgacgagt tatgggtaga attacgacat cagcatatcg ctgtagtgtc gcagagtgtg   1020
acgaaaaact tgaagaaatt taccgattca aaacgaatga cccaaagtga taaacaatca   1080
atgaaagatc tgtcacaaat gattaagaaa atgccccaat atcaaaagga gttatctaaa   1140
tatgctacac acttgcatct tgctgaagac tgcatgaaat cttaccaagg atatgttgac   1200
aaattatgta aagttgaaca agacctagca atgggtacag atgcagaagg agaaaaaatt   1260
aaagaccata tgcgtaacat cgtaccgatt ttacttgatc caaaaaataac aaacgaatat   1320
gacaaaatga gaataattgc tctatatgca atgattaaaa atggcataac cgacgaaaat   1380
ttatcaaaac ttgctactca tgcccaaata aaagacaaac aaactattgc taatttgcaa   1440
ttcttgggag ttaatgttat caatgatggt gggaaccgga aaaaaccgta ttcggtgcca   1500
agaaaagagc gtattactga acaaacgtat caaatgtcta gatggacgcc tgtaattaag   1560
gatattatgg aagacgctat tgaagataaa ttagatcaaa aacactttcc atttttagct   1620
ggccgagcgc aaaccagtgc ttaccacgcc ccaacaagtg ctcgatatgg tcattggcat   1680
aaagacaagg cccagcagac agtgaaaaat gtgcccagaa taattgtctt cattgttgga   1740
ggcatgagtt tttcagaaat cagatgtgcg tatgaggtaa caaacgccca aaaaaattgg   1800
gaggtcatta ttggatcctc caacattttg actccccaaa gttttcttaa ggatttaaac   1860
actcttacag tctaggattc aggaaaaaaa gttactttta atatacctga taattaaaaa   1920
tgctttcgtc atgtgaattt gattgcttaa gataaatggt tagttttact ggaattttta   1980
attgtagttg acattttgag atatttgtac ctactaacgt taaaaatgtg cagacctaag   2040
caagatatta caatataatc ttggatgcta gtctatcttc cctttctaaa aataactttt   2100
atttttaata attataattc tggattgaaa aataaaatgt atgtaaagta cttaagggaa   2160
ctgattattt tttttatttt ttaagttgag cagtctcaca caaacaatac attactcgtg   2220
cgccagcgca cttcatagac ttctaaaaaa aacattgggt ataaaaaact gttctcaatt   2280
tactaacgga acatttaaat ttattttaag cccctaagct ttaattatta aaaattgtat   2340
aaatgttgtt agaaataaag taagttttca aaggcgttat ataaatgttt agcgtgttat   2400
ggcgtttaac accataattc aaaaatatca aatatttaaa gttatttatc acgtttttat   2460
tgttatttct tgttataagt agttttttag atacttaaac ttgtattgta ttcagtattt   2520
cttttcaata gttatacatg tattatattc                                    2550
```

<210> SEQ ID NO 123
<211> LENGTH: 586
<212> TYPE: PRT
<213> ORGANISM: Meligethes aeneus

<400> SEQUENCE: 123

Met Ala Leu Lys Gly Gln Val Gly Gln Lys Ile Met Asn Glu Val Ile

-continued

```
1               5                   10                  15

Lys His Lys Pro Lys Lys Asn Gly Pro Ala His Gly Val Glu Trp Arg
            20                  25                  30

Val Leu Val Val Asp Gln Leu Ala Met Arg Met Val Ser Ala Cys Cys
        35                  40                  45

Lys Met His Asp Ile Ser Ala Glu Gly Ile Thr Leu Val Glu Asp Ile
    50                  55                  60

Asn Lys Lys Arg Glu Pro Leu Asn Thr Met Glu Ala Ile Tyr Leu Ile
65                  70                  75                  80

Thr Pro Ser Glu Lys Ser Val His Ser Leu Met Asn Asp Phe Glu Ser
                85                  90                  95

Pro Arg Leu Met Tyr Lys Gly Ala His Val Phe Phe Thr Glu Ala Cys
            100                 105                 110

Pro Asp Asn Leu Phe Gln Lys Leu Ser Gln His Pro Val Val Lys Tyr
        115                 120                 125

Ile Lys Thr Cys Lys Glu Ile Asn Ile Ala Phe Ile Pro Asn Glu Ser
    130                 135                 140

Gln Val Phe Ser Leu Asp Cys Pro Glu Thr Phe Gln Cys Ser Tyr Asp
145                 150                 155                 160

Pro Ala Met Glu Ala Ala Arg Asn Ala Asn Met Glu Arg Met Ala Glu
                165                 170                 175

Gln Ile Ala Thr Leu Cys Ala Thr Leu Gly Glu Tyr Pro Ser Val Arg
            180                 185                 190

Tyr Arg Ser Asp Trp Glu Arg Asn Val Glu Leu Ala Gln Met Ile Gln
        195                 200                 205

Gln Lys Leu Asp Ala Tyr Lys Ala Asp Glu Pro Thr Met Gly Glu Gly
    210                 215                 220

Pro Glu Lys Ala Arg Ser Gln Leu Leu Ile Leu Asp Arg Gly Phe Asp
225                 230                 235                 240

Cys Val Ser Pro Met Leu His Glu Leu Thr Phe Gln Ala Met Ala Tyr
                245                 250                 255

Asp Leu Leu Pro Ile Glu Asn Asp Val Tyr Lys Tyr Glu Ala Ser Ala
            260                 265                 270

Gly Val Phe Lys Glu Val Leu Leu Asp Glu Asn Asp Glu Leu Trp Val
        275                 280                 285

Glu Leu Arg His Gln His Ile Ala Val Val Ser Gln Ser Val Thr Lys
    290                 295                 300

Asn Leu Lys Lys Phe Thr Asp Ser Lys Arg Met Thr Gln Ser Asp Lys
305                 310                 315                 320

Gln Ser Met Lys Asp Leu Ser Gln Met Ile Lys Lys Met Pro Gln Tyr
                325                 330                 335

Gln Lys Glu Leu Ser Lys Tyr Ala Thr His Leu His Leu Ala Glu Asp
            340                 345                 350

Cys Met Lys Ser Tyr Gln Gly Tyr Val Asp Lys Leu Cys Lys Val Glu
        355                 360                 365

Gln Asp Leu Ala Met Gly Thr Asp Ala Glu Gly Glu Lys Ile Lys Asp
    370                 375                 380

His Met Arg Asn Ile Val Pro Ile Leu Leu Asp Pro Lys Ile Thr Asn
385                 390                 395                 400

Glu Tyr Asp Lys Met Arg Ile Ile Ala Leu Tyr Ala Met Ile Lys Asn
                405                 410                 415

Gly Ile Thr Asp Glu Asn Leu Ser Lys Leu Ala Thr His Ala Gln Ile
            420                 425                 430
```

```
Lys Asp Lys Gln Thr Ile Ala Asn Leu Gln Phe Leu Gly Val Asn Val
        435                 440                 445

Ile Asn Asp Gly Gly Asn Arg Lys Lys Pro Tyr Ser Val Pro Arg Lys
    450                 455                 460

Glu Arg Ile Thr Glu Gln Thr Tyr Gln Met Ser Arg Trp Thr Pro Val
465                 470                 475                 480

Ile Lys Asp Ile Met Glu Asp Ala Ile Glu Asp Lys Leu Asp Gln Lys
                485                 490                 495

His Phe Pro Phe Leu Ala Gly Arg Ala Gln Thr Ser Ala Tyr His Ala
            500                 505                 510

Pro Thr Ser Ala Arg Tyr Gly His Trp His Lys Asp Lys Ala Gln Gln
        515                 520                 525

Thr Val Lys Asn Val Pro Arg Ile Ile Val Phe Ile Val Gly Gly Met
    530                 535                 540

Ser Phe Ser Glu Ile Arg Cys Ala Tyr Glu Val Thr Asn Ala Gln Lys
545                 550                 555                 560

Asn Trp Glu Val Ile Ile Gly Ser Ser Asn Ile Leu Thr Pro Gln Ser
                565                 570                 575

Phe Leu Lys Asp Leu Asn Thr Leu Thr Val
            580                 585


<210> SEQ ID NO 124
<211> LENGTH: 3746
<212> TYPE: DNA
<213> ORGANISM: Meligethes aeneus

<400> SEQUENCE: 124

gttgatattg ttgttgaggg ggttgatatt gttgttgagg gggttgatat tgttgtggat     60

caacttgcca tgagaatggt ttcagcctgt tgtaaaatgc acgatatttc agctgagggc    120

atcacattgg ttgaagatat aaacaagaaa agagaaccct taaacaccat ggaagcaata    180

tatctaataa caccatctga aaaatctgtt cactcactga tgaacgattt tgaatcgcca    240

agacttatgt acaaaggggc acatgtattt tttactgaag tctgtcccga agaactcttc    300

aatgagttgt gtaaatcttg tgctgcaagg aaaattaaaa cgctaaagga aatcaacatt    360

gccttcttgc cctatgaatc acaggtgttt tctttggact gcccagaaac attccaatgc    420

agttatgatc ctgctatgga agcagccaga aatgcaaaca tggagagaat ggcagaacaa    480

attgctacat tgtgtgcaac tctgggagaa tacccttcag taagataccg aagtgattgg    540

gaacgcaacg tggaactagc gcagatgatt cagcaaaagt tggatgccta taaagcggat    600

gagcccacaa tgggagaggg gcctgaaaaa gcgagatcgc aacttttgat tcttgaccgc    660

ggcttcgact gcgtatcacc catgctgcac gaacttacat tccaggcaat ggcctacgat    720

ttgctgccaa tcgaaaacga cgtgtacaaa tatgaagctt cagcgggagt atttaaggaa    780

gtgttgctcg acgaaaacga cgagttatgg gtagaattac gacatcagca tatcgctgta    840

gtgtcgcaga gtgtgacgaa aaacttgaag aaatttaccg attcaaaacg aatgacccaa    900

agtgataaac aatcaatgaa agatctgtca caaatgatta agaaaatgcc ccaatatcaa    960

aaggagttat ctaaatatgc tacacacttg catcttgctg aagactgcat gaaatcttac   1020

caaggatatg ttgacaaatt atgtaaagtt gaacaagacc tagcaatggg tacagatgca   1080

gaaggagaaa aaattaaaga ccatatgcgt aacatcgtac cgattttact tgatccaaaa   1140

ataacaaacg aatatgacaa aatgagaata attgctctat atgcaatgat taaaaatggc   1200
```

-continued

```
ataaccgacg aaaatttatc aaaacttgct actcatgccc aaataaaaga caaacaaact   1260
attgctaatt tgcaattctt gggagttaat gttatcaatg atggtgggaa ccggaaaaaa   1320
ccgtattcgg tgccaagaaa agagcgtatt actgaacaaa cgtatcaaat gtctagatgg   1380
acgcctgtaa ttaaggatat tatggaagac gctattgaag ataaattaga tcaaaaacac   1440
tttccatttt tagctggccg agcgcaaacc agtgcttacc acgccccaac aagtgctcga   1500
tatggtcatt ggcataaaga caaggcccag cagacagtga aaaatgtgcc cagaataatt   1560
gtcttcattg ttggaggcat gagtttttca gaaatcagat gtgcgtatga ggtaacaaac   1620
gcccaaaaaa attgggaggt cattattgga tcctccaaca ttttgactcc ccaaagtttt   1680
cttaaggatt taaacactct tacagtctag gattcaggaa aaaaagttac ttttaatata   1740
cctgataatt aaaaatgctt tcgtcatgtg aatttgattg cttaagataa atggttagtt   1800
ttactggaat ttttaattgt agttgacatt ttgagatatt tgtacctact aacgttaaaa   1860
atgtgcagac ctaagcaaga tattacaata taatcttgga tgctagtcta tcttcccttt   1920
ctaaaaataa cttttatttt taataattat aattctggat tgaaaaataa aatgtatgta   1980
aagtacttaa gggaactgat tatttttttt atttttaag ttgagcagtc tcacacaaac    2040
aatacattac tcgtgcgcca gcgcacttca tagacttcta aaaaaaacat tgggtataaa   2100
aaactgttct caatttacta acggaacatt taaatttatt ttaagcccct aagctttaat   2160
tattaaaaat tgtataaatg ttgttagaaa taaagtaagt tttcaaaggc gttatataaa   2220
tgtttagcgt gttatggcgt ttaacaccat aattcaaaaa tatcaaatat ttaaagttat   2280
ttatcacgtt tttattgtta tttcttgtta taagtagttt tttagatact taaacttgta   2340
ttgtattcag tatttctttt caatagttat acatgtattt tttttttttt taatttagca   2400
aaattaaaat tgtcaatttt attaagatat agtatagtat tttgtctttt taagacaaaa   2460
tgtaacataa ttaaatttta tccgaattca taaaaatatt gttgttcctt tcatgacaaa   2520
gtggccaagt ccagttttat ttaaaaatgt aatacaaaat atagctgctt ttaacacaga   2580
atactgtaca taaaatctac ctaaaaaata cagtgtgctt tattgacaac aaatgtaatt   2640
ttttgtatat atgcagacac caccactact ggacttggta atccaattct cataaaagga   2700
atcttataag attcctatat atattatgtt aaagtaaggt tgtggttcta tctcatcttg   2760
agagaataat aatttttacc ttgttacacc actccaaaaa aatgcctgat tatacaaaat   2820
tggcaacaaa aactatggat acaagttatt tcagtaactt ataactattg taatgctata   2880
atggtaccta caaaaaagaa aagcccactt accacactac tatagtaggc tttataaagc   2940
ctttgttttt atattaggtt tgtacagggt gaatcacaac tttcatcccg gacaacaatc   3000
gggatttcct ggtgaagtca tgatgatatc acaacgtgat tttttttatc acgctgtgat   3060
atcctgagtg catacacatg cttcatccca gtgatatcat gtagaactca cggtgtgata   3120
tttgcaaaat tttcgcatgc gtatgagccc tgcgaactgc gaatttaaaa cctagtttgt   3180
tattcctatt acaccgttat aatttataaa acgttgtttg catatcacga atgttgtccg   3240
ggttcaatta attagtttat ttcttgaatg acaacattcg tgatattcat acgaacatca   3300
cgtcgtgatt ttcacaaatt ttattcatac tgatatcata cggaagtcac cgcgtgataa   3360
ataaaaatca tacgaacgtc acgtcgtgat tttcacaaat tttattcata cggacatcat   3420
ccggatgtca ctgcgtgaga aataaaaatc atgtcgtgat tttttatgcc atcgctgttt   3480
gcgattgacc gatggcacaa aaaatcatgt cgtgattttt tatgccaacg gtgtttggat   3540
aatcattttt gcgctgcgtt cgtacactaa gagaaaaatt atgttgaatc aacagttttt   3600
```

-continued gcggttaaat actttcaaaa tcatgtcgtg ttttttaggc caccggtcaa tcgcaaacag 3660
cgatggcaca aaaaatcacg acatgatttt gaaagtattt aaccgcaaaa actgttgatt 3720
caacataatt tttctcttag tgtacg 3746

<210> SEQ ID NO 125
<211> LENGTH: 569
<212> TYPE: PRT
<213> ORGANISM: Meligethes aeneus

<400> SEQUENCE: 125

Val Asp Ile Val Val Glu Gly Val Asp Ile Val Val Glu Gly Val Asp
1 5 10 15

Ile Val Val Asp Gln Leu Ala Met Arg Met Val Ser Ala Cys Cys Lys
20 25 30

Met His Asp Ile Ser Ala Glu Gly Ile Thr Leu Val Glu Asp Ile Asn
35 40 45

Lys Lys Arg Glu Pro Leu Asn Thr Met Glu Ala Ile Tyr Leu Ile Thr
50 55 60

Pro Ser Glu Lys Ser Val His Ser Leu Met Asn Asp Phe Glu Ser Pro
65 70 75 80

Arg Leu Met Tyr Lys Gly Ala His Val Phe Phe Thr Glu Val Cys Pro
85 90 95

Glu Glu Leu Phe Asn Glu Leu Cys Lys Ser Cys Ala Ala Arg Lys Ile
100 105 110

Lys Thr Leu Lys Glu Ile Asn Ile Ala Phe Leu Pro Tyr Glu Ser Gln
115 120 125

Val Phe Ser Leu Asp Cys Pro Glu Thr Phe Gln Cys Ser Tyr Asp Pro
130 135 140

Ala Met Glu Ala Ala Arg Asn Ala Asn Met Glu Arg Met Ala Glu Gln
145 150 155 160

Ile Ala Thr Leu Cys Ala Thr Leu Gly Glu Tyr Pro Ser Val Arg Tyr
165 170 175

Arg Ser Asp Trp Glu Arg Asn Val Glu Leu Ala Gln Met Ile Gln Gln
180 185 190

Lys Leu Asp Ala Tyr Lys Ala Asp Glu Pro Thr Met Gly Glu Gly Pro
195 200 205

Glu Lys Ala Arg Ser Gln Leu Leu Ile Leu Asp Arg Gly Phe Asp Cys
210 215 220

Val Ser Pro Met Leu His Glu Leu Thr Phe Gln Ala Met Ala Tyr Asp
225 230 235 240

Leu Leu Pro Ile Glu Asn Asp Val Tyr Lys Tyr Glu Ala Ser Ala Gly
245 250 255

Val Phe Lys Glu Val Leu Leu Asp Glu Asn Asp Glu Leu Trp Val Glu
260 265 270

Leu Arg His Gln His Ile Ala Val Val Ser Gln Ser Val Thr Lys Asn
275 280 285

Leu Lys Lys Phe Thr Asp Ser Lys Arg Met Thr Gln Ser Asp Lys Gln
290 295 300

Ser Met Lys Asp Leu Ser Gln Met Ile Lys Lys Met Pro Gln Tyr Gln
305 310 315 320

Lys Glu Leu Ser Lys Tyr Ala Thr His Leu His Leu Ala Glu Asp Cys
325 330 335

Met Lys Ser Tyr Gln Gly Tyr Val Asp Lys Leu Cys Lys Val Glu Gln

```
            340                 345                 350

Asp Leu Ala Met Gly Thr Asp Ala Glu Gly Glu Lys Ile Lys Asp His
        355                 360                 365

Met Arg Asn Ile Val Pro Ile Leu Leu Asp Pro Lys Ile Thr Asn Glu
    370                 375                 380

Tyr Asp Lys Met Arg Ile Ile Ala Leu Tyr Ala Met Ile Lys Asn Gly
385                 390                 395                 400

Ile Thr Asp Glu Asn Leu Ser Lys Leu Ala Thr His Ala Gln Ile Lys
                405                 410                 415

Asp Lys Gln Thr Ile Ala Asn Leu Gln Phe Leu Gly Val Asn Val Ile
            420                 425                 430

Asn Asp Gly Gly Asn Arg Lys Lys Pro Tyr Ser Val Pro Arg Lys Glu
        435                 440                 445

Arg Ile Thr Glu Gln Thr Tyr Gln Met Ser Arg Trp Thr Pro Val Ile
    450                 455                 460

Lys Asp Ile Met Glu Asp Ala Ile Glu Asp Lys Leu Asp Gln Lys His
465                 470                 475                 480

Phe Pro Phe Leu Ala Gly Arg Ala Gln Thr Ser Ala Tyr His Ala Pro
                485                 490                 495

Thr Ser Ala Arg Tyr Gly His Trp His Lys Asp Lys Ala Gln Gln Thr
            500                 505                 510

Val Lys Asn Val Pro Arg Ile Ile Val Phe Ile Val Gly Gly Met Ser
        515                 520                 525

Phe Ser Glu Ile Arg Cys Ala Tyr Glu Val Thr Asn Ala Gln Lys Asn
    530                 535                 540

Trp Glu Val Ile Ile Gly Ser Ser Asn Ile Leu Thr Pro Gln Ser Phe
545                 550                 555                 560

Leu Lys Asp Leu Asn Thr Leu Thr Val
                565


<210> SEQ ID NO 126
<211> LENGTH: 3504
<212> TYPE: DNA
<213> ORGANISM: Meligethes aeneus

<400> SEQUENCE: 126

gttgatattg ttgttgaggg ggttgatatt gttgttgagg gggttgatat tgttgtggat      60

caacttgcca tgagaatggt ttcagcctgt tgtaaaatgc acgatatttc agctgagggc     120

atcacattgg ttgaagatat aaacaagaaa agagaaccct taaacaccat ggaagcaata     180

tatctaataa caccatctga aaaatctgtt cactcactga tgaacgattt tgaatcgcca     240

agacttatgt acaaaggggc acatgtattt tttactgaag catgccctga taatttattt     300

caaaaattgt ctcaacatcc agtagtgaaa tatattaaaa cttgtaaaga aatcaacatt     360

gcatttatac caaatgaatc acaggtgttt tctttggact gcccagaaac attccaatgc     420

agttatgatc ctgctatgga agcagccaga aatgcaaaca tggagagaat ggcagaacaa     480

attgctacat tgtgtgcaac tctgggagaa taccccttcag taagataccg aagtgattgg     540

gaacgcaacg tggaactagc gcagatgatt cagcaaaagt tggatgccta taaagcggat     600

gagcccacaa tgggagaggg gcctgaaaaa gcgagatcgc aacttttgat tcttgaccgc     660

ggcttcgact gcgtatcacc catgctgcac gaacttacat tccaggcaat ggcctacgat     720

ttgctgccaa tcgaaaacga cgtgtacaaa tatgaagctt cagcgggagt atttaaggaa     780

gtgttgctcg acgaaaacga cgagttatgg gtagaattac gacatcagca tatcgctgta     840
```

```
gtgtcgcaga gtgtgacgaa aaacttgaag aaatttaccg attcaaaacg aatgacccaa    900
agtgataaac aatcaatgaa agatctgtca caaatgatta agaaaatgcc ccaatatcaa    960
aaggagttat ctaaatatgc tacacacttg catcttgctg aagactgcat gaaatcttac   1020
caaggatatg ttgacaaatt atgtaaagtt gaacaagacc tagcaatggg tacagatgca   1080
gaaggagaaa aaattaaaga ccatatgcgt aacatcgtac cgattttact tgatccaaaa   1140
ataacaaacg aatatgacaa aatgagaata attgctctat atgcaatgat taaaaatggc   1200
ataaccgacg aaaatttatc aaaacttgct actcatgccc aaataaaaga caaacaaact   1260
attgctaatt tgcaattctt gggagttaat gttatcaatg atggtgggaa ccggaaaaaa   1320
ccgtattcgg tgccaagaaa agagcgtatt actgaacaaa cgtatcaaat gtctagatgg   1380
acgcctgtaa ttaaggatat tatggaagac gctattgaag ataaattaga tcaaaaacac   1440
tttccatttt tagctggccg agcgcaaacc agtgcttacc acgccccaac aagtgctcga   1500
tatggtcatt ggcataaaga caaggcccag cagacagtga aaaatgtgcc cagaataatt   1560
gtcttcattg ttggaggcat gagtttttca gaaatcagat gtgcgtatga ggtaacaaac   1620
gcccaaaaaa attgggaggt cattattgga tcctccaaca ttttgactcc ccaaagtttt   1680
cttaaggatt taaacactct tacagtctag gattcaggaa aaaaagttac ttttaatata   1740
cctgataatt aaaaatgctt tcgtcatgtg aatttgattg cttaagataa atggttagtt   1800
ttactggaat ttttaattgt agttgacatt ttgagatatt tgtacctact aacgttaaaa   1860
atgtgcagac ctaagcaaga tattacaata taatcttgga tgctagtcta tcttcccttt   1920
ctaaaaataa cttttatttt taataattat aattctggat tgaaaaataa aatgtatgta   1980
aagtacttaa gggaactgat tattttttt attttttaag ttgagcagtc tcacacaaac   2040
aatacattac tcgtgcgcca gcgcacttca tagacttcta aaaaaaacat tgggtataaa   2100
aaactgttct caatttacta acggaacatt taaatttatt ttaagcccct aagctttaat   2160
tattaaaaat tgtataaatg ttgttagaaa taaagtaagt tttcaaaggc gttatataaa   2220
tgtttagcgt gttatggcgt ttaacaccat aattcaaaaa tatcaaatat ttaaagttat   2280
ttatcacgtt tttattgtta tttcttgtta taagtagttt tttagatact taaacttgta   2340
ttgtattcag tatttctttt caatagttat acatgtattt tttttttttt taatttagca   2400
aaattaaaat tgtcaatttt attaagatat agtatagtat tttgtctttt taagacaaaa   2460
tgtaacataa ttaaatttta tccgaattca taaaaatatt gttgttcctt tcatgacaaa   2520
gtggccaagt ccagttttat ttaaaaatgt aatacaaaat atagctgctt ttaacacaga   2580
atactgtaca taaaatctac ctaaaaaata cagtgtgctt tattgacaac aaatgtaatt   2640
ttttgtatat atgcagacac caccactact ggacttggta atccaattct cataaaagga   2700
atcttataag attcctatat atattatgtt aaagtaaggt tgtggttcta tctcatcttg   2760
agagaataat aatttttacc ttgttacacc actccaaaaa aatgcctgat tatacaaaat   2820
tggcaacaaa aactatggat acaagttatt tcagtaactt ataactattg taatgctata   2880
atggtaccta caaaaaagaa aagcccactt accacactac tatagtaggc tttataaagc   2940
ctttgttttt atattaggtt tgtacagggt gaatcacaac tttcatcccg gacaacaatc   3000
gggatttcct ggtgaagtca tgatgatatc acaacgtgat tttttttatc acgctgtgaa   3060
atcctgagtg catacacatg cttcatccca gtgatatcat gtagaactca cggtgtgata   3120
tttgcaaaat gttcgcatgc ctatgagacc tgcgaactgc gaatttaaaa cctagtttgt   3180
```

-continued

```
tattcatatt acaccgttat aatttataaa acgttgtttg catatcacga atgttgtccg   3240

ggttcaatta aaaaggatat ttcaaaaaaa aacaaaacgt gaacgttttg aacgcagggc   3300

tcatatattc ctgatattca tacgaacatc atgtcgtgat tttttacaaa ttttattcaa   3360

actgataaca tacggaagtc accgtgtgat aaatgaaaat aatacgaatg tcacgtcgtg   3420

attttcacac ggacatcatc cggatgtcac tgcgtgagaa atgaaaatca tgtcgtgatt   3480

ttttatgcca acagtgtttg gata                                          3504


<210> SEQ ID NO 127
<211> LENGTH: 569
<212> TYPE: PRT
<213> ORGANISM: Meligethes aeneus

<400> SEQUENCE: 127

Val Asp Ile Val Val Glu Gly Val Asp Ile Val Val Glu Gly Val Asp
1               5                   10                  15

Ile Val Val Asp Gln Leu Ala Met Arg Met Val Ser Ala Cys Cys Lys
            20                  25                  30

Met His Asp Ile Ser Ala Glu Gly Ile Thr Leu Val Glu Asp Ile Asn
        35                  40                  45

Lys Lys Arg Glu Pro Leu Asn Thr Met Glu Ala Ile Tyr Leu Ile Thr
    50                  55                  60

Pro Ser Glu Lys Ser Val His Ser Leu Met Asn Asp Phe Glu Ser Pro
65                  70                  75                  80

Arg Leu Met Tyr Lys Gly Ala His Val Phe Phe Thr Glu Ala Cys Pro
                85                  90                  95

Asp Asn Leu Phe Gln Lys Leu Ser Gln His Pro Val Val Lys Tyr Ile
            100                 105                 110

Lys Thr Cys Lys Glu Ile Asn Ile Ala Phe Ile Pro Asn Glu Ser Gln
        115                 120                 125

Val Phe Ser Leu Asp Cys Pro Glu Thr Phe Gln Cys Ser Tyr Asp Pro
    130                 135                 140

Ala Met Glu Ala Ala Arg Asn Ala Asn Met Glu Arg Met Ala Glu Gln
145                 150                 155                 160

Ile Ala Thr Leu Cys Ala Thr Leu Gly Glu Tyr Pro Ser Val Arg Tyr
                165                 170                 175

Arg Ser Asp Trp Glu Arg Asn Val Glu Leu Ala Gln Met Ile Gln Gln
            180                 185                 190

Lys Leu Asp Ala Tyr Lys Ala Asp Glu Pro Thr Met Gly Glu Gly Pro
        195                 200                 205

Glu Lys Ala Arg Ser Gln Leu Leu Ile Leu Asp Arg Gly Phe Asp Cys
    210                 215                 220

Val Ser Pro Met Leu His Glu Leu Thr Phe Gln Ala Met Ala Tyr Asp
225                 230                 235                 240

Leu Leu Pro Ile Glu Asn Asp Val Tyr Lys Tyr Glu Ala Ser Ala Gly
                245                 250                 255

Val Phe Lys Glu Val Leu Leu Asp Glu Asn Asp Glu Leu Trp Val Glu
            260                 265                 270

Leu Arg His Gln His Ile Ala Val Val Ser Gln Ser Val Thr Lys Asn
        275                 280                 285

Leu Lys Lys Phe Thr Asp Ser Lys Arg Met Thr Gln Ser Asp Lys Gln
    290                 295                 300

Ser Met Lys Asp Leu Ser Gln Met Ile Lys Lys Met Pro Gln Tyr Gln
305                 310                 315                 320
```

```
Lys Glu Leu Ser Lys Tyr Ala Thr His Leu His Leu Ala Glu Asp Cys
                325                 330                 335

Met Lys Ser Tyr Gln Gly Tyr Val Asp Lys Leu Cys Lys Val Glu Gln
            340                 345                 350

Asp Leu Ala Met Gly Thr Asp Ala Glu Gly Glu Lys Ile Lys Asp His
        355                 360                 365

Met Arg Asn Ile Val Pro Ile Leu Leu Asp Pro Lys Ile Thr Asn Glu
    370                 375                 380

Tyr Asp Lys Met Arg Ile Ile Ala Leu Tyr Ala Met Ile Lys Asn Gly
385                 390                 395                 400

Ile Thr Asp Glu Asn Leu Ser Lys Leu Ala Thr His Ala Gln Ile Lys
                405                 410                 415

Asp Lys Gln Thr Ile Ala Asn Leu Gln Phe Leu Gly Val Asn Val Ile
            420                 425                 430

Asn Asp Gly Gly Asn Arg Lys Lys Pro Tyr Ser Val Pro Arg Lys Glu
        435                 440                 445

Arg Ile Thr Glu Gln Thr Tyr Gln Met Ser Arg Trp Thr Pro Val Ile
    450                 455                 460

Lys Asp Ile Met Glu Asp Ala Ile Glu Asp Lys Leu Asp Gln Lys His
465                 470                 475                 480

Phe Pro Phe Leu Ala Gly Arg Ala Gln Thr Ser Ala Tyr His Ala Pro
                485                 490                 495

Thr Ser Ala Arg Tyr Gly His Trp His Lys Asp Lys Ala Gln Gln Thr
            500                 505                 510

Val Lys Asn Val Pro Arg Ile Ile Val Phe Ile Val Gly Gly Met Ser
        515                 520                 525

Phe Ser Glu Ile Arg Cys Ala Tyr Glu Val Thr Asn Ala Gln Lys Asn
    530                 535                 540

Trp Glu Val Ile Ile Gly Ser Ser Asn Ile Leu Thr Pro Gln Ser Phe
545                 550                 555                 560

Leu Lys Asp Leu Asn Thr Leu Thr Val
                565
```

<210> SEQ ID NO 128
<211> LENGTH: 401
<212> TYPE: DNA
<213> ORGANISM: Meligethes aeneus

<400> SEQUENCE: 128

```
ggactgccca gaaacattcc aatgcagtta tgatcctgct atggaagcag ccagaaatgc      60

aaacatggag agaatggcag aacaaattgc tacattgtgt gcaactctgg gagaataccc     120

ttcagtaaga taccgaagtg attgggaacg caacgtggaa ctagcgcaga tgattcagca     180

aaagttggat gcctataaag cggatgagcc cacaatggga gaggggcctg aaaaagcgag     240

atcgcaactt ttgattcttg accgcggctt cgactgcgta tcacccatgc tgcacgaact     300

tacattccag gcaatggcct acgatctgct gccaatcgaa aacgacgtgt acaaatatga     360

agcttcagcg ggagtattta aggaagtgtt gctcgacgaa a                         401
```

<210> SEQ ID NO 129
<211> LENGTH: 45
<212> TYPE: DNA
<213> ORGANISM: Artificial Sequence
<220> FEATURE:
<223> OTHER INFORMATION: Forward primer to amplify Rop reg1

<400> SEQUENCE: 129
taatacgact cactataggg agatttcgtc gagcaacact tcctt 45

<210> SEQ ID NO 130
<211> LENGTH: 44
<212> TYPE: DNA
<213> ORGANISM: Artificial Sequence
<220> FEATURE:
<223> OTHER INFORMATION: Reverse primer to amplify Rop reg 1

<400> SEQUENCE: 130
taatacgact cactataggg agaggactgc ccagaaacat tcca 44

<210> SEQ ID NO 131
<211> LENGTH: 2487
<212> TYPE: DNA
<213> ORGANISM: Meligethes aeneus

<400> SEQUENCE: 131
aggtgttttc tttggactgc ccagaaacat tccaatgcag ttatgatcct gctatggaag 60
cagccagaaa tgcaaacatg gagagaatgg cagaacaaat tgctacattg tgtgcaactc 120
tgggagaata cccttcagta agataccgaa gtgattggga acgcaacgtg gaactagcgc 180
agatgattca gcaaaagttg gatgcctata aagcggatga gcccacaatg ggagaggggc 240
ctgaaaaagc gagatcgcaa cttttgattc ttgaccgcgg cttcgactgc gtatcaccca 300
tgctgcacga acttacattc caggcaatgg cctacgattt gctgccaatc gaaaacgacg 360
tgtacaaata tgaagcttca gcgggagtat ttaaggaagt gttgctcgac gaaaacgacg 420
agttatgggt agaattacga catcagcata tcgctgtagt gtcgcagagt gtgacgaaaa 480
acttgaagaa atttaccgat tcaaaacgaa tgacccaaag tgataaacaa tcaatgaaag 540
atctgtcaca aatgattaag aaaatgcccc aatatcaaaa ggagttatct aaatatgcta 600
cacacttgca tcttgctgaa gactgcatga aatcttacca aggatatgtt gacaaattat 660
gtaaagttga acaagaccta gcaatgggta cagatgcaga aggagaaaaa attaaagacc 720
atatgcgtaa catcgtaccg attttacttg atccaaaaat aacaaacgaa tatgacaaaa 780
tgagaataat tgctctatat gcaatgatta aaaatggcat aaccgacgaa aatttatcaa 840
aacttgctac tcatgcccaa ataaaagaca aacaaactat tgctaatttg caattcttgg 900
gagttaatgt tatcaatgat ggtgggaacc ggaaaaaacc gtattcggtg ccaagaaaag 960
agcgtattac tgaacaaacg tatcaaatgt ctagatggac gcctgtaatt aaggatatta 1020
tggaagacgc tattgaagat aaattagatc aaaaacactt tccattttta gctggccgag 1080
cgcaaaccag tgcttaccac gccccaacaa gtgctcgata tggtcattgg cataaagaca 1140
aggcccagca gacagtgaaa aatgtgccca gaataattgt cttcattgtt ggaggcatga 1200
gtttttcaga aatcagatgt gcgtatgagg taacaaacgc ccaaaaaaat tgggaggtca 1260
ttattggatc ctccaacatt ttgactcccc aaagttttct taaggattta aacactctta 1320
cagtctagga ttcaggaaaa aaagttactt ttaatatacc tgataattaa aaatgctttc 1380
gtcatgtgaa tttgattgct taagataaat ggttagtttt actggaattt ttaattgtag 1440
ttgacatttt gagatatttg tacctactaa cgttaaaaat gtgcagacct aagcaagata 1500
ttacaatata atcttggatg ctagtctatc ttccctttct aaaaataact tttattttta 1560
ataattataa ttctggattg aaaaataaaa tgtatgtaaa gtacttaagg gaactgatta 1620
ttttttttat tttttaagtt gagcagtctc acacaaacaa tacattactc gtgcgccagc 1680

-continued

```
gcacttcata gacttctaaa aaaaacattg ggtataaaaa actgttctca atttactaac   1740

ggaacattta aatttatttt aagcccctaa gctttaatta ttaaaaattg tataaatgtt   1800

gttagaaata aagtaagttt tcaaaggcgt tatataaatg tttagcgtgt tatggcgttt   1860

aacaccataa ttcaaaaata tcaaatattt aaagttattt atcacgtttt tattgttatt   1920

tcttgttata agtagttttt tagatactta aacttgtatt gtattcagta tttcttttca   1980

atagttatac atgtattata ttctacaata aatttagcaa aattaaaatt gtcaatttta   2040

ttaagatata gtatagtatt ttgtcttttt aagacaaaat gtaacataat taaattttat   2100

ccgaattcat aaaaatattg ttgttccttt catgacaaag tggccaagtc cagttttatt   2160

taaaaatgta atacaaaata tagctgcttt taacacagaa tactgtacat aaaatctacc   2220

taaaaaatac agtgtgcttt attgacaaca aatgtaattt tttgtatata tgcagacacc   2280

accacactgg acttggtaat ccaattctca taaaaggaat cttatatgtt aaagtaaggt   2340

tgtggttcat ctcatcttga gagaataata atttttacct tgttacacca ctccaaaaaa   2400

atgcctgatt atacaaaatt ggcaacaaaa actatggata caagttattt cagtaactta   2460

taactattgt aatgctataa tggtacc                                       2487
```

<210> SEQ ID NO 132
<211> LENGTH: 441
<212> TYPE: PRT
<213> ORGANISM: Meligethes aeneus

<400> SEQUENCE: 132

```
Val Phe Ser Leu Asp Cys Pro Glu Thr Phe Gln Cys Ser Tyr Asp Pro
1               5                   10                  15

Ala Met Glu Ala Ala Arg Asn Ala Asn Met Glu Arg Met Ala Glu Gln
            20                  25                  30

Ile Ala Thr Leu Cys Ala Thr Leu Gly Glu Tyr Pro Ser Val Arg Tyr
        35                  40                  45

Arg Ser Asp Trp Glu Arg Asn Val Glu Leu Ala Gln Met Ile Gln Gln
    50                  55                  60

Lys Leu Asp Ala Tyr Lys Ala Asp Glu Pro Thr Met Gly Glu Gly Pro
65                  70                  75                  80

Glu Lys Ala Arg Ser Gln Leu Leu Ile Leu Asp Arg Gly Phe Asp Cys
                85                  90                  95

Val Ser Pro Met Leu His Glu Leu Thr Phe Gln Ala Met Ala Tyr Asp
            100                 105                 110

Leu Leu Pro Ile Glu Asn Asp Val Tyr Lys Tyr Glu Ala Ser Ala Gly
        115                 120                 125

Val Phe Lys Glu Val Leu Leu Asp Glu Asn Asp Glu Leu Trp Val Glu
    130                 135                 140

Leu Arg His Gln His Ile Ala Val Val Ser Gln Ser Val Thr Lys Asn
145                 150                 155                 160

Leu Lys Lys Phe Thr Asp Ser Lys Arg Met Thr Gln Ser Asp Lys Gln
                165                 170                 175

Ser Met Lys Asp Leu Ser Gln Met Ile Lys Lys Met Pro Gln Tyr Gln
            180                 185                 190

Lys Glu Leu Ser Lys Tyr Ala Thr His Leu His Leu Ala Glu Asp Cys
        195                 200                 205

Met Lys Ser Tyr Gln Gly Tyr Val Asp Lys Leu Cys Lys Val Glu Gln
    210                 215                 220
```

-continued

```
Asp Leu Ala Met Gly Thr Asp Ala Glu Gly Glu Lys Ile Lys Asp His
225                 230                 235                 240

Met Arg Asn Ile Val Pro Ile Leu Leu Asp Pro Lys Ile Thr Asn Glu
                245                 250                 255

Tyr Asp Lys Met Arg Ile Ile Ala Leu Tyr Ala Met Ile Lys Asn Gly
            260                 265                 270

Ile Thr Asp Glu Asn Leu Ser Lys Leu Ala Thr His Ala Gln Ile Lys
        275                 280                 285

Asp Lys Gln Thr Ile Ala Asn Leu Gln Phe Leu Gly Val Asn Val Ile
    290                 295                 300

Asn Asp Gly Gly Asn Arg Lys Lys Pro Tyr Ser Val Pro Arg Lys Glu
305                 310                 315                 320

Arg Ile Thr Glu Gln Thr Tyr Gln Met Ser Arg Trp Thr Pro Val Ile
                325                 330                 335

Lys Asp Ile Met Glu Asp Ala Ile Glu Asp Lys Leu Asp Gln Lys His
            340                 345                 350

Phe Pro Phe Leu Ala Gly Arg Ala Gln Thr Ser Ala Tyr His Ala Pro
        355                 360                 365

Thr Ser Ala Arg Tyr Gly His Trp His Lys Asp Lys Ala Gln Gln Thr
    370                 375                 380

Val Lys Asn Val Pro Arg Ile Ile Val Phe Ile Val Gly Gly Met Ser
385                 390                 395                 400

Phe Ser Glu Ile Arg Cys Ala Tyr Glu Val Thr Asn Ala Gln Lys Asn
                405                 410                 415

Trp Glu Val Ile Ile Gly Ser Ser Asn Ile Leu Thr Pro Gln Ser Phe
            420                 425                 430

Leu Lys Asp Leu Asn Thr Leu Thr Val
        435                 440
```

<210> SEQ ID NO 133
<211> LENGTH: 2635
<212> TYPE: DNA
<213> ORGANISM: Meligethes aeneus

<400> SEQUENCE: 133

```
taaaaaaata aaagtttttct gtcagtgcat acttattgac tttttaaatg tggcatcctt      60

gcattcctat ttgacattta atgataattg tgcagtgggt gctattaaaa attatattgt     120

ttaaataggt agttaaaata ttataaaata ttgttagagt gttcatcaca aattatatgc     180

aatatggcgt taaaaggaca agttgggcaa aaaattatga acgaggtaat aaagcataaa     240

ccaaagaaaa atggacccgc tcatggagtg gaatggagag ttttggttgt ggatcaactt     300

gccatgagaa tggtttcagc ctgttgtaaa atgcacgata tttcagctga gggcatcaca     360

ttggttgaag atataaacaa gaaaagagaa cccttaaaca ccatggaagc aatatatcta     420

ataacaccat ctgaaaaatc tgttcactca ctgatgaacg attttgaatc gccaagactt     480

atgtacaaag ggcacatgt attttttact gaagcatgcc ctgataattt atttcaaaaa     540

ttgtctcaac atccagtagt gaaatatatt aaaacttgta aagaaatcaa cattgcattt     600

ataccaaatg aatcacaggt gttttctttg gactgcccag aaacattcca atgcagttat     660

gatcctgcta tggaagcagc cagaaatgca aacatggaga gaatggcaga acaaattgct     720

acattgtgtg caactctggg agaataccct tcagtaagat accgaagtga ttgggaacgc     780

aacgtggaac tagcgcagat gattcagcaa aagttggatg cctataaagc ggatgagccc     840

acaatgggag aggggcctga aaaagcgaga tcgcaacttt tgattcttga ccgcggcttc     900
```

```
gactgcgtat cacccatgct gcacgaactt acattccagg caatggccta cgatttgctg    960

ccaatcgaaa acgacgtgta caaatatgaa gcttcagcgg gagtatttaa ggaagtgttg   1020

ctcgacgaaa acgacgagtt atgggtagaa ttacgacatc agcatatcgc tgtagtgtcg   1080

cagagtgtga cgaaaaactt gaagaaattt accgattcaa aacgaatgac ccaaagtgat   1140

aaacaatcaa tgaaagatct gtcacaaatg attaagaaaa tgccccaata tcaaaaggag   1200

ttatctaaat atgctacaca cttgcatctt gctgaagact gcatgaaatc ttaccaagga   1260

tatgttgaca aattatgtaa agttgaacaa gacctagcaa tgggtacaga tgcagaagga   1320

gaaaaaatta aagaccatat gcgtaacatc gtaccgattt tacttgatcc aaaaataaca   1380

aacgaatatg acaaaatgag aataattgct ctatatgcaa tgattaaaaa tggcataacc   1440

gacgaaaatt tatcaaaact tgctactcat gcccaaataa aagacaaaca aactattgct   1500

aatttgcaat tcttgggagt taatgttatc aatgatggtg ggaaccggaa aaaaccgtat   1560

tcggtgccaa gaaaagagcg tattactgaa caaacgtatc aaatgtctag atggacgcct   1620

gtaattaagg atattatgga agacgctatt gaagataaat tagatcaaaa acactttcca   1680

tttttagctg gccgagcgca aaccagtgct taccacgccc caacaagtgc tcgatatggt   1740

cattggcata aagacaaggc ccagcagaca gtgaaaaatg tgcccagaat aattgtcttc   1800

attgttggag gcatgagttt ttcagaaatc agatgtgcgt atgaggtaac aaacgcccaa   1860

aaaaattggg aggtcattat tggatcctcc aacattttga ctccccaaag ttttcttaag   1920

gatttaaaca ctcttacagt ctaggattca ggaaaaaaag ttacttttaa tatacctgat   1980

aattaaaaat gctttcgtca tgtgaatttg attgcttaag ataaatggtt agttttactg   2040

gaatttttaa ttgtagttga cattttgaga tatttgtacc tactaacgtt aaaaatgtgc   2100

agacctaagc aagatattac aatataatct tggatgctag tctatcttcc ctttctaaaa   2160

ataactttta tttttaataa ttataattct ggattgaaaa ataaaatgta tgtaaagtac   2220

ttaagggaac tgattatttt ttttattttt taagttgagc agtctcacac aaacaataca   2280

ttactcgtgc gccagcgcac ttcatagact tctaaaaaaa acattgggta taaaaaactg   2340

ttctcaattt actaacggaa catttaaatt tattttaagc ccctaagctt taattattaa   2400

aaattgtata aatgttgtta gaaataaagt aagttttcaa aggcgttata taaatgttta   2460

gcgtgttatg gcgtttaaca ccataattca aaaatatcaa atatttaaag ttatttatca   2520

cgtttttatt gttatttctt gttataagta gttttttaga tacttaaact tgtattgtat   2580

tcagtatttc ttttcaatag ttatacatgt attatattct acaataaatt tagca        2635
```

<210> SEQ ID NO 134
<211> LENGTH: 586
<212> TYPE: PRT
<213> ORGANISM: Meligethes aeneus

<400> SEQUENCE: 134

```
Met Ala Leu Lys Gly Gln Val Gly Gln Lys Ile Met Asn Glu Val Ile
1               5                   10                  15

Lys His Lys Pro Lys Lys Asn Gly Pro Ala His Gly Val Glu Trp Arg
            20                  25                  30

Val Leu Val Val Asp Gln Leu Ala Met Arg Met Val Ser Ala Cys Cys
        35                  40                  45

Lys Met His Asp Ile Ser Ala Glu Gly Ile Thr Leu Val Glu Asp Ile
    50                  55                  60
```

-continued

```
Asn Lys Lys Arg Glu Pro Leu Asn Thr Met Glu Ala Ile Tyr Leu Ile
65                  70                  75                  80

Thr Pro Ser Glu Lys Ser Val His Ser Leu Met Asn Asp Phe Glu Ser
                85                  90                  95

Pro Arg Leu Met Tyr Lys Gly Ala His Val Phe Phe Thr Glu Ala Cys
            100                 105                 110

Pro Asp Asn Leu Phe Gln Lys Leu Ser Gln His Pro Val Val Lys Tyr
        115                 120                 125

Ile Lys Thr Cys Lys Glu Ile Asn Ile Ala Phe Ile Pro Asn Glu Ser
    130                 135                 140

Gln Val Phe Ser Leu Asp Cys Pro Glu Thr Phe Gln Cys Ser Tyr Asp
145                 150                 155                 160

Pro Ala Met Glu Ala Ala Arg Asn Ala Asn Met Glu Arg Met Ala Glu
                165                 170                 175

Gln Ile Ala Thr Leu Cys Ala Thr Leu Gly Glu Tyr Pro Ser Val Arg
            180                 185                 190

Tyr Arg Ser Asp Trp Glu Arg Asn Val Glu Leu Ala Gln Met Ile Gln
        195                 200                 205

Gln Lys Leu Asp Ala Tyr Lys Ala Asp Glu Pro Thr Met Gly Glu Gly
    210                 215                 220

Pro Glu Lys Ala Arg Ser Gln Leu Leu Ile Leu Asp Arg Gly Phe Asp
225                 230                 235                 240

Cys Val Ser Pro Met Leu His Glu Leu Thr Phe Gln Ala Met Ala Tyr
                245                 250                 255

Asp Leu Leu Pro Ile Glu Asn Asp Val Tyr Lys Tyr Glu Ala Ser Ala
            260                 265                 270

Gly Val Phe Lys Glu Val Leu Leu Asp Glu Asn Asp Glu Leu Trp Val
        275                 280                 285

Glu Leu Arg His Gln His Ile Ala Val Val Ser Gln Ser Val Thr Lys
    290                 295                 300

Asn Leu Lys Lys Phe Thr Asp Ser Lys Arg Met Thr Gln Ser Asp Lys
305                 310                 315                 320

Gln Ser Met Lys Asp Leu Ser Gln Met Ile Lys Lys Met Pro Gln Tyr
                325                 330                 335

Gln Lys Glu Leu Ser Lys Tyr Ala Thr His Leu His Leu Ala Glu Asp
            340                 345                 350

Cys Met Lys Ser Tyr Gln Gly Tyr Val Asp Lys Leu Cys Lys Val Glu
        355                 360                 365

Gln Asp Leu Ala Met Gly Thr Asp Ala Glu Gly Glu Lys Ile Lys Asp
    370                 375                 380

His Met Arg Asn Ile Val Pro Ile Leu Leu Asp Pro Lys Ile Thr Asn
385                 390                 395                 400

Glu Tyr Asp Lys Met Arg Ile Ile Ala Leu Tyr Ala Met Ile Lys Asn
                405                 410                 415

Gly Ile Thr Asp Glu Asn Leu Ser Lys Leu Ala Thr His Ala Gln Ile
            420                 425                 430

Lys Asp Lys Gln Thr Ile Ala Asn Leu Gln Phe Leu Gly Val Asn Val
        435                 440                 445

Ile Asn Asp Gly Gly Asn Arg Lys Lys Pro Tyr Ser Val Pro Arg Lys
    450                 455                 460

Glu Arg Ile Thr Glu Gln Thr Tyr Gln Met Ser Arg Trp Thr Pro Val
465                 470                 475                 480

Ile Lys Asp Ile Met Glu Asp Ala Ile Glu Asp Lys Leu Asp Gln Lys
```

-continued

```
                485                 490                 495

His Phe Pro Phe Leu Ala Gly Arg Ala Gln Thr Ser Ala Tyr His Ala
            500                 505                 510

Pro Thr Ser Ala Arg Tyr Gly His Trp His Lys Asp Lys Ala Gln Gln
        515                 520                 525

Thr Val Lys Asn Val Pro Arg Ile Ile Val Phe Ile Val Gly Gly Met
    530                 535                 540

Ser Phe Ser Glu Ile Arg Cys Ala Tyr Glu Val Thr Asn Ala Gln Lys
545                 550                 555                 560

Asn Trp Glu Val Ile Ile Gly Ser Ser Asn Ile Leu Thr Pro Gln Ser
                565                 570                 575

Phe Leu Lys Asp Leu Asn Thr Leu Thr Val
            580                 585
```

RAS OPPOSITE (ROP) AND RELATED NUCLEIC ACID MOLECULES THAT CONFER RESISTANCE TO COLEOPTERAN AND/OR HEMIPTERAN PESTS

PRIORITY CLAIM

This application claims the benefit of the filing date of U.S. Provisional Patent Application Ser. No. 61/919,322, filed Dec. 20, 2013, for "RAS OPPOSITE (ROP) AND RELATED NUCLEIC ACID MOLECULES THAT CONFER RESISTANCE TO COLEOPTERAN AND/OR HEMIPTERAN PESTS."

TECHNICAL FIELD

Field of the Invention

The present invention relates generally to control of plant damage caused by coleopteran and hemipteran pests. In particular embodiments, the present invention relates to identification of target coding and non-coding sequences, and the use of for post-transcriptionally repressing or inhibiting expression of target coding and non-coding sequences in the cells of a coleopteran or hemipteran pest to provide a plant protective effect.

Background

The western corn rootworm (WCR), *Diabrotica virgifera virgifera* LeConte, is one of the most devastating corn rootworm species in North America and is a particular concern in corn-growing areas of the Midwestern United States. The northern corn rootworm (NCR), *Diabrotica barberi* Smith and Lawrence, is a closely-related species that co-inhabits much of the same range as WCR. There are several other related subspecies of *Diabrotica* that are significant pests in North America: the Mexican corn rootworm (MCR), *D. virgifera zeae* Krysan and Smith; the southern corn rootworm (SCR), *D. undecimpunctata howardi* Barber; *D. balteata* LeConte; *D. undecimpunctata tenella*; and *D. u. undecimpunctata* Mannerheim. The United States Department of Agriculture currently estimates that corn rootworms cause $1 billion in lost revenue each year, including $800 million in yield loss and $200 million in treatment costs.

Both WCR and NCR eggs are deposited in the soil during the summer. The insects remain in the egg stage throughout the winter. The eggs are oblong, white, and less than 0.004 inch in length. The larvae hatch in late May or early June, with the precise timing of egg hatching varying from year to year due to temperature differences and location. The newly hatched larvae are white worms that are less than 0.125 inch in length. Once hatched, the larvae begin to feed on corn roots. Corn rootworms go through three larval instars. After feeding for several weeks, the larvae molt into the pupal stage. They pupate in the soil, and then they emerge from the soil as adults in July and August. Adult rootworms are about 0.25 inch in length.

Corn rootworm larvae complete development on corn and several other species of grasses. Larvae reared on yellow foxtail emerge later and have a smaller head capsule size as adults than larvae reared on corn. Ellsbury et al. (2005) Environ. Entomol. 34:627-634. WCR adults feed on corn silk, pollen, and kernels on exposed ear tips. If WCR adults emerge before corn reproductive tissues are present, they may feed on leaf tissue, thereby slowing plant growth and occasionally killing the host plant. However, the adults will quickly shift to preferred silks and pollen when they become available. NCR adults also feed on reproductive tissues of the corn plant, but in contrast rarely feed on corn leaves.

Most of the rootworm damage in corn is caused by larval feeding. Newly hatched rootworms initially feed on fine corn root hairs and burrow into root tips. As the larvae grow larger, they feed on and burrow into primary roots. When corn rootworms are abundant, larval feeding often results in the pruning of roots all the way to the base of the corn stalk. Severe root injury interferes with the roots' ability to transport water and nutrients into the plant, reduces plant growth, and results in reduced grain production, thereby often drastically reducing overall yield. Severe root injury also often results in lodging of corn plants, which makes harvest more difficult and further decreases yield. Furthermore, feeding by adults on the corn reproductive tissues can result in pruning of silks at the ear tip. If this "silk clipping" is severe enough during pollen shed, pollination may be disrupted.

Control of corn rootworms may be attempted by crop rotation, chemical insecticides, biopesticides (e.g., the spore-forming gram-positive bacterium, *Bacillus thuringiensis*), or a combination thereof. Crop rotation suffers from the significant disadvantage of placing unwanted restrictions upon the use of farmland. Moreover, oviposition of some rootworm species may occur in soybean fields, thereby mitigating the effectiveness of crop rotation practiced with corn and soybean.

Chemical insecticides are the most heavily relied upon strategy for achieving corn rootworm control. Chemical insecticide use, though, is an imperfect corn rootworm control strategy; over $1 billion may be lost in the United States each year due to corn rootworm when the costs of the chemical insecticides are added to the costs of the rootworm damage that may occur despite the use of the insecticides. High populations of larvae, heavy rains, and improper application of the insecticide(s) may all result in inadequate corn rootworm control. Furthermore, the continual use of insecticides may select for insecticide-resistant rootworm strains, as well as raise significant environmental concerns due to the toxicity of many of them to non-target species.

Stink bugs (Hemiptera; Pentatomidae) comprise another important agricultural pest complex. Worldwide over 50 closely related species of stink bugs are known to cause crop damage. McPherson & McPherson, R. M. (2000) *Stink bugs of economic importance in America north of Mexico* CRC Press. These insects are present in a large number of important crops including maize, soybean, fruit, vegetables, and cereals. The Neotropical brown stink bug, *Euchistus heros*, the red banded stink bug, *Piezodorus guildinii*, brown marmorated stink bug, *Halyomorpha halys*, and the Southern green stink bug, *Nezara viridula*, are of particular concern.

Stink bugs go through multiple nymph stages before reaching the adult stage. The time to develop from eggs to adults is about 30-40 days. Multiple generations occur in warm climates resulting in significant insect pressure.

Both nymphs and adults feed on sap from soft tissues into which they also inject digestive enzymes causing extra-oral tissue digestion and necrosis. Digested plant material and nutrients are then ingested. Depletion of water and nutrients from the plant vascular system results in plant tissue damage. Damage to developing grain and seeds is the most significant as yield and germination are significantly reduced.

Current management of stink bugs relies on insecticide treatment on an individual field basis. Therefore, alternative management strategies are urgently needed to minimize ongoing crop losses.

European pollen beetles (EPB) are serious pests in oilseed rape, both the larvae and adults feed on flowers and pollen.

Pollen beetle damage to the crop can cause 20-40% yield loss. The primary pest species is *Meligethes aeneus*. Currently, pollen beetle control in oilseed rape relies mainly on pyrethroids which are expected to be phased out soon because of their environmental and regulatory profile. Moreover, pollen beetle resistance to existing chemical insecticides has been reported. Therefore, urgently needed are environmentally friendly pollen beetle control solutions with novel modes of action.

In nature, pollen beetles overwinter as adults in the soil or under leaf litter. In spring the adults emerge from hibernation and start feeding on flowers of weeds, and migrate onto flowering oilseed rape plants. The eggs are laid in oilseed rape. The larvae feed and develop in the buds and on the flowers. Late stage larvae find a pupation site in the soil. The second generation of adults emerge in July and August and feed on various flowering plants before finding sites for overwintering.

RNA interference (RNAi) is a process utilizing endogenous cellular pathways, whereby an interfering RNA (iRNA) molecule (e.g., a double-stranded RNA (dsRNA) molecule) that is specific for all, or any portion of adequate size, of a target gene sequence results in the degradation of the mRNA encoded thereby. In recent years, RNAi has been used to perform gene "knockdown" in a number of species and experimental systems; for example, *Caenorhabitis elegans*, plants, insect embryos, and cells in tissue culture. See, e.g., Fire et al. (1998) Nature 391:806-811; Martinez et al. (2002) Cell 110:563-574; McManus and Sharp (2002) Nature Rev. Genetics 3:737-747.

RNAi accomplishes degradation of mRNA through an endogenous pathway including the DICER protein complex. DICER cleaves long dsRNA molecules into short fragments of approximately 20 nucleotides, termed small interfering RNA (siRNA). The siRNA is unwound into two single-stranded RNAs: the passenger strand and the guide strand. The passenger strand is degraded, and the guide strand is incorporated into the RNA-induced silencing complex (RISC). Micro ribonucleic acid (miRNA) molecules may be similarly incorporated into RISC. Post-transcriptional gene silencing occurs when the guide strand binds specifically to a complementary sequence of an mRNA molecule and induces cleavage by Argonaute, the catalytic component of the RISC complex. This process is known to spread systemically throughout the organism despite initially limited concentrations of siRNA and/or miRNA in some eukaryotes such as plants, nematodes, and some insects.

Only transcripts complementary to the siRNA and/or miRNA are cleaved and degraded, and thus the knock-down of mRNA expression is sequence-specific. In plants, several functional groups of DICER genes exist. The gene silencing effect of RNAi persists for days and, under experimental conditions, can lead to a decline in abundance of the targeted transcript of 90% or more, with consequent reduction in levels of the corresponding protein.

U.S. Pat. No. 7,612,194 and U.S. Patent Publication Nos. 2007/0050860, 2010/0192265, and 2011/0154545 disclose a library of 9112 expressed sequence tag (EST) sequences isolated from *D. v. virgifera* LeConte pupae. It is suggested in U.S. Pat. No. 7,612,194 and U.S. Patent Publication No. 2007/0050860 to operably link to a promoter a nucleic acid molecule that is complementary to one of several particular partial sequences of *D. v. virgifera* vacuolar-type $H^+$-ATPase (V-ATPase) disclosed therein for the expression of antisense RNA in plant cells. U.S. Patent Publication No. 2010/0192265 suggests operably linking a promoter to a nucleic acid molecule that is complementary to a particular partial sequence of a *D. v. virgifera* gene of unknown and undisclosed function (the partial sequence is stated to be 58% identical to C56C10.3 gene product in *C. elegans*) for the expression of anti-sense RNA in plant cells. U.S. Patent Publication No. 2011/0154545 suggests operably linking a promoter to a nucleic acid molecule that is complementary to two particular partial sequences of *D. v. virgifera* coatomer beta subunit genes for the expression of anti-sense RNA in plant cells. Further, U.S. Pat. No. 7,943,819 discloses a library of 906 expressed sequence tag (EST) sequences isolated from *D. v. virgifera* LeConte larvae, pupae, and dissected midguts, and suggests operably linking a promoter to a nucleic acid molecule that is complementary to a particular partial sequence of a *D. v. virgifera* charged multivesicular body protein 4b gene for the expression of double-stranded RNA in plant cells.

No further suggestion is provided in U.S. Pat. No. 7,612,194, and U.S. Patent Publication Nos. 2007/0050860, 2010/0192265 and 2011/0154545 to use any particular sequence of the more than nine thousand sequences listed therein for RNA interference, other than the several particular partial sequences of V-ATPase and the particular partial sequences of genes of unknown function. Furthermore, none of U.S. Pat. No. 7,612,194, and U.S. Patent Publication Nos. 2007/0050860 and 2010/0192265, and 2011/0154545 provides any guidance as to which other of the over nine thousand sequences provided would be lethal, or even otherwise useful, in species of corn rootworm when used as dsRNA or siRNA. U.S. Pat. No. 7,943,819 provides no suggestion to use any particular sequence of the more than nine hundred sequences listed therein for RNA interference, other than the particular partial sequence of a charged multivesicular body protein 4b gene. Furthermore, U.S. Pat. No. 7,943,819 provides no guidance as to which other of the over nine hundred sequences provided would be lethal, or even otherwise useful, in species of corn rootworm when used as dsRNA or siRNA. U.S. Patent Application Publication No. U.S. 2013/040173 and PCT Application Publication No. WO 2013/169923 describe the use of a sequence derived from a *Diabrotica virgifera* Snf7 gene for RNA interference in maize. (Also disclosed in Bolognesi et al. (2012) PLos ONE 7(10): e47534. doi:10.1371/journal.pone.0047534).

The overwhelming majority of sequences complementary to corn rootworm DNAs (such as the foregoing) are not lethal in species of corn rootworm when used as dsRNA or siRNA. For example, Baum et al. (2007, Nature Biotechnology 25:1322-1326), describe the effects of inhibiting several WCR gene targets by RNAi. These authors reported that the 8 of 26 target genes they tested were not able to provide experimentally significant coleopteran pest mortality at a very high iRNA (e.g., dsRNA) concentration of more than 520 ng/$cm^2$.

SUMMARY OF THE DISCLOSURE

Overview of Several Embodiments

Disclosed herein are nucleic acid molecules (e.g., target genes, DNAs, dsRNAs, siRNAs, miRNAs, shRNAs, and hpRNAs), and methods of use thereof, for the control of coleopteran pests, including, for example, *D. v. virgifera* LeConte (western corn rootworm, "WCR"); *D. barberi* Smith and Lawrence (northern corn rootworm, "NCR"); *D. u. howardi* Barber (southern corn rootworm, "SCR"); *D. v. zeae* Krysan and Smith (Mexican corn rootworm, "MCR"); *D. balteata* LeConte; *D. u. tenella; D. u. undecimpunctata* Mannerheim; *Meligethes aeneus* Fabricius (pollen beetle, "PB"); and hemipteran pests, including, for example, *Euschistus heros* (Fabr.) (Neotropical brown stink bug), *Nezara viridula* (L.) (Southern Green Stink Bug), *Piezodorus guildinii* (Westwood) (red-banded stink bug) *Halyomorpha halys* (brown marmorated stink bug), *Acrosternum hilare* (Green Stink Bug), and *Euschistus servus* (Brown Stink Bug). In particular examples, exemplary nucleic acid molecules are disclosed that may be homologous to at least a portion of one or more native nucleic acid sequences in a coleopteran and/or hemipteran pest.

In these and further examples, the native nucleic acid sequence may be a target gene, the product of which may be, for example and without limitation: involved in a metabolic process; involved in a reproductive process; or involved in larval development. In some examples, post-translational inhibition of the expression of a target gene by a nucleic acid molecule comprising a sequence homologous thereto may be lethal in coleopteran and/or hemipteran pests, or result in reduced growth and/or reproduction. In specific examples, a gene encoding Ras-opposite (the encoded protein referred to herein as "ROP;" and a nucleic acid encoding ROP referred to herein as "rop") may be selected as a target gene for post-transcriptional silencing. In particular examples, a target gene useful for post-transcriptional inhibition is the novel gene rop. An isolated nucleic acid molecule comprising rop; the complement of the nucleotide sequence encoding rop; and fragments of any of the foregoing is, therefore, disclosed herein. Examples of rop include, but are not limited to SEQ ID NOs:1, 115, 120, 122, 124, 126, 131, and 133.

Also disclosed are nucleic acid molecules comprising a nucleotide sequence that encodes a polypeptide that is at least 85% identical to an amino acid sequence within a target gene product (for example, ROP). For example, a nucleic acid molecule may comprise a nucleotide sequence encoding a polypeptide that is at least 85% identical to an amino acid sequence of SEQ ID NOs:2, 116, 121, 123, 125, 127, 132, or 134 (a ROP). In particular examples, a nucleic acid molecule comprises a nucleotide sequence encoding a polypeptide that is at least 85% identical to an amino acid sequence within ROP. Further disclosed are nucleic acid molecules comprising a nucleotide sequence that is the reverse complement of a nucleotide sequence that encodes a polypeptide at least 85% identical to an amino acid sequence within a target gene product.

Also disclosed are cDNA sequences that may be used for the production of iRNA (e.g., dsRNA, siRNA, shRNA, miRNA, and hpRNA) molecules that are complementary to all or part of a coleopteran and/or hemipteran pest target gene, for example: rop. In particular embodiments, dsRNAs, siRNAs, shRNA, miRNAs, and/or hpRNAs may be produced in vitro, or in vivo by a genetically-modified organism, such as a plant or bacterium. In particular examples, cDNA molecules are disclosed that may be used to produce iRNA molecules that are complementary to all or part of rop (e.g. SEQ ID NOs:1, 115, 120, 122, 124, 126, 131, and 133).

Further disclosed are means for inhibiting expression of an essential gene in a coleopteran and/or hemipteran pest, and means for providing coleopteran and/or hemipteran pest resistance to a plant. Examples of a means for inhibiting expression of an essential gene in a coleopteran and/or hemipteran pest include a single- or double-stranded RNA molecule consisting of at least one of SEQ ID NO:3 (*Diabrotica rop* region 1 or rop reg1), SEQ ID NO:4 (*Diabrotica rop* region 2 or rop reg2), SEQ ID NO:114 (*Diabrotica rop* region v3 or rop v3), SEQ ID NO:119 (*Euschistus rop* region 1 or BSB rop reg1), SEQ ID NO:128 (*Meligethes rop* region 1 or EPB rop reg1), or the complement thereof. Functional equivalents of means for inhibiting expression of an essential gene in a coleopteran and/or hemipteran pest include single- or double-stranded RNA molecules that are substantially homologous to all or part of rop (for example, a WCR gene comprising SEQ ID NOs:1 or 115). Functional equivalents of means for inhibiting expression of an essential gene in a coleopteran and/or hemipteran pest include single- or double-stranded RNA molecules that are substantially homologous to all or part of rop (for example, a PB gene comprising SEQ ID NOs:120, 122, 124, 126, 131, or 133). Another example of means for providing coleopteran and/or hemipteran pest resistance to a plant is a DNA molecule comprising a nucleic acid sequence encoding a means for inhibiting expression of an essential gene in a coleopteran and/or hemipteran pest operably linked to a promoter, wherein the DNA molecule is capable of being integrated into the genome of a maize or soybean plant.

Disclosed are methods for controlling a population of a coleopteran and/or hemipteran pest, comprising providing to a coleopteran and/or hemipteran pest an iRNA (e.g., dsRNA, siRNA, shRNA, miRNA, and hpRNA) molecule that functions upon being taken up by the coleopteran and/or hemipteran pest to inhibit a biological function within the coleopteran and/or hemipteran pest. For example, an iRNA molecule comprising all or part of a nucleotide sequence selected from the group consisting of: SEQ ID NO:1, SEQ ID NO:3, SEQ ID NO:4, SEQ ID NO:114, SEQ ID NO:115, SEQ ID NO:119, SEQ ID NO:120, SEQ ID NO:122, SEQ ID NO:124, SEQ ID NO:126, SEQ ID NO:128, SEQ ID NO:131, and SEQ ID NO:133; the complement of SEQ ID NO:1, SEQ ID NO:3, SEQ ID NO:4, and SEQ ID NO:114, SEQ ID NO:115, SEQ ID NO:119, SEQ ID NO:120, SEQ ID NO:122, SEQ ID NO:124, SEQ ID NO:126, SEQ ID NO:128, SEQ ID NO:131, and SEQ ID NO:133; a native coding sequence of a *Diabrotica* organism (e.g., WCR) or hemipteran organism (e.g. BSB) or *Meligethes* organism (e.g., EPB) comprising all or part of any of SEQ ID NO:1, SEQ ID NO:3, SEQ ID NO:4, SEQ ID NO:114, SEQ ID NO:115, SEQ ID NO:119, SEQ ID NO:120, SEQ ID NO:122, SEQ ID NO:124, SEQ ID NO:126, SEQ ID NO:128, SEQ ID NO:131, and SEQ ID NO:133; the complement of a native coding sequence of a *Diabrotica* organism or hemipteran organism or *Meligethes* organism comprising all or part of any of SEQ ID NO:1, SEQ ID NO:3, SEQ ID NO:4, SEQ ID NO:114, SEQ ID NO:115, SEQ ID NO:119, SEQ ID NO:120, SEQ ID NO:122, SEQ ID NO:124, SEQ ID NO:126, SEQ ID NO:128, SEQ ID NO:131, and SEQ ID NO:133; a native non-coding sequence of a *Diabrotica* organism or hemipteran organism or *Meligethes* organism that is transcribed into a native RNA molecule comprising all or part of any of SEQ ID NO:1, SEQ ID NO:3, SEQ ID NO:4, SEQ ID NO:114, SEQ ID NO:115, SEQ ID NO:119, SEQ ID NO:120, SEQ ID NO:122, SEQ ID NO:124, SEQ ID NO:126, SEQ ID NO:128, SEQ ID NO:131, and SEQ ID NO:133; and the complement of a native non-coding sequence of a *Diabrotica* organism or hemipteran organism or *Meligethes* organism that is transcribed into a native RNA molecule comprising all or part of any of SEQ ID NO:1, SEQ ID NO:3, SEQ ID NO:4, SEQ ID NO:114, SEQ ID NO:115, and SEQ ID NO:119, SEQ ID NO:120, SEQ ID NO:122, SEQ ID NO:124, SEQ ID NO:126, SEQ ID NO:128, SEQ ID NO:131, and SEQ ID NO:133.

Also disclosed herein are methods wherein dsRNAs, siRNAs, shRNAs, miRNAs, and/or hpRNAs may be provided to a coleopteran and/or hemipteran pest in a, or in genetically-modified plant cells expressing the dsRNAs, siRNAs, shRNAs, miRNAs, and/or hpRNAs. In these and further examples, the dsRNAs, siRNAs, shRNAs, miRNAs, and/or hpRNAs may be ingested by coleopteran and/or hemipteran pest larvae. Ingestion of dsRNAs, siRNA, shRNAs, miRNAs, and/or hpRNAs of the invention may then result in RNAi in the larvae, which in turn may result in silencing of a gene essential for viability of the coleopteran and/or hemipteran pest and leading ultimately to larval mortality. Thus, methods are disclosed wherein nucleic acid molecules comprising exemplary nucleic acid sequence(s) useful for control of coleopteran and/or hemipteran pests are provided to a coleopteran and/or hemipteran pest. In particular examples, the coleopteran and/or hemipteran pest controlled by use of nucleic acid molecules of the invention may be WCR, NCR, *Meligethes aeneus, Euchistus heros, Piezodorus guildinii, Halyomorpha halys, Nezara viridula Acrosternum hilare*, and *Euschistus servus.*

BRIEF DESCRIPTION OF THE SEQUENCES IN THE LISTING

Figure 1:
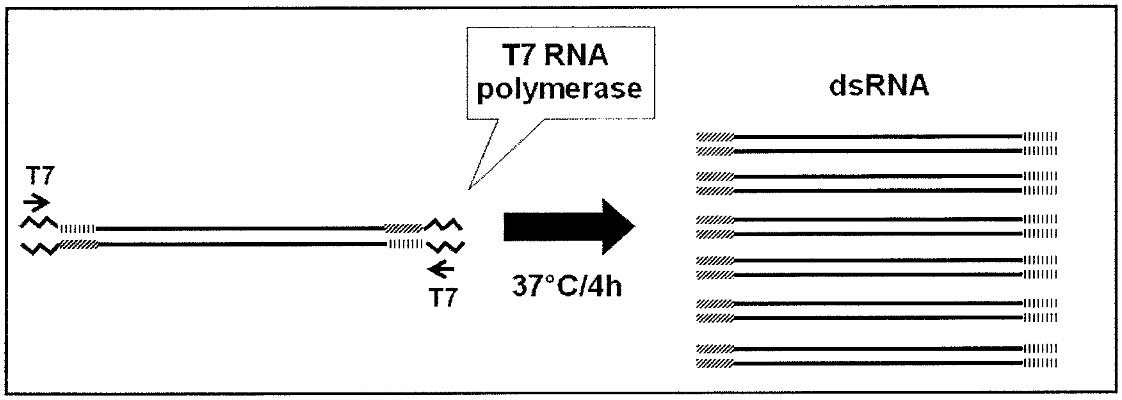
FIG. 1 is a pictorial representation of a strategy for the generation of dsRNA from a single transcription template.

The nucleic acid sequences listed in the accompanying sequence listing are shown using standard letter abbreviations for nucleotide bases and amino acids, as defined in 37 C.F.R. § 1.822. Only one strand of each nucleic acid sequence is shown, but the complementary strand and reverse complementary strand are understood as included by any reference to the displayed strand. In the accompanying sequence listing:

SEQ ID NO:1 shows a DNA sequence of rop from *Diabrotica virgifera.*

SEQ ID NO:2 shows an amino acid sequence of a ROP from *Diabrotica virgifera.*

SEQ ID NO:3 shows a DNA sequence of rop reg1 (region 1) from *Diabrotica virgifera* that was used for in vitro dsRNA synthesis (T7 promoter sequences at 5' and 3' ends not shown).

SEQ ID NO:4 shows a DNA sequence of rop reg2 (region 2) from *Diabrotica virgifera* that was used for in vitro dsRNA synthesis (T7 promoter sequences at 5' and 3' ends not shown).

SEQ ID NO:5 shows a DNA sequence of a T7 phage promoter.

SEQ ID NO:6 shows a DNA sequence of a YFP coding region segment that was used for in vitro dsRNA synthesis (T7 promoter sequences at 5' and 3' ends not shown).

SEQ ID NOS:7-12 show primers used to amplify portions of a rop sequence from *Diabrotica virgifera* comprising rop reg1, rop reg2, and primers used to amplify a YFP coding region segment.

SEQ ID NO:13 presents an rop v1 from *Diabrotica virgifera* hairpin-RNA-forming sequence as found in pDAB114515. Upper case bases are rop sense strand, underlined lower case bases comprise ST-LS1 intron, non-underlined lower case bases are rop antisense strand.

```
TCAGCATGCTGTAAAATGCATGATATATCAGCAGAAGGCATTACATTGGT
TGAAGATATTATGAAGAAAAGGGAACCGCTTGGTACCATGGAAGCTGTGT
```

-continued

```
ACTTGATAACACCTTCAGAAAAGTCAGTTCATGCTCTTATGAATGACTTT
GAACCACCAAGACAGATGTACAGAGGGGCACACGTGTTTTTACAGAAGC
GTGTCCAGACgactagtaccggttgggaaaggtatgtttctgcttctacc
tttgatatatatataataattatcactaattagtagtaatatagtatttc
aagtatttttttcaaaataaaagaatgtagtatatagctattgcttttct
gtagtttataagtgtgtatattttaatttataacttttctaatatatgac
caaaacatggtgatgtgcaggttgatccgcggttagtctggacacgcttc
tgtaaaaaacacgtgtgcccctctgtacatctgtcttggtggttcaaagt
cattcataagagcatgaactgacttttctgaaggtgttatcaagtacaca
gcttccatggtaccaagcggttccctttcttcataatatcttcaaccaa
tgtaatgccttctgctgatatatcatgcattttacagcatgctga
```

SEQ ID NO:14 presents an rop v3 from *Diabrotica virgifera* hairpin-RNA-forming sequence as found in pDAB115770. Upper case bases are rop sense strand, underlined lower case bases comprise ST-LS1 intron, non-underlined lower case bases are rop antisense strand.

```
CAAGTATGCTACGCATCTTCATCTCGCTGAAGACTGCATGAAGGCCTATC
AGGGGTATATAGACAAGTTGTGTAAAGTTGAGCAGGATTTGGCAATGGGA
ACTGATGCCGAAGGCGAGAAAATCAAGGATCACATGCGCAACATCGTCCC
CATCTTGCTAGATCCCAAAATCACCAATGAATACGATAAGAgactagtac
cggttgggaaaggtatgtttctgcttctacctttgatatatatataataa
ttatcactaattagtagtaatatagtatttcaagtatttttttcaaaata
aaagaatgtagtatatagctattgcttttctgtagtttataagtgtgtat
attttaatttataacttttctaatatatgaccaaaacatggtgatgtgca
ggttgatccgcggttatcttatcgtattcattggtgattttgggatctag
caagatggggacgatgttgcgcatgtgatccttgattttctcgccttcgg
catcagttcccattgccaaatcctgctcaactttacacaacttgtctata
taccccctgataggccttcatgcagtcttcagcgagatgaagatgcgtagc
atacttg
```

SEQ ID NO:15 shows a YFP hairpin-RNA-forming sequence v2 as found in pDAB110853. Upper case bases are YFP sense strand, underlined bases comprise ST-LS1 intron, lower case, non-underlined bases are YFP antisense strand.

```
ATGTCATCTGGAGCACTTCTCTTTCATGGGAAGATTCCTTACGTTGTGGA
GATGGAAGGGAATGTTGATGGCCACACCTTTAGCATACGTGGGAAAGGCT
ACGGAGATGCCTCAGTGGGAAAGgactagtaccggttgggaaaggtatgt
ttctgcttctacctttgatatatatataataattatcactaattagtagt
aatatagtatttcaagtatttttttcaaaataaaagaatgtagtatatag
ctattgcttttctgtagtttataagtgtgtatattttaatttataacttt
tctaatatatgaccaaaacatggtgatgtgcaggttgatccgcggttact
ttcccactgaggcatctccgtagcctttcccacgtatgctaaaggtgtgg
```

-continued ccatcaacattcccttccatctccacaacgtaaggaatcttcccatgaaa gagaagtgctccagatgacat SEQ ID NO:16 shows a DNA sequence comprising an ST-LS1 intron.

SEQ ID NO:17 shows a YFP coding sequence as found in pDAB110556.

SEQ ID NO:18 shows a DNA sequence of Annexin region 1.

SEQ ID NO:19 shows a DNA sequence of Annexin region 2.

SEQ ID NO:20 shows a DNA sequence of Beta Spectrin 2 region 1.

SEQ ID NO:21 shows a DNA sequence of Beta Spectrin 2 region 2.

SEQ ID NO:22 shows a DNA sequence of mtRP-L4 region 1.

SEQ ID NO:23 shows a DNA sequence of mtRP-L4 region 2.

SEQ ID NOs:24-47 show primers used to amplify gene regions of Annexin, Beta spectrin 2, mtRP-L4, and YFP for dsRNA synthesis.

SEQ ID NO:48 shows a maize DNA sequence encoding a TIP41-like protein.

SEQ ID NO:49 shows a DNA sequence of oligonucleotide T20NV.

SEQ ID NOs:50-54 show primers and probes used to measure maize transcript levels.

SEQ ID NO:55 shows a DNA sequence of a portion of a SpecR coding region used for binary vector backbone detection.

SEQ ID NO:56 shows a DNA sequence of a portion of an AAD1 coding region used for genomic copy number analysis.

SEQ ID NO:57 shows a DNA sequence of a maize invertase gene.

SEQ ID NOs:58 to 69 show sequences of primers and probes used for gene copy number analyses.

SEQ ID NOs:70 to 111 show *Diabrotica* transcript sequences that encode proteins having sequence homology to SEQ ID NO:2 by means of a Sec1 domain.

SEQ ID NOs:112 and 113 show primers used to amplify portions of a *Diabrotica rop* sequence comprising rop v3 (region v3).

SEQ ID NO:114 shows a DNA sequence of rop region v3 from *Diabrotica virgifera* (rop v3) that was used for in vitro dsRNA synthesis (T7 promoter sequences at 5' and 3' ends not shown).

SEQ ID NO:115 shows a DNA sequence of rop from a Neotropical Brown Stink Bug (*Euschistus heros*).

SEQ ID NO: 116 shows a *Euschistus heros* ROP protein

SEQ ID NOs: 117 and 118 show primers used to amplify a portion of a *Euschistus heros* rop sequence comprising BSB_rop reg1

SEQ ID NO:119 shows a DNA sequence of BSB_rop reg1

SEQ ID NO:120 shows a DNA sequence comprising rop from *Meligethes aeneus.*

SEQ ID NO:121 shows an amino acid sequence of a ROP protein from *Meligethes aeneus.*

SEQ ID NO:122 shows a DNA sequence comprising rop from *Meligethes aeneus.*

SEQ ID NO:123 shows an amino acid sequence of a ROP protein from *Meligethes aeneus.*

SEQ ID NO:124 shows a DNA sequence comprising rop from *Meligethes aeneus.*

SEQ ID NO:125 shows an amino acid sequence of a ROP protein from *Meligethes aeneus.*

SEQ ID NO:126 shows a DNA sequence comprising rop from *Meligethes aeneus.*

SEQ ID NO:127 shows an amino acid sequence of a ROP protein from *Meligethes aeneus.*

SEQ ID NO:128 shows a DNA sequence of rop reg1 (region 1) from *Meligethes aeneus* that was used for in vitro dsRNA synthesis (T7 promoter sequences at 5' and 3' ends not shown).

SEQ ID NOs:129 and 130 show primers used to amplify portions of a *Meligethes rop* sequence comprising rop reg1 (region 1).

SEQ ID NO:131 shows a DNA sequence comprising rop-1 from *Meligethes aeneus.*

SEQ ID NO:132 shows an amino acid sequence of a ROP-1 protein from *Meligethes aeneus.*

SEQ ID NO:133 shows a DNA sequence comprising rop-2 from *Meligethes aeneus.*

SEQ ID NO:134 shows an amino acid sequence of a ROP-2 protein from *Meligethes aeneus.*

DETAILED DESCRIPTION

Disclosed herein are methods and compositions for control of coleopteran and/or hemipteran pest infestations. Methods for identifying one or more gene(s) essential to the lifecycle of a coleopteran and/or hemipteran pest for use as a target gene for RNAi-mediated control of a coleopteran and/or hemipteran pest population are also provided. DNA plasmid vectors encoding one or more dsRNA molecules may be designed to suppress one or more target gene(s) essential for growth, survival, development, and/or reproduction. In some embodiments, methods are provided for post-transcriptional repression of expression or inhibition of a target gene via nucleic acid molecules that are complementary to a coding or non-coding sequence of the target gene in a coleopteran and/or hemipteran pest. In these and further embodiments, a coleopteran and/or hemipteran pest may ingest one or more dsRNA, siRNA, shRNA, miRNA, and/or hpRNA molecules transcribed from all or a portion of a nucleic acid molecule that is complementary to a coding or non-coding sequence of a target gene, thereby providing a plant-protective effect.

Thus, some embodiments involve sequence-specific inhibition of expression of target gene products, using dsRNA, siRNA, shRNA, miRNA and/or hpRNA that is complementary to coding and/or non-coding sequences of the target gene(s) to achieve at least partial control of a coleopteran and/or hemipteran pest. Disclosed is a set of isolated and purified nucleic acid molecules comprising a nucleotide sequence, for example, as set forth in any of SEQ ID NO:1, SEQ ID NO:3, SEQ ID NO:4, SEQ ID NO:114, SEQ ID NO:115, SEQ ID NO:119, SEQ ID NO:120, SEQ ID NO:122, SEQ ID NO:124, SEQ ID NO:126, SEQ ID NO:128, SEQ ID NO:131, and SEQ ID NO:133, and fragments thereof. In some embodiments, a stabilized dsRNA molecule may be expressed from this sequence, fragments thereof, or a gene comprising one of these sequences, for the post-transcriptional silencing or inhibition of a target gene. In certain embodiments, isolated and purified nucleic acid molecules comprise all or part of SEQ ID NO:1. In other embodiments, isolated and purified nucleic acid molecules comprise all or part of SEQ ID NO:3. In yet other embodiments, isolated and purified nucleic acid molecules comprise all or part of SEQ ID NO:4. In still further embodiments, isolated and purified nucleic acid molecules comprise all or part of SEQ ID NO:114. In other embodiments, isolated and purified nucleic acid molecules comprise all or part of SEQ ID NO:115. In yet other embodiments, isolated and purified nucleic acid molecules comprise all or part of SEQ ID NO:119, SEQ ID NO:120, SEQ ID NO:122, SEQ ID NO:124, SEQ ID NO:126, SEQ ID NO:128, SEQ ID NO:131, or SEQ ID NO:133.

Some embodiments involve a recombinant host cell (e.g., a plant cell) having in its genome at least one recombinant DNA sequence encoding at least one iRNA (e.g., dsRNA) molecule(s). In particular embodiments, the dsRNA molecule(s) may be produced when ingested by a coleopteran and/or hemipteran pest to post-transcriptionally silence or inhibit the expression of a target gene in the coleopteran and/or hemipteran pest. The recombinant DNA sequence may comprise, for example, one or more of any of SEQ ID NO:1, SEQ ID NO:3, SEQ ID NO:4, SEQ ID NO:114, SEQ ID NO:115, SEQ ID NO:119, SEQ ID NO:120, SEQ ID NO:122, SEQ ID NO:124, SEQ ID NO:126, SEQ ID NO:128, SEQ ID NO:131, or SEQ ID NO:133; fragments of any of SEQ ID NO:1, SEQ ID NO:3, SEQ ID NO:4, SEQ ID NO:114, SEQ ID NO:115, SEQ ID NO:119, SEQ ID NO:120, SEQ ID NO:122, SEQ ID NO:124, SEQ ID NO:126, SEQ ID NO:128, SEQ ID NO:131, or SEQ ID NO:133 or a partial sequence of a gene comprising one or more of SEQ ID NO:1, SEQ ID NO:3, SEQ ID NO:4, SEQ ID NO:114, SEQ ID NO:115, SEQ ID NO:119 SEQ ID NO:120, SEQ ID NO:122, SEQ ID NO:124, SEQ ID NO:126, SEQ ID NO:128, SEQ ID NO:131, or SEQ ID NO:133; or complements thereof.

Particular embodiments involve a recombinant host cell having in its genome a recombinant nucleic acid sequence encoding at least one iRNA (e.g., dsRNA) molecule(s) comprising all or part of SEQ ID NOs:1, 115, 120, 122, 124, 126, 131, and/or 133. When ingested by a coleopteran and/or hemipteran pest, the iRNA molecule(s) may silence or inhibit the expression of a target gene comprising SEQ ID NO:1, SEQ ID NO:115, SEQ ID NO:120, SEQ ID NO:122, SEQ ID NO:124, SEQ ID NO:126, SEQ ID NO:131, or SEQ ID NO:133, in the coleopteran and/or hemipteran pest, and thereby result in cessation of growth, development, reproduction, and/or feeding in the coleopteran and/or hemipteran pest.

In some embodiments, a recombinant host cell having in its genome at least one recombinant nucleic acid sequence encoding at least one dsRNA molecule may be a transformed plant cell. Some embodiments involve transgenic plants comprising such a transformed plant cell. In addition to such transgenic plants, progeny plants of any transgenic plant generation, transgenic seeds, and transgenic plant products, are all provided, each of which comprises recombinant nucleic acid sequence(s). In particular embodiments, a dsRNA molecule of the invention may be expressed in a transgenic plant cell. Therefore, in these and other embodiments, a dsRNA molecule of the invention may be isolated from a transgenic plant cell. In particular embodiments, the transgenic plant is a plant selected from the group comprising corn (*Zea mays*), soybean (*Glycine max*), and plants of the family Poaceae.

Some embodiments involve a method for modulating the expression of a target gene in a coleopteran and/or hemipteran pest cell. In these and other embodiments, a nucleic acid molecule may be provided, wherein the nucleic acid molecule comprises a nucleotide sequence encoding a dsRNA molecule. In particular embodiments, a nucleotide sequence encoding a dsRNA molecule may be operatively linked to a promoter, and may also be operatively linked to a transcription termination sequence. In particular embodiments, a method for modulating the expression of a target gene in a coleopteran and/or hemipteran pest cell may comprise: (a) transforming a plant cell with a vector comprising a nucleotide sequence encoding a dsRNA molecule; (b) culturing the transformed plant cell under conditions sufficient to allow for development of a plant cell culture comprising a plurality of transformed plant cells; (c) selecting for a transformed plant cell that has integrated the vector into its genome; and (d) determining that the selected transformed plant cell comprises the dsRNA molecule encoded by the nucleotide sequence of the vector. A plant may be regenerated from a plant cell that has the vector integrated in its genome and comprises the dsRNA molecule encoded by the nucleotide sequence of the vector.

Thus, also disclosed is a transgenic plant comprising a vector having a nucleotide sequence encoding a dsRNA molecule integrated in its genome, wherein the transgenic plant comprises the dsRNA molecule encoded by the nucleotide sequence of the vector. In particular embodiments, expression of a dsRNA molecule in the plant is sufficient to modulate the expression of a target gene in a cell of a coleopteran and/or hemipteran pest that contacts the transformed plant or plant cell, for example, by feeding on the transformed plant, a part of the plant (e.g., root) or plant cell. Transgenic plants disclosed herein may display resistance and/or enhanced tolerance to coleopteran and/or hemipteran pest infestations. Particular transgenic plants may display resistance and/or enhanced tolerance to one or more coleopteran and/or hemipteran pests selected from the group consisting of: WCR; NCR; SCR; MCR; D. balteata LeConte; *D. u. tenella; D. u. undecimpunctata* Mannerheim, *Meligethes aeneus* Fabricius, *Euchistus heros, Piezodorus guildinii, Halyomorpha halys*, and *Nezara viridula, Acrosternum hilare*, and *Euschistus servus*.

Also disclosed herein are methods for delivery of control agents, such as an iRNA molecule, to a coleopteran and/or hemipteran pest. Such control agents may cause, directly or indirectly, an impairment in the ability of the coleopteran and/or hemipteran pest to feed, grow or otherwise cause damage in a host. In some embodiments, a method of inhibiting expression of a target gene in a coleopteran and/or hemipteran pest may result in the cessation of growth, development, reproduction, and/or feeding in the coleopteran and/or hemipteran pest. In some embodiments, the method may eventually result in death of the coleopteran and/or hemipteran pest.

In some embodiments, compositions (e.g., a topical composition) are provided that comprise an iRNA (e.g., dsRNA) molecule of the invention for use in plants, animals, and/or the environment of a plant or animal to achieve the elimination or reduction of a coleopteran and/or hemipteran pest infestation. In particular embodiments, the composition may be a nutritional composition or food source to be fed to the coleopteran and/or hemipteran pest. Some embodiments comprise making the nutritional composition or food source available to the coleopteran and/or hemipteran pest. Ingestion of a composition comprising iRNA molecules may result in the uptake of the molecules by one or more cells of the coleopteran and/or hemipteran pest, which may in turn result in the inhibition of expression of at least one target gene in cell(s) of the coleopteran and/or hemipteran pest. Ingestion of or damage to a plant or plant cell by a coleopteran and/or hemipteran pest may be limited or eliminated in or on any host tissue or environment in which the coleopteran and/or hemipteran pest is present by providing one or more compositions comprising an iRNA molecule of the invention in the host of the coleopteran and/or hemipteran pest.

The compositions and methods disclosed herein may be used together in combinations with other methods and compositions for controlling damage by coleopteran and/or hemipteran pests. For example, an iRNA molecule as described herein for protecting plants from coleopteran and/or hemipteran pests may be used in a method comprising the additional use of one or more chemical agents effective against a coleopteran and/or hemipteran pest, biopesticides effective against a coleopteran and/or hemipteran pest, crop rotation, or recombinant genetic techniques that exhibit features different from the features of the RNAi-mediated methods and RNAi compositions of the invention (e.g., recombinant production of proteins in plants that are harmful to a coleopteran and/or hemipteran pest (e.g., Bt toxins)).

II. Abbreviations dsRNA a ribonucleic acid where at least a portion of the ribonucleic acid is double stranded GI growth inhibition NCBI National Center for Biotechnology Information gDNA genomic DNA iRNA inhibitory ribonucleic acid ORF open reading frame RNAi ribonucleic acid interference miRNA micro ribonucleic acid siRNA small interfering ribonucleic acid shRNA small hairpin ribonucleic acid hpRNA hairpin containing ribonucleic acid UTR untranslated region WCR western corn rootworm (*Diabrotica virgifera virgifera* LeConte)

NCR northern corn rootworm (*Diabrotica barberi* Smith and Lawrence)

MCR Mexican corn rootworm (*Diabrotica virgifera zeae* Krysan and Smith)

PCR Polymerase chain reaction

RISC RNA-induced Silencing Complex

SCR southern corn rootworm (*Diabrotica undecimpunctata* howardi Barber)

BSB Neotropical brown stink bug (*Euschistus heros* Fabricius)

PB Pollen beetle (*Meligethes aeneus* Fabricius)

III. Terms

In the description and tables which follow, a number of terms are used. In order to provide a clear and consistent understanding of the specification and claims, including the scope to be given such terms, the following definitions are provided:

Coleopteran pest: As used herein, the term "coleopteran pest" refers to insects of the genus *Diabrotica*, which feed upon corn and other true grasses. In particular examples, a coleopteran pest is selected from the list comprising *D. v. virgifera* LeConte (WCR); *D. barberi* Smith and Lawrence (NCR); *D. u. howardi* (SCR); *D. v. zeae* (MCR); *D. balteata* LeConte; *D. u. tenella; D. u. undecimpunctata* Mannerheim; and *Meligethes aeneus* Fabricius.

Hemipteran pest: As used herein, the term "hemipteran pest" refers to insects of the family Pentatomidae, which feed on wide range of host plants and have piercing and sucking mouth parts. In particular examples, a hemipteran pest is selected from the list comprising, *Euschistus heros* (Fabr.) (Neotropical brown stink bug), *Nezara viridula* (L.) (Southern Green Stink Bug), *Piezodorus guildinii* (Westwood) (red-banded stink bug) *Halyomorpha halys* brown marmorated stink bug, *Acrosternum hilare* (Green Stink Bug), and *Euschistus serous* (Brown Stink Bug).

Contact (with an organism): As used herein, the term "contact with" or "uptake by" an organism (e.g., a coleopteran and/or hemipteran pest), with regard to a nucleic acid molecule, includes internalization of the nucleic acid molecule into the organism, for example and without limitation: ingestion of the molecule by the organism (e.g., by feeding); contacting the organism with a composition comprising the nucleic acid molecule; and soaking of organisms with a solution comprising the nucleic acid molecule.

Contig: As used herein, the term "contig" refers to a nucleic acid sequence that is reconstructed from a set of overlapping nucleic acid segments derived from a single genetic source.

Corn plant: As used herein, the term "corn plant" refers to a plant of the species, *Zea mays* (maize).

Encoding a dsRNA: As used herein, the term "encoding a dsRNA" includes a gene whose RNA transcription product is capable of forming an intramolecular dsRNA structure (e.g., a hairpin) or intermolecular dsRNA structure (e.g., by hybridizing to a target RNA molecule).

Expression: As used herein, "expression" of a sequence (for example, a gene or a transgene) refers to the process by which the coded information of a nucleic acid transcriptional unit (including, e.g., genomic DNA or cDNA) is converted into an operational, non-operational, or structural part of a cell, often including the synthesis of a protein. Gene expression can be influenced by external signals; for example, exposure of a cell, tissue, or organism to an agent that increases or decreases gene expression. Expression of a gene can also be regulated anywhere in the pathway from DNA to RNA to protein. Regulation of gene expression occurs, for example, through controls acting on transcription, translation, RNA transport and processing, degradation of intermediary molecules such as mRNA, or through activation, inactivation, compartmentalization, or degradation of specific protein molecules after they have been made, or by combinations thereof. Gene expression can be measured at the RNA level or the protein level by any method known in the art, including, without limitation, northern (RNA) blot, RT-PCR, western (immuno-) blot, or in vitro, in situ, or in vivo protein activity assay(s).

Genetic material: As used herein, the term "genetic material" includes all genes and nucleic acid molecules, such as DNA and RNA.

Inhibition: As used herein, the term "inhibition," when used to describe an effect on a coding sequence (for example, a gene), refers to a measurable decrease in the cellular level of mRNA transcribed from the coding sequence and/or peptide, polypeptide, or protein product of the coding sequence. In some examples, expression of a coding sequence may be inhibited such that expression is approximately eliminated. "Specific inhibition" refers to the inhibition of a target coding sequence without consequently affecting expression of other coding sequences (e.g., genes) in the cell wherein the specific inhibition is being accomplished.

Isolated: An "isolated" biological component (such as a nucleic acid or protein) has been substantially separated, produced apart from, or purified away from other biological components in the cell of the organism in which the component naturally occurs (i.e., other chromosomal and extrachromosomal DNA and RNA, and proteins). Nucleic acid molecules and proteins that have been "isolated" include nucleic acid molecules and proteins purified by standard purification methods. The term also embraces nucleic acids and proteins prepared by recombinant expression in a host cell, as well as chemically-synthesized nucleic acid molecules, proteins, and peptides.

Nucleic acid molecule: As used herein, the term "nucleic acid molecule" may refer to a polymeric form of nucleotides, which may include both sense and anti-sense strands of RNA, cDNA, genomic DNA, and synthetic forms and mixed polymers of the above. A nucleotide may refer to a ribonucleotide, deoxyribonucleotide, or a modified form of either type of nucleotide. A "nucleic acid molecule," as used herein, is synonymous with "nucleic acid" and "polynucleotide." A nucleic acid molecule is usually at least 10 bases in length, unless otherwise specified. By convention, the nucleotide sequence of a nucleic acid molecule is read from the 5' to the 3' end of the molecule. The "complement" of a nucleotide sequence refers to the sequence, from 5' to 3', of the nucleobases which form base pairs with the nucleobases of the nucleotide sequence (i.e., A-T/U, and G-C). The "reverse complement" of a nucleic acid sequence refers to the sequence, from 3' to 5', of the nucleobases which form base pairs with the nucleobases of the nucleotide sequence.

"Nucleic acid molecules" include single- and double-stranded forms of DNA; single-stranded forms of RNA; and double-stranded forms of RNA (dsRNA). The term "nucleotide sequence" or "nucleic acid sequence" refers to both the sense and antisense strands of a nucleic acid as either individual single strands or in the duplex. The term "ribonucleic acid" (RNA) is inclusive of iRNA (inhibitory RNA), dsRNA (double-stranded RNA), siRNA (small interfering RNA), shRNA (small hairpin RNA), mRNA (messenger RNA), miRNA (microRNA), hpRNA (hairpin RNA), tRNA (transfer RNA, whether charged or discharged with a corresponding acylated amino acid), and cRNA (complementary RNA). The term "deoxyribonucleic acid" (DNA) is inclusive of cDNA, genomic DNA, and DNA-RNA hybrids. The terms "nucleic acid segment" and "nucleotide sequence segment," or more generally "segment" will be understood by those in the art as a functional term that includes both genomic sequences, ribosomal RNA sequences, transfer RNA sequences, messenger RNA sequences, operon sequences, and smaller engineered nucleotide sequences that encode or may be adapted to encode, peptides, polypeptides, or proteins.

Oligonucleotide: An oligonucleotide is a short nucleic acid polymer. Oligonucleotides may be formed by cleavage of longer nucleic acid segments, or by polymerizing individual nucleotide precursors. Automated synthesizers allow the synthesis of oligonucleotides up to several hundred bases in length. Because oligonucleotides may bind to a complementary nucleotide sequence, they may be used as probes for detecting DNA or RNA. Oligonucleotides composed of DNA (oligodeoxyribonucleotides) may be used in PCR, a technique for the amplification of DNA and RNA (reverse transcribed into a cDNA) sequences. In PCR, the oligonucleotide is typically referred to as a "primer," which allows a DNA polymerase to extend the oligonucleotide and replicate the complementary strand.

A nucleic acid molecule may include either or both naturally occurring and modified nucleotides linked together by naturally occurring and/or non-naturally occurring nucleotide linkages. Nucleic acid molecules may be modified chemically or biochemically, or may contain non-natural or derivatized nucleotide bases, as will be readily appreciated by those of skill in the art. Such modifications include, for example, labels, methylation, substitution of one or more of the naturally occurring nucleotides with an analog, internucleotide modifications (e.g., uncharged linkages: for example, methyl phosphonates, phosphotriesters, phosphoramidates, carbamates, etc.; charged linkages: for example, phosphorothioates, phosphorodithioates, etc.; pendent moieties: for example, peptides; intercalators: for example, acridine, psoralen, etc.; chelators; alkylators; and modified linkages: for example, alpha anomeric nucleic acids, etc.). The term "nucleic acid molecule" also includes any topological conformation, including single-stranded, double-stranded, partially duplexed, triplexed, hairpinned, circular, and padlocked conformations.

As used herein, with respect to DNA, the term "coding sequence," "sequence encoding." "structural nucleotide sequence," or "structural nucleic acid molecule" refers to a nucleotide sequence that is ultimately translated into a polypeptide, via transcription and mRNA, when placed under the control of appropriate regulatory sequences. With respect to RNA, the term "coding sequence" refers to a nucleotide sequence that is translated into a peptide, polypeptide, or protein. The boundaries of a coding sequence are determined by a translation start codon at the 5'-terminus and a translation stop codon at the 3'-terminus. Coding sequences include, but are not limited to: genomic DNA; cDNA; EST; and recombinant nucleotide sequences.

Genome: As used herein, the term "genome" refers to chromosomal DNA found within the nucleus of a cell, and also refers to organelle DNA found within subcellular components of the cell. In some embodiments of the invention, a DNA molecule may be introduced into a plant cell such that the DNA molecule is integrated into the genome of the plant cell. In these and further embodiments, the DNA molecule may be either integrated into the nuclear DNA of the plant cell, or integrated into the DNA of the chloroplast or mitochondrion of the plant cell. The term "genome" as it applies to bacteria refers to both the chromosome and plasmids within the bacterial cell. In some embodiments of the invention, a DNA molecule may be introduced into a bacterium such that the DNA molecule is integrated into the genome of the bacterium. In these and further embodiments, the DNA molecule may be either chromosomally-integrated or located as or in a stable plasmid.

Sequence identity: The term "sequence identity" or "identity," as used herein, in the context of two nucleic acid or polypeptide sequences, refers to the residues in the two sequences that are the same when aligned for maximum correspondence over a specified comparison window.

As used herein, the term "percentage of sequence identity" may refer to the value determined by comparing two optimally aligned sequences (e.g., nucleic acid sequences or polypeptide sequences) over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleotide or amino acid residue occurs in both sequences to yield the number of matched positions, dividing the number of matched positions by the total number of positions in the comparison window, and multiplying the result by 100 to yield the percentage of sequence identity. A sequence that is identical at every position in comparison to a reference sequence is said to be 100% identical to the reference sequence, and vice-versa.

Methods for aligning sequences for comparison are well-known in the art. Various programs and alignment algorithms are described in, for example: Smith and Waterman (1981) Adv. Appl. Math. 2:482; Needleman and Wunsch (1970) J. Mol. Biol. 48:443; Pearson and Lipman (1988) Proc. Natl. Acad. Sci. U.S.A. 85:2444; Higgins and Sharp (1988) Gene 73:237-244; Higgins and Sharp (1989) CABIOS 5:151-153; Corpet et al. (1988) Nucleic Acids Res. 16:10881-10890; Huang et al. (1992) Comp. Appl. Biosci. 8:155-165; Pearson et al. (1994) Methods Mol. Biol. 24:307-331; Tatiana et al. (1999) FEMS Microbiol. Lett. 174:247-250. A detailed consideration of sequence alignment methods and homology calculations can be found in, e.g., Altschul et al. (1990) J. Mol. Biol. 215:403-410.

The National Center for Biotechnology Information (NCBI) Basic Local Alignment Search Tool (BLAST™; Altschul et al. (1990)) is available from several sources, including the National Center for Biotechnology Information (Bethesda, Md.), and on the internet, for use in connection with several sequence analysis programs. A description of how to determine sequence identity using this program is available on the internet under the "help" section for BLAST™. For comparisons of nucleic acid sequences, the "Blast 2 sequences" function of the BLAST™ (Blastn) program may be employed using the default BLOSUM62 matrix set to default parameters. Nucleic acid sequences with even greater similarity to the reference sequences will show increasing percentage identity when assessed by this method.

Specifically hybridizable/Specifically complementary: As used herein, the terms "Specifically hybridizable" and "Specifically complementary" are terms that indicate a sufficient degree of complementarity such that stable and specific binding occurs between the nucleic acid molecule and a target nucleic acid molecule. Hybridization between two nucleic acid molecules involves the formation of an anti-parallel alignment between the nucleic acid sequences of the two nucleic acid molecules. The two molecules are then able to form hydrogen bonds with corresponding bases on the opposite strand to form a duplex molecule that, if it is sufficiently stable, is detectable using methods well known in the art. A nucleic acid molecule need not be 100% complementary to its target sequence to be specifically hybridizable. However, the amount of sequence complementarity that must exist for hybridization to be specific is a function of the hybridization conditions used.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ and/or $Mg^{++}$ concentration) of the hybridization will determine the stringency of hybridization. The ionic strength of the wash buffer and the wash temperature also influence stringency. Calculations regarding hybridization conditions required for attaining particular degrees of stringency are known to those of ordinary skill in the art, and are discussed, for example, in Sambrook et al. (ed.) *Molecular Cloning: A Laboratory Manual*, $2^{nd}$ ed., vol. 1-3, Cold Spring Harbor Laboratory Press, Cold Spring Harbor, N.Y., 1989, chapters 9 and 11, and updates; and Hames and Higgins (eds.) *Nucleic Acid Hybridization*, IRL Press, Oxford, 1985. Further detailed instruction and guidance with regard to the hybridization of nucleic acids may be found, for example, in Tijssen, "Overview of principles of hybridization and the strategy of nucleic acid probe assays," in *Laboratory Techniques in Biochemistry and Molecular Biology—Hybridization with Nucleic Acid Probes*, Part I, Chapter 2, Elsevier, N.Y., 1993; and Ausubel et al., Eds., *Current Protocols in Molecular Biology*, Chapter 2, Greene Publishing and Wiley-Interscience, NY, 1995, and updates.

As used herein, "stringent conditions" encompass conditions under which hybridization will occur only if there is more than 80% sequence match between the hybridization molecule and a homologous sequence within the target nucleic acid molecule. "Stringent conditions" include further particular levels of stringency. Thus, as used herein, "moderate stringency" conditions are those under which molecules with more than 80% sequence match (i.e. having less than 20% mismatch) will hybridize; conditions of "high stringency" are those under which sequences with more than 90% match (i.e. having less than 10% mismatch) will hybridize; and conditions of "very high stringency" are those under which sequences with more than 95% match (i.e. having less than 5% mismatch) will hybridize.

The following are representative, non-limiting hybridization conditions.

High Stringency condition (detects sequences that share at least 90% sequence identity): Hybridization in 5×SSC buffer at 65° C. for 16 hours; wash twice in 2×SSC buffer at room temperature for 15 minutes each; and wash twice in 0.5×SSC buffer at 65° C. for 20 minutes each.

Moderate Stringency condition (detects sequences that share at least 80% sequence identity): Hybridization in 5× to 6×SSC buffer at 65-70° C. for 16-20 hours; wash twice in 2×SSC buffer at room temperature for 5-20 minutes each; and wash twice in 1×SSC buffer at 55-70° C. for 30 minutes each.

Non-stringent control condition (sequences that share at least 50% sequence identity will hybridize): Hybridization in 6×SSC buffer at room temperature to 55° C. for 16-20 hours; wash at least twice in 2× to 3×SSC buffer at room temperature to 55° C. for 20-30 minutes each.

As used herein, the term "substantially homologous" or "substantial homology," with regard to a contiguous nucleic acid sequence, refers to contiguous nucleotide sequences that are borne by nucleic acid molecules that hybridize under stringent conditions to a nucleic acid molecule having the reference nucleic acid sequence. For example, nucleic acid molecules having sequences that are substantially homologous to a reference nucleic acid sequence of SEQ ID NO:1 are those nucleic acid molecules that hybridize under stringent conditions (e.g., the Moderate Stringency conditions set forth, supra) to nucleic acid molecules having the reference nucleic acid sequence of SEQ ID NO:1. Substantially homologous sequences may have at least 80% sequence identity. For example, substantially homologous sequences may have from about 80% to 100% sequence identity, such as about 81%; about 82%; about 83%; about 84%; about 85%; about 86%; about 87%; about 88%; about 89%; about 90%; about 91%; about 92%; about 93%; about 94% about 95%; about 96%; about 97%; about 98%; about 98.5%; about 99%; about 99.5%; and about 100%. The property of substantial homology is closely related to specific hybridization. For example, a nucleic acid molecule is specifically hybridizable when there is a sufficient degree of complementarity to avoid non-specific binding of the nucleic acid to non-target sequences under conditions where specific binding is desired, for example, under stringent hybridization conditions.

As used herein, the term "ortholog" refers to a gene in two or more species that has evolved from a common ancestral nucleotide sequence, and may retain the same function in the two or more species.

As used herein, two nucleic acid sequence molecules are said to exhibit "complete complementarity" when every nucleotide of a sequence read in the 5' to 3' direction is complementary to every nucleotide of the other sequence when read in the 3' to 5' direction. A nucleotide sequence that is complementary to a reference nucleotide sequence will exhibit a sequence identical to the reverse complement sequence of the reference nucleotide sequence. These terms and descriptions are well defined in the art and are easily understood by those of ordinary skill in the art.

Operably linked: A first nucleotide sequence is operably linked with a second nucleic acid sequence when the first nucleic acid sequence is in a functional relationship with the second nucleic acid sequence. When recombinantly produced, operably linked nucleic acid sequences are generally contiguous, and, where necessary, two protein-coding regions may be joined in the same reading frame (e.g., in a translationally fused ORF). However, nucleic acids need not be contiguous to be operably linked.

The term, "operably linked," when used in reference to a regulatory sequence and a coding sequence, means that the regulatory sequence affects the expression of the linked coding sequence. "Regulatory sequences," or "control elements," refer to nucleotide sequences that influence the timing and level/amount of transcription, RNA processing or stability, or translation of the associated coding sequence. Regulatory sequences may include promoters; translation leader sequences; introns; enhancers; stem-loop structures; repressor binding sequences; termination sequences; polyadenylation recognition sequences; etc. Particular regulatory sequences may be located upstream and/or downstream of a coding sequence operably linked thereto. Also, particular regulatory sequences operably linked to a coding sequence may be located on the associated complementary strand of a double-stranded nucleic acid molecule.

Promoter: As used herein, the term "promoter" refers to a region of DNA that may be upstream from the start of transcription, and that may be involved in recognition and binding of RNA polymerase and other proteins to initiate transcription. A promoter may be operably linked to a coding sequence for expression in a cell, or a promoter may be operably linked to a nucleotide sequence encoding a signal sequence which may be operably linked to a coding sequence for expression in a cell. A "plant promoter" may be a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters which initiate transcription only in certain tissues are referred to as "tissue-specific." A "cell type-specific" promoter primarily drives expression in certain cell types in one or more organs, for example, vascular cells in roots or leaves. An "inducible" promoter may be a promoter which may be under environmental control. Examples of environmental conditions that may initiate transcription by inducible promoters include anaerobic conditions and the presence of light. Tissue-specific, tissue-preferred, cell type specific, and inducible promoters constitute the class of "non-constitutive" promoters. A "constitutive" promoter is a promoter which may be active under most environmental conditions or in most tissue or cell types.

Any inducible promoter can be used in some embodiments of the invention. See Ward et al. (1993) Plant Mol. Biol. 22:361-366. With an inducible promoter, the rate of transcription increases in response to an inducing agent. Exemplary inducible promoters include, but are not limited to: Promoters from the ACEI system that respond to copper; In2 gene from maize that responds to benzenesulfonamide herbicide safeners; Tet repressor from Tn10; and the inducible promoter from a steroid hormone gene, the transcriptional activity of which may be induced by a glucocorticosteroid hormone (Schena et al. (1991) Proc. Natl. Acad. Sci. USA 88:10421-10425).

Exemplary constitutive promoters include, but are not limited to: Promoters from plant viruses, such as the 35S promoter from Cauliflower Mosaic Virus (CaMV); promoters from rice actin genes; ubiquitin promoters; pEMU; MAS; maize H3 histone promoter; and the ALS promoter, XbaI/NcoI fragment 5' to the *Brassica napus* ALS3 structural gene (or a nucleotide sequence similar to said XbaI/NcoI fragment) (U.S. Pat. No. 5,659,026).

Additionally, any tissue-specific or tissue-preferred promoter may be utilized in some embodiments of the invention. Plants transformed with a nucleic acid molecule comprising a coding sequence operably linked to a tissue-specific promoter may produce the product of the coding sequence exclusively, or preferentially, in a specific tissue. Exemplary tissue-specific or tissue-preferred promoters include, but are not limited to: A seed-preferred promoter, such as that from the phaseolin gene; a leaf-specific and light-induced promoter such as that from cab or rubisco; an anther-specific promoter such as that from LAT52; a pollen-specific promoter such as that from Zm13; and a microspore-preferred promoter such as that from apg.

Soybean plant: As used herein, the term "soybean plant" refers to a plant of the species *Glycine* sp., including *Glycine max*.

Transformation: As used herein, the term "transformation" or "transduction" refers to the transfer of one or more nucleic acid molecule(s) into a cell. A cell is "transformed" by a nucleic acid molecule transduced into the cell when the nucleic acid molecule becomes stably replicated by the cell, either by incorporation of the nucleic acid molecule into the cellular genome, or by episomal replication. As used herein, the term "transformation" encompasses all techniques by which a nucleic acid molecule can be introduced into such a cell. Examples include, but are not limited to: transfection with viral vectors; transformation with plasmid vectors; electroporation (Fromm et al. (1986) Nature 319:791-793); lipofection (Feigner et al. (1987) Proc. Natl. Acad. Sci. USA 84:7413-7417); microinjection (Mueller et al. (1978) Cell 15:579-585); *Agrobacterium*-mediated transfer (Fraley et al. (1983) Proc. Natl. Acad. Sci. USA 80:4803-4807); direct DNA uptake; and microprojectile bombardment (Klein et al. (1987) Nature 327:70).

Transgene: An exogenous nucleic acid sequence. In some examples, a transgene may be a sequence that encodes one or both strand(s) of a dsRNA molecule that comprises a nucleotide sequence that is complementary to a nucleic acid molecule found in a coleopteran and/or hemipteran pest. In further examples, a transgene may be an antisense nucleic acid sequence, wherein expression of the antisense nucleic acid sequence inhibits expression of a target nucleic acid sequence. In still further examples, a transgene may be a gene sequence (e.g., a herbicide-resistance gene), a gene encoding an industrially or pharmaceutically useful compound, or a gene encoding a desirable agricultural trait. In these and other examples, a transgene may contain regulatory sequences (e.g., a promoter) operably linked to a coding sequence of the transgene.

Vector: A nucleic acid molecule as introduced into a cell, for example, to produce a transformed cell. A vector may include nucleic acid sequences that permit it to replicate in the host cell, such as an origin of replication. Examples of vectors include, but are not limited to: a plasmid; cosmid; bacteriophage; or virus that carries exogenous DNA into a cell. A vector may also be an RNA molecule. A vector may also include one or more genes, antisense sequences, and/or selectable marker genes and other genetic elements known in the art. A vector may transduce, transform, or infect a cell, thereby causing the cell to express the nucleic acid molecules and/or proteins encoded by the vector. A vector optionally includes materials to aid in achieving entry of the nucleic acid molecule into the cell (e.g., a liposome, protein coating, etc.).

Yield: A stabilized yield of about 100% or greater relative to the yield of check varieties in the same growing location growing at the same time and under the same conditions. In particular embodiments, "improved yield" or "improving yield" means a cultivar having a stabilized yield of 105% to 115% or greater relative to the yield of check varieties in the same growing location containing significant densities of coleopteran and/or hemipteran pests that are injurious to that crop growing at the same time and under the same conditions.

Unless specifically indicated or implied, the terms "a," "an," and "the" signify "at least one," as used herein.

Unless otherwise specifically explained, all technical and scientific terms used herein have the same meaning as commonly understood by those of ordinary skill in the art to which this disclosure belongs. Definitions of common terms in molecular biology can be found in, for example, Lewin's *Genes X*, Jones & Bartlett Publishers, 2009 (ISBN 10 0763766321); Krebs et al. (eds.), *The Encyclopedia of Molecular Biology*, Blackwell Science Ltd., 1994 (ISBN 0-632-02182-9); and Meyers R. A. (ed.), *Molecular Biology and Biotechnology: A Comprehensive Desk Reference*, VCH Publishers, Inc., 1995 (ISBN 1-56081-569-8). All percentages are by weight and all solvent mixture proportions are by volume unless otherwise noted. All temperatures are in degrees Celsius.

IV. Nucleic Acid Molecules Comprising a Coleopteran and/or Hemipteran Pest Sequence

A. Overview

Described herein are nucleic acid molecules useful for the control of coleopteran and/or hemipteran pests. Described nucleic acid molecules include target sequences (e.g., native genes, and non-coding sequences), dsRNAs, siRNAs, shRNAs, hpRNAs, and miRNAs. For example, dsRNA, siRNA, shRNA, miRNA and/or hpRNA molecules are described in some embodiments that may be specifically complementary to all or part of one or more native nucleic acid sequences in a coleopteran and/or hemipteran pest. In these and further embodiments, the native nucleic acid sequence(s) may be one or more target gene(s), the product of which may be, for example and without limitation: involved in a metabolic process; involved in a reproductive process; or involved in larval development. Nucleic acid molecules described herein, when introduced into a cell comprising at least one native nucleic acid sequence(s) to which the nucleic acid molecules are specifically complementary, may initiate RNAi in the cell, and consequently reduce or eliminate expression of the native nucleic acid sequence(s). In some examples, reduction or elimination of the expression of a target gene by a nucleic acid molecule comprising a sequence specifically complementary thereto may be lethal in coleopteran and/or hemipteran pests, or result in reduced growth and/or reproduction.

In some embodiments, at least one target gene in a coleopteran and/or hemipteran pest may be selected, wherein the target gene comprises a nucleotide sequence comprising rop (SEQ ID NO:1, SEQ ID NO:115, SEQ ID NO:120, SEQ ID NO:122, SEQ ID NO:124, SEQ ID NO:126, SEQ ID NO:131, or SEQ ID NO:133). In particular examples, a target gene in a coleopteran and/or hemipteran pest is selected, wherein the target gene comprises a novel nucleotide sequence comprising rop (SEQ ID NO:1, SEQ ID NO:115, SEQ ID NO:120, SEQ ID NO:122, SEQ ID NO:124, SEQ ID NO:126, SEQ ID NO:131, or SEQ ID NO:133).

In some embodiments, a target gene may be a nucleic acid molecule comprising a nucleotide sequence that encodes a polypeptide comprising a contiguous amino acid sequence that is at least 85% identical (e.g., about 90%, about 95%, about 96%, about 97%, about 98%, about 99%, about 100%, or 100% identical) to the amino acid sequence of a protein product of rop (SEQ ID NO:1, SEQ ID NO:115, SEQ ID NO:120, SEQ ID NO:122, SEQ ID NO:124, SEQ ID NO:126, SEQ ID NO:131, or SEQ ID NO:133). A target gene may be any nucleic acid sequence in a coleopteran and/or hemipteran pest, the post-transcriptional inhibition of which has a deleterious effect on the coleopteran and/or hemipteran pest, or provides a protective benefit against the coleopteran and/or hemipteran pest to a plant. In particular examples, a target gene is a nucleic acid molecule comprising a nucleotide sequence that encodes a polypeptide comprising a contiguous amino acid sequence that is at least 85% identical, about 90% identical, about 95% identical, about 96% identical, about 97% identical, about 98% identical, about 99% identical, about 100% identical, or 100% identical to the amino acid sequence of a protein product of novel nucleotide sequence SEQ ID NO:1, SEQ ID NO:115, SEQ ID NO:120, SEQ ID NO:122, SEQ ID NO:124, SEQ ID NO:126, SEQ ID NO:131, or SEQ ID NO:133.

Provided according to the invention are nucleotide sequences, the expression of which results in an RNA molecule comprising a nucleotide sequence that is specifically complementary to all or part of a native RNA molecule that is encoded by a coding sequence in a coleopteran and/or hemipteran pest. In some embodiments, after ingestion of the expressed RNA molecule by a coleopteran and/or hemipteran pest, down-regulation of the coding sequence in cells of the coleopteran and/or hemipteran pest may be obtained. In particular embodiments, down-regulation of the coding sequence in cells of the coleopteran and/or hemipteran pest may result in a deleterious effect on the growth, viability, proliferation, and/or reproduction of the coleopteran and/or hemipteran pest.

In some embodiments, target sequences include transcribed non-coding RNA sequences, such as 5'UTRs; 3'UTRs; spliced leader sequences; intron sequences; outron sequences (e.g., 5'UTR RNA subsequently modified in trans splicing); donatron sequences (e.g., non-coding RNA required to provide donor sequences for trans splicing); and other non-coding transcribed RNA of target coleopteran and/or hemipteran pest genes. Such sequences may be derived from both mono-cistronic and poly-cistronic genes.

Thus, also described herein in connection with some embodiments are iRNA molecules (e.g., dsRNAs, siRNAs, shRNAs, miRNAs and hpRNAs) that comprise at least one nucleotide sequence that is specifically complementary to all or part of a target sequence in a coleopteran and/or hemipteran pest. In some embodiments an iRNA molecule may comprise nucleotide sequence(s) that are complementary to all or part of a plurality of target sequences; for example, 2, 3, 4, 5, 6, 7, 8, 9, 10, or more target sequences. In particular embodiments, an iRNA molecule may be produced in vitro, or in vivo by a genetically-modified organism, such as a plant or bacterium. Also disclosed are cDNA sequences that may be used for the production of dsRNA molecules, siRNA molecules, shRNA molecules, miRNA molecules, and/or hpRNA molecules that are specifically complementary to all or part of a target sequence in a coleopteran and/or hemipteran pest. Further described are recombinant DNA constructs for use in achieving stable transformation of particular host targets. Transformed host targets may express effective levels of dsRNA, siRNA, shRNA, miRNA and/or hpRNA molecules from the recombinant DNA constructs. Therefore, also described is a plant transformation vector comprising at least one nucleotide sequence operably linked to a heterologous promoter functional in a plant cell, wherein expression of the nucleotide sequence(s) results in an RNA molecule comprising a nucleotide sequence that is specifically complementary to all or part of a target sequence in a coleopteran and/or hemipteran pest.

In some embodiments, nucleic acid molecules useful for the control of coleopteran and/or hemipteran pests may include: all or part of a native nucleic acid sequence isolated from a *Diabrotica, Meligethes*, or hemipteran organism comprising rop (e.g., SEQ ID NO:1, SEQ ID NO:115, SEQ ID NO:120, SEQ ID NO:122, SEQ ID NO:124, SEQ ID NO:126, SEQ ID NO:131, or SEQ ID NO:133); nucleotide sequences that when expressed result in an RNA molecule comprising a nucleotide sequence that is specifically complementary to all or part of a native RNA molecule that is encoded by rop (e.g., SEQ ID NO:1, SEQ ID NO:115, SEQ ID NO:120, SEQ ID NO:122, SEQ ID NO:124, SEQ ID NO:126, SEQ ID NO:131, or SEQ ID NO:133); iRNA molecules (e.g., dsRNAs, siRNAs, shRNAs, miRNAs and hpRNAs) that comprise at least one nucleotide sequence that is specifically complementary to all or part of a rop coding sequence (e.g., SEQ ID NO:1, SEQ ID NO:115, SEQ ID NO:120, SEQ ID NO:122, SEQ ID NO:124, SEQ ID NO:126, SEQ ID NO:131, or SEQ ID NO:133); cDNA sequences that may be used for the production of dsRNA molecules, siRNA molecules, miRNA and/or hpRNA molecules that are specifically complementary to all or part of pre-mRNA or mRNA by rop (e.g., SEQ ID NO:1, SEQ ID NO:115, SEQ ID NO:120, SEQ ID NO:122, SEQ ID NO:124, SEQ ID NO:126, SEQ ID NO:131, or SEQ ID NO:133); and recombinant DNA constructs for use in achieving stable transformation of particular host targets, wherein a transformed host target comprises one or more of the foregoing nucleic acid molecules.

B. Nucleic Acid Molecules

The present invention provides, inter alia, iRNA (e.g., dsRNA, siRNA, shRNA, miRNA and hpRNA) molecules that inhibit target gene expression in a cell, tissue, or organ of a coleopteran and/or hemipteran pest; and DNA molecules capable of being expressed as an iRNA molecule in a cell or microorganism to inhibit target gene expression in a cell, tissue, or organ of a coleopteran and/or hemipteran pest.

Some embodiments of the invention provide an isolated nucleic acid molecule comprising at least one (e.g., one, two, three, or more) nucleotide sequence(s) selected from the group consisting of: SEQ ID NO:1, SEQ ID NO:115, SEQ ID NO:120, SEQ ID NO:122, SEQ ID NO:124, SEQ ID NO:126, SEQ ID NO:131, or SEQ ID NO:133; the complement of SEQ ID NO:1, SEQ ID NO:115, SEQ ID NO:120, SEQ ID NO:122, SEQ ID NO:124, SEQ ID NO:126, SEQ ID NO:131, or SEQ ID NO:133; a fragment of at least 15 contiguous nucleotides of SEQ ID NO:1, SEQ ID NO:115, SEQ ID NO:120, SEQ ID NO:122, SEQ ID NO:124, SEQ ID NO:126, SEQ ID NO:131, or SEQ ID NO:133; the complement of a fragment of at least 15 contiguous nucleotides of SEQ ID NO:1, SEQ ID NO:115, SEQ ID NO:120, SEQ ID NO:122, SEQ ID NO:124, SEQ ID NO:126, SEQ ID NO:131, or SEQ ID NO:133; a native coding sequence of a *Diabrotica* organism (e.g., WCR) comprising SEQ ID NO:1; a native coding sequence of a hemipteran organism comprising SEQ ID NO:115; a native coding sequence of a *Meligethes* organism comprising SEQ ID NO:120, SEQ ID NO:122, SEQ ID NO:124, SEQ ID NO:126, SEQ ID NO:131, or SEQ ID NO:133; the complement of a native coding sequence of a *Diabrotica* organism comprising SEQ ID NO:1; the complement of a native coding sequence of a hemipteran organism comprising SEQ ID NO:115; the complement of a native coding sequence of a *Meligethes* organism comprising SEQ ID NO:120, SEQ ID NO:122, SEQ ID NO:124, SEQ ID NO:126, SEQ ID NO:131, or SEQ ID NO:133; a native non-coding sequence of a *Diabrotica* organism that is transcribed into a native RNA molecule comprising SEQ ID NO:1; a native non-coding sequence of a hemipteran organism that is transcribed into a native RNA molecule comprising SEQ ID NO:115; a native non-coding sequence of a *Meligethes* organism that is transcribed into a native RNA molecule comprising SEQ ID NO:120, SEQ ID NO:122, SEQ ID NO:124, SEQ ID NO:126, SEQ ID NO:131, or SEQ ID NO:133; the complement of a native non-coding sequence of a *Diabrotica* organism that is transcribed into a native RNA molecule comprising SEQ ID NO:1; the complement of a native non-coding sequence of a hemipteran organism that is transcribed into a native RNA molecule comprising SEQ ID NO:115; the complement of a native non-coding sequence of a *Meligethes* organism that is transcribed into a native RNA molecule comprising SEQ ID NO:120, SEQ ID NO:122, SEQ ID NO:124, SEQ ID NO:126, SEQ ID NO:131, or SEQ ID NO:133; a fragment of at least 15 contiguous nucleotides of a native coding sequence of a *Diabrotica* organism comprising SEQ ID NO:1; a fragment of at least 15 contiguous nucleotides of a native coding sequence of a hemipteran organism comprising SEQ ID NO:115; a fragment of at least 15 contiguous nucleotides of a native coding sequence of a *Meligethes* organism comprising SEQ ID NO:120, SEQ ID NO:122, SEQ ID NO:124, SEQ ID NO:126, SEQ ID NO:131, or SEQ ID NO:133; the complement of a fragment of at least 15 contiguous nucleotides of a native coding sequence of a *Diabrotica* organism comprising SEQ ID NO:1; the complement of a fragment of at least 15 contiguous nucleotides of a native coding sequence of a hemipteran organism comprising SEQ ID NO:115; the complement of a fragment of at least 15 contiguous nucleotides of a native coding sequence of a *Meligethes* organism comprising SEQ ID NO:120, SEQ ID NO:122, SEQ ID NO:124, SEQ ID NO:126, SEQ ID NO:131, or SEQ ID NO:133; a fragment of at least 15 contiguous nucleotides of a native non-coding sequence of a *Diabrotica* organism that is transcribed into a native RNA molecule comprising SEQ ID NO:1; a fragment of at least 15 contiguous nucleotides of a native non-coding sequence of a hemipteran organism that is transcribed into a native RNA molecule comprising SEQ ID NO:115; a fragment of at least 15 contiguous nucleotides of a native non-coding sequence of a *Meligethes* organism that is transcribed into a native RNA molecule comprising SEQ ID NO:120, SEQ ID NO:122, SEQ ID NO:124, SEQ ID NO:126, SEQ ID NO:131, or SEQ ID NO:133; the complement of a fragment of at least 15 contiguous nucleotides of a native non-coding sequence of a *Diabrotica* organism that is transcribed into a native RNA molecule comprising SEQ ID NO:1; the complement of a fragment of at least 15 contiguous nucleotides of a native non-coding sequence of a hemipteran organism that is transcribed into a native RNA molecule comprising SEQ ID NO:115, and the complement of a fragment of at least 15 contiguous nucleotides of a native non-coding sequence of a *Meligethes* organism that is transcribed into a native RNA molecule comprising SEQ ID NO:120, SEQ ID NO:122, SEQ ID NO:124, SEQ ID NO:126, SEQ ID NO:131, or SEQ ID NO:133. In particular embodiments, contact with or uptake by a coleopteran and/or hemipteran pest of the isolated nucleic acid sequence inhibits the growth, development, reproduction and/or feeding of the coleopteran and/or hemipteran pest.

In some embodiments, a nucleic acid molecule of the invention may comprise at least one (e.g., one, two, three, or more) DNA sequence(s) capable of being expressed as an iRNA molecule in a cell or microorganism to inhibit target gene expression in a cell, tissue, or organ of a coleopteran and/or hemipteran pest. Such DNA sequence(s) may be operably linked to a promoter sequence that functions in a cell comprising the DNA molecule to initiate or enhance the transcription of the encoded RNA capable of forming a dsRNA molecule(s). In one embodiment, the at least one (e.g., one, two, three, or more) DNA sequence(s) may be derived from a nucleotide sequence comprising SEQ ID NO:1, SEQ ID NO:115, SEQ ID NO:120, SEQ ID NO:122, SEQ ID NO:124, SEQ ID NO:126, SEQ ID NO:131, or SEQ ID NO:133. Derivatives of SEQ ID NO:1, SEQ ID NO:115, SEQ ID NO:120, SEQ ID NO:122, SEQ ID NO:124, SEQ ID NO:126, SEQ ID NO:131, or SEQ ID NO:133 include fragments of SEQ ID NO:1, SEQ ID NO:115, SEQ ID NO:120, SEQ ID NO:122, SEQ ID NO:124, SEQ ID NO:126, SEQ ID NO:131, or SEQ ID NO:133. In some embodiments, such a fragment may comprise, for example, at least about 15 contiguous nucleotides of SEQ ID NO:1, SEQ ID NO:115, SEQ ID NO:120, SEQ ID NO:122, SEQ ID NO:124, SEQ ID NO:126, SEQ ID NO:131, or SEQ ID NO:133, or a complement thereof. Thus, such a fragment may comprise, for example, 15, 16, 17, 18, 19, 20, 21, 22, 23, 24, 25, 26, 27, 28, 29, 30, 40, 50, 60, 70, 80, 90, 100, 110, 120, 130, 140, 150, 160, 170, 180, 190, 200 or more contiguous nucleotides of SEQ ID NO:1, SEQ ID NO:115, SEQ ID NO:120, SEQ ID NO:122, SEQ ID NO:124, SEQ ID NO:126, SEQ ID NO:131, or SEQ ID NO:133, or a complement thereof. In these and further embodiments, such a fragment may comprise, for example, more than about 15 contiguous nucleotides of SEQ ID NO:1, SEQ ID NO:115, SEQ ID NO:120, SEQ ID NO:122, SEQ ID NO:124, SEQ ID NO:126, SEQ ID NO:131, or SEQ ID NO:133, or a complement thereof. Thus, a fragment of SEQ ID NO:1, SEQ ID NO:115, SEQ ID NO:120, SEQ ID NO:122, SEQ ID NO:124, SEQ ID NO:126, SEQ ID NO:131, or SEQ ID NO:133 may comprise, for example, 15, 16, 17, 18, 19, 20, 21, about 25, (e.g., 22, 23, 24, 25, 26, 27, 28, and 29), about 30, about 40, (e.g., 35, 36, 37, 38, 39, 40, 41, 42, 43, 44, and 45), about 50, about 60, about 70, about 80, about 90, about 100, about 110, about 120, about 130, about 140, about 150, about 160, about 170, about 180, about 190, about 200 or more contiguous nucleotides of SEQ ID NO:1, SEQ ID NO:115, SEQ ID NO:120, SEQ ID NO:122, SEQ ID NO:124, SEQ ID NO:126, SEQ ID NO:131, or SEQ ID NO:133, or a complement thereof.

Some embodiments comprise introducing partial- or fully-stabilized dsRNA molecules into a coleopteran and/or hemipteran pest to inhibit expression of a target gene in a cell, tissue, or organ of the coleopteran and/or hemipteran pest. When expressed as an iRNA molecule (e.g., dsRNA, siRNA, shRNA, miRNA, and hpRNA) and taken up by a coleopteran and/or hemipteran pest, nucleic acid sequences comprising one or more fragments of SEQ ID NO:1, SEQ ID NO:115, SEQ ID NO:120, SEQ ID NO:122, SEQ ID NO:124, SEQ ID NO:126, SEQ ID NO:131, or SEQ ID NO:133 may cause one or more of death, growth inhibition, change in sex ratio, reduction in brood size, cessation of infection, and/or cessation of feeding by a coleopteran and/or hemipteran pest. For example, in some embodiments, a dsRNA molecule comprising a nucleotide sequence including about 15 to about 300 or about 19 to about 25 nucleotides that are substantially homologous to a coleopteran and/or hemipteran pest target gene sequence and comprising one or more fragments of a nucleotide sequence comprising SEQ ID NO:1, SEQ ID NO:115, SEQ ID NO:120, SEQ ID NO:122, SEQ ID NO:124, SEQ ID NO:126, SEQ ID NO:131, or SEQ ID NO:133 is provided. Expression of such a dsRNA molecule may, for example, lead to mortality and/or growth inhibition in a coleopteran and/or hemipteran pest that takes up the dsRNA molecule.

In certain embodiments, dsRNA molecules provided by the invention comprise nucleotide sequences complementary to a target gene comprising SEQ ID NO:1, SEQ ID NO:115, SEQ ID NO:120, SEQ ID NO:122, SEQ ID NO:124, SEQ ID NO:126, SEQ ID NO:131, or SEQ ID NO:133 and/or nucleotide sequences complementary to a fragment of SEQ ID NO:1, SEQ ID NO:115, SEQ ID NO:120, SEQ ID NO:122, SEQ ID NO:124, SEQ ID NO:126, SEQ ID NO:131, or SEQ ID NO:133, the inhibition of which target gene in a coleopteran and/or hemipteran pest results in the reduction or removal of a protein or nucleotide sequence agent that is essential for the coleopteran and/or hemipteran pest's growth, development, or other biological function. A selected nucleotide sequence may exhibit from about 80% to about 100% sequence identity to SEQ ID NO:1, SEQ ID NO:115, SEQ ID NO:120, SEQ ID NO:122, SEQ ID NO:124, SEQ ID NO:126, SEQ ID NO:131, or SEQ ID NO:133, a contiguous fragment of the nucleotide sequence set forth in SEQ ID NO:1, SEQ ID NO:115, SEQ ID NO:120, SEQ ID NO:122, SEQ ID NO:124, SEQ ID NO:126, SEQ ID NO:131, or SEQ ID NO:133, or the complement of either of the foregoing. For example, a selected nucleotide sequence may exhibit about 81%; about 82%; about 83%; about 84%; about 85%; about 86%; about 87%; about 88%; about 89%; about 90%; about 91%; about 92%; about 93%; about 94% about 95%; about 96%; about 97%; about 98%; about 98.5%; about 99%; about 99.5%; or about 100% sequence identity to SEQ ID NO:1, SEQ ID NO:115, SEQ ID NO:120, SEQ ID NO:122, SEQ ID NO:124, SEQ ID NO:126, SEQ ID NO:131, or SEQ ID NO:133, a contiguous fragment of the nucleotide sequence set forth in SEQ ID NO:1, SEQ ID NO:115, SEQ ID NO:120, SEQ ID NO:122, SEQ ID NO:124, SEQ ID NO:126, SEQ ID NO:131, or SEQ ID NO:133, or the complement of either of the foregoing.

In some embodiments, a DNA molecule capable of being expressed as an iRNA molecule in a cell or microorganism to inhibit target gene expression may comprise a single nucleotide sequence that is specifically complementary to all or part of a native nucleic acid sequence found in one or more target coleopteran and/or hemipteran pest species, or the DNA molecule can be constructed as a chimera from a plurality of such specifically complementary sequences.

In some embodiments, a nucleic acid molecule may comprise a first and a second nucleotide sequence separated by a "spacer sequence." A spacer sequence may be a region comprising any sequence of nucleotides that facilitates secondary structure formation between the first and second nucleotide sequences, where this is desired. In one embodiment, the spacer sequence is part of a sense or antisense coding sequence for mRNA. The spacer sequence may alternatively comprise any combination of nucleotides or homologues thereof that are capable of being linked covalently to a nucleic acid molecule.

For example, in some embodiments, the DNA molecule may comprise a nucleotide sequence coding for one or more different RNA molecules, wherein each of the different RNA molecules comprises a first nucleotide sequence and a second nucleotide sequence, wherein the first and second nucleotide sequences are complementary to each other. The first and second nucleotide sequences may be connected within an RNA molecule by a spacer sequence. The spacer sequence may constitute part of the first nucleotide sequence or the second nucleotide sequence. Expression of an RNA molecule comprising the first and second nucleotide sequences may lead to the formation of a dsRNA molecule of the present invention, by specific base-pairing of the first and second nucleotide sequences. The first nucleotide sequence or the second nucleotide sequence may be substantially identical to a nucleic acid sequence native to a coleopteran and/or hemipteran pest (e.g., a target gene, or transcribed non-coding sequence), a derivative thereof, or a complementary sequence thereto.

dsRNA nucleic acid molecules comprise double strands of polymerized ribonucleotide sequences, and may include modifications to either the phosphate-sugar backbone or the nucleoside. Modifications in RNA structure may be tailored to allow specific inhibition. In one embodiment, dsRNA molecules may be modified through a ubiquitous enzymatic process so that siRNA molecules may be generated. This enzymatic process may utilize an RNAse III enzyme, such as DICER in eukaryotes, either in vitro or in vivo. See Elbashir et al. (2001) Nature 411:494-498; and Hamilton and Baulcombe (1999) Science 286(5441):950-952. DICER or functionally-equivalent RNAse III enzymes cleave larger dsRNA strands and/or hpRNA molecules into smaller oligonucleotides (e.g., siRNAs), each of which is typically about 19-25 nucleotides in length. The siRNA molecules produced by these enzymes have 2 to 3 nucleotide 3' overhangs, and 5' phosphate and 3' hydroxyl termini. The siRNA molecules generated by RNAse III enzymes are unwound and separated into single-stranded RNA in the cell. The siRNA molecules then specifically hybridize with RNA sequences transcribed from a target gene, and both RNA molecules are subsequently degraded by an inherent cellular RNA-degrading mechanism. This process may result in the effective degradation or removal of the RNA sequence encoded by the target gene in the target organism. The outcome is the post-transcriptional silencing of the targeted gene. In some embodiments, siRNA molecules produced by endogenous RNAse III enzymes from heterologous nucleic acid molecules may efficiently mediate the down-regulation of target genes in coleopteran and/or hemipteran pests.

In some embodiments, a nucleic acid molecule of the invention may include at least one non-naturally occurring nucleotide sequence that can be transcribed into a single-stranded RNA molecule capable of forming a dsRNA molecule in vivo through intermolecular hybridization. Such dsRNA sequences typically self-assemble, and can be provided in the nutrition source of a coleopteran and/or hemipteran pest to achieve the post-transcriptional inhibition of a target gene. In these and further embodiments, a nucleic acid molecule of the invention may comprise two different non-naturally occurring nucleotide sequences, each of which is specifically complementary to a different target gene in a coleopteran and/or hemipteran pest. When such a nucleic acid molecule is provided as a dsRNA molecule to a coleopteran and/or hemipteran pest, the dsRNA molecule inhibits the expression of at least two different target genes in the coleopteran and/or hemipteran pest.

C. Obtaining Nucleic Acid Molecules

A variety of native sequences in coleopteran and/or hemipteran pests may be used as target sequences for the design of nucleic acid molecules of the invention, such as iRNAs and DNA molecules encoding iRNAs. Selection of native sequences is not, however, a straight-forward process. Only a small number of native sequences in the coleopteran and/or hemipteran pest will be effective targets. For example, it cannot be predicted with certainty whether a particular native sequence can be effectively down-regulated by nucleic acid molecules of the invention, or whether down-regulation of a particular native sequence will have a detrimental effect on the growth, viability, proliferation, and/or reproduction of the coleopteran and/or hemipteran pest. The vast majority of native coleopteran and/or hemipteran pest sequences, such as ESTs isolated therefrom (for example, as listed in U.S. Pat. No. 7,612,194 and U.S. Pat. No. 7,943,819), do not have a detrimental effect on the growth, viability, proliferation, and/or reproduction of the coleopteran and/or hemipteran pest, such as WCR, NCR, *Meligethes aeneus, Euschistus heros, Nezara viridula, Piezodorus guildinii, Halyomorpha halys, Acrosternum hilare*, and *Euschistus servus*.

Neither is it predictable which of the native sequences which may have a detrimental effect on a coleopteran and/or hemipteran pest are able to be used in recombinant techniques for expressing nucleic acid molecules complementary to such native sequences in a host plant and providing the detrimental effect on the coleopteran and/or hemipteran pest upon feeding without causing harm to the host plant.

In some embodiments, nucleic acid molecules of the invention (e.g., dsRNA molecules to be provided in the host plant of a coleopteran and/or hemipteran pest) are selected to target cDNA sequences that encode proteins or parts of proteins essential for coleopteran and/or hemipteran pest survival, such as amino acid sequences involved in metabolic or catabolic biochemical pathways, cell division, reproduction, energy metabolism, digestion, host plant recognition, and the like. As described herein, ingestion of compositions by a target organism containing one or more dsRNAs, at least one segment of which is specifically complementary to at least a substantially identical segment of RNA produced in the cells of the target pest organism, can result in the death or other inhibition of the target. A nucleotide sequence, either DNA or RNA, derived from a coleopteran and/or hemipteran pest can be used to construct plant cells resistant to infestation by the coleopteran and/or hemipteran pests. The host plant of the coleopteran and/or hemipteran pest (e.g., *Z. mays* or *G. max*), for example, can be transformed to contain one or more of the nucleotide sequences derived from the coleopteran and/or hemipteran pest as provided herein. The nucleotide sequence transformed into the host may encode one or more RNAs that form into a dsRNA sequence in the cells or biological fluids within the transformed host, thus making the dsRNA available if/when the coleopteran and/or hemipteran pest forms a nutritional relationship with the transgenic host. This may result in the suppression of expression of one or more genes in the cells of the coleopteran and/or hemipteran pest, and ultimately death or inhibition of its growth or development.

Thus, in some embodiments, a gene is targeted that is essentially involved in the growth, development and reproduction of a coleopteran and/or hemipteran pest. Other target genes for use in the present invention may include, for example, those that play important roles in coleopteran and/or hemipteran pest viability, movement, migration, growth, development, infectivity, establishment of feeding sites and reproduction. A target gene may, therefore, be a housekeeping gene or a transcription factor. Additionally, a native coleopteran and/or hemipteran pest nucleotide sequence for use in the present invention may also be derived from a homolog (e.g., an ortholog), of a plant, viral, bacterial or insect gene, the function of which is known to those of skill in the art, and the nucleotide sequence of which is specifically hybridizable with a target gene in the genome of the target coleopteran and/or hemipteran pest. Methods of identifying a homolog of a gene with a known nucleotide sequence by hybridization are known to those of skill in the art.

In some embodiments, the invention provides methods for obtaining a nucleic acid molecule comprising a nucleotide sequence for producing an iRNA (e.g., dsRNA, siRNA, shRNA, miRNA, and hpRNA) molecule. One such embodiment comprises: (a) analyzing one or more target gene(s) for their expression, function, and phenotype upon dsRNA-mediated gene suppression in a coleopteran and/or hemipteran pest; (b) probing a cDNA or gDNA library with a probe comprising all or a portion of a nucleotide sequence or a homolog thereof from a targeted coleopteran and/or hemipteran pest that displays an altered (e.g., reduced) growth or development phenotype in a dsRNA-mediated suppression analysis; (c) identifying a DNA clone that specifically hybridizes with the probe; (d) isolating the DNA clone identified in step (b); (e) sequencing the cDNA or gDNA fragment that comprises the clone isolated in step (d), wherein the sequenced nucleic acid molecule comprises all or a substantial portion of the RNA sequence or a homolog thereof; and (f) chemically synthesizing all or a substantial portion of a gene sequence, or a siRNA, or shRNA, or miRNA or hpRNA or mRNA or dsRNA.

In further embodiments, a method for obtaining a nucleic acid fragment comprising a nucleotide sequence for producing a substantial portion of an iRNA (e.g., dsRNA, siRNA, shRNA, miRNA, and hpRNA) molecule includes: (a) synthesizing first and second oligonucleotide primers specifically complementary to a portion of a native nucleotide sequence from a targeted coleopteran and/or hemipteran pest; and (b) amplifying a cDNA or gDNA insert present in a cloning vector using the first and second oligonucleotide primers of step (a), wherein the amplified nucleic acid molecule comprises a substantial portion of a siRNA or miRNA or shRNA or hpRNA or mRNA or dsRNA molecule.

Nucleic acids of the invention can be isolated, amplified, or produced by a number of approaches. For example, an iRNA (e.g., dsRNA, siRNA, shRNA, miRNA, and hpRNA) molecule may be obtained by PCR amplification of a target nucleic acid sequence (e.g., a target gene or a target transcribed non-coding sequence) derived from a gDNA or cDNA library, or portions thereof. DNA or RNA may be extracted from a target organism, and nucleic acid libraries may be prepared therefrom using methods known to those ordinarily skilled in the art. gDNA or cDNA libraries generated from a target organism may be used for PCR amplification and sequencing of target genes. A confirmed PCR product may be used as a template for in vitro transcription to generate sense and antisense RNA with minimal promoters. Alternatively, nucleic acid molecules may be synthesized by any of a number of techniques (See, e.g., Ozaki et al. (1992) Nucleic Acids Research, 20: 5205-5214; and Agrawal et al. (1990) Nucleic Acids Research, 18: 5419-5423), including use of an automated DNA synthesizer (for example, a P. E. Biosystems, Inc. (Foster City, Calif.) model 392 or 394 DNA/RNA Synthesizer), using standard chemistries, such as phosphoramidite chemistry. See, e.g., Beaucage et al. (1992) Tetrahedron, 48: 2223-2311; U.S. Pat. Nos. 4,415,732, 4,458,066, 4,725,677, 4,973,679, and 4,980,460. Alternative chemistries resulting in non-natural backbone groups, such as phosphorothioate, phosphoramidate, and the like, can also be employed.

An RNA, dsRNA, siRNA, shRNA, miRNA, or hpRNA molecule of the present invention may be produced chemically or enzymatically by one skilled in the art through manual or automated reactions, or in vivo in a cell comprising a nucleic acid molecule comprising a sequence encoding the RNA, dsRNA, siRNA, shRNA, miRNA, or hpRNA molecule. RNA may also be produced by partial or total organic synthesis—any modified ribonucleotide can be introduced by in vitro enzymatic or organic synthesis. An RNA molecule may be synthesized by a cellular RNA polymerase or a bacteriophage RNA polymerase (e.g., T3 RNA polymerase, T7 RNA polymerase, and SP6 RNA polymerase). Expression constructs useful for the cloning and expression of nucleotide sequences are known in the art. See, e.g., U.S. Pat. Nos. 5,593,874, 5,693,512, 5,698,425, 5,712,135, 5,789,214, and 5,804,693. RNA molecules that are synthesized chemically or by in vitro enzymatic synthesis may be purified prior to introduction into a cell. For example, RNA molecules can be purified from a mixture by extraction with a solvent or resin, precipitation, electrophoresis, chromatography, or a combination thereof. Alternatively, RNA molecules that are synthesized chemically or by in vitro enzymatic synthesis may be used with no or a minimum of purification, for example, to avoid losses due to sample processing. The RNA molecules may be dried for storage or dissolved in an aqueous solution. The solution may contain buffers or salts to promote annealing, and/or stabilization of dsRNA molecule duplex strands.

In certain embodiments, a dsRNA molecule may be formed by a single self-complementary RNA strand or from two complementary RNA strands. dsRNA molecules may be synthesized either in vivo or in vitro. An endogenous RNA polymerase of the cell may mediate transcription of the one or two RNA strands in vivo, or cloned RNA polymerase may be used to mediate transcription in vivo or in vitro. Post-transcriptional inhibition of a target gene in a coleopteran and/or hemipteran pest may be host-targeted by specific transcription in an organ, tissue, or cell type of the host (e.g., by using a tissue-specific promoter); stimulation of an environmental condition in the host (e.g., by using an inducible promoter that is responsive to infection, stress, temperature, and/or chemical inducers); and/or engineering transcription at a developmental stage or age of the host (e.g., by using a developmental stage-specific promoter). RNA strands that form a dsRNA molecule, whether transcribed in vitro or in vivo, may or may not be polyadenylated, and may or may not be capable of being translated into a polypeptide by a cell's translational apparatus.

D. Recombinant Vectors and Host Cell Transformation

In some embodiments, the invention also provides a DNA molecule for introduction into a cell (e.g., a bacterial cell, a yeast cell, or a plant cell), wherein the DNA molecule comprises a nucleotide sequence that, upon expression to RNA and ingestion by a coleopteran and/or hemipteran pest, achieves suppression of a target gene in a cell, tissue, or organ of the coleopteran and/or hemipteran pest. Thus, some embodiments provide a recombinant nucleic acid molecule comprising a nucleic acid sequence capable of being expressed as an iRNA (e.g., dsRNA, siRNA, shRNA, miRNA, and hpRNA) molecule in a plant cell to inhibit target gene expression in a coleopteran and/or hemipteran pest. In order to initiate or enhance expression, such recombinant nucleic acid molecules may comprise one or more regulatory sequences, which regulatory sequences may be operably linked to the nucleic acid sequence capable of being expressed as an iRNA. Methods to express a gene suppression molecule in plants are known, and may be used to express a nucleotide sequence of the present invention. See, e.g., International PCT Publication No. WO06/073727; and U.S. Patent Publication No. 2006/0200878 A1).

In specific embodiments, a recombinant DNA molecule of the invention may comprise a nucleic acid sequence encoding a dsRNA molecule. Such recombinant DNA molecules may encode dsRNA molecules capable of inhibiting the expression of endogenous target gene(s) in a coleopteran and/or hemipteran pest cell upon ingestion. In many embodiments, a transcribed RNA may form a dsRNA molecule that may be provided in a stabilized form; e.g., as a hairpin and stem and loop structure.

In these and further embodiments, one strand of a dsRNA molecule may be formed by transcription from a nucleotide sequence which is substantially homologous to a nucleotide sequence consisting of SEQ ID NO:1; the complement of SEQ ID NO:1; a fragment of at least 15 contiguous nucleotides of SEQ ID NO:1; the complement of a fragment of at least 15 contiguous nucleotides of SEQ ID NO:1; a native coding sequence of a *Diabrotica* organism (e.g., WCR) comprising SEQ ID NO:1; the complement of a native coding sequence of a *Diabrotica* organism comprising SEQ ID NO:1; a native non-coding sequence of a *Diabrotica* organism that is transcribed into a native RNA molecule comprising SEQ ID NO:1; the complement of a native non-coding sequence of a *Diabrotica* organism that is transcribed into a native RNA molecule comprising SEQ ID NO:1; a fragment of at least 15 contiguous nucleotides of a native coding sequence of a *Diabrotica* organism (e.g., WCR) comprising SEQ ID NO:1; the complement of a fragment of at least 15 contiguous nucleotides of a native coding sequence of a *Diabrotica* organism comprising SEQ ID NO:1; a fragment of at least 15 contiguous nucleotides of a native non-coding sequence of a *Diabrotica* organism that is transcribed into a native RNA molecule comprising SEQ ID NO:1; and the complement of a fragment of at least 15 contiguous nucleotides of a native non-coding sequence of a *Diabrotica* organism that is transcribed into a native RNA molecule comprising SEQ ID NO:1.

In other embodiments, one strand of a dsRNA molecule may be formed by transcription from a nucleotide sequence which is substantially homologous to a nucleotide sequence consisting of SEQ ID NO:115; the complement of SEQ ID NO:115; a fragment of at least 19 contiguous nucleotides of SEQ ID NO:115; the complement of a fragment of at least 19 contiguous nucleotides of SEQ ID NO:115; a native coding sequence of a hemipteran organism comprising SEQ ID NO:115; the complement of a native coding sequence of a hemipteran organism comprising SEQ ID NO:115; a native non-coding sequence of a hemipteran organism that is transcribed into a native RNA molecule comprising SEQ ID NO:115; the complement of a native non-coding sequence of a hemipteran organism that is transcribed into a native RNA molecule comprising SEQ ID NO:115; a fragment of at least 19 contiguous nucleotides of a native coding sequence of a hemipteran organism comprising SEQ ID NO:115; the complement of a fragment of at least 19 contiguous nucleotides of a native coding sequence of a hemipteran organism comprising SEQ ID NO:115; a fragment of at least 19 contiguous nucleotides of a native non-coding sequence of a hemipteran organism that is transcribed into a native RNA molecule comprising SEQ ID NO:115; and the complement of a fragment of at least 19 contiguous nucleotides of a native non-coding sequence of a hemipteran organism that is transcribed into a native RNA molecule comprising SEQ ID NO:115.

In these and further embodiments, one strand of a dsRNA molecule may be formed by transcription from a nucleotide sequence which is substantially homologous to a nucleotide sequence consisting of SEQ ID NO:120, SEQ ID NO:122, SEQ ID NO:124, SEQ ID NO:126, SEQ ID NO:131, or SEQ ID NO:133; the complement of SEQ ID NO:120, SEQ ID NO:122, SEQ ID NO:124, SEQ ID NO:126, SEQ ID NO:131, or SEQ ID NO:133; a fragment of at least 15 contiguous nucleotides of SEQ ID NO:120, SEQ ID NO:122, SEQ ID NO:124, SEQ ID NO:126, SEQ ID NO:131, or SEQ ID NO:133; the complement of a fragment of at least 15 contiguous nucleotides of SEQ ID NO:120, SEQ ID NO:122, SEQ ID NO:124, SEQ ID NO:126, SEQ ID NO:131, or SEQ ID NO:133; a native coding sequence of a *Meligethes* organism (e.g., PB) comprising SEQ ID NO:120, SEQ ID NO:122, SEQ ID NO:124, SEQ ID NO:126, SEQ ID NO:131, or SEQ ID NO:133; the complement of a native coding sequence of a *Meligethes* organism comprising SEQ ID NO:120, SEQ ID NO:122, SEQ ID NO:124, SEQ ID NO:126, SEQ ID NO:131, or SEQ ID NO:133; a native non-coding sequence of a *Meligethes* organism that is transcribed into a native RNA molecule comprising SEQ ID NO:120, SEQ ID NO:122, SEQ ID NO:124, SEQ ID NO:126, SEQ ID NO:131, or SEQ ID NO:133; the complement of a native non-coding sequence of a *Meligethes* organism that is transcribed into a native RNA molecule comprising SEQ ID NO:120, SEQ ID NO:122, SEQ ID NO:124, SEQ ID NO:126, SEQ ID NO:131, or SEQ ID NO:133; a fragment of at least 15 contiguous nucleotides of a native coding sequence of a *Meligethes* organism (e.g., PB) comprising SEQ ID NO:120, SEQ ID NO:122, SEQ ID NO:124, SEQ ID NO:126, SEQ ID NO:131, or SEQ ID NO:133; the complement of a fragment of at least 15 contiguous nucleotides of a native coding sequence of a *Meligethes* organism comprising SEQ ID NO:120, SEQ ID NO:122, SEQ ID NO:124, SEQ ID NO:126, SEQ ID NO:131, or SEQ ID NO:133; a fragment of at least 15 contiguous nucleotides of a native non-coding sequence of a Meligethes organism that is transcribed into a native RNA molecule comprising SEQ ID NO:120, SEQ ID NO:122, SEQ ID NO:124, SEQ ID NO:126, SEQ ID NO:131, or SEQ ID NO:133; and the complement of a fragment of at least 15 contiguous nucleotides of a native non-coding sequence of a Meligethes organism that is transcribed into a native RNA molecule comprising SEQ ID NO:120, SEQ ID NO:122, SEQ ID NO:124, SEQ ID NO:126, SEQ ID NO:131, or SEQ ID NO:133.

In particular embodiments, a recombinant DNA molecule encoding a dsRNA molecule may comprise at least two nucleotide sequence segments within a transcribed sequence, such sequences arranged such that the transcribed sequence comprises a first nucleotide sequence segment in a sense orientation, and a second nucleotide sequence segment (comprising the complement of the first nucleotide sequence segment) is in an antisense orientation, relative to at least one promoter, wherein the sense nucleotide sequence segment and the antisense nucleotide sequence segment are linked or connected by a spacer sequence segment of from about five (~5) to about one thousand (~1000) nucleotides. The spacer sequence segment may form a loop between the sense and antisense sequence segments. The sense nucleotide sequence segment or the antisense nucleotide sequence segment may be substantially homologous to the nucleotide sequence of a target gene (e.g., a gene comprising SEQ ID NO:1, SEQ ID NO:115, SEQ ID NO:120, SEQ ID NO:122, SEQ ID NO:124, SEQ ID NO:126, SEQ ID NO:131, or SEQ ID NO:133) or fragment thereof. In some embodiments, however, a recombinant DNA molecule may encode a dsRNA molecule without a spacer sequence. In embodiments, a sense coding sequence and an antisense coding sequence may be different lengths.

Sequences identified as having a deleterious effect on coleopteran and/or hemipteran pests or a plant-protective effect with regard to coleopteran and/or hemipteran pests may be readily incorporated into expressed dsRNA molecules through the creation of appropriate expression cassettes in a recombinant nucleic acid molecule of the invention. For example, such sequences may be expressed as a hairpin with stem and loop structure by taking a first segment corresponding to a target gene sequence (e.g., SEQ ID NO:1, SEQ ID NO:115, SEQ ID NO:120, SEQ ID NO:122, SEQ ID NO:124, SEQ ID NO:126, SEQ ID NO:131, or SEQ ID NO:133 and fragments thereof); linking this sequence to a second segment spacer region that is not homologous or complementary to the first segment; and linking this to a third segment, wherein at least a portion of the third segment is substantially complementary to the first segment. Such a construct forms a stem and loop structure by intramolecular base-pairing of the first segment with the third segment, wherein the loop structure forms and comprises the second segment. See, e.g., U.S. Patent Publication Nos. 2002/0048814 and 2003/0018993; and International PCT Publication Nos. WO94/01550 and WO98/05770. A dsRNA molecule may be generated, for example, in the form of a double-stranded structure such as a stem-loop structure (e.g., hairpin), whereby production of siRNA targeted for a native coleopteran and/or hemipteran pest sequence is enhanced by co-expression of a fragment of the targeted gene, for instance on an additional plant expressible cassette, that leads to enhanced siRNA production, or reduces methylation to prevent transcriptional gene silencing of the dsRNA hairpin promoter.

Embodiments of the invention include introduction of a recombinant nucleic acid molecule of the present invention into a plant (i.e., transformation) to achieve coleopteran and/or hemipteran pest-inhibitory levels of expression of one or more iRNA molecules. A recombinant DNA molecule may, for example, be a vector, such as a linear or a closed circular plasmid. The vector system may be a single vector or plasmid, or two or more vectors or plasmids that together contain the total DNA to be introduced into the genome of a host. In addition, a vector may be an expression vector. Nucleic acid sequences of the invention can, for example, be suitably inserted into a vector under the control of a suitable promoter that functions in one or more hosts to drive expression of a linked coding sequence or other DNA sequence. Many vectors are available for this purpose, and selection of the appropriate vector will depend mainly on the size of the nucleic acid to be inserted into the vector and the particular host cell to be transformed with the vector. Each vector contains various components depending on its function (e.g., amplification of DNA or expression of DNA) and the particular host cell with which it is compatible.

To impart coleopteran and/or hemipteran pest resistance to a transgenic plant, a recombinant DNA may, for example, be transcribed into an iRNA molecule (e.g., an RNA molecule that forms a dsRNA molecule) within the tissues or fluids of the recombinant plant. An iRNA molecule may comprise a nucleotide sequence that is substantially homologous and specifically hybridizable to a corresponding transcribed nucleotide sequence within a coleopteran and/or hemipteran pest that may cause damage to the host plant species. The coleopteran and/or hemipteran pest may contact the iRNA molecule that is transcribed in cells of the transgenic host plant, for example, by ingesting cells or fluids of the transgenic host plant that comprise the iRNA molecule. Thus, expression of a target gene is suppressed by the iRNA molecule within coleopteran and/or hemipteran pests that infest the transgenic host plant. In some embodiments, suppression of expression of the target gene in the target coleopteran and/or hemipteran pest may result in the plant being resistant to attack by the pest.

In order to enable delivery of iRNA molecules to a coleopteran and/or hemipteran pest in a nutritional relationship with a plant cell that has been transformed with a recombinant nucleic acid molecule of the invention, expression (i.e., transcription) of iRNA molecules in the plant cell is required. Thus, a recombinant nucleic acid molecule may comprise a nucleotide sequence of the invention operably linked to one or more regulatory sequences, such as a heterologous promoter sequence that functions in a host cell, such as a bacterial cell wherein the nucleic acid molecule is to be amplified, and a plant cell wherein the nucleic acid molecule is to be expressed.

Promoters suitable for use in nucleic acid molecules of the invention include those that are inducible, viral, synthetic, or constitutive, all of which are well known in the art. Non-limiting examples describing such promoters include U.S. Pat. No. 6,437,217 (maize RS81 promoter); U.S. Pat. No. 5,641,876 (rice actin promoter); U.S. Pat. No. 6,426,446 (maize RS324 promoter); U.S. Pat. No. 6,429,362 (maize PR-1 promoter); U.S. Pat. No. 6,232,526 (maize A3 promoter); U.S. Pat. No. 6,177,611 (constitutive maize promoters); U.S. Pat. Nos. 5,322,938, 5,352,605, 5,359,142, and 5,530,196 (CaMV 35S promoter); U.S. Pat. No. 6,433,252 (maize L3 oleosin promoter); U.S. Pat. No. 6,429,357 (rice actin 2 promoter, and rice actin 2 intron); U.S. Pat. No. 6,294,714 (light-inducible promoters); U.S. Pat. No. 6,140,078 (salt-inducible promoters); U.S. Pat. No. 6,252,138 (pathogen-inducible promoters); U.S. Pat. No. 6,175,060 (phosphorous deficiency-inducible promoters); U.S. Pat. No. 6,388,170 (bidirectional promoters); U.S. Pat. No. 6,635,806 (gamma-coixin promoter); and U.S. Patent Publication No. 2009/757,089 (maize chloroplast aldolase promoter). Additional promoters include the nopaline synthase (NOS) promoter (Ebert et al. (1987) Proc. Natl. Acad. Sci. USA 84(16):5745-5749) and the octopine synthase (OCS) promoters (which are carried on tumor-inducing plasmids of *Agrobacterium tumefaciens*); the caulimovirus promoters such as the cauliflower mosaic virus (CaMV) 19S promoter (Lawton et al. (1987) Plant Mol. Biol. 9:315-324); the CaMV 35S promoter (Odell et al. (1985) Nature 313:810-812; the figwort mosaic virus 35S-promoter (Walker et al.

(1987) Proc. Natl. Acad. Sci. USA 84(19):6624-6628); the sucrose synthase promoter (Yang and Russell (1990) Proc. Natl. Acad. Sci. USA 87:4144-4148); the R gene complex promoter (Chandler et al. (1989) Plant Cell 1:1175-1183); the chlorophyll a/b binding protein gene promoter; CaMV 35S (U.S. Pat. Nos. 5,322,938, 5,352,605, 5,359,142, and 5,530,196); FMV 35S (U.S. Pat. Nos. 5,378,619 and 6,051,753); a PC1SV promoter (U.S. Pat. No. 5,850,019); the SCP1 promoter (U.S. Pat. No. 6,677,503); and AGRtu.nos promoters (GENBANK® Accession No. V00087; Depicker et al. (1982) J. Mol. Appl. Genet. 1:561-573; Bevan et al. (1983) Nature 304:184-187).

In particular embodiments, nucleic acid molecules of the invention comprise a tissue-specific promoter, such as a root-specific promoter. Root-specific promoters drive expression of operably-linked coding sequences exclusively or preferentially in root tissue. Examples of root-specific promoters are known in the art. See, e.g., U.S. Pat. Nos. 5,110,732; 5,459,252 and 5,837,848; and Opperman et al. (1994) Science 263:221-3; and Hirel et al. (1992) Plant Mol. Biol. 20:207-18. In some embodiments, a nucleotide sequence or fragment for coleopteran and/or hemipteran pest control according to the invention may be cloned between two root-specific promoters oriented in opposite transcriptional directions relative to the nucleotide sequence or fragment, and which are operable in a transgenic plant cell and expressed therein to produce RNA molecules in the transgenic plant cell that subsequently may form dsRNA molecules, as described, supra. The iRNA molecules expressed in plant tissues may be ingested by a coleopteran and/or hemipteran pest so that suppression of target gene expression is achieved.

Additional regulatory sequences that may optionally be operably linked to a nucleic acid molecule of interest include 5'UTRs that function as a translation leader sequence located between a promoter sequence and a coding sequence. The translation leader sequence is present in the fully-processed mRNA, and it may affect processing of the primary transcript, and/or RNA stability. Examples of translation leader sequences include maize and petunia heat shock protein leaders (U.S. Pat. No. 5,362,865), plant virus coat protein leaders, plant rubisco leaders, and others. See, e.g., Turner and Foster (1995) Molecular Biotech. 3(3):225-36. Non-limiting examples of 5'UTRs include GmHsp (U.S. Pat. No. 5,659,122); PhDnaK (U.S. Pat. No. 5,362,865); AtAnt1; TEV (Carrington and Freed (1990) J. Virol. 64:1590-7); and AGRtumos (GENBANK® Accession No. V00087; and Bevan et al. (1983) Nature 304:184-7).

Other regulatory sequences that may optionally be operably linked to a nucleic acid molecule of interest also include 3' non-translated sequences, 3' transcription termination regions, or poly-adenylation regions. These are genetic elements located downstream of a nucleotide sequence, and include polynucleotides that provide polyadenylation signal, and/or other regulatory signals capable of affecting transcription or mRNA processing. The polyadenylation signal functions in plants to cause the addition of polyadenylate nucleotides to the 3' end of the mRNA precursor. The polyadenylation sequence can be derived from a variety of plant genes, or from T-DNA genes. A non-limiting example of a 3' transcription termination region is the nopaline synthase 3' region (nos 3; Fraley et al. (1983) Proc. Natl. Acad. Sci. USA 80:4803-7). An example of the use of different 3' nontranslated regions is provided in Ingelbrecht et al., (1989) Plant Cell 1:671-80. Non-limiting examples of polyadenylation signals include one from a *Pisum sativum* RbcS2 gene (Ps.RbcS2-E9; Coruzzi et al. (1984) EMBO J. 3:1671-9) and AGRtu.nos (GENBANK® Accession No. E01312).

Some embodiments may include a plant transformation vector that comprises an isolated and purified DNA molecule comprising at least one of the above-described regulatory sequences operatively linked to one or more nucleotide sequences of the present invention. When expressed, the one or more nucleotide sequences result in one or more RNA molecule(s) comprising a nucleotide sequence that is specifically complementary to all or part of a native RNA molecule in a coleopteran and/or hemipteran pest. Thus, the nucleotide sequence(s) may comprise a segment encoding all or part of a ribonucleotide sequence present within a targeted coleopteran and/or hemipteran pest RNA transcript, and may comprise inverted repeats of all or a part of a targeted coleopteran and/or hemipteran pest transcript. A plant transformation vector may contain sequences specifically complementary to more than one target sequence, thus allowing production of more than one dsRNA for inhibiting expression of two or more genes in cells of one or more populations or species of target coleopteran and/or hemipteran pests. Segments of nucleotide sequence specifically complementary to nucleotide sequences present in different genes can be combined into a single composite nucleic acid molecule for expression in a transgenic plant. Such segments may be contiguous or separated by a spacer sequence.

In some embodiments, a plasmid of the present invention already containing at least one nucleotide sequence(s) of the invention can be modified by the sequential insertion of additional nucleotide sequence(s) in the same plasmid, wherein the additional nucleotide sequence(s) are operably linked to the same regulatory elements as the original at least one nucleotide sequence(s). In some embodiments, a nucleic acid molecule may be designed for the inhibition of multiple target genes. In some embodiments, the multiple genes to be inhibited can be obtained from the same coleopteran and/or hemipteran pest species, which may enhance the effectiveness of the nucleic acid molecule. In other embodiments, the genes can be derived from different coleopteran and/or hemipteran pests, which may broaden the range of coleopteran and/or hemipteran pests against which the agent(s) is/are effective. When multiple genes are targeted for suppression or a combination of expression and suppression, a polycistronic DNA element can be fabricated.

A recombinant nucleic acid molecule or vector of the present invention may comprise a selectable marker that confers a selectable phenotype on a transformed cell, such as a plant cell. Selectable markers may also be used to select for plants or plant cells that comprise a recombinant nucleic acid molecule of the invention. The marker may encode biocide resistance, antibiotic resistance (e.g., kanamycin, Geneticin (G418), bleomycin, hygromycin, etc.), or herbicide resistance (e.g., glyphosate, etc.). Examples of selectable markers include, but are not limited to: a neo gene which codes for kanamycin resistance and can be selected for using kanamycin, G418, etc.; a bar gene which codes for bialaphos resistance; a mutant EPSP synthase gene which encodes glyphosate resistance; a nitrilase gene which confers resistance to bromoxynil; a mutant acetolactate synthase (ALS) gene which confers imidazolinone or sulfonylurea resistance; and a methotrexate resistant DHFR gene. Multiple selectable markers are available that confer resistance to ampicillin, bleomycin, chloramphenicol, gentamycin, hygromycin, kanamycin, lincomycin, methotrexate, phosphinothricin, puromycin, spectinomycin, rifampicin, streptomycin and tetracycline, and the like. Examples of such selectable markers are illustrated in, e.g., U.S. Pat. Nos. 5,550,318; 5,633,435; 5,780,708 and 6,118,047.

A recombinant nucleic acid molecule or vector of the present invention may also include a screenable marker. Screenable markers may be used to monitor expression. Exemplary screenable markers include a β-glucuronidase or uidA gene (GUS) which encodes an enzyme for which various chromogenic substrates are known (Jefferson et al. (1987) Plant Mol. Biol. Rep. 5:387-405); an R-locus gene, which encodes a product that regulates the production of anthocyanin pigments (red color) in plant tissues (Dellaporta et al. (1988) "Molecular cloning of the maize R-nj allele by transposon tagging with Ac." In 18$^{th}$ *Stadler Genetics Symposium,* P. Gustafson and R. Appels, eds. (New York: Plenum), pp. 263-82); a β-lactamase gene (Sutcliffe et al. (1978) Proc. Natl. Acad. Sci. USA 75:3737-41); a gene which encodes an enzyme for which various chromogenic substrates are known (e.g., PADAC, a chromogenic cephalosporin); a luciferase gene (Ow et al. (1986) Science 234:856-9); an xylE gene that encodes a catechol dioxygenase that can convert chromogenic catechols (Zukowski et al. (1983) Gene 46(2-3):247-55); an amylase gene (Ikatu et al. (1990) Bio/Technol. 8:241-2); a tyrosinase gene which encodes an enzyme capable of oxidizing tyrosine to DOPA and dopaquinone which in turn condenses to melanin (Katz et al. (1983) J. Gen. Microbiol. 129:2703-14); and an α-galactosidase.

In some embodiments, recombinant nucleic acid molecules, as described, supra, may be used in methods for the creation of transgenic plants and expression of heterologous nucleic acids in plants to prepare transgenic plants that exhibit reduced susceptibility to coleopteran and/or hemipteran pests. Plant transformation vectors can be prepared, for example, by inserting nucleic acid molecules encoding iRNA molecules into plant transformation vectors and introducing these into plants.

Suitable methods for transformation of host cells include any method by which DNA can be introduced into a cell, such as by transformation of protoplasts (See, e.g., U.S. Pat. No. 5,508,184), by desiccation/inhibition-mediated DNA uptake (See, e.g., Potrykus et al. (1985) Mol. Gen. Genet. 199:183-8), by electroporation (See, e.g., U.S. Pat. No. 5,384,253), by agitation with silicon carbide fibers (See, e.g., U.S. Pat. Nos. 5,302,523 and 5,464,765), by *Agrobacterium*-mediated transformation (See, e.g., U.S. Pat. Nos. 5,563,055; 5,591,616; 5,693,512; 5,824,877; 5,981,840; and 6,384,301) and by acceleration of DNA-coated particles (See, e.g., U.S. Pat. Nos. 5,015,580, 5,550,318, 5,538,880, 6,160,208, 6,399,861, and 6,403,865), etc. Techniques that are particularly useful for transforming corn are described, for example, in U.S. Pat. Nos. 5,591,616, 7,060,876 and 7,939,3281. Through the application of techniques such as these, the cells of virtually any species may be stably transformed. In some embodiments, transforming DNA is integrated into the genome of the host cell. In the case of multicellular species, transgenic cells may be regenerated into a transgenic organism. Any of these techniques may be used to produce a transgenic plant, for example, comprising one or more nucleic acid sequences encoding one or more iRNA molecules in the genome of the transgenic plant.

The most widely utilized method for introducing an expression vector into plants is based on the natural transformation system of various *Agrobacterium* species. *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. The Ti (tumor-inducing)-plasmids contain a large segment, known as T-DNA, which is transferred to transformed plants. Another segment of the Ti plasmid, the Vir region, is responsible for T-DNA transfer. The T-DNA region is bordered by terminal repeats. In modified binary vectors, the tumor-inducing genes have been deleted, and the functions of the Vir region are utilized to transfer foreign DNA bordered by the T-DNA border sequences. The T-region may also contain a selectable marker for efficient recovery of transgenic cells and plants, and a multiple cloning site for inserting sequences for transfer such as a dsRNA encoding nucleic acid.

Thus, in some embodiments, a plant transformation vector is derived from a Ti plasmid of *A. tumefaciens* (See, e.g., U.S. Pat. Nos. 4,536,475, 4,693,977, 4,886,937, and 5,501,967; and European Patent No. EP 0 122 791) or a Ri plasmid of *A. rhizogenes*. Additional plant transformation vectors include, for example and without limitation, those described by Herrera-Estrella et al. (1983) Nature 303:209-13; Bevan et al. (1983) Nature 304:184-7; Klee et al. (1985) Bio/Technol. 3:637-42; and in European Patent No. EP 0 120 516, and those derived from any of the foregoing. Other bacteria such as *Sinorhizobium, Rhizobium*, and *Mesorhizobium* that interact with plants naturally can be modified to mediate gene transfer to a number of diverse plants. These plant-associated symbiotic bacteria can be made competent for gene transfer by acquisition of both a disarmed Ti plasmid and a suitable binary vector.

After providing exogenous DNA to recipient cells, transformed cells are generally identified for further culturing and plant regeneration. In order to improve the ability to identify transformed cells, one may desire to employ a selectable or screenable marker gene, as previously set forth, with the transformation vector used to generate the transformant. In the case where a selectable marker is used, transformed cells are identified within the potentially transformed cell population by exposing the cells to a selective agent or agents. In the case where a screenable marker is used, cells may be screened for the desired marker gene trait.

Cells that survive the exposure to the selective agent, or cells that have been scored positive in a screening assay, may be cultured in media that supports regeneration of plants. In some embodiments, any suitable plant tissue culture media (e.g., MS and N6 media) may be modified by including further substances, such as growth regulators. Tissue may be maintained on a basic medium with growth regulators until sufficient tissue is available to begin plant regeneration efforts, or following repeated rounds of manual selection, until the morphology of the tissue is suitable for regeneration (e.g., typically about 2 weeks), then transferred to media conducive to shoot formation. Cultures are transferred periodically until sufficient shoot formation has occurred. Once shoots are formed, they are transferred to media conducive to root formation. Once sufficient roots are formed, plants can be transferred to soil for further growth and maturation.

To confirm the presence of a nucleic acid molecule of interest (for example, a DNA sequence encoding one or more iRNA molecules that inhibit target gene expression in a coleopteran and/or hemipteran pest) in the regenerating plants, a variety of assays may be performed. Such assays include, for example: molecular biological assays, such as Southern and northern blotting, PCR, and nucleic acid sequencing; biochemical assays, such as detecting the presence of a protein product, e.g., by immunological means (ELISA and/or immuno blots) or by enzymatic function;

plant part assays, such as leaf or root assays; and analysis of the phenotype of the whole regenerated plant.

Integration events may be analyzed, for example, by PCR amplification using, e.g., oligonucleotide primers specific for a nucleic acid molecule of interest. PCR genotyping is understood to include, but not be limited to, polymerase-chain reaction (PCR) amplification of genomic DNA derived from isolated host plant callus tissue predicted to contain a nucleic acid molecule of interest integrated into the genome, followed by standard cloning and sequence analysis of PCR amplification products. Methods of PCR genotyping have been well described (for example, Rios, G. et al. (2002) Plant J. 32:243-53) and may be applied to genomic DNA derived from any plant species (e.g., *Z. mays* or *G. max*) or tissue type, including cell cultures.

A transgenic plant formed using *Agrobacterium*-dependent transformation methods typically contains a single recombinant DNA sequence inserted into one chromosome. The single recombinant DNA sequence is referred to as a "transgenic event" or "integration event." Such transgenic plants are hemizygous for the inserted exogenous sequence. In some embodiments, a transgenic plant homozygous with respect to a transgene may be obtained by sexually mating (selfing) an independent segregant transgenic plant that contains a single exogenous gene sequence to itself, for example a $T_0$ plant, to produce $T_1$ seed. One fourth of the $T_1$ seed produced will be homozygous with respect to the transgene. Germinating $T_1$ seed results in plants that can be tested for heterozygosity, typically using an SNP assay or a thermal amplification assay that allows for the distinction between heterozygotes and homozygotes (i.e., a zygosity assay).

In particular embodiments, at least 2, 3, 4, 5, 6, 7, 8, 9 or 10 or more different iRNA molecules that have a coleopteran and/or hemipteran pest-inhibitory effect are produced in a plant cell. The iRNA molecules (e.g., dsRNA molecules) may be expressed from multiple nucleic acid sequences introduced in different transformation events, or from a single nucleic acid sequence introduced in a single transformation event. In some embodiments, a plurality of iRNA molecules are expressed under the control of a single promoter. In other embodiments, a plurality of iRNA molecules are expressed under the control of multiple promoters. Single iRNA molecules may be expressed that comprise multiple nucleic acid sequences that are each homologous to different loci within one or more coleopteran and/or hemipteran pests (for example, the locus defined by SEQ ID NO:1, SEQ ID NO:115, SEQ ID NO:120, SEQ ID NO:122, SEQ ID NO:124, SEQ ID NO:126, SEQ ID NO:131, or SEQ ID NO:133), both in different populations of the same species of coleopteran and/or hemipteran pest, or in different species of coleopteran and/or hemipteran pests.

In addition to direct transformation of a plant with a recombinant nucleic acid molecule, transgenic plants can be prepared by crossing a first plant having at least one transgenic event with a second plant lacking such an event. For example, a recombinant nucleic acid molecule comprising a nucleotide sequence that encodes an iRNA molecule may be introduced into a first plant line that is amenable to transformation to produce a transgenic plant, which transgenic plant may be crossed with a second plant line to introgress the nucleotide sequence that encodes the iRNA molecule into the second plant line.

The invention also includes commodity products containing one or more of the sequences of the present invention. Particular embodiments include commodity products produced from a recombinant plant or seed containing one or more of the nucleotide sequences of the present invention. A commodity product containing one or more of the sequences of the present invention is intended to include, but not be limited to, meals, oils, crushed or whole grains or seeds of a plant, or any food or animal feed product comprising any meal, oil, or crushed or whole grain of a recombinant plant or seed containing one or more of the sequences of the present invention. The detection of one or more of the sequences of the present invention in one or more commodity or commodity products contemplated herein is de facto evidence that the commodity or commodity product is produced from a transgenic plant designed to express one or more of the nucleotides sequences of the present invention for the purpose of controlling coleopteran and/or hemipteran plant pests using dsRNA-mediated gene suppression methods.

In some aspects, seeds and commodity products produced by transgenic plants derived from transformed plant cells are included, wherein the seeds or commodity products comprise a detectable amount of a nucleic acid sequence of the invention. In some embodiments, such commodity products may be produced, for example, by obtaining transgenic plants and preparing food or feed from them. Commodity products comprising one or more of the nucleic acid sequences of the invention includes, for example and without limitation: meals, oils, crushed or whole grains or seeds of a plant, and any food product comprising any meal, oil, or crushed or whole grain of a recombinant plant or seed comprising one or more of the nucleic acid sequences of the invention. The detection of one or more of the sequences of the invention in one or more commodity or commodity products is de facto evidence that the commodity or commodity product is produced from a transgenic plant designed to express one or more of the iRNA molecules of the invention for the purpose of controlling coleopteran and/or hemipteran pests.

In some embodiments, a transgenic plant or seed comprising a nucleic acid molecule of the invention also may comprise at least one other transgenic event in its genome, including without limitation: a transgenic event from which is transcribed an iRNA molecule targeting a locus in a coleopteran and/or hemipteran pest other than the one defined by SEQ ID NO:1, SEQ ID NO:115, SEQ ID NO:120, SEQ ID NO:122, SEQ ID NO:124, SEQ ID NO:126, SEQ ID NO:131, or SEQ ID NO:133, such as, for example, one or more loci selected from the group consisting of Caf1-180 (U.S. Patent Application Publication No. 2012/0174258), VatpaseC (U.S. Patent Application Publication No. 2012/0174259), Rho1 (U.S. Patent Application Publication No. 2012/0174260), VatpaseH (U.S. Patent Application Publication No. 2012/0198586), PPI-87B (U.S. Patent Application Publication No. 2013/0091600), RPA70 (U.S. Patent Application Publication No. 2013/0091601), and RPS6 (U.S. Patent Application Publication No. 2013/0097730); a transgenic event from which is transcribed an iRNA molecule targeting a gene in an organism other than a coleopteran and/or hemipteran pest (e.g., a plant-parasitic nematode); a gene encoding an insecticidal protein (e.g., a *Bacillus thuringiensis* insecticidal protein, such as, for example, Cry34Ab1 (U.S. Pat. Nos. 6,127,180, 6,340,593, and 6,624,145), Cry35Ab 1 (U.S. Pat. Nos. 6,083,499, 6,340,593, and 6,548,291), a "Cry34/35Ab1" combination in a single event (e.g., maize event DAS-59122-7; U.S. Pat. No. 7,323,556), Cry3A (e.g., U.S. Pat. No. 7,230,167), Cry3B (e.g., U.S. Pat. No. 8,101,826), Cry6A (e.g., U.S. Pat. No. 6,831,062), and combinations thereof (e.g., U.S. Patent Application Nos. 2013/0167268, 2013/0167269, and 2013/

0180016); an herbicide tolerance gene (e.g., a gene providing tolerance to glyphosate, glufosinate, dicamba or 2,4-D (e.g., U.S. Pat. No. 7,838,733)); and a gene contributing to a desirable phenotype in the transgenic plant, such as increased yield, altered fatty acid metabolism, or restoration of cytoplasmic male sterility). In particular embodiments, sequences encoding iRNA molecules of the invention may be combined with other insect control or with disease resistance traits in a plant to achieve desired traits for enhanced control of insect damage and plant disease. Combining insect control traits that employ distinct modes-of-action may provide protected transgenic plants with superior durability over plants harboring a single control trait, for example, because of the reduced probability that resistance to the trait(s) will develop in the field.

V. Target Gene Suppression in a Coleopteran and/or Hemipteran Pest

A. Overview

In some embodiments of the invention, at least one nucleic acid molecule useful for the control of coleopteran and/or hemipteran pests may be provided to a coleopteran and/or hemipteran pest, wherein the nucleic acid molecule leads to RNAi-mediated gene silencing in the coleopteran and/or hemipteran pest. In particular embodiments, an iRNA molecule (e.g., dsRNA, siRNA, shRNA, miRNA, and hpRNA) may be provided to the coleopteran and/or hemipteran pest. In some embodiments, a nucleic acid molecule useful for the control of coleopteran and/or hemipteran pests may be provided to a coleopteran and/or hemipteran pest by contacting the nucleic acid molecule with the coleopteran and/or hemipteran pest. In these and further embodiments, a nucleic acid molecule useful for the control of coleopteran and/or hemipteran pests may be provided in a feeding substrate of the coleopteran and/or hemipteran pest, for example, a nutritional composition. In these and further embodiments, a nucleic acid molecule useful for the control of coleopteran and/or hemipteran pests may be provided through ingestion of plant material comprising the nucleic acid molecule that is ingested by the coleopteran and/or hemipteran pest. In certain embodiments, the nucleic acid molecule is present in plant material through expression of a recombinant nucleic acid sequence introduced into the plant material, for example, by transformation of a plant cell with a vector comprising the recombinant nucleic acid sequence and regeneration of a plant material or whole plant from the transformed plant cell.

B. RNAi-Mediated Target Gene Suppression

In embodiments, the invention provides iRNA molecules (e.g., dsRNA, siRNA, shRNA, miRNA, and hpRNA) that may be designed to target essential native nucleotide sequences (e.g., essential genes) in the transcriptome of a coleopteran and/or hemipteran pest (e.g., WCR, NCR, *Meligethes aeneus, Euschistus heros, Nezara viridula, Piezodorus guildinii, Halyomorpha halys, Acrosternum hilare*, and *Euschistus servus*), for example by designing an iRNA molecule that comprises at least one strand comprising a nucleotide sequence that is specifically complementary to the target sequence. The sequence of an iRNA molecule so designed may be identical to the target sequence, or may incorporate mismatches that do not prevent specific hybridization between the iRNA molecule and its target sequence.

iRNA molecules of the invention may be used in methods for gene suppression in a coleopteran and/or hemipteran pest, thereby reducing the level or incidence of damage caused by the pest on a plant (for example, a protected transformed plant comprising an iRNA molecule). As used herein, the term "gene suppression" refers to any of the well-known methods for reducing the levels of protein produced as a result of gene transcription to mRNA and subsequent translation of the mRNA, including the reduction of protein expression from a gene or a coding sequence including post-transcriptional inhibition of expression and transcriptional suppression. Post-transcriptional inhibition is mediated by specific homology between all or a part of an mRNA transcribed from a gene targeted for suppression and the corresponding iRNA molecule used for suppression. Additionally, post-transcriptional inhibition refers to the substantial and measurable reduction of the amount of mRNA available in the cell for binding by ribosomes.

In some embodiments where an iRNA molecule is a dsRNA molecule, the dsRNA molecule may be cleaved by the enzyme, DICER, into short siRNA molecules (approximately 20 nucleotides in length). The double-stranded siRNA molecule generated by DICER activity upon the dsRNA molecule may be separated into two single-stranded siRNAs; the "passenger strand" and the "guide strand." The passenger strand may be degraded, and the guide strand may be incorporated into RISC. Post-transcriptional inhibition occurs by specific hybridization of the guide strand with a specifically complementary sequence of an mRNA molecule, and subsequent cleavage by the enzyme, Argonaute (catalytic component of the RISC complex).

In other embodiments of the invention, any form of iRNA molecule may be used. Those of skill in the art will understand that dsRNA molecules typically are more stable than are single-stranded RNA molecules, during preparation and during the step of providing the iRNA molecule to a cell, and are typically also more stable in a cell. Thus, while siRNA and miRNA molecules, for example, may be equally effective in some embodiments, a dsRNA molecule may be chosen due to its stability.

In particular embodiments, a nucleic acid molecule is provided that comprises a nucleotide sequence, which nucleotide sequence may be expressed in vitro to produce an iRNA molecule that is substantially homologous to a nucleic acid molecule encoded by a nucleotide sequence within the genome of a coleopteran and/or hemipteran pest. In certain embodiments, the in vitro transcribed iRNA molecule may be a stabilized dsRNA molecule that comprises a stem-loop structure. After a coleopteran and/or hemipteran pest contacts the in vitro transcribed iRNA molecule, post-transcriptional inhibition of a target gene in the coleopteran and/or hemipteran pest (for example, an essential gene) may occur.

In some embodiments of the invention, expression of a nucleic acid molecule comprising at least 15 contiguous nucleotides of a nucleotide sequence is used in a method for post-transcriptional inhibition of a target gene in a coleopteran and/or hemipteran pest, wherein the nucleotide sequence is selected from the group consisting of: SEQ ID NO:1; the complement of SEQ ID NO:1; a fragment of at least 15 contiguous nucleotides of SEQ ID NO:1; the complement of a fragment of at least 15 contiguous nucleotides of SEQ ID NO:1; a native coding sequence of a *Diabrotica* organism (e.g., WCR) comprising SEQ ID NO:1; the complement of a native coding sequence of a *Diabrotica* organism comprising SEQ ID NO:1; a native non-coding sequence of a *Diabrotica* organism that is transcribed into a native RNA molecule comprising SEQ ID NO:1; the complement of a native non-coding sequence of a *Diabrotica* organism that is transcribed into a native RNA molecule comprising SEQ ID NO:1; the complement of a native non-coding sequence of a *Diabrotica* organism that is transcribed into a native RNA molecule comprising SEQ ID NO:1; a fragment of at least 15 contiguous nucleotides of a native coding sequence of a *Diabrotica* organism (e.g., WCR) comprising SEQ ID NO:1; the complement of a fragment of at least 15 contiguous nucleotides of a native coding sequence of a *Diabrotica* organism comprising SEQ ID NO:1; a fragment of at least 15 contiguous nucleotides of a native non-coding sequence of a *Diabrotica* organism that is transcribed into a native RNA molecule comprising SEQ ID NO:1; and the complement of a fragment of at least 15 contiguous nucleotides of a native non-coding sequence of a *Diabrotica* organism that is transcribed into a native RNA molecule comprising SEQ ID NO:1. In certain embodiments, expression of a nucleic acid molecule that is at least 80% identical (e.g., 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100%, and 100%) with any of the foregoing may be used. In these and further embodiments, a nucleic acid molecule may be expressed that specifically hybridizes to an RNA molecule present in at least one cell of a coleopteran and/or hemipteran pest.

In certain embodiments of the invention, expression of a nucleic acid molecule comprising at least 15 contiguous nucleotides of a nucleotide sequence is used in a method for post-transcriptional inhibition of a target gene in a coleopteran pest, wherein the nucleotide sequence is selected from the group consisting of: SEQ ID NO:115; the complement of SEQ ID NO:115; a fragment of at least 15 contiguous nucleotides of SEQ ID NO:115; the complement of a fragment of at least 15 contiguous nucleotides of SEQ ID NO:115; a native coding sequence of a hemipteran organism SEQ ID NO:115; the complement of a native coding sequence of a hemipteran organism comprising SEQ ID NO:115; a native non-coding sequence of a hemipteran organism that is transcribed into a native RNA molecule comprising SEQ ID NO:115; the complement of a native non-coding sequence of a hemipteran organism that is transcribed into a native RNA molecule comprising SEQ ID NO:115; the complement of a native non-coding sequence of a hemipteran organism that is transcribed into a native RNA molecule comprising SEQ ID NO:115; a fragment of at least 15 contiguous nucleotides of a native coding sequence of a hemipteran organism comprising SEQ ID NO:115; the complement of a fragment of at least 15 contiguous nucleotides of a native coding sequence of a hemipteran organism comprising SEQ ID NO:115; a fragment of at least 15 contiguous nucleotides of a native non-coding sequence of a hemipteran organism that is transcribed into a native RNA molecule comprising SEQ ID NO:115; and the complement of a fragment of at least 15 contiguous nucleotides of a native non-coding sequence of a hemipteran organism that is transcribed into a native RNA molecule comprising SEQ ID NO:115. In certain embodiments, expression of a nucleic acid molecule that is at least 80% identical (e.g., 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100%, and 100%) with any of the foregoing may be used. In these and further embodiments, a nucleic acid molecule may be expressed that specifically hybridizes to an RNA molecule present in at least one cell of a coleopteran pest.

In some embodiments of the invention, expression of a nucleic acid molecule comprising at least 15 contiguous nucleotides of a nucleotide sequence is used in a method for post-transcriptional inhibition of a target gene in a coleopteran and/or hemipteran pest, wherein the nucleotide sequence is selected from the group consisting of: SEQ ID NO:120, SEQ ID NO:122, SEQ ID NO:124, SEQ ID NO:126, SEQ ID NO:131, or SEQ ID NO:133; the complement of SEQ ID NO:120, SEQ ID NO:122, SEQ ID NO:124, SEQ ID NO:126, SEQ ID NO:131, or SEQ ID NO:133; a fragment of at least 15 contiguous nucleotides of SEQ ID NO:120, SEQ ID NO:122, SEQ ID NO:124, SEQ ID NO:126, SEQ ID NO:131, or SEQ ID NO:133; the complement of a fragment of at least 15 contiguous nucleotides of SEQ ID NO:120, SEQ ID NO:122, SEQ ID NO:124, SEQ ID NO:126, SEQ ID NO:131, or SEQ ID NO:133; a native coding sequence of a *Meligethes* organism (e.g., EPB) comprising SEQ ID NO:120, SEQ ID NO:122, SEQ ID NO:124, SEQ ID NO:126, SEQ ID NO:131, or SEQ ID NO:133; the complement of a native coding sequence of a *Meligethes* organism comprising SEQ ID NO:120, SEQ ID NO:122, SEQ ID NO:124, SEQ ID NO:126, SEQ ID NO:131, or SEQ ID NO:133; a native non-coding sequence of a *Meligethes* organism that is transcribed into a native RNA molecule comprising SEQ ID NO:120, SEQ ID NO:122, SEQ ID NO:124, SEQ ID NO:126, SEQ ID NO:131, or SEQ ID NO:133; the complement of a native non-coding sequence of a *Meligethes* organism that is transcribed into a native RNA molecule comprising SEQ ID NO:120, SEQ ID NO:122, SEQ ID NO:124, SEQ ID NO:126, SEQ ID NO:131, or SEQ ID NO:133; the complement of a native non-coding sequence of a *Meligethes* organism that is transcribed into a native RNA molecule comprising SEQ ID NO:120, SEQ ID NO:122, SEQ ID NO:124, SEQ ID NO:126, SEQ ID NO:131, or SEQ ID NO:133; a fragment of at least 15 contiguous nucleotides of a native coding sequence of a *Meligethes* organism (e.g., EPB) comprising SEQ ID NO:120, SEQ ID NO:122, SEQ ID NO:124, SEQ ID NO:126, SEQ ID NO:131, or SEQ ID NO:133; the complement of a fragment of at least 15 contiguous nucleotides of a native coding sequence of a *Meligethes* organism comprising SEQ ID NO:120, SEQ ID NO:122, SEQ ID NO:124, SEQ ID NO:126, SEQ ID NO:131, or SEQ ID NO:133; a fragment of at least 15 contiguous nucleotides of a native non-coding sequence of a *Meligethes* organism that is transcribed into a native RNA molecule comprising SEQ ID NO:120, SEQ ID NO:122, SEQ ID NO:124, SEQ ID NO:126, SEQ ID NO:131, or SEQ ID NO:133; and the complement of a fragment of at least 15 contiguous nucleotides of a native non-coding sequence of a *Meligethes* organism that is transcribed into a native RNA molecule comprising SEQ ID NO:120, SEQ ID NO:122, SEQ ID NO:124, SEQ ID NO:126, SEQ ID NO:131, or SEQ ID NO:133. In certain embodiments, expression of a nucleic acid molecule that is at least 80% identical (e.g., 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100%, and 100%) with any of the foregoing may be used. In these and further embodiments, a nucleic acid molecule may be expressed that specifically hybridizes to an RNA molecule present in at least one cell of a coleopteran and/or hemipteran pest.

In other embodiments, expression of at least one nucleic acid molecule comprising at least 19 contiguous nucleotides of a nucleotide sequence may be used in a method for post-transcriptional inhibition of a target gene in a coleopteran and/or hemipteran pest, wherein the nucleotide sequence is selected from the group consisting of: SEQ ID NO:1; the complement of SEQ ID NO:1; a fragment of at least 19 contiguous nucleotides of SEQ ID NO:1; the complement of a fragment of at least 19 contiguous nucleotides of SEQ ID NO:1; a native coding sequence of a *Diabrotica* organism (e.g., WCR) comprising SEQ ID NO:1; the complement of a native coding sequence of a *Diabrotica* organism (e.g., WCR) comprising SEQ ID NO:1; a native non-coding sequence of a *Diabrotica* organism that is transcribed into a native RNA molecule comprising SEQ ID NO:1; the complement of a native non-coding sequence of a *Diabrotica* organism that is transcribed into a native RNA molecule comprising SEQ ID NO:1; a fragment of at least 19 contiguous nucleotides of a native coding sequence of a *Diabrotica* organism (e.g., WCR) comprising SEQ ID NO:1; the complement of a fragment of at least 19 contiguous nucleotides of a native coding sequence of a *Diabrotica* organism comprising SEQ ID NO:1; a fragment of at least 19 contiguous nucleotides of a native non-coding sequence of a *Diabrotica* organism that is transcribed into a native RNA molecule comprising SEQ ID NO:1; and the complement of a fragment of at least 19 contiguous nucleotides of a native non-coding sequence of a *Diabrotica* organism that is transcribed into a native RNA molecule comprising SEQ ID NO:1. In certain embodiments, expression of a nucleic acid molecule that is at least 80% identical (e.g., 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100%, and 100%) with any of the foregoing may be used. In these and further embodiments, a nucleic acid molecule may be expressed that specifically hybridizes to an RNA molecule present in at least one cell of a coleopteran and/or hemipteran pest. In particular examples, such a nucleic acid molecule may comprise a nucleotide sequence comprising SEQ ID NO:1.

In particular embodiments, expression of at least one nucleic acid molecule comprising at least 19 contiguous nucleotides of a nucleotide sequence may be used in a method for post-transcriptional inhibition of a target gene in a coleopteran pest, wherein the nucleotide sequence is selected from the group consisting of: SEQ ID NO:115; the complement of SEQ ID NO:115; a fragment of at least 19 contiguous nucleotides of SEQ ID NO:115; the complement of a fragment of at least 19 contiguous nucleotides of SEQ ID NO:115; a native coding sequence of a hemipteran organism comprising SEQ ID NO:115; the complement of a native coding sequence of a hemipteran organism comprising SEQ ID NO:115; a native non-coding sequence of a hemipteran organism that is transcribed into a native RNA molecule comprising SEQ ID NO:115; the complement of a native non-coding sequence of a hemipteran organism that is transcribed into a native RNA molecule comprising SEQ ID NO:115; a fragment of at least 19 contiguous nucleotides of a native coding sequence of a hemipteran organism comprising SEQ ID NO:115; the complement of a fragment of at least 19 contiguous nucleotides of a native coding sequence of a hemipteran organism comprising SEQ ID NO:115; a fragment of at least 19 contiguous nucleotides of a native non-coding sequence of a hemipteran organism that is transcribed into a native RNA molecule comprising SEQ ID NO:115; and the complement of a fragment of at least 19 contiguous nucleotides of a native non-coding sequence of a hemipteran organism that is transcribed into a native RNA molecule comprising SEQ ID NO:115. In certain embodiments, expression of a nucleic acid molecule that is at least 80% identical (e.g., 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100%, and 100%) with any of the foregoing may be used. In these and further embodiments, a nucleic acid molecule may be expressed that specifically hybridizes to an RNA molecule present in at least one cell of a coleopteran pest. In particular examples, such a nucleic acid molecule may comprise a nucleotide sequence comprising SEQ ID NO:115.

In other embodiments, expression of at least one nucleic acid molecule comprising at least 19 contiguous nucleotides of a nucleotide sequence may be used in a method for post-transcriptional inhibition of a target gene in a coleopteran and/or hemipteran pest, wherein the nucleotide sequence is selected from the group consisting of: SEQ ID NO:120, SEQ ID NO:122, SEQ ID NO:124, SEQ ID NO:126, SEQ ID NO:131, or SEQ ID NO:133; the complement of SEQ ID NO:120, SEQ ID NO:122, SEQ ID NO:124, SEQ ID NO:126, SEQ ID NO:131, or SEQ ID NO:133; a fragment of at least 19 contiguous nucleotides of SEQ ID NO:120, SEQ ID NO:122, SEQ ID NO:124, SEQ ID NO:126, SEQ ID NO:131, or SEQ ID NO:133; the complement of a fragment of at least 19 contiguous nucleotides of SEQ ID NO:120, SEQ ID NO:122, SEQ ID NO:124, SEQ ID NO:126, SEQ ID NO:131, or SEQ ID NO:133; a native coding sequence of a *Meligethes* organism (e.g., EPB) comprising SEQ ID NO:120, SEQ ID NO:122, SEQ ID NO:124, or SEQ ID NO:126, SEQ ID NO:131, or SEQ ID NO:133; the complement of a native coding sequence of a *Meligethes* organism (e.g., EPB) comprising SEQ ID NO:120, SEQ ID NO:122, SEQ ID NO:124, SEQ ID NO:126, SEQ ID NO:131, or SEQ ID NO:133; a native non-coding sequence of a *Meligethes* organism that is transcribed into a native RNA molecule comprising SEQ ID NO:120, SEQ ID NO:122, SEQ ID NO:124, SEQ ID NO:126, SEQ ID NO:131, or SEQ ID NO:133; the complement of a native non-coding sequence of a *Meligethes* organism that is transcribed into a native RNA molecule comprising SEQ ID NO:120, SEQ ID NO:122, SEQ ID NO:124, SEQ ID NO:126, SEQ ID NO:131, or SEQ ID NO:133; a fragment of at least 19 contiguous nucleotides of a native coding sequence of a *Meligethes* organism (e.g., EPB) comprising SEQ ID NO:120, SEQ ID NO:122, SEQ ID NO:124, SEQ ID NO:126, SEQ ID NO:131, or SEQ ID NO:133; the complement of a fragment of at least 19 contiguous nucleotides of a native coding sequence of a *Meligethes* organism comprising SEQ ID NO:120, SEQ ID NO:122, SEQ ID NO:124, SEQ ID NO:126, SEQ ID NO:131, or SEQ ID NO:133; a fragment of at least 19 contiguous nucleotides of a native non-coding sequence of a *Meligethes* organism that is transcribed into a native RNA molecule comprising SEQ ID NO:120, SEQ ID NO:122, SEQ ID NO:124, SEQ ID NO:126, SEQ ID NO:131, or SEQ ID NO:133; and the complement of a fragment of at least 19 contiguous nucleotides of a native non-coding sequence of a *Meligethes* organism that is transcribed into a native RNA molecule comprising SEQ ID NO:120, SEQ ID NO:122, SEQ ID NO:124, SEQ ID NO:126, SEQ ID NO:131, or SEQ ID NO:133. In certain embodiments, expression of a nucleic acid molecule that is at least 80% identical (e.g., 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100%, and 100%) with any of the foregoing may be used. In these and further embodiments, a nucleic acid molecule may be expressed that specifically hybridizes to an RNA molecule present in at least one cell of a coleopteran and/or hemipteran pest. In particular examples, such a nucleic acid molecule may comprise a nucleotide sequence comprising SEQ ID NO:120, SEQ ID NO:122, SEQ ID NO:124, SEQ ID NO:126, SEQ ID NO:131, or SEQ ID NO:133.

It is an important feature of some embodiments of the invention that the RNAi post-transcriptional inhibition system is able to tolerate sequence variations among target genes that might be expected due to genetic mutation, strain polymorphism, or evolutionary divergence. The introduced nucleic acid molecule may not need to be absolutely homologous to either a primary transcription product or a fully-processed mRNA of a target gene, so long as the introduced nucleic acid molecule is specifically hybridizable to either a primary transcription product or a fully-processed mRNA of the target gene. Moreover, the introduced nucleic acid molecule may not need to be full-length, relative to either a primary transcription product or a fully processed mRNA of the target gene.

Inhibition of a target gene using the iRNA technology of the present invention is sequence-specific; i.e., nucleotide sequences substantially homologous to the iRNA molecule (s) are targeted for genetic inhibition. In some embodiments, an RNA molecule comprising a nucleotide sequence identical to a portion of a target gene sequence may be used for inhibition. In these and further embodiments, an RNA molecule comprising a nucleotide sequence with one or more insertion, deletion, and/or point mutations relative to a target gene sequence may be used. In particular embodiments, an iRNA molecule and a portion of a target gene may share, for example, at least from about 80%, at least from about 81%, at least from about 82%, at least from about 83%, at least from about 84%, at least from about 85%, at least from about 86%, at least from about 87%, at least from about 88%, at least from about 89%, at least from about 90%, at least from about 91%, at least from about 92%, at least from about 93%, at least from about 94%, at least from about 95%, at least from about 96%, at least from about 97%, at least from about 98%, at least from about 99%, at least from about 100%, and 100% sequence identity. Alternatively, the duplex region of a dsRNA molecule may be specifically hybridizable with a portion of a target gene transcript. In specifically hybridizable molecules, a less than full length sequence exhibiting a greater homology compensates for a longer, less homologous sequence. The length of the nucleotide sequence of a duplex region of a dsRNA molecule that is identical to a portion of a target gene transcript may be at least about 15, 16, 7, 18, 19, 20, 21, 22, 23, 24, 25, 26, 27, 28, 29, 30, 35, 40, 45, 50, 100, 200, 300, 400, 500, or at least about 1000 bases. In some embodiments, a sequence of greater than 15 to 100 nucleotides may be used. In other embodiments, a sequence of greater than 100 to 200 nucleotides may be used. In particular embodiments, a sequence of greater than about 200 to 300 nucleotides may be used. In alternative embodiments, a sequence of greater than 300 to 500 nucleotides may be used. In particular embodiments, a sequence of greater than about 500 to 1000 nucleotides may be used, depending on the size of the target gene.

In certain embodiments, expression of a target gene in a coleopteran and/or hemipteran pest may be inhibited by at least 10%; at least 33%; at least 50%; or at least 80% within a cell of the coleopteran and/or hemipteran pest, such that a significant inhibition takes place. Significant inhibition refers to inhibition over a threshold that results in a detectable phenotype (e.g., cessation of growth, cessation of feeding, cessation of development, induced mortality, etc.), or a detectable decrease in RNA and/or gene product corresponding to the target gene being inhibited. Although in certain embodiments of the invention inhibition occurs in substantially all cells of the coleopteran and/or hemipteran pest, in other embodiments inhibition occurs only in a subset of cells expressing the target gene.

In some embodiments, transcriptional suppression in a cell is mediated by the presence of a dsRNA molecule exhibiting substantial sequence identity to a promoter DNA sequence or the complement thereof, to effect what is referred to as "promoter trans suppression." Gene suppression may be effective against target genes in a coleopteran and/or hemipteran pest that may ingest or contact such dsRNA molecules, for example, by ingesting or contacting plant material containing the dsRNA molecules. dsRNA molecules for use in promoter trans suppression may be specifically designed to inhibit or suppress the expression of one or more homologous or complementary sequences in the cells of the coleopteran and/or hemipteran pest. Post-transcriptional gene suppression by antisense or sense oriented RNA to regulate gene expression in plant cells is disclosed in U.S. Pat. Nos. 5,107,065, 5,231,020, 5,283,184, and 5,759,829.

C. Expression of iRNA Molecules Provided to a Coleopteran and/or Hemipteran Pest Expression of iRNA molecules for RNAi-mediated gene inhibition in a coleopteran and/or hemipteran pest may be carried out in any one of many in vitro or in vivo formats. The iRNA molecules may then be provided to a coleopteran and/or hemipteran pest, for example, by contacting the iRNA molecules with the pest, or by causing the pest to ingest or otherwise internalize the iRNA molecules. Some embodiments of the invention include transformed host plants of a coleopteran and/or hemipteran pest, transformed plant cells, and progeny of transformed plants. The transformed plant cells and transformed plants may be engineered to express one or more of the iRNA molecules, for example, under the control of a heterologous promoter, to provide a pest-protective effect. Thus, when a transgenic plant or plant cell is consumed by a coleopteran and/or hemipteran pest during feeding, the pest may ingest iRNA molecules expressed in the transgenic plants or cells. The nucleotide sequences of the present invention may also be introduced into a wide variety of prokaryotic and eukaryotic microorganism hosts to produce iRNA molecules. The term "microorganism" includes prokaryotic and eukaryotic species, such as bacteria and fungi.

Modulation of gene expression may include partial or complete suppression of such expression. In another embodiment, a method for suppression of gene expression in a coleopteran and/or hemipteran pest comprises providing in the tissue of the host of the pest a gene-suppressive amount of at least one dsRNA molecule formed following transcription of a nucleotide sequence as described herein, at least one segment of which is complementary to an mRNA sequence within the cells of the coleopteran and/or hemipteran pest. A dsRNA molecule, including its modified form such as an siRNA, shRNA, miRNA, or hpRNA molecule, ingested by a coleopteran and/or hemipteran pest in accordance with the invention, may be at least from about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100%, or 100% identical to an RNA molecule transcribed from a nucleic acid molecule comprising a nucleotide sequence comprising SEQ ID NO:1, SEQ ID NO:115, SEQ ID NO:120, SEQ ID NO:122, SEQ ID NO:124, SEQ ID NO:126, SEQ ID NO:131, or SEQ ID NO:133. Isolated and substantially purified nucleic acid molecules including, but not limited to, non-naturally occurring nucleotide sequences and recombinant DNA constructs for providing dsRNA molecules of the present invention are, therefore, provided, which suppress or inhibit the expression of an endogenous coding sequence or a target coding sequence in the coleopteran and/or hemipteran pest when introduced thereto.

Particular embodiments provide a delivery system for the delivery of iRNA molecules for the post-transcriptional inhibition of one or more target gene(s) in a coleopteran and/or hemipteran plant pest and control of a population of the coleopteran and/or hemipteran plant pest. In some embodiments, the delivery system comprises ingestion of a host transgenic plant cell or contents of the host cell comprising RNA molecules transcribed in the host cell. In these and further embodiments, a transgenic plant cell or a transgenic plant is created that contains a recombinant DNA construct providing a stabilized dsRNA molecule of the invention. Transgenic plant cells and transgenic plants comprising nucleic acid sequences encoding a particular iRNA molecule may be produced by employing recombinant DNA technologies (which basic technologies are well-known in the art) to construct a plant transformation vector comprising a nucleotide sequence encoding an iRNA molecule of the invention (e.g., a stabilized dsRNA molecule); to transform a plant cell or plant; and to generate the transgenic plant cell or the transgenic plant that contains the transcribed iRNA molecule.

To impart coleopteran and/or hemipteran pest resistance to a transgenic plant, a recombinant DNA molecule may, for example, be transcribed into an iRNA molecule, such as a dsRNA molecule, an siRNA molecule, an shRNA molecule, an miRNA molecule, or an hpRNA molecule. In some embodiments, an RNA molecule transcribed from a recombinant DNA molecule may form a dsRNA molecule within the tissues or fluids of the recombinant plant. Such a dsRNA molecule may be comprised in part of a nucleotide sequence that is identical to a corresponding nucleotide sequence transcribed from a DNA sequence within a coleopteran and/or hemipteran pest of a type that may infest the host plant. Expression of a target gene within the coleopteran and/or hemipteran pest is suppressed by the ingested dsRNA molecule, and the suppression of expression of the target gene in the coleopteran and/or hemipteran pest results in, for example, cessation of feeding by the coleopteran and/or hemipteran pest, with an ultimate result being, for example, that the transgenic plant is protected from further damage by the coleopteran and/or hemipteran pest. The modulatory effects of dsRNA molecules have been shown to be applicable to a variety of genes expressed in pests, including, for example, endogenous genes responsible for cellular metabolism or cellular transformation, including house-keeping genes; transcription factors; molting-related genes; and other genes which encode polypeptides involved in cellular metabolism or normal growth and development.

For transcription from a transgene in vivo or an expression construct, a regulatory region (e.g., promoter, enhancer, silencer, and polyadenylation signal) may be used in some embodiments to transcribe the RNA strand (or strands). Therefore, in some embodiments, as set forth, supra, a nucleotide sequence for use in producing iRNA molecules may be operably linked to one or more promoter sequences functional in a plant host cell. The promoter may be an endogenous promoter, normally resident in the host genome. The nucleotide sequence of the present invention, under the control of an operably linked promoter sequence, may further be flanked by additional sequences that advantageously affect its transcription and/or the stability of a resulting transcript. Such sequences may be located upstream of the operably linked promoter, downstream of the 3' end of the expression construct, and may occur both upstream of the promoter and downstream of the 3' end of the expression construct.

Some embodiments provide methods for reducing the damage to a host plant (e.g., a corn or soybean plant) caused by a coleopteran and/or hemipteran pest that feeds on the plant, wherein the method comprises providing in the host plant a transformed plant cell expressing at least one nucleic acid molecule of the invention, wherein the nucleic acid molecule(s) functions upon being taken up by the coleopteran and/or hemipteran pest to inhibit the expression of a target sequence within the coleopteran and/or hemipteran pest, which inhibition of expression results in mortality, reduced growth, and/or reduced reproduction of the coleopteran and/or hemipteran pest, thereby reducing the damage to the host plant caused by the coleopteran and/or hemipteran pest. In some embodiments, the nucleic acid molecule(s) comprise dsRNA molecules. In these and further embodiments, the nucleic acid molecule(s) comprise dsRNA molecules that each comprise more than one nucleotide sequence that is specifically hybridizable to a nucleic acid molecule expressed in a coleopteran and/or hemipteran pest cell. In some embodiments, the nucleic acid molecule(s) consist of one nucleotide sequence that is specifically hybridizable to a nucleic acid molecule expressed in a coleopteran and/or hemipteran pest cell.

In other embodiments, a method for increasing the yield of a corn or soybean crop is provided, wherein the method comprises introducing into a corn or soybean plant at least one nucleic acid molecule of the invention; cultivating the corn or soybean plant to allow the expression of an iRNA molecule comprising the nucleic acid sequence, wherein expression of an iRNA molecule comprising the nucleic acid sequence inhibits coleopteran and/or hemipteran pest growth and/or coleopteran and/or hemipteran pest damage, thereby reducing or eliminating a loss of yield due to coleopteran and/or hemipteran pest infestation. In some embodiments, the iRNA molecule is a dsRNA molecule. In these and further embodiments, the nucleic acid molecule(s) comprise dsRNA molecules that each comprise more than one nucleotide sequence that is specifically hybridizable to a nucleic acid molecule expressed in a coleopteran and/or hemipteran pest cell. In some embodiments, the nucleic acid molecule(s) consists of one nucleotide sequence that is specifically hybridizable to a nucleic acid molecule expressed in a coleopteran and/or hemipteran pest cell.

In particular embodiments, a method for modulating the expression of a target gene in a coleopteran and/or hemipteran pest is provided, the method comprising: transforming a plant cell with a vector comprising a nucleic acid sequence encoding at least one nucleic acid molecule of the invention, wherein the nucleotide sequence is operatively-linked to a promoter and a transcription termination sequence; culturing the transformed plant cell under conditions sufficient to allow for development of a plant cell culture including a plurality of transformed plant cells; selecting for transformed plant cells that have integrated the nucleic acid molecule into their genomes; screening the transformed plant cells for expression of an iRNA molecule encoded by the integrated nucleic acid molecule; selecting a transgenic plant cell that expresses the iRNA molecule; and feeding the selected transgenic plant cell to the coleopteran and/or hemipteran pest. Plants may also be regenerated from transformed plant cells that express an iRNA molecule encoded by the integrated nucleic acid molecule. In some embodiments, the iRNA molecule is a dsRNA molecule. In these and further embodiments, the nucleic acid molecule(s) comprise dsRNA molecules that each comprise more than one nucleotide sequence that is specifically hybridizable to a nucleic acid molecule expressed in a coleopteran and/or hemipteran pest cell. In some embodiments, the nucleic acid molecule(s) consists of one nucleotide sequence that is specifically hybridizable to a nucleic acid molecule expressed in a coleopteran and/or hemipteran pest cell.

iRNA molecules of the invention can be incorporated within the seeds of a plant species (e.g., corn or soybean), either as a product of expression from a recombinant gene incorporated into a genome of the plant cells, or incorporated into a coating or seed treatment that is applied to the seed before planting. A plant cell comprising a recombinant gene is considered to be a transgenic event. Also included in embodiments of the invention are delivery systems for the delivery of iRNA molecules to coleopteran and/or hemipteran pests. For example, the iRNA molecules of the invention may be directly introduced into the cells of a coleopteran and/or hemipteran pest. Methods for introduction may include direct mixing of iRNA with plant tissue from a host for the coleopteran and/or hemipteran pest, as well as application of compositions comprising iRNA molecules of the invention to host plant tissue. For example, iRNA molecules may be sprayed onto a plant surface. Alternatively, an iRNA molecule may be expressed by a microorganism, and the microorganism may be applied onto the plant surface, or introduced into a root or stem by a physical means such as an injection. As discussed, supra, a transgenic plant may also be genetically engineered to express at least one iRNA molecule in an amount sufficient to kill the coleopteran and/or hemipteran pests known to infest the plant. iRNA molecules produced by chemical or enzymatic synthesis may also be formulated in a manner consistent with common agricultural practices, and used as spray-on products for controlling plant damage by a coleopteran and/or hemipteran pest. The formulations may include the appropriate stickers and wetters required for efficient foliar coverage, as well as UV protectants to protect iRNA molecules (e.g., dsRNA molecules) from UV damage. Such additives are commonly used in the bioinsecticide industry, and are well known to those skilled in the art. Such applications may be combined with other spray-on insecticide applications (biologically based or otherwise) to enhance plant protection from coleopteran and/or hemipteran pests.

All references, including publications, patents, and patent applications, cited herein are hereby incorporated by reference to the extent they are not inconsistent with the explicit details of this disclosure, and are so incorporated to the same extent as if each reference were individually and specifically indicated to be incorporated by reference and were set forth in its entirety herein. The references discussed herein are provided solely for their disclosure prior to the filing date of the present application. Nothing herein is to be construed as an admission that the inventors are not entitled to antedate such disclosure by virtue of prior invention.

The following EXAMPLES are provided to illustrate certain particular features and/or aspects. These EXAMPLES should not be construed to limit the disclosure to the particular features or aspects described.

EXAMPLES

Example 1

Identification of Candidate Target Genes

Multiple stages of WCR (*Diabrotica virgifera virgifera* LeConte) development were selected for pooled transcriptome generation to provide candidate target gene sequences for control by RNAi transgenic plant insect resistance technology.

In one exemplification, total RNA was isolated from about 0.9 gm whole first-instar WCR larvae; (4 to 5 days post-hatch; held at 16° C.), and purified using the following phenol/TRI REAGENT®-based method (MOLECULAR RESEARCH CENTER, Cincinnati, Ohio):

Larvae were homogenized at room temperature in a 15 mL homogenizer with 10 mL of TRI REAGENT® until a homogenous suspension was obtained. Following 5 min. incubation at room temperature, the homogenate was dispensed into 1.5 mL microfuge tubes (1 mL per tube), 200 μL of chloroform was added, and the mixture was vigorously shaken for 15 seconds. After allowing the extraction to sit at room temperature for 10 min, the phases were separated by centrifugation at 12,000×g at 4° C. The upper phase (comprising about 0.6 mL) was carefully transferred into another sterile 1.5 mL tube, and an equal volume of room temperature isopropanol was added. After incubation at room temperature for 5 to 10 min, the mixture was centrifuged 8 min at 12,000×g (4° C. or 25° C.).

The supernatant was carefully removed and discarded, and the RNA pellet was washed twice by vortexing with 75% ethanol, with recovery by centrifugation for 5 min at 7,500×g (4° C. or 25° C.) after each wash. The ethanol was carefully removed, the pellet was allowed to air-dry for 3 to 5 min, and then was dissolved in nuclease-free sterile water. RNA concentration was determined by measuring the absorbance (A) at 260 nm and 280 nm. A typical extraction from about 0.9 gm of larvae yielded over 1 mg of total RNA, with an $A_{260}/A_{280}$ ratio of 1.9. The RNA thus extracted was stored at −80° C. until further processed.

RNA quality was determined by running an aliquot through a 1% agarose gel. The agarose gel solution was made using autoclaved 10×TAE buffer (Tris-acetate EDTA; 1× concentration is 0.04 M Tris-acetate, 1 mM EDTA (ethylenediamine tetra-acetic acid sodium salt), pH 8.0) diluted with DEPC (diethyl pyrocarbonate)-treated water in an autoclaved container. 1×TAE was used as the running buffer. Before use, the electrophoresis tank and the well-forming comb were cleaned with RNase AWAY® (INVITROGEN INC., Carlsbad, Calif.). Two μL of RNA sample were mixed with 8 L of TE buffer (10 mM Tris HCl pH 7.0; 1 mM EDTA) and 10 μL of RNA sample buffer (NOVAGEN® Catalog No 70606; EMD4 Bioscience, Gibbstown, N.J.). The sample was heated at 70° C. for 3 min, cooled to room temperature, and 5 μL (containing 1 μg to 2 μg RNA) were loaded per well. Commercially available RNA molecular weight markers were simultaneously run in separate wells for molecular size comparison. The gel was run at 60 volts for 2 hr.

A normalized cDNA library was prepared from the larval total RNA by a commercial service provider (EUROFINS MWG Operon, Huntsville, Ala.), using random priming. The normalized larval cDNA library was sequenced at ½ plate scale by GS FLX 454 Titanium™ series chemistry at EUROFINS MWG Operon, which resulted in over 600,000 reads with an average read length of 348 bp. 350,000 reads were assembled into over 50,000 contigs. Both the unassembled reads and the contigs were converted into BLASTab1e databases using the publicly available program, FORMATDB (available from NCBI).

Total RNA and normalized cDNA libraries were similarly prepared from materials harvested at other WCR developmental stages. A pooled transcriptome library for target gene screening was constructed by combining cDNA library members representing the various developmental stages.

Candidate genes for RNAi targeting were selected using information regarding lethal RNAi effects of particular genes in other insects such as *Drosophila* and *Hemipteran*. These genes were hypothesized to be essential for survival and growth in coleopteran and/or hemipteran insects. Selected target gene homologs were identified in the transcriptome sequence database as described below. Full-length or partial sequences of the target genes were amplified by PCR to prepare templates for double-stranded RNA (dsRNA) production.

TBLASTN searches using candidate protein coding sequences were run against BLASTable databases containing the unassembled *Diabrotica* sequence reads or the assembled contigs. Significant hits to a *Diabrotica* sequence (defined as better than $e^{-20}$ for contigs homologies and better than $e^{-10}$ for unassembled sequence reads homologies) were confirmed using BLASTX against the NCBI non-redundant database. The results of this BLASTX search confirmed that the *Diabrotica* homolog candidate gene sequences identified in the TBLASTN search indeed comprised *Diabrotica* genes, or were the best hit to the non-*Diabrotica* candidate gene sequence present in the *Diabrotica* sequences. In most cases, *Hemipteran* candidate genes which were annotated as encoding a protein gave an unambiguous sequence homology to a sequence or sequences in the *Diabrotica* transcriptome sequences. In a few cases, it was clear that some of the *Diabrotica* contigs or unassembled sequence reads selected by homology to a non-*Diabrotica* candidate gene overlapped, and that the assembly of the contigs had failed to join these overlaps. In those cases, SEQUENCHER® v4.9 (GENE CODES CORPORATION, Ann Arbor, Mich.) was used to assemble the sequences into longer contigs.

A candidate target gene encoding *Diabrotica rop* (SEQ ID NO:1) was identified as a gene that may lead to coleopteran pest mortality, inhibition of growth, inhibition of development, or inhibition of reproduction in WCR.

Genes with Homology to WCR rop

ROP contains a conserved domain of the Sec1 family (pfam00995). Sec1 family proteins are known to be involved in synaptic transmission and general secretion. Other *Diabrotica virgifera* proteins that also contain this domain may share structural and/or functional properties, and thus a gene that encodes one of these proteins may comprise a candidate target gene that may lead to coleopteran pest mortality, inhibition of growth, inhibition of development, or inhibition of reproduction in WCR.

In *Drosophila melanogaster*, genes encoding Ras and Ras opposite (rop) are divergently transcribed from a bidirectional promoter (Harrison et al., (1995) Genetics 139:1701-1709). The 68 kDa ROP protein shares sequence homology with *Saccharomyces cerevisiae* proteins SLT1, SEC1 and SLP1, all of which are involved in vesicle trafficking among yeast cellular compartments (Salzberg et al., (1993) Development 117:1309-1319). Further, ROP regulates neurotransmitter release in a dosage-dependent manner (Wu et al., (1998) EMBO Journal 17:127-139). rop dsRNA transgenes can be combined with other dsRNA molecules to provide redundant RNAi targeting and synergistic RNAi effects. Transgenic corn events expressing dsRNA that targets rop are useful for preventing root feeding damage by corn rootworm. rop dsRNA transgenes represent new modes of action for combining with *Bacillus thuringiensis* insecticidal protein technology in Insect Resistance Management gene pyramids to mitigate against the development of rootworm populations resistant to either of these rootworm control technologies.

Full-length or partial clones of sequences of a *Diabrotica* candidate gene, rop, were used to generate PCR amplicons for dsRNA synthesis.

SEQ ID NO:1 shows a 4816 bp DNA sequence of *Diabrotica* rop.

SEQ ID NO:3 shows a 392 bp DNA sequence of rop reg1.

SEQ ID NO:4 shows a 627 bp DNA sequence of rop reg2.

SEQ ID NO:114 shows a 201 bp DNA sequence of rop v3.

Example 2

Amplification of Target Genes to Produce dsRNA

Primers were designed to amplify portions of coding regions of each target gene by PCR. (See Table 1 and SEQ ID NOs:112 and 113). Where appropriate, a T7 phage promoter sequence (TTAATACGACTCACTATAGGGAGA; SEQ ID NO:5) was incorporated into the 5' ends of the amplified sense or antisense strands. See Table 1. Total RNA was extracted from WCR, and first-strand cDNA was used as template for PCR reactions using opposing primers positioned to amplify all or part of the native target gene sequence. dsRNA was also amplified from a DNA clone comprising the coding region for a yellow fluorescent protein (YFP) (SEQ ID NO:6; Shagin et al. (2004) Mol. Biol. Evol. 21(5):841-50).

TABLE 1

Primers and Primer Pairs used to amplify portions of coding regions of exemplary rop target gene and YFP negative control gene.

| | Gene ID | Primer ID | SEQ ID NO: | Sequence |
|---|---|---|---|---|
| Pair 1 | rop reg1 | ROP-F1T7 | 7 | TTAATACGACTCACTATAGGGAGAACCATGGCGTTAAAGAACCAAG |
| | | ROP-R1T7 | 8 | TTAATACGACTCACTATAGGGAGAGGGTGGTGGCACAAGGTACT |
| Pair 2 | rop reg2 | ROP-F2T7 | 9 | TTAATACGACTCACTATAGGGAGACTCGACCGAGGTTTCGAC |
| | | ROP-R2T7 | 10 | TTAATACGACTCACTATAGGGAGATAACTGAAGGTTGGCGATGGTC |
| Pair 3 | YFP | YFP-F_T7 | 11 | TTAATACGACTCACTATAGGGAGACACCATGGGCTCCAGCGGCGCCC |
| | | YFP-R_T7 | 12 | TTAATACGACTCACTATAGGGAGAAGATCTTGAAGGCGCTCTTCAGG |

Example 3

RNAi Constructs

Template Preparation by PCR and dsRNA Synthesis.

A strategy used to provide specific templates for rop and YFP dsRNA production is shown in FIG. 1. Template DNAs intended for use in rop dsRNA synthesis were prepared by PCR using the primer pairs in Table 1 and (as PCR template) first-strand cDNA prepared from total RNA isolated from WCR first-instar larvae. For each selected rop and YFP target gene region, PCR amplifications introduced a T7 promoter sequence at the 5' ends of the amplified sense and antisense strands (the YFP segment was amplified from a DNA clone of the YFP coding region). The two PCR amplified fragments for each region of the target genes were then mixed in approximately equal amounts, and the mixture was used as transcription template for dsRNA production. See FIG. 1. The sequences of the dsRNA templates amplified with the particular primer pairs were: SEQ ID NO:3 (rop reg1), SEQ ID NO:4 (rop reg2), SEQ ID NO:114 (rop v3), and YFP (SEQ ID NO:6). Double-stranded RNA for insect bioassay was synthesized and purified using an AMBION® MEGASCRIPT® RNAi kit following the manufacturer's instructions (INVITROGEN). The concentrations of dsRNAs were measured using a NANODROP® 8000 spectrophotometer (THERMO SCIENTIFIC, Wilmington, Del.).

Construction of Plant Transformation Vectors.

Entry vectors (pDAB112649 and pDAB115766) harboring a target gene construct for hairpin formation comprising segments of rop (SEQ ID NO:1) were assembled using a combination of chemically synthesized fragments (DNA2.0, Menlo Park, Calif.) and standard molecular cloning methods. Intramolecular hairpin formation by RNA primary transcripts was facilitated by arranging (within a single transcription unit) two copies of a target gene segment in opposite orientation to one another, the two segments being separated by an ST-LS1 intron sequence (SEQ ID NO:16) (Vancanneyt et al. (1990) Mol. Gen. Genet. 220(2):245-50). Thus, the primary mRNA transcript contains the two rop gene segment sequences as large inverted repeats of one another, separated by the intron sequence. A copy of a maize ubiquitin 1 promoter (U.S. Pat. No. 5,510,474) was used to drive production of the primary mRNA hairpin transcript, and a fragment comprising a 3' untranslated region from a maize peroxidase 5 gene (ZmPer5 3'UTR v2; U.S. Pat. No. 6,699,984) was used to terminate transcription of the hairpin-RNA-expressing gene.

Entry vector pDAB112649 comprises a rop v1 hairpin-RNA construct (SEQ ID NO:13) that comprises a segment of rop (SEQ ID NO:1)

Entry vector pDAB115766 comprises a rop v3 hairpin-RNA construct (SEQ ID NO:14) that comprises a segment of rop (SEQ ID NO:1) distinct from that found in pDAB112649.

Entry vectors pDAB112649 and pDAB115766 described above were used in standard GATEWAY® recombination reactions with a typical binary destination vector (pDAB109805) to produce rop hairpin RNA expression transformation vectors for *Agrobacterium*-mediated maize embryo transformations (pDAB114515 and pDAB115770), respectively).

A negative control binary vector, pDAB110853, which comprises a gene that expresses a YFP hairpin dsRNA, was constructed by means of standard GATEWAY® recombination reactions with a typical binary destination vector (pDAB109805) and entry vector pDAB101670. Entry Vector pDAB101670 comprises a YFP hairpin sequence (SEQ ID NO:15) under the expression control of a maize ubiquitin 1 promoter (as above) and a fragment comprising a 3' untranslated region from a maize peroxidase 5 gene (as above).

Binary destination vector pDAB109805 comprises a herbicide resistance gene (aryloxyalknoate dioxygenase; AAD-1 v3) (U.S. Pat. No. 7,838,733(B2), and Wright et al. (2010) Proc. Natl. Acad. Sci. U.S.A. 107:20240-5) under the regulation of a sugarcane bacilliform badnavirus (ScBV) promoter (Schenk et al. (1999) Plant Molec. Biol. 39:1221-30). A synthetic 5'UTR sequence, comprised of sequences from a Maize Streak Virus (MSV) coat protein gene 5'UTR and intron 6 from a maize Alcohol Dehydrogenase 1 (ADH1) gene, is positioned between the 3' end of the SCBV promoter segment and the start codon of the AAD-1 coding region. A fragment comprising a 3' untranslated region from a maize lipase gene (ZmLip 3'UTR; U.S. Pat. No. 7,179,902) was used to terminate transcription of the AAD-1 mRNA.

A further negative control binary vector, pDAB110556, which comprises a gene that expresses a YFP protein, was constructed by means of standard GATEWAY® recombination reactions with a typical binary destination vector (pDAB9989) and entry vector pDAB100287. Binary destination vector pDAB9989 comprises a herbicide resistance gene (aryloxyalknoate dioxygenase; AAD-1 v3) (as above) under the expression regulation of a maize ubiquitin 1 promoter (as above) and a fragment comprising a 3' untranslated region from a maize lipase gene (ZmLip 3'UTR; as above). Entry Vector pDAB100287 comprises a YFP coding region (SEQ ID NO:17) under the expression control of a maize ubiquitin 1 promoter (as above) and a fragment comprising a 3' untranslated region from a maize peroxidase 5 gene (as above).

SEQ ID NO:13 presents an rop v1 hairpin-RNA-forming sequence as found in pDAB114515.

SEQ ID NO:14 presents an rop v3 hairpin-RNA-forming sequence as found in pDAB115770.

Example 4

Insect Diet Bioassays

Sample Preparation and Bioassays

A number of dsRNA molecules (including those corresponding to rop reg1 (SEQ ID NO:3), rop reg2 (SEQ ID NO:4), and rop v3 (SEQ ID NO:114)) were synthesized and purified using a MEGASCRIPT® RNAi kit. The purified dsRNA molecules were prepared in TE buffer, and all bioassays contained a control treatment consisting of this buffer, which served as a background check for mortality or growth inhibition of WCR (*Diabrotica virgifera virgifera* LeConte). The concentrations of dsRNA molecules in the bioassay buffer were measured using a NANODROP® 8000 spectrophotometer (THERMO SCIENTIFIC, Wilmington, Del.).

Samples were tested for insect activity in bioassays conducted with neonate insect larvae on artificial insect diet. WCR eggs were obtained from CROP CHARACTERISTICS, INC. (Farmington, Minn.).

The bioassays were conducted in 128-well plastic trays specifically designed for insect bioassays (C-D INTERNATIONAL, Pitman, N.J.). Each well contained approximately 1.0 mL of an artificial diet designed for growth of coleopteran insects. A 60 μL aliquot of dsRNA sample was delivered by pipette onto the surface of the diet of each well (40 μL/$cm^2$). dsRNA sample concentrations were calculated as the amount of dsRNA per square centimeter (ng/$cm^2$) of surface area (1.5 $cm^2$) in the well. The treated trays were held in a fume hood until the liquid on the diet surface evaporated or was absorbed into the diet.

Within a few hours of eclosion, individual larvae were picked up with a moistened camel hair brush and deposited on the treated diet (one or two larvae per well). The infested wells of the 128-well plastic trays were then sealed with adhesive sheets of clear plastic, and vented to allow gas exchange. Bioassay trays were held under controlled environmental conditions (28° C., ~40% Relative Humidity, 16:8 (Light:Dark)) for 9 days, after which time the total number of insects exposed to each sample, the number of dead insects, and the weight of surviving insects were recorded. Average percent mortality and average growth inhibition were calculated for each treatment. Growth inhibition (GI) was calculated as follows:

$$GI=[1-(TWIT/TNIT)/(TWIBC/TNIBC)]$$

where TWIT is the Total Weight of live Insects in the Treatment;

TNIT is the Total Number of Insects in the Treatment;

TWIBC is the Total Weight of live Insects in the Background Check (Buffer control); and TNIBC is the Total Number of Insects in the Background Check (Buffer control).

Statistical analysis was done using JMP® software (SAS, Cary, N.C.).

$LC_{50}$ (Lethal Concentration) is defined as the dosage at which 50% of the test insects are killed. $GI_{50}$ (Growth Inhibition) is defined as the dosage at which the mean growth (e.g. live weight) of the test insects is 50% of the mean value seen in Background Check samples.

Replicated bioassays demonstrated that ingestion of particular samples resulted in a surprising and unexpected mortality and growth inhibition of corn rootworm larvae.

Example 5

Screening of Candidate Target Genes

Synthetic dsRNA designed to inhibit target gene sequences identified in EXAMPLE 1 caused mortality and growth inhibition when administered to WCR in diet-based assays. rop reg1, rop reg2, and rop v3 were observed to exhibit greatly increased efficacy in this assay over other dsRNAs screened.

Replicated bioassays demonstrated that ingestion of dsRNA preparations derived from rop reg1, rop reg2, and rop v3 each resulted in mortality and/or growth inhibition of western corn rootworm larvae. Table 2 and Table 3 show the results of diet-based feeding bioassays of WCR larvae following 9-day exposure to these dsRNAs, as well as the results obtained with a negative control sample of dsRNA prepared from a yellow fluorescent protein (YFP) coding region (SEQ ID NO:6).

It has previously been suggested that certain genes of *Diabrotica* spp. may be exploited for RNAi-mediated insect control. See U.S. Patent Publication No. 2007/0124836, which discloses 906 sequences, and U.S. Pat. No. 7,614,924, which discloses 9,112 sequences. However, it was determined that many genes suggested to have utility for RNAi-mediated insect control are not efficacious in controlling *Diabrotica*. It was also determined that sequences rop reg1, rop reg2, and rop v3 each provide surprising and unexpected superior control of *Diabrotica*, compared to other genes suggested to have utility for RNAi-mediated insect control.

For example, Annexin, Beta spectrin 2, and mtRP-L4 were each suggested in U.S. Pat. No. 7,614,924 to be efficacious in RNAi-mediated insect control. SEQ ID NO:18 is the DNA sequence of Annexin region 1 (Reg 1), and SEQ ID NO:19 is the DNA sequence of Annexin region 2 (Reg 2). SEQ ID NO:20 is the DNA sequence of Beta spectrin 2 region 1 (Reg 1), and SEQ ID NO:21 is the DNA sequence of Beta spectrin 2 region 2 (Reg2). SEQ ID NO:22 is the DNA sequence of mtRP-L4 region 1 (Reg 1), and SEQ ID NO:23 is the DNA sequence of mtRP-L4 region 2 (Reg 2). A YFP sequence (SEQ ID NO:6) was also used to produce dsRNA as a negative control.

Figure 2:
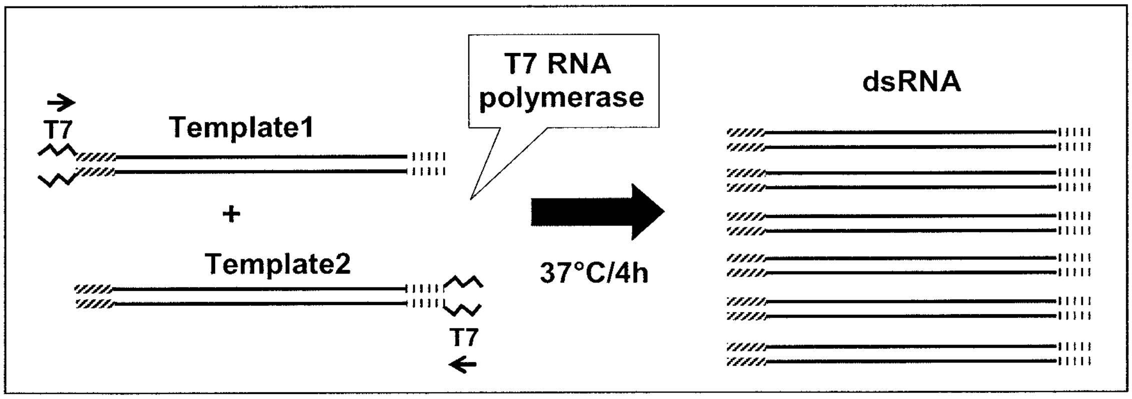
FIG. 2 is a pictorial representation of a strategy for the generation of dsRNA from two transcription templates.

Each of the aforementioned sequences was used to produce dsRNA by the methods of EXAMPLE 3. The strategy used to provide specific templates for dsRNA production is shown in FIG. 2. Template DNAs intended for use in dsRNA synthesis were prepared by PCR using the primer pairs in Table 4 and (as PCR template) first-strand cDNA prepared from total RNA isolated from WCR first-instar larvae. (YFP was amplified from a DNA clone.) For each selected target gene region, two separate PCR amplifications were performed. The first PCR amplification introduced a T7 promoter sequence at the 5' end of the amplified sense strands. The second reaction incorporated the T7 promoter sequence at the 5' ends of the antisense strands. The two PCR amplified fragments for each region of the target genes were then mixed in approximately equal amounts, and the mixture was used as transcription template for dsRNA production.

TABLE 2

Results of rop dsRNA diet feeding assays obtained with western corn rootworm larvae after 9 days of feeding. ANOVA analysis found significance differences in Mean % Mortality and Mean % Growth Inhibition (GI). Means were separated using the Tukey-Kramer test.

| Gene Name | Dose ($ng/cm^2$) | No. Rows | Mean (% Mortality) ± SEM* | Mean (GI) ± SEM |
|---|---|---|---|---|
| rop reg1 | 500 | 4 | 83.23 ± 1.75 A | 0.90 ± 0.01 A |
| rop reg2 | 500 | 4 | 86.37 ± 5.54 A | 0.88 ± 0.10 A |
| rop v3 | 500 | 14 | 79.84 ± 4.16 A | 0.94 ± 0.02 A |
| TE** | 0 | 4 | 13.23 ± 2.81 B | 0.00 ± 0.00 B |
| WATER | 0 | 4 | 9.01 ± 2.8 B | 0.0 ± 0.00 B |
| YFP*** | 500 | 4 | 8.82 ± 5.63 B | 0.09 ± 0.08 B |

*SEM = Standard Error of the Mean. Letters in parentheses designate statistical levels. Levels not connected by same letter are significantly different ($P < 0.05$).

**TE = Tris HCl (10 mM) plus EDTA (1 mM) buffer, pH 8.

***YFP = Yellow Fluorescent Protein

TABLE 3

Summary of oral potency of rop dsRNA on WCR larvae ($ng/cm^2$).

| Gene Name | $LC_{50}$ | Range | $GI_{50}$ | Range |
|---|---|---|---|---|
| rop reg1 | 20.4 | 13.63 to 30.11 | 5.91 | 4.29 to 8.15 |
| rop reg2 | 29.67 | 19.32 to 45.41 | 7.07 | 2.15 to 23.22 |
| rop v3 | 25.35 | 18.46 to 34.47 | 10.06 | 6.32 to 16.00 |

See FIG. 2. Double-stranded RNA was synthesized and purified using an AMBION® MEGAscript® RNAi kit following the manufacturer's instructions (INVITROGEN). The concentrations of dsRNAs were measured using a NANODROP® 8000 spectrophotometer (THERMO SCIENTIFIC, Wilmington, Del.). and the dsRNAs were each tested by the same diet-based bioassay methods described above. Table 4 lists the sequences of the primers used to produce the Annexin Reg1, Annexin Reg2, Beta spectrin 2

Reg1, Beta spectrin 2 Reg2, mtRP-L4 Reg1, and mtRP-L4 Reg2 dsRNA molecules. YFP primer sequences for use in the method depicted in FIG. 2. are also listed in Table 4. Table 5 presents the results of diet-based feeding bioassays of WCR larvae following 9-day exposure to these dsRNA molecules. Replicated bioassays demonstrated that ingestion of these dsRNAs resulted in no mortality or growth inhibition of western corn rootworm larvae above that seen with control samples of TE buffer, Water, or YFP protein.

TABLE 4

Primers and Primer Pairs used to amplify portions of coding regions of genes.

| | Gene (Region) | Primer ID | SEQ ID NO: | Sequence |
|---|---|---|---|---|
| Pair 4 | Annexin (Reg 1) | Ann-F1_T7 | 24 | TTAATACGACTCACTATAGGGAGAGCTC CAACAGTGGTTCCTTATC |
| | Annexin (Reg 1) | Ann-R1 | 25 | CTAATAATTCTTTTTTAATGTTCCTGAGG |
| Pair 5 | Annexin (Reg 1) | Ann-F1 | 26 | GCTCCAACAGTGGTTCCTTATC |
| | Annexin (Reg 1) | Ann-R1_T7 | 27 | TTAATACGACTCACTATAGGGAGACTAA TAATTCTTTTTTAATGTTCCTGAGG |
| Pair 6 | Annexin (Reg 2) | Ann-F2_T7 | 28 | TTAATACGACTCACTATAGGGAGATTGT TACAAGCTGGAGAACTTCTC |
| | Annexin (Reg 2) | Ann-R2 | 29 | CTTAACCAACAACGGCTAATAAGG |
| Pair 7 | Annexin (Reg 2) | Ann-F2 | 30 | TTGTTACAAGCTGGAGAACTTCTC |
| | Annexin (Reg 2) | Ann-R2T7 | 31 | TTAATACGACTCACTATAGGGAGACTTA ACCAACAACGGCTAATAAGG |
| Pair 8 | Beta-spect2 (Reg 1) | Betasp2-F1_T7 | 32 | TTAATACGACTCACTATAGGGAGAAGAT GTTGGCTGCATCTAGAGAA |
| | Beta-spect2 (Reg 1) | Betasp2-R1 | 33 | GTCCATTCGTCCATCCACTGCA |
| Pair 9 | Beta-spect2 (Reg 1) | Betasp2-F1 | 34 | AGATGTTGGCTGCATCTAGAGAA |
| | Beta-spect2 (Reg 1) | Betasp2-R1_T7 | 35 | TTAATACGACTCACTATAGGGAGAGTCC ATTCGTCCATCCACTGCA |
| Pair 10 | Beta-spect2 (Reg 2) | Betasp2-F2_T7 | 36 | TTAATACGACTCACTATAGGGAGAGCAG ATGAACACCAGCGAGAAA |
| | Beta-spect2 (Reg 2) | Betasp2-R2 | 37 | CTGGGCAGCTTCTTGTTTCCTC |
| Pair 11 | Beta-spect2 (Reg 2) | Betasp2-F2 | 38 | GCAGATGAACACCAGCGAGAAA |
| | Beta-spect2 (Reg 2) | Betasp2-R2_T7 | 39 | TTAATACGACTCACTATAGGGAGACTGG GCAGCTTCTTGTTTCCTC |
| Pair 12 | mtRP-L4 (Reg 1) | L4-F1_T7 | 40 | TTAATACGACTCACTATAGGGAGAAGTG AAATGTTAGCAAATATAACATCC |
| | mtRP-L4 (Reg 1) | L4-R1 | 41 | ACCTCTCACTTCAAATCTTGACTTTG |
| Pair 13 | mtRP-L4 (Reg 1) | L4-F1 | 42 | AGTGAAATGTTAGCAAATATAACATCC |
| | mtRP-L4 (Reg 1) | L4-R1_T7 | 43 | TTAATACGACTCACTATAGGGAGAACCT CTCACTTCAAATCTTGACTTTG |
| Pair 14 | mtRP-L4 (Reg 2) | L4-F2_T7 | 44 | TTAATACGACTCACTATAGGGAGACAAA GTCAAGATTTGAAGTGAGAGGT |
| | mtRP-L4 (Reg 2) | L4-R2 | 45 | CTACAAATAAAACAAGAAGGACCCC |
| Pair 15 | mtRP-L4 (Reg 2) | L4-F2 | 46 | CAAAGTCAAGATTTGAAGTGAGAGGT |
| | mtRP-L4 (Reg 2) | L4-R2_T7 | 47 | TTAATACGACTCACTATAGGGAGACTAC AAATAAAACAAGAAGGACCCC |

TABLE 5

Results of diet feeding assays obtained with western corn rootworm larvae after 9 days.

| Gene Name | Dose ($ng/cm^2$) | Mean Live Larval Weight (mg) | Mean % Mortality | Mean Growth Inhibition |
|---|---|---|---|---|
| Annexin-Reg 1 | 1000 | 0.545 | 0 | −0.262 |
| Annexin-Reg 2 | 1000 | 0.565 | 0 | −0.301 |
| Beta spectrin2 Reg 1 | 1000 | 0.340 | 12 | −0.014 |
| Beta spectrin2 Reg 2 | 1000 | 0.465 | 18 | −0.367 |
| mtRP-L4 Reg 1 | 1000 | 0.305 | 4 | −0.168 |
| mtRP-L4 Reg 2 | 1000 | 0.305 | 7 | −0.180 |
| TE buffer* | 0 | 0.430 | 13 | 0.000 |
| Water | 0 | 0.535 | 12 | 0.000 |
| YFP** | 1000 | 0.480 | 9 | −0.386 |

*TE = Tris HCl (10 mM) plus EDTA (1 mM) buffer, pH 8.
**YFP = Yellow Fluorescent Protein

Example 6

Production of Transgenic Maize Tissues Comprising Insecticidal Hairpin dsRNAs

*Agrobacterium*-Mediated Transformation

Transgenic maize cells, tissues, and plants that produce one or more insecticidal dsRNA molecules (for example, at least one dsRNA molecule including a dsRNA molecule targeting a gene comprising rop; SEQ ID NO:1) through expression of a chimeric gene stably-integrated into the plant genome were produced following *Agrobacterium*-mediated transformation. Maize transformation methods employing superbinary or binary transformation vectors are known in the art, as described, for example, in U.S. Pat. No. 8,304,604, which is herein incorporated by reference in its entirety. Transformed tissues were selected by their ability to grow on Haloxyfop-containing medium and were screened for dsRNA production, as appropriate. Portions of such transformed tissue cultures may be presented to neonate corn rootworm larvae for bioassay, essentially as described in EXAMPLE 4.

*Agrobacterium* Culture Initiation

Glycerol stocks of *Agrobacterium* strain DAt13192 cells (WO 2012/016222A2) harboring a binary transformation vector pDAB114515, pDAB115770, pDAB110853 or pDAB110556 described above (EXAMPLE 3) were streaked on AB minimal medium plates (Watson, et al., (1975) J. Bacteriol. 123:255-264) containing appropriate antibiotics and were grown at 20° C. for 3 days. The cultures were then streaked onto YEP plates (gm/L: yeast extract, 10; Peptone, 10; NaCl 5) containing the same antibiotics and were incubated at 20° C. for 1 day.

*Agrobacterium* Culture

On the day of an experiment, a stock solution of Inoculation Medium and acetosyringone was prepared in a volume appropriate to the number of constructs in the experiment and pipetted into a sterile, disposable, 250 mL flask. Inoculation Medium (Frame et al. (2011) *Genetic Transformation Using Maize Immature Zygotic Embryos.* IN Plant Embryo Culture Methods and Protocols: Methods in Molecular Biology. T. A. Thorpe and E. C. Yeung, (Eds), Springer Science and Business Media, LLC. pp 327-341) contained: 2.2 gm/L MS salts; 1×ISU Modified MS Vitamins (Frame et al., ibid.) 68.4 gm/L sucrose; 36 gm/L glucose; 115 mg/L L-proline; and 100 mg/L myo-inositol; at pH 5.4.) Acetosyringone was added to the flask containing Inoculation Medium to a final concentration of 200 μM from a 1 M stock solution in 100% dimethyl sulfoxide and the solution was thoroughly mixed.

For each construct, 1 or 2 inoculating loops-full of *Agrobacterium* from the YEP plate were suspended in 15 mL of the Inoculation Medium/acetosyringone stock solution in a sterile, disposable, 50 mL centrifuge tube, and the optical density of the solution at 550 nm ($OD_{550}$) was measured in a spectrophotometer. The suspension was then diluted to $OD_{550}$ of 0.3 to 0.4 using additional Inoculation Medium/acetosyringone mixture. The tube of *Agrobacterium* suspension was then placed horizontally on a platform shaker set at about 75 rpm at room temperature and shaken for 1 to 4 hours while embryo dissection was performed.

Ear Sterilization and Embryo Isolation

Maize immature embryos were obtained from plants of *Zea mays* inbred line B104 (Hallauer et al. (1997) Crop Science 37:1405-1406) grown in the greenhouse and self- or sib-pollinated to produce ears. The ears were harvested approximately 10 to 12 days post-pollination. On the experimental day, de-husked ears were surface-sterilized by immersion in a 20% solution of commercial bleach (ULTRA CLOROX® Germicidal Bleach, 6.15% sodium hypochlorite; with two drops of TWEEN 20) and shaken for 20 to 30 min, followed by three rinses in sterile deionized water in a laminar flow hood. Immature zygotic embryos (1.8 to 2 2 mm long) were aseptically dissected from each ear and randomly distributed into microcentrifuge tubes containing 2.0 mL of a suspension of appropriate *Agrobacterium* cells in liquid Inoculation Medium with 200 μM acetosyringone, into which 2 μL, of 10% BREAK-THRU® 5233 surfactant (EVONIK INDUSTRIES; Essen, Germany) had been added. For a given set of experiments, embryos from pooled ears were used for each transformation.

*Agrobacterium* Co-Cultivation

Following isolation, the embryos were placed on a rocker platform for 5 minutes. The contents of the tube were then poured onto a plate of Co-cultivation Medium, which contained 4.33 gm/L MS salts; 1×ISU Modified MS Vitamins; 30 gm/L sucrose; 700 mg/L L-proline; 3.3 mg/L Dicamba in KOH (3,6-dichloro-o-anisic acid or 3,6-dichloro-2-methoxybenzoic acid); 100 mg/L myo-inositol; 100 mg/L Casein Enzymatic Hydrolysate; 15 mg/L $AgNO_3$; 200 μM acetosyringone in DMSO; and 3 gm/L GELZAN™, at pH 5.8. The liquid *Agrobacterium* suspension was removed with a sterile, disposable, transfer pipette. The embryos were then oriented with the scutellum facing up using sterile forceps with the aid of a microscope. The plate was closed, sealed with 3M® MICROPORE® medical tape, and placed in an incubator at 25° C. with continuous light at approximately 60 $\mu mol\ m^{-2}s^{-1}$ of Photosynthetically Active Radiation (PAR).

Callus Selection and Regeneration of Transgenic Events

Following the Co-Cultivation period, embryos were transferred to Resting Medium, which was composed of 4.33 gm/L MS salts; 1×ISU Modified MS Vitamins; 30 gm/L sucrose; 700 mg/L L-proline; 3.3 mg/L Dicamba in KOH; 100 mg/L myo-inositol; 100 mg/L Casein Enzymatic Hydrolysate; 15 mg/L $AgNO_3$; 0.5 gm/L MES (2-(N-morpholino) ethanesulfonic acid monohydrate; PHYTOTECHNOLOGIES LABR.; Lenexa, Kans.); 250 mg/L Carbenicillin; and 2.3 gm/L GELZAN™; at pH 5.8. No more than 36 embryos were moved to each plate. The plates were placed in a clear plastic box and incubated at 27° C. with continuous light at approximately 50 $\mu mol\ m^{-2}s^{-1}$ PAR for 7 to 10 days. Callused embryos were then transferred (<18/plate) onto Selection Medium I, which was comprised of Resting Medium (above) with 100 nM R-Haloxyfop acid (0.0362 mg/L; for selection of calli harboring the AAD-1 gene). The plates were returned to clear boxes and incubated at 27° C.

with continuous light at approximately 50 μmol $m^{-2}s^{-1}$ PAR for 7 days. Callused embryos were then transferred (<12/plate) to Selection Medium II, which is comprised of Resting Medium (above) with 500 nM R-Haloxyfop acid (0.181 mg/L). The plates were returned to clear boxes and incubated at 27° C. with continuous light at approximately 50 μmol $m^{-2}s^{-1}$ PAR for 14 days. This selection step allowed transgenic callus to further proliferate and differentiate.

Proliferating, embryogenic calli were transferred (<9/plate) to Pre-Regeneration medium. Pre-Regeneration Medium contained 4.33 gm/L MS salts; 1×ISU Modified MS Vitamins; 45 gm/L sucrose; 350 mg/L L-proline; 100 mg/L myo-inositol; 50 mg/L Casein Enzymatic Hydrolysate; 1.0 mg/L $AgNO_3$; 0.25 gm/L MES; 0.5 mg/L naphthaleneacetic acid in NaOH; 2.5 mg/L abscisic acid in ethanol; 1 mg/L 6-benzylaminopurine; 250 mg/L Carbenicillin; 2.5 gm/L GELZAN™; and 0.181 mg/L Haloxyfop acid; at pH 5.8. The plates were stored in clear boxes and incubated at 27° C. with continuous light at approximately 50 μmol $m^{-2}s^{-1}$ PAR for 7 days. Regenerating calli were then transferred (<6/plate) to Regeneration Medium in PHYTATRAYS™ (SIGMA-ALDRICH) and incubated at 28° C. with 16 hours light/8 hours dark per day (at approximately 160 μmol $m^{-2}s^{-1}$ PAR) for 14 days or until shoots and roots developed. Regeneration Medium contained 4.33 gm/L MS salts; 1×ISU Modified MS Vitamins; 60 gm/L sucrose; 100 mg/L myo-inositol; 125 mg/L Carbenicillin; 3 gm/L GELLAN™ gum; and 0.181 mg/L R-Haloxyfop acid; at pH 5.8. Small shoots with primary roots were then isolated and transferred to Elongation Medium without selection. Elongation Medium contained 4.33 gm/L MS salts; 1×ISU Modified MS Vitamins; 30 gm/L sucrose; and 3.5 gm/L GELRITE®: at pH 5.8.

Transformed plant shoots selected by their ability to grow on medium containing Haloxyfop were transplanted from PHYTATRAYS™ to small pots filled with growing medium (PROMIX BX; PREMIER TECH HORTICULTURE), covered with cups or HUMI-DOMES (ARCO PLASTICS), and then hardened-off in a CONVIRON growth chamber (27° C. day/24° C. night, 16-hour photoperiod, 50-70% RH, 200 μmol $m^{-2}s^{-1}$ PAR). In some instances, putative transgenic plantlets were analyzed for transgene relative copy number by quantitative real-time PCR assays using primers designed to detect the AAD1 herbicide tolerance gene integrated into the maize genome. Further, RNA qPCR assays were used to detect the presence of the ST-LS1 intron sequence in expressed dsRNAs of putative transformants. Selected transformed plantlets were then moved into a greenhouse for further growth and testing.

Transfer and Establishment of $T_0$ Plants in the Greenhouse for Bioassay and Seed Production When plants reached the V3-V4 stage, they were transplanted into IE CUSTOM BLEND (PROFILE/METRO MIX 160) soil mixture and grown to flowering in the greenhouse (Light Exposure Type: Photo or Assimilation; High Light Limit: 1200 PAR; 16-hour day length; 27° C. day/24° C. night).

Plants to be used for insect bioassays were transplanted from small pots to TINUS™ 350-4 ROOTRAINERS® (SPENCER-LEMAIRE INDUSTRIES, Acheson, Alberta, Canada;) (one plant per event per ROOTRAINER®). Approximately four days after transplanting to ROOTRAINERS®, plants were infested for bioassay.

Plants of the $T_1$ generation were obtained by pollinating the silks of $T_0$ transgenic plants with pollen collected from plants of non-transgenic elite inbred line B104 or other appropriate pollen donors, and planting the resultant seeds. Reciprocal crosses were performed when possible.

Example 7

Molecular Analyses of Transgenic Maize Tissues

Molecular analyses (e.g. RNA qPCR) of maize tissues were performed on samples from leaves and roots that were collected from greenhouse grown plants on the same days that root feeding damage was assessed.

Results of RNA qPCR assays for the Per5 3'UTR were used to validate expression of hairpin transgenes. (A low level of Per5 3'UTR detection is expected in nontransformed maize plants, since there is usually expression of the endogenous Per5 gene in maize tissues.) Results of RNA qPCR assays for the ST-LS1 intron sequence (which is integral to the formation of dsRNA hairpin molecules) in expressed RNAs were used to validate the presence of hairpin transcripts. Transgene RNA expression levels were measured relative to the RNA levels of an endogenous maize gene.

DNA qPCR analyses to detect a portion of the AAD1 coding region in genomic DNA were used to estimate transgene insertion copy number. Samples for these analyses were collected from plants grown in environmental chambers. Results were compared to DNA qPCR results of assays designed to detect a portion of a single-copy native gene, and simple events (having one or two copies of the transgenes) were advanced for further studies in the greenhouse.

Additionally, qPCR assays designed to detect a portion of the spectinomycin-resistance gene (SpecR; harbored on the binary vector plasmids outside of the T-DNA) were used to determine if the transgenic Plants Contained Extraneous Integrated Plasmid Backbone Sequences.

Hairpin RNA transcript expression level: Per 5 3'UTR qPCR

Callus cell events or transgenic plants were analyzed by real time quantitative PCR (qPCR) of the Per 5 3'UTR sequence to determine the relative expression level of the full length hairpin transcript, as compared to the transcript level of an internal maize gene (SEQ ID NO:48; GENBANK® Accession No. BT069734), which encodes a TIP41-like protein (i.e. a maize homolog of GENBANK® Accession No. AT4G34270; having a tBLASTX score of 74% identity). RNA was isolated using an RNAEASY™ 96 kit (QIAGEN, Valencia, Calif.). Following elution, the total RNA was subjected to a DNAse1 treatment according to the kit's suggested protocol. The RNA was then quantified on a NANODROP® 8000 spectrophotometer (THERMO SCIENTIFIC) and concentration was normalized to 25 ng/μL. First strand cDNA was prepared using a HIGH CAPACITY cDNA SYNTHESIS KIT (INVITROGEN) in a 10 μL reaction volume with 5 μL denatured RNA, substantially according to the manufacturer's recommended protocol. The protocol was modified slightly to include the addition of 10 μL of 100 μM T20VN oligonucleotide (IDT) (SEQ ID NO:49; TTTTTTTTTTTTTTTTTTTTVN, where V is A, C, or G, and N is A, C, G, or T/U) into the 1 mL tube of random primer stock mix, in order to prepare a working stock of combined random primers and oligo dT.

Following cDNA synthesis, samples were diluted 1:3 with nuclease-free water, and stored at −20° C. until assayed.

Separate real-time PCR assays for the Per5 3' UTR and TIP41-like transcript were performed on a LIGHTCYCLER™ 480 (ROCHE DIAGNOSTICS, Indianapolis, Ind.) in 10 μL reaction volumes. For the Per5 3'UTR assay, reactions were run with Primers P5U76S (F) (SEQ ID NO:50) and P5U76A (R) (SEQ ID NO:51), and a ROCHE UNIVERSAL PROBE™ (UPL76; Catalog No. 4889960001; labeled with FAM). For the TIP41-like reference gene assay, primers TIPmxF (SEQ ID NO:52) and TIPmxR (SEQ ID NO:53), and Probe HXTIP (SEQ ID NO:54) labeled with HEX (hexachlorofluorescein) were used.

All assays included negative controls of no-template (mix only). For the standard curves, a blank (water in source well) was also included in the source plate to check for sample cross-contamination. Primer and probe sequences are set forth in Table 6. Reaction components recipes for detection of the various transcripts are disclosed in Table 7, and PCR reactions conditions are summarized in Table 8. The FAM (6-Carboxy Fluorescein Amidite) fluorescent moiety was excited at 465 nm and fluorescence was measured at 510 nm; the corresponding values for the HEX (hexachlorofluorescein) fluorescent moiety were 533 nm and 580 nm.

TABLE 6

Primer sequences used for molecular analyses of transcript levels in transgenic maize.

| Target | Oligo-nucleotide | SEQ ID NO. | Sequence |
|---|---|---|---|
| Per5 3' UTR | P5U76S (F) | 50 | TTGTGATGTTGGTGGCGTAT |
| Per5 3' UTR | P5U76A (R) | 51 | TGTTAAATAAAACCCCAAAGATCG |
| Per5 3' UTR | Roche UPL76 (FAM-Probe) | NAv** | Roche Diagnostics Catalog Number 488996001 |
| TIP41 | TIPmxF | 52 | TGAGGGTAATGCCAACTGGTT |
| TIP41 | TIPmxR | 53 | GCAATGTAACCGAGTGTCTCTCAA |
| TIP41 | HXTIP (HEX-Probe) | 54 | TTTTTGGCTTAGAGTTGATGGTGTACTGATGA |

*TIP41-like protein.
**NAv Sequence Not Available from the supplier.

TABLE 7

PCR reaction recipes for transcript detection.

| Component | Final Concentration | |
|---|---|---|
| | Per5 3'UTR | TIP-like Gene |
| Roche Buffer | 1X | 1X |
| P5U76S (F) | 0.4 μM | 0 |
| P5U76A (R) | 0.4 μM | 0 |
| Roche UPL76 (FAM) | 0.2 μM | 0 |
| HEXtipZM F | 0 | 0.4 μM |
| HEXtipZM R | 0 | 0.4 μM |
| HEXtipZMP (HEX) | 0 | 0.2 μM |
| cDNA (2.0 μL) | NA | NA |
| Water | To 10 μL | To 10 μL |

TABLE 8

Thermocycler conditions for qPCR. TIP41-like Gene and Per5 3'UTR Detection

| Process | Temp | Time | No. Cycles |
|---|---|---|---|
| Target Activation | 95° C. | 10 min | 1 |
| Denature | 95° C. | 10 sec | 40 |
| Extend | 60° C. | 40 sec | |
| Acquire/FAM or HEX | 72° C. | 1 sec | |
| Cool | 40° C. | 10 sec | 1 |

Data were analyzed using LIGHTCYCLER™ Software v1.5 by relative quantification using a second derivative max algorithm for calculation of Cq values according to the supplier's recommendations. For expression analyses, expression values were calculated using the ΔΔCt method (i.e., 2-(Cq TARGET−Cq REF)), which relies on the comparison of differences of Cq values between two targets, with the base value of 2 being selected under the assumption that, for optimized PCR reactions, the product doubles every cycle.

Hairpin Transcript Size and Integrity: Northern Blot Assay

In some instances, additional molecular characterization of the transgenic plants is obtained by the use of Northern Blot (RNA blot) analysis to determine the molecular size of the rop hairpin RNA in transgenic plants expressing a rop hairpin dsRNA.

All materials and equipment are treated with RNAZAP (AMBION/INVITROGEN) before use. Tissue samples (100 mg to 500 mg) are collected in 2 mL SAFELOCK EPPENDORF tubes, disrupted with a KLECKO™ tissue pulverizer (GARCIA MANUFACTURING, Visalia, Calif.) with three tungsten beads in 1 mL of TRIZOL (INVITROGEN) for 5 min, then incubated at room temperature (RT) for 10 min. Optionally, the samples are centrifuged for 10 min at 4° C. at 11,000 rpm and the supernatant is transferred into a fresh 2 mL SAFELOCK EPPENDORF tube. After 200 μL of chloroform are added to the homogenate, the tube is mixed by inversion for 2 to 5 min, incubated at RT for 10 minutes, and centrifuged at 12,000×g for 15 min at 4° C. The top phase is transferred into a sterile 1.5 mL EPPENDORF tube, 600 μL of 100% isopropanol are added, followed by incubation at RT for 10 min to 2 hr, then centrifuged at 12,000×g for 10 min at 4° to 25° C. The supernatant is discarded and the RNA pellet is washed twice with 1 mL of 70% ethanol, with centrifugation at 7,500×g for 10 min at 4° to 25° C. between washes. The ethanol is discarded and the pellet is briefly air dried for 3 to 5 min before resuspending in 50 μL of nuclease-free water.

Total RNA is quantified using the NANODROP® 8000 (THERMO-FISHER) and samples are normalized to 5 μg/10 μL. 10 μL of glyoxal (AMBION/INVITROGEN) are then added to each sample. Five to 14 ng of DIG RNA standard marker mix (ROCHE APPLIED SCIENCE, Indianapolis, Ind.) are dispensed and added to an equal volume of glyoxal. Samples and marker RNAs are denatured at 50° C. for 45 min and stored on ice until loading on a 1.25% SEAKEM GOLD agarose (LONZA, Allendale, N.J.) gel in NORTHERNMAX 10× glyoxal running buffer (AMBION/INVITROGEN) RNAs are separated by electrophoresis at 65 volts/30 mA for 2 hr and 15 min.

Following electrophoresis, the gel is rinsed in 2×SSC for 5 min and imaged on a GEL DOC station (BIORAD, Hercules, Calif.), then the RNA is passively transferred to a nylon membrane (MILLIPORE) overnight at RT, using 10×SSC as the transfer buffer (20×SSC consists of 3 M sodium chloride and 300 mM trisodium citrate, pH 7.0).

Following the transfer, the membrane is rinsed in 2×SSC for 5 minutes, the RNA is UV-crosslinked to the membrane (AGILENT/STRATAGENE), and the membrane is allowed to dry at RT for up to 2 days.

The membrane is prehybridized in ULTRAHYB buffer (AMBION/INVITROGEN) for 1 to 2 hr. The probe consists of a PCR amplified product containing the sequence of interest, (for example, the antisense sequence portion of SEQ ID NO:13 or SEQ ID NO:14, as appropriate) labeled with digoxygenin by means of a ROCHE APPLIED SCIENCE DIG procedure. Hybridization in recommended buffer is overnight at a temperature of 60° C. in hybridization tubes. Following hybridization, the blot is subjected to DIG washes, wrapped, exposed to film for 1 to 30 minutes, then the film is developed, all by methods recommended by the supplier of the DIG kit.

Transgene Copy Number Determination

Maize leaf pieces approximately equivalent to 2 leaf punches were collected in 96-well collection plates (QIAGEN). Tissue disruption was performed with a KLECKO™ tissue pulverizer (GARCIA MANUFACTURING, Visalia, Calif.) in BIOSPRINT96 AP1 lysis buffer (supplied with a BIOSPRINT96 PLANT KIT; QIAGEN) with one stainless steel bead. Following tissue maceration, genomic DNA (gDNA) was isolated in high throughput format using a BIOSPRINT96 PLANT KIT and a BIOSPRINT96 extraction robot. Genomic DNA was diluted 2:3 DNA:water prior to setting up the qPCR reaction.

qPCR Analysis

Transgene detection by hydrolysis probe assay was performed by real-time PCR using a LIGHTCYCLER®480 system. Oligonucleotides to be used in hydrolysis probe assays to detect the ST-LS1 intron sequence (SEQ ID NO:16), or to detect a portion of the SpecR gene (i.e. the spectinomycin resistance gene borne on the binary vector plasmids; SEQ ID NO:55; SPC1 oligonucleotides in Table 9), were designed using LIGHTCYCLER® PROBE DESIGN SOFTWARE 2.0. Further, oligonucleotides to be used in hydrolysis probe assays to detect a segment of the AAD-1 herbicide tolerance gene (SEQ ID NO:56; GAAD1 oligonucleotides in Table 9) were designed using PRIMER EXPRESS software (APPLIED BIOSYSTEMS). Table 9 shows the sequences of the primers and probes. Assays were multiplexed with reagents for an endogenous maize chromosomal gene (Invertase (SEQ ID NO:57; GENBANK® Accession No: U16123; referred to herein as IVR1), which served as an internal reference sequence to ensure gDNA was present in each assay. For amplification, LIGHTCYCLER®480 PROBES MASTER mix (ROCHE APPLIED SCIENCE) was prepared at 1× final concentration in a 10 μL volume multiplex reaction containing 0.4 μM of each primer and 0.2 μM of each probe (Table 10). A two step amplification reaction was performed as outlined in Table 11. Fluorophore activation and emission for the FAM- and HEX-labeled probes were as described above; CY5 conjugates are excited maximally at 650 nm and fluoresce maximally at 670 nm.

Cp scores (the point at which the fluorescence signal crosses the background threshold) were determined from the real time PCR data using the fit points algorithm (LIGHTCYCLER® SOFTWARE release 1.5) and the Relative Quant module (based on the ΔΔCt method). Data were handled as described previously (above; RNA qPCR).

TABLE 9

Sequences of primers and probes (with fluorescent conjugate) used for gene copy number determinations and binary vector plasmid backbone detection.

| Name | SEQ ID NO: | Sequence |
|---|---|---|
| GAAD1-F | 61 | TGTTCGGTTCCCTCTACCAA |
| GAAD1-R | 62 | CAACATCCATCACCTTGACTGA |
| GAAD1-P (FAM) | 63 | CACAGAACCGTCGCTTCAGCAACA |
| IVR1-F | 64 | TGGCGGACGACGACTTGT |
| IVR1-R | 65 | AAAGTTTGGAGGCTGCCGT |
| IVR1-P (HEX) | 66 | CGAGCAGACCGCCGTGTACTTCTACC |
| SPC1A | 67 | CTTAGCTGGATAACGCCAC |
| SPC1S | 68 | GACCGTAAGGCTTGATGAA |
| TQSPEC (CY5*) | 69 | CGAGATTCTCCGCGCTGTAGA |

CY5 = Cyanine-5

TABLE 10

Reaction components for gene copy number analyses and plasmid backbone detection.

| Component | Amt. (μL) | Stock | Final Conc'n |
|---|---|---|---|
| 2X Buffer | 5.0 | 2X | 1X |
| Appropriate Forward Primer | 0.4 | 10 μM | 0.4 |
| Appropriate Reverse Primer | 0.4 | 10 μM | 0.4 |
| Appropriate Probe | 0.4 | 5 μM | 0.2 |
| IVR1-Forward Primer | 0.4 | 10 μM | 0.4 |
| IVR1-Reverse Primer | 0.4 | 10 μM | 0.4 |
| IVR1-Probe | 0.4 | 5 μM | 0.2 |
| $H_2O$ | 0.6 | NA* | NA |
| gDNA | 2.0 | ND** | ND |
| Total | 10.0 | | |

*NA = Not Applicable
**ND = Not Determined

TABLE 11

Thermocycler conditions for DNA qPCR Genomic copy number analyses

| Process | Temp. | Time | No. Cycles |
|---|---|---|---|
| Target Activation | 95° C. | 10 min | 1 |
| Denature | 95° C. | 10 sec | 40 |
| Extend & Acquire FAM, HEX, or CY5 | 60° C. | 40 sec | |
| Cool | 40° C. | 10 sec | 1 |

Example 8

Bioassay of Transgenic Maize

In Vitro Insect Bioassays

Bioactivity of dsRNA of the subject invention produced in plant cells is demonstrated by bioassay methods. See, e.g., Baum et al. (2007) Nat. Biotechnol. 25(11):1322-1326. One is able to demonstrate efficacy, for example, by feeding various plant tissues or tissue pieces derived from a plant producing an insecticidal dsRNA to target insects in a controlled feeding environment. Alternatively, extracts are prepared from various plant tissues derived from a plant producing the insecticidal dsRNA and the extracted nucleic acids are dispensed on top of artificial diets for bioassays as previously described herein. The results of such feeding assays are compared to similarly conducted bioassays that employ appropriate control tissues from host plants that do not produce an insecticidal dsRNA, or to other control samples.

Insect bioassays with Transgenic Maize Events

Two western corn rootworm larvae (1 to 3 days old) hatched from washed eggs are selected and placed into each well of the bioassay tray. The wells are then covered with a "PULL N' PEEL" tab cover (BIO-CV-16, BIO-SERV) and placed in a 28° C. incubator with an 18 hr/6 hr light/dark cycle. Nine days after the initial infestation, the larvae are assessed for mortality, which is calculated as the percentage of dead insects out of the total number of insects in each treatment. The insect samples are frozen at −20° C. for two days, then the insect larvae from each treatment are pooled and weighed. The percent of growth inhibition is calculated as the mean weight of the experimental treatments divided by the mean of the average weight of two control well treatments. The data are expressed as a Percent Growth Inhibition (of the Negative Controls). Mean weights that exceed the control mean weight are normalized to zero.

Insect Bioassays in the Greenhouse

Western corn rootworm (WCR, *Diabrotica virgifera virgifera* LeConte) eggs were received in soil from CROP CHARACTERISTICS (Farmington, Minn.). WCR eggs were incubated at 28° C. for 10 to 11 days. Eggs were washed from the soil, placed into a 0.15% agar solution, and the concentration was adjusted to approximately 75 to 100 eggs per 0.25 mL aliquot. A hatch plate was set up in a Petri dish with an aliquot of egg suspension to monitor hatch rates.

The soil around the maize plants growing in ROOTRAINERS® was infested with 150 to 200 WCR eggs. The insects were allowed to feed for 2 weeks, after which time a "Root Rating" was given to each plant. A Node-Injury Scale was utilized for grading essentially according to Oleson et al. (2005, J. Econ. Entomol. 98:1-8). Plants which passed this bioassay were transplanted to 5-gallon pots for seed production. Transplants were treated with insecticide to prevent further rootworm damage and insect release in the greenhouses. Plants were hand pollinated for seed production. Seeds produced by these plants were saved for evaluation at the $T_1$ and subsequent generations of plants.

Greenhouse bioassays included two kinds of negative control plants. Transgenic negative control plants were generated by transformation with vectors harboring genes designed to produce a yellow fluorescent protein (YFP) or a YFP hairpin dsRNA (See Example 4). Nontransformed negative control plants were grown from seeds of lines 7sh382 or B104. Bioassays were conducted on two separate dates, with negative controls included in each set of plant materials.

Table 12 shows the combined results of molecular analyses and bioassays for rop-hairpin plants. Examination of the bioassay results summarized in Table 12 reveals the surprising and unexpected observation that the majority of the transgenic maize plants harboring constructs that express an rop hairpin dsRNA comprising segments of SEQ ID NO:1, for example, as exemplified in SEQ ID NO:13 and SEQ ID NO:14, are protected against root damage incurred by feeding of western corn rootworm larvae. Twenty-two of the 37 graded events had a root rating of 0.5 or lower. Table 13 shows the combined results of molecular analyses and bioassays for negative control plants. Most of the plants had no protection against WCR larvae feeding, although five of the 34 graded plants had a root rating of 0.75 or lower. The presence of some plants having low root ratings scores amongst the negative control plant set is sometimes observed and reflects the variability and difficulty of conducting this type of bioassay in a greenhouse setting.

TABLE 12

Greenhouse bioassay and molecular analyses results of rop-hairpin-expressing maize plants.

| | Leaf Tissue | | Root Tissue | | |
|---|---|---|---|---|---|
| Sample ID | ST-LS1 RTL* | PER5 UTR RTL | ST-LS1 RTL* | PER5 UTR RTL | Root Rating |
| rop v1 Hairpin Events | | | | | |
| 114515[1]-001.001 | 0.162 | 62.7 | 0.026 | 89.9 | 0.05 |
| 114515[1]-005.001 | 0.170 | 131.6 | 0.082 | 30.1 | 0.05 |
| 114515[1]-008.001 | 0.268 | 194.0 | 0.068 | 113.8 | 0.75 |
| 114515[1]-009.001 | 0.262 | 121.1 | 0.146 | 52.0 | 0.75 |
| 114515[1]-010.001 | 1.028 | 56.5 | 0.110 | 8.7 | 1 |
| 114515[1]-012.001 | 0.133 | 103.3 | 0.051 | 28.1 | 0.5 |
| 114515[1]-013.001 | 0.145 | 63.6 | 0.059 | 168.9 | 1 |
| 114515[1]-014.001 | 0.203 | 172.4 | 0.072 | 104.0 | 0.25 |
| 114515[1]-015.001 | 0.257 | 127.1 | 0.021 | 89.3 | 0.25 |
| 114515[1]-016.001 | 0.363 | 235.6 | 0.129 | 213.8 | 0.1 |
| 114515[1]-017.001 | 0.225 | 128.9 | 0.037 | 115.4 | 0.25 |
| 114515[1]-018.001 | 0.110 | 81.0 | 0.093 | 200.9 | 0.5 |
| 114515[1]-019.001 | 0.122 | 87.4 | 0.013 | 85.0 | 0.1 |
| 114515[1]-020.001 | 0.221 | 65.3 | 0.142 | 27.3 | 1 |
| 114515[1]-022.001 | 0.486 | 91.8 | 0.063 | 36.8 | 0.25 |
| 114515[1]-023.001 | 0.257 | 117.8 | 0.043 | 117.0 | 1 |

TABLE 12-continued

Greenhouse bioassay and molecular analyses results of rop-hairpin-expressing maize plants.

| Sample ID | Leaf Tissue ST-LS1 RTL* | Leaf Tissue PER5 UTR RTL | Root Tissue ST-LS1 RTL* | Root Tissue PER5 UTR RTL | Root Rating |
|---|---|---|---|---|---|
| 114515[1]-024.001 | 2.042 | 240.5 | 0.000 | 1.0 | 0.25 |
| 114515[1]-026.001 | 0.000 | 68.6 | 0.028 | 33.4 | 1 |
| 114515[1]-027.001 | 0.374 | 69.1 | 0.451 | 26.9 | 1 |
| 114515[1]-028.001 | 0.204 | 68.6 | 0.076 | 163.1 | 1 |
| rop v3 Hairpin Events | | | | | |
| 115770[1]-001.001 | 0.227 | 242.2 | 0.113 | 404.5 | 0.01 |
| 115770[1]-002.001 | 0.163 | 128.0 | 0.283 | 404.5 | 0.05 |
| 115770[1]-004.001 | 0.174 | 90.5 | 0.222 | 148.1 | 0.05 |
| 115770[1]-005.001 | 0.159 | 143.0 | 0.166 | 96.3 | 0.05 |
| 115770[1]-007.001 | 0.072 | 88.0 | 0.274 | 238.9 | 0.01 |
| 115770[1]-008.001 | 0.101 | 117.8 | 0.068 | 68.6 | 0.1 |
| 115770[1]-012.001 | 0.920 | 298.2 | 0.146 | 199.5 | 0.5 |
| 115770[1]-014.001 | 2.497 | 467.9 | 5.134 | 424.6 | 0.75 |
| 115770[1]-015.001 | 1.310 | 266.9 | 0.179 | 226.0 | 0.75 |
| 115770[1]-018.001 | 0.871 | 245.6 | 0.222 | 238.9 | 0.75 |
| 115770[1]-019.001 | 0.959 | 243.9 | 0.366 | 296.1 | 0.5 |
| 115770[1]-020.001 | 0.889 | 252.5 | 0.398 | 369.6 | 0.75 |
| 115770[1]-022.001 | 0.824 | 296.1 | 0.176 | 498.0 | 0.1 |
| 115770[1]-024.001 | 0.707 | 333.1 | 0.145 | 261.4 | 0.25 |
| 115770[1]-027.001 | 0.566 | 337.8 | 0.312 | 487.8 | 0.75 |
| 115770[1]-028.001 | 0.366 | 166.6 | 0.080 | 121.1 | 0.75 |
| 115770[1]-029.001 | 1.125 | 252.5 | 0.268 | 315.2 | 0.5 |

*RTL = Relative Transcript Level as measured against TIP4-like gene transcript levels.

TABLE 13

Greenhouse bioassay and molecular analyses results of negative control plants comprising transgenic and nontransformed maize plants.

| Sample ID | Leaf Tissue ST-LS1 RTL* | Leaf Tissue PER5 UTR RTL | Root Tissue ST-LS1 RTL* | Root Tissue PER5 UTR RTL | Root Rating |
|---|---|---|---|---|---|
| YFP protein Events | | | | | |
| 101556[679]-10513.001 | 0.000 | 0.0 | 0.000 | 32.7 | 1 |
| 101556[679]-10514.001 | 0.173 | 171.3 | 0.240 | 202.3 | 1 |
| 101556[679]-10515.001 | 0.000 | 42.5 | 0.000 | 45.6 | 1 |
| 101556[679]-10516.001 | 0.000 | 18.9 | 0.000 | 65.3 | 0.75 |
| 101556[677]-10524.001 | 0.000 | 315.2 | 0.000 | 364.6 | 1 |
| 101556[677]-10525.001 | 0.000 | 184.8 | 0.000 | 95.0 | 1 |
| 101556[677]-10526.001 | 0.000 | 0.2 | 0.000 | 0.3 | 1 |
| 101556[677]-10527.001 | 0.000 | 170.1 | 0.000 | 128.0 | 1 |
| 101556[677]-10528.001 | 0.000 | 179.8 | 0.067 | 104.0 | 1 |
| 101556[677]-10529.001 | 0.000 | 98.4 | 0.000 | 38.9 | 1 |
| YFP hairpin Events | | | | | |
| 110853[8]-289.001 | 0.117 | 97.0 | 0.122 | 65.3 | 0.5 |
| 110853[8]-290.001 | 0.098 | 70.0 | 0.272 | 79.3 | 1 |
| 110853[8]-291.001 | 0.084 | 36.3 | 0.107 | 86.2 | 1 |
| 110853[8]-293.001 | 0.088 | 79.9 | 0.624 | 101.1 | 0.05 |
| 110853[8]-294.001 | 0.079 | 35.8 | 0.117 | 54.2 | 1 |
| 110853[8]-295.001 | 0.095 | 82.7 | 0.114 | 145.0 | 1 |
| 110853[8]-296.001 | 0.097 | 59.7 | 0.158 | 79.9 | 1 |
| 110853[8]-297.001 | 0.106 | 0.1 | 0.000 | 2.5 | 1 |
| 110853[8]-298.001 | 0.000 | 0.1 | 0.000 | 32.9 | 1 |
| 110853[8]-299.001 | 0.354 | 143.0 | 0.308 | 101.8 | 1 |
| 110853[8]-300.001 | 0.500 | 159.8 | 0.085 | 139.1 | 1 |
| 110853[8]-301.001 | 0.304 | 174.9 | 1.007 | 111.4 | 1 |
| Nontransformed Plants | | | | | |
| 7sh382 | 0.000 | 0.1 | 0.000 | 0.2 | 0.75 |
| 7sh382 | 0.000 | 0.1 | 0.000 | 0.1 | 1 |
| 7sh382 | 0.000 | 0.1 | 0.000 | 6.1 | NG** |
| 7sh382 | 0.000 | 0.4 | 0.000 | 1.6 | 1 |
| 7sh382 | 0.287 | 0.0 | 0.000 | ND*** | 1 |

TABLE 13-continued

Greenhouse bioassay and molecular analyses results of negative control plants comprising transgenic and nontransformed maize plants.

| | Leaf Tissue | | Root Tissue | | |
|---|---|---|---|---|---|
| Sample ID | ST-LS1 RTL* | PER5 UTR RTL | ST-LS1 RTL* | PER5 UTR RTL | Root Rating |
| 7sh382 | 0.000 | 0.2 | 0.000 | 0.3 | 0.75 |
| B104 | 0.000 | 0.2 | 0.000 | 0.2 | 1 |
| B104 | 0.000 | 0.0 | 0.000 | 0.6 | 1 |
| B104 | 0.000 | 0.1 | 0.000 | 0.3 | 1 |
| B104 | 0.000 | 0.4 | 1.000 | 1.0 | 1 |
| B104 | 0.000 | 0.1 | 0.000 | 0.5 | 1 |
| B104 | 0.000 | 0.0 | 0.000 | 205.1 | 1 |
| B104 | 0.077 | 0.1 | 0.000 | 4.4 | 1 |

*RTL = Relative Transcript Level as measured against TIP4-like gene transcript levels.

**NG = Not Graded due to small plant size.

***ND = Not Done.

Example 9

Transgenic *Zea mays* Comprising Coleopteran Pest Sequences

Ten to 20 transgenic $T_0$ *Zea mays* plants are generated as described in EXAMPLE 6. A further 10-20 $T_1$ *Zea mays* independent lines expressing hairpin dsRNA for an RNAi construct are obtained for corn rootworm challenge. Hairpin dsRNA may be derived as set forth in SEQ ID NO:13, SEQ ID NO:14, or otherwise further comprising SEQ ID NO:1. Additional hairpin dsRNAs may be derived, for example, from coleopteran pest sequences such as, for example, Caf1-180 (U.S. Patent Application Publication No. 2012/0174258), VatpaseC (U.S. Patent Application Publication No. 2012/0174259), Rho1 (U.S. Patent Application Publication No. 2012/0174260), VatpaseH (U.S. Patent Application Publication No. 2012/0198586), PPI-87B (U.S. Patent Application Publication No. 2013/0091600), RPA70 (U.S. Patent Application Publication No. 2013/0091601), or RPS6 (U.S. Patent Application Publication No. 2013/0097730). These are confirmed through RT-PCR or other molecular analysis methods. Total RNA preparations from selected independent $T_1$ lines are optionally used for RT-PCR with primers designed to bind in the ST-LS1 intron of the hairpin expression cassette in each of the RNAi constructs. In addition, specific primers for each target gene in an RNAi construct are optionally used to amplify and confirm the production of the pre-processed mRNA required for siRNA production in planta. The amplification of the desired bands for each target gene confirms the expression of the hairpin RNA in each transgenic *Zea mays* plant. Processing of the dsRNA hairpin of the target genes into siRNA is subsequently optionally confirmed in independent transgenic lines using RNA blot hybridizations.

Moreover, RNAi molecules having mismatch sequences with more than 80% sequence identity to target genes affect corn rootworms in a way similar to that seen with RNAi molecules having 100% sequence identity to the target genes The pairing of mismatch sequence with native sequences to form a hairpin dsRNA in the same RNAi construct delivers plant-processed siRNAs capable of affecting the growth, development and viability of feeding coleopteran pests.

In planta delivery of dsRNA, siRNA shRNA, or miRNA corresponding to target genes and the subsequent uptake by coleopteran pests through feeding results in down-regulation of the target genes in the coleopteran pest through RNA-mediated gene silencing. When the function of a target gene is important at one or more stages of development, the growth, development, and reproduction of the coleopteran pest is affected, and in the case of at least one of WCR, NCR, SCR, MCR, *D. balteata* LeConte, *D. u. tenella*, and *D. u. undecimpunctata* Mannerheim, leads to failure to successfully infest, feed, develop, and/or reproduce, or leads to death of the coleopteran pest. The choice of target genes and the successful application of RNAi is then used to control coleopteran pests.

Phenotypic Comparison of Transgenic RNAi Lines and Nontransformed *Zea mays*

Target coleopteran pest genes or sequences selected for creating hairpin dsRNA have no similarity to any known plant gene sequence. Hence it is not expected that the production or the activation of (systemic) RNAi by constructs targeting these coleopteran pest genes or sequences will have any deleterious effect on transgenic plants. However, development and morphological characteristics of transgenic lines are compared with nontransformed plants, as well as those of transgenic lines transformed with an "empty" vector having no hairpin-expressing gene. Plant root, shoot, foliage and reproduction characteristics are compared. There is no observable difference in root length and growth patterns of transgenic and nontransformed plants. Plant shoot characteristics such as height, leaf numbers and sizes, time of flowering, floral size and appearance are similar. In general, there are no observable morphological differences between transgenic lines and those without expression of target iRNA molecules when cultured in vitro and in soil in the glasshouse.

Example 10

Transgenic *Zea mays* Comprising a Coleopteran Pest Sequence and Additional RNAi Constructs A transgenic *Zea mays* plant comprising a heterologous coding sequence in its genome that is transcribed into an iRNA molecule that targets an organism other than a coleopteran pest is secondarily transformed via *Agrobacterium* or WHISKERS™ methodologies (see Petolino and Arnold (2009) Methods Mol. Biol. 526:59-67) to produce one or more insecticidal dsRNA molecules (for example, at least one dsRNA molecule including a dsRNA molecule targeting a gene comprising SEQ ID NO:1). Plant transformation plasmid vectors prepared essentially as described in EXAMPLE 3 are delivered via *Agrobacterium* or WHISKERS™-mediated transformation methods into maize suspension cells or immature maize embryos obtained from a transgenic Hi II or B104 *Zea mays* plant comprising a heterologous coding sequence in its genome that is transcribed into an iRNA molecule that targets an organism other than a coleopteran pest.

Example 11

Transgenic *Zea mays* Comprising an RNAi Construct and Additional Coleopteran Pest Control Sequences A transgenic *Zea mays* plant comprising a heterologous coding sequence in its genome that is transcribed into an iRNA molecule that targets a coleopteran pest organism (for example, at least one dsRNA molecule including a dsRNA molecule targeting a gene comprising SEQ ID NO:1) is secondarily transformed via *Agrobacterium* or WHISKERS™ methodologies (see Petolino and Arnold (2009) Methods Mol. Biol. 526:59-67) to produce one or more insecticidal protein molecules, for example, Cry3, or Cry34 and Cry35Ab1 insecticidal proteins. Plant transformation plasmid vectors prepared essentially as described in EXAMPLE 3 are delivered via *Agrobacterium* or WHISKERS™-mediated transformation methods into maize suspension cells or immature maize embryos obtained from a transgenic B104 *Zea mays* plant comprising a heterologous coding sequence in its genome that is transcribed into an iRNA molecule that targets a coleopteran pest organism. Doubly-transformed plants are obtained that produce iRNA molecules and insecticidal proteins for control of coleopteran pests.

Example 12

Other *Diabrotica* Sequences Having Homology to ROP

ROP protein (SEQ ID NO:2) contains a conserved domain of the Sec1 family (pfam00995). Sec1 family proteins are known to be involved in synaptic transmission and general secretion. hmmscan was used for PFAM domain prediction in the WCR transcriptome sequences. Protein homology analyses using a Sec1 domain identified 42 other *Diabrotica virgifera* sequences (SEQ ID NOs:70 to 111) that encode proteins that contain a Sec1 domain and may consequently share structural and/or functional properties with ROP protein. Thus, the genes (i.e. SEQ ID NOs:70-111) encoding these proteins are additional candidates for RNAi-mediated control of *Diabrotica* species, including at least one of WCR, NCR, SCR, MCR, *D. balteata* LeConte, *D. u. tenella*, and *D. u. undecimpunctata* Mannerheim, by methods described herein.

Example 13

Mortality of Neotropical Brown Stink Bug (*Euschistus heros*) following rop RNAi injection Insect Rearing Neotropical Brown Stink Bugs (BSB; *Euschistus heros*) were reared on BSB artificial diet prepared as follows (used within two weeks of preparation). Lyophilized green beans were blended to a fine powder in a MAGIC BULLET® blender while raw (organic) peanuts were blended in a separate MAGIC BULLET® blender. Blended dry ingredients were combined (weight percentages: green beans, 35%; peanuts, 35%; sucrose, 5%; Vitamin complex (e.g. Vanderzant Vitamin Mixture for insects, SIGMA-ALDRICH, Catalog No. V1007), 0.9%); in a large MAGIC BULLET® blender, which was capped and shaken well to mix the ingredients. The mixed dry ingredients were then added to a mixing bowl. In a separate container, water and benomyl anti-fungal agent (50 ppm; 25 μL of a 20,000 ppm solution/50 mL diet solution) were mixed well and then added to the dry ingredient mixture. All ingredients were mixed by hand until the solution was fully blended. The diet was shaped into desired sizes, wrapped loosely in aluminum foil, heated for 4 hours at 60° C., then cooled and stored at 4° C.

RNAi Target Selection

Six stages of BSB development were selected for mRNA library preparation. Total RNA was extracted from insects frozen at −70° C. and homogenized in 10 volumes of Lysis/Binding buffer in Lysing MATRIX A 2 mL tubes (MP BIOMEDICALS, Santa Ana, Calif.) on a FastPrep®-24 Instrument (MP BIOMEDICALS). Total mRNA was extracted using a mirVana™ miRNA Isolation Kit (AMBION; INVITROGEN) according to the manufacturer's protocol. RNA sequencing using an Illumina® HiSeq™ system (San Diego, Calif.) provided candidate target gene sequences for use in RNAi insect control technology. HiSeq™ generated a total of about 378 million reads for the six samples. The reads were assembled individually for each sample using TRINITY assembler software (Grabherr et al. (2011) Nature Biotech. 29:644-652). The assembled transcripts were combined to generate a pooled transcriptome. This BSB pooled transcriptome contains 378,457 sequences.

BSB Rop Ortholog Identification

A tBLASTn search of the BSB pooled transcriptome was performed using as query sequence a *Drosophila* ROP protein (ROP-PA; GENBANK® Accession No. AAF47844.1). BSB rop (SEQ ID NO:115) was identified as a Brown Stink Bug candidate target gene.

Template Preparation and dsRNA Synthesis cDNA was prepared from total BSB RNA extracted from a single young adult insect (about 90 mg) using TRIzol® Reagent (LIFE TECHNOLOGIES). The insect was homogenized at room temperature in a 1.5 mL microcentrifuge tube with 200 μL of TRIzol® using a pellet pestle (FISHERBRAND Catalog No. 12-141-363) and Pestle Motor Mixer (COLE-PARMER, Vernon Hills, Ill.). Following homogenization, an additional 800 μL of TRIzol® was added, the homogenate was vortexed, and then incubated at room temperature for five minutes. Cell debris was removed by centrifugation and the supernatant was transferred to a new tube. 200 μL of chloroform were added and the mixture was vortexed for 15 seconds. After allowing the extraction to sit at room temperature for 2 to 3 min, the phases were separated by centrifugation at 12,000×g at 4° C. for 15 minutes. The upper aqueous phase was carefully transferred into another nuclease-free 1.5 mL microcentrifuge tube, and the RNA was precipitated with 500 μL of room temperature isopropanol. After ten-minute incubation at room temperature, the mixture was centrifuged for 10 minutes as above. The RNA pellet was rinsed with 1 mL of room-temperature 75% ethanol and centrifuged for an additional 10 minutes as above. The RNA pellet was dried at room temperature and resuspended in 200 μL of Tris Buffer from a GFX PCR DNA AND GEL EXTRACTION KIT (Illustra™; GE HEALTHCARE LIFE SCIENCES) using Elution Buffer Type 4 (i.e. 10 mM Tris-HCl pH8.0). RNA concentration was determined using a NANODROP® 8000 spectrophotometer (THERMO SCIENTIFIC, Wilmington, Del.).

cDNA was reverse-transcribed from 5 μg of BSB total RNA template and oligo dT primer using a SUPERSCRIPT III FIRST-STRAND SYNTHESIS SYSTEM™ for RT-PCR (INVITROGEN), following the supplier's recommended protocol. The final volume of the transcription reaction was brought to 100 μL with nuclease-free water.

Primers BSB_Rop-1-For (SEQ ID NO:117) and BSB_Rop-1-Rev (SEQ ID NO:118) were used in touch-down PCR (annealing temperature lowered from 60° C. to 50° C. in a 1° C./cycle decrease) with 1 μL of cDNA (above) as the template. Fragments comprising a 499 by segment of rop (i.e. BSB rop region1; SEQ ID NO:119) were generated during 35 cycles of PCR. The BSB_Rop primers comprised a T7 phage promoter sequence (SEQ ID NO:5) at their 5' ends, and thus enabled the use of BSB rop reg1 DNA fragments for dsRNA transcription.

dsRNA was synthesized using 2 μL of PCR product (above) as the template with a MEGAscript™ RNAi kit (AMBION) used according to the manufacturer's instructions. (See FIG. 1). dsRNA was quantified on a NANO-DROP® 8000 spectrophotometer and diluted to 500 ng/μL in nuclease-free 0.1× TE buffer (1 mM Tris HCL, 0.1 mM EDTA, pH7.4).

Injection of dsRNA into BSB Hemocoel

BSB were reared on artificial diet (above) in a 27° C. incubator at 65% relative humidity and 16:8 hour light:dark photoperiod. Second instar nymphs (each weighing 1 to 1.5 mg) were gently handled with a small brush to prevent injury and were placed in a Petri dish on ice to chill and immobilize the insects. Each insect was injected with 55.2 nL of a 500 ng/μL dsRNA solution (i.e. 27.6 ng dsRNA; dosage of 18.4 to 27.6 μg/g body weight). Injections were performed using a NANOJECT™ II injector (DRUMMOND SCIENTIFIC, Broomhall, Pa.) equipped with an injection needle pulled from a Drummond 3.5 inches #3-000=203-G/X glass capillary. The needle tip was broken and the capillary was backfilled with light mineral oil, then filled with 2 to 3 μL of dsRNA. dsRNA was injected into the abdomen of the nymphs (10 insects injected per dsRNA per trial), and the trials were repeated on three different days. Injected insects (5 per well) were transferred into 32-well trays (Bio-RT-32 Rearing Tray; BIO-SERV, Frenchtown, N.J.) containing a pellet of artificial BSB diet and covered with Pull-N-Peel™ tabs (BIO-CV-4; BIO-SERV). Moisture was supplied by means of 1.25 mL of water in a 1.5 mL microcentrifuge tube with a cotton wick. The trays were incubated at 26.5° C., 60% humidity and 16:8 light:dark photoperiod. Viability counts and weights were taken on day 7 after the injections.

Injections Identified BSB Rop as a Lethal dsRNA Target dsRNA homologous to a YFP coding region (prepared as in EXAMPLE 2) was used as a negative control in BSB injection experiments. As summarized in Table 13, 27.6 ng of BSB_Rop reg1 dsRNA injected into the hemocoel of $2^{nd}$ instar BSB nymphs produced high mortality within seven days. The mortality caused by BSB_rop reg1 dsRNA was significantly different from that seen with the same amount of injected YFP dsRNA (negative control).

TABLE 13

Results of BSB_rop reg1 dsRNA injection into the hemocoel of $2^{nd}$ instar Brown Stink Bug nymphs seven days after injection.

| Treatment* | Mean % Mortality | SEM | N trials | t-test (p) |
|---|---|---|---|---|
| BSB_rop reg1 dsRNA | 90 | 5.8 | 3 | 6.08E−04 |
| YFP v2 dsRNA | 13 | 3.3 | 3 | 6.43E−01 |
| Not injected | 10 | 5.8 | 3 | |

*Ten insects injected per trial for each dsRNA.

Example 14

Transgenic *Zea mays* Comprising Hemipteran Pest Sequences

Ten to 20 transgenic $T_0$ *Zea mays* plants harboring expression vectors for nucleic acids comprising SEQ ID NO: 115 and/or SEQ ID NO 119 are generated as described in EXAMPLE 6. A further 10-20 $T_1$ *Zea mays* independent lines expressing hairpin dsRNA for an RNAi construct are obtained for BSB challenge. Hairpin dsRNA may be derived as set forth in SEQ ID NO:119 or otherwise further comprising SEQ ID NO:115. These are confirmed through RT-PCR or other molecular analysis methods. Total RNA preparations from selected independent $T_1$ lines are optionally used for RT-PCR with primers designed to bind in the ST-LS1 intron of the hairpin expression cassette in each of the RNAi constructs. In addition, specific primers for each target gene in an RNAi construct are optionally used to amplify and confirm the production of the pre-processed mRNA required for siRNA production in planta. The amplification of the desired bands for each target gene confirms the expression of the hairpin RNA in each transgenic *Zea mays* plant. Processing of the dsRNA hairpin of the target genes into siRNA is subsequently optionally confirmed in independent transgenic lines using RNA blot hybridizations.

Moreover, RNAi molecules having mismatch sequences with more than 80% sequence identity to target genes affect corn rootworms in a way similar to that seen with RNAi molecules having 100% sequence identity to the target genes. The pairing of mismatch sequence with native sequences to form a hairpin dsRNA in the same RNAi construct delivers plant-processed siRNAs capable of affecting the growth, development and viability of feeding hemipteran pests.

In planta delivery of dsRNA, siRNA, shRNA, or miRNA corresponding to target genes and the subsequent uptake by hemipteran pests through feeding results in down-regulation of the target genes in the hemipteran pest through RNA-mediated gene silencing. When the function of a target gene is important at one or more stages of development, the growth, development, and reproduction of the hemipteran pest is affected, and in the case of at least one of *Euchistus heros, Piezodorus guildinii, Halyomorpha halys, Nezara viridula, Acrosternum hilare*, and *Euschistus servus* leads to failure to successfully infest, feed, develop, and/or reproduce, or leads to death of the hemipteran pest. The choice of target genes and the successful application of RNAi is then used to control hemipteran pests.

Phenotypic Comparison of Transgenic RNAi Lines and Nontransformed *Zea mays*

Target hemipteran pest genes or sequences selected for creating hairpin dsRNA have no similarity to any known plant gene sequence. Hence it is not expected that the production or the activation of (systemic) RNAi by constructs targeting these hemipteran pest genes or sequences will have any deleterious effect on transgenic plants. However, development and morphological characteristics of transgenic lines are compared with nontransformed plants, as well as those of transgenic lines transformed with an "empty" vector having no hairpin-expressing gene. Plant root, shoot, foliage and reproduction characteristics are compared. There is no observable difference in root length and growth patterns of transgenic and nontransformed plants. Plant shoot characteristics such as height, leaf numbers and sizes, time of flowering, floral size and appearance are similar. In general, there are no observable morphological differences between transgenic lines and those without expression of target iRNA molecules when cultured in vitro and in soil in the glasshouse.

Example 15

Transgenic *Glycine max* Comprising Hemipteran Pest Sequences

Ten to 20 transgenic $T_0$ *Glycine max* plants harboring expression vectors for nucleic acids comprising SEQ ID NO: 115 and/or SEQ ID NO 119 are generated as is known in the art, including for example by *Agrobacterium*-mediated transformation, as follows. Mature soybean (*Glycine max*) seeds are sterilized overnight with chlorine gas for sixteen hours. Following sterilization with chlorine gas, the seeds are placed in an open container in a LAMINAR™ flow hood to dispel the chlorine gas. Next, the sterilized seeds are imbibed with sterile $H_2O$ for sixteen hours in the dark using a black box at 24° C.

Preparation of Split-Seed Soybeans.

The split soybean seed comprising a portion of an embryonic axis protocol required preparation of soybean seed material which is cut longitudinally, using a #10 blade affixed to a scalpel, along the hilum of the seed to separate and remove the seed coat, and to split the seed into two cotyledon sections. Careful attention is made to partially remove the embryonic axis, wherein about ½-⅓ of the embryo axis remains attached to the nodal end of the cotyledon.

Inoculation.

The split soybean seeds comprising a partial portion of the embryonic axis are then immersed for about 30 minutes in a solution of *Agrobacterium tumefaciens* (e.g., strain EHA 101 or EHA 105) containing binary plasmid comprising SEQ ID NO: 115 and/or SEQ ID NO 119. The *Agrobacterium tumefaciens* solution is diluted to a final concentration of $\lambda$=0.6 $OD_{650}$ before immersing the cotyledons comprising the embryo axis.

Co-Cultivation.

Following inoculation, the split soybean seed is allowed to co-cultivate with the *Agrobacterium tumefaciens* strain for 5 days on co-cultivation medium (Wang, Kan. *Agrobacterium Protocols*. 2. 1. New Jersey: Humana Press, 2006. Print.) in a Petri dish covered with a piece of filter paper.

Shoot Induction.

After 5 days of co-cultivation, the split soybean seeds are washed in liquid Shoot Induction (SI) media consisting of B5 salts, B5 vitamins, 28 mg/L Ferrous, 38 mg/L $Na_2$EDTA, 30 g/L sucrose, 0.6 g/L MES, 1.11 mg/L BAP, 100 mg/L TIMENTIN™, 200 mg/L cefotaxime, and 50 mg/L vancomycin (pH 5.7). The split soybean seeds are then cultured on Shoot Induction I (SI I) medium consisting of B5 salts, B5 vitamins, 7 g/L Noble agar, 28 mg/L Ferrous, 38 mg/L $Na_2$EDTA, 30 g/L sucrose, 0.6 g/L MES, 1.11 mg/L BAP, 50 mg/L TIMENTIN™, 200 mg/L cefotaxime, 50 mg/L vancomycin (pH 5.7), with the flat side of the cotyledon facing up and the nodal end of the cotyledon imbedded into the medium. After 2 weeks of culture, the explants from the transformed split soybean seed are transferred to the Shoot Induction II (SI II) medium containing SI I medium supplemented with 6 mg/L glufosinate (LIBERTY®).

Shoot Elongation.

After 2 weeks of culture on SI II medium, the cotyledons are removed from the explants and a flush shoot pad containing the embryonic axis are excised by making a cut at the base of the cotyledon. The isolated shoot pad from the cotyledon is transferred to Shoot Elongation (SE) medium. The SE medium consists of MS salts, 28 mg/L Ferrous, 38 mg/L $Na_2$EDTA, 30 g/L sucrose and 0.6 g/L MES, 50 mg/L asparagine, 100 mg/L L-pyroglutamic acid, 0.1 mg/L IAA, 0.5 mg/L GA3, 1 mg/L zeatin riboside, 50 mg/L TIMENTIN™, 200 mg/L cefotaxime, 50 mg/L vancomycin, 6 mg/L glufosinate, 7 g/L Noble agar, (pH 5.7). The cultures are transferred to fresh SE medium every 2 weeks. The cultures are grown in a CONVIRON™ growth chamber at 24° C. with an 18 h photoperiod at a light intensity of 80-90 $\mu$mol/$m^2$sec.

Rooting.

Elongated shoots which developed from the cotyledon shoot pad are isolated by cutting the elongated shoot at the base of the cotyledon shoot pad, and dipping the elongated shoot in 1 mg/L IBA (Indole 3-butyric acid) for 1-3 minutes to promote rooting. Next, the elongated shoots are transferred to rooting medium (MS salts, B5 vitamins, 28 mg/L Ferrous, 38 mg/L $Na_2$EDTA, 20 g/L sucrose and 0.59 g/L MES, 50 mg/L asparagine, 100 mg/L L-pyroglutamic acid 7 g/L Noble agar, pH 5.6) in phyta trays.

Cultivation.

Following culture in a CONVIRON™ growth chamber at 24° C., 18 h photoperiod, for 1-2 weeks, the shoots which have developed roots are transferred to a soil mix in a covered sundae cup and placed in a CONVIRON™ growth chamber (models CMP4030 and CMP3244, Controlled Environments Limited, Winnipeg, Manitoba, Canada) under long day conditions (16 hours light/8 hours dark) at a light intensity of 120-150 $\mu$mol/$m^2$sec under constant temperature (22° C.) and humidity (40-50%) for acclimatization of plantlets. The rooted plantlets are acclimated in sundae cups for several weeks before they are transferred to the greenhouse for further acclimatization and establishment of robust transgenic soybean plants.

A further 10-20 $T_1$ *Glycine max* independent lines expressing hairpin dsRNA for an RNAi construct are obtained for BSB challenge. Hairpin dsRNA may be derived as set forth in SEQ ID NO:119 or otherwise further comprising SEQ ID NO:115. These are confirmed through RT-PCR or other molecular analysis methods. Total RNA preparations from selected independent $T_1$ lines are optionally used for RT-PCR with primers designed to bind in the ST-LS1 intron of the hairpin expression cassette in each of the RNAi constructs. In addition, specific primers for each target gene in an RNAi construct are optionally used to amplify and confirm the production of the pre-processed mRNA required for siRNA production in planta. The amplification of the desired bands for each target gene confirms the expression of the hairpin RNA in each transgenic *Glycine max* plant. Processing of the dsRNA hairpin of the target genes into siRNA is subsequently optionally confirmed in independent transgenic lines using RNA blot hybridizations.

Moreover, RNAi molecules having mismatch sequences with more than 80% sequence identity to target genes affect corn rootworms in a way similar to that seen with RNAi molecules having 100% sequence identity to the target genes. The pairing of mismatch sequence with native sequences to form a hairpin dsRNA in the same RNAi construct delivers plant-processed siRNAs capable of affecting the growth, development and viability of feeding hemipteran pests.

In planta delivery of dsRNA, siRNA, shRNA, or miRNA corresponding to target genes and the subsequent uptake by hemipteran pests through feeding results in down-regulation of the target genes in the hemipteran pest through RNA-mediated gene silencing. When the function of a target gene is important at one or more stages of development, the growth, development, and reproduction of the hemipteran pest is affected, and in the case of at least one of *Euchistus heros, Piezodorus guildinii, Halyomorpha halys, Nezara viridula, Acrosternum hilare*, and *Euschistus servus* leads to failure to successfully infest, feed, develop, and/or reproduce, or leads to death of the hemipteran pest. The choice of target genes and the successful application of RNAi is then used to control hemipteran pests.

Phenotypic comparison of transgenic RNAi lines and nontransformed *Glycine max* Target hemipteran pest genes or sequences selected for creating hairpin dsRNA have no similarity to any known plant gene sequence. Hence it is not expected that the production or the activation of (systemic) RNAi by constructs targeting these hemipteran pest genes or sequences will have any deleterious effect on transgenic plants. However, development and morphological characteristics of transgenic lines are compared with nontransformed plants, as well as those of transgenic lines transformed with an "empty" vector having no hairpin-expressing gene. Plant root, shoot, foliage and reproduction characteristics are compared. There is no observable difference in root length and growth patterns of transgenic and nontransformed plants. Plant shoot characteristics such as height, leaf numbers and sizes, time of flowering, floral size and appearance are similar. In general, there are no observable morphological differences between transgenic lines and those without expression of target iRNA molecules when cultured in vitro and in soil in the glasshouse.

Example 16

Pollen Beetle Transcriptome

Insects: Larvae and adult pollen beetles were collected from fields with flowering rapeseed plants (Giessen, Germany). Young adult beetles (each per treatment group: n=20; 3 replicates) were challenged by injecting a mixture of two different bacteria (*Staphylococcus aureus* and *Pseudomonas aeruginosa*), one yeast (*Saccharomyces cerevisiae*) and bacterial LPS. Bacterial cultures were grown at 37° C. with agitation, and the optical density was monitored at 600 nm (OD600). The cells were harvested at OD600 ~1 by centrifugation and resuspended in phosphate-buffered saline. The mixture was introduced ventrolaterally by pricking the abdomen of pollen beetle imagoes using a dissecting needle dipped in an aqueous solution of 10 mg/ml LPS (purified *E. coli* endotoxin; Sigma, Taufkirchen, Germany) and the bacterial and yeast cultures. Along with the immune challenged beetles naïve beetles and larvae were collected (n=20 per and 3 replicates each) at the same time point.

RNA Isolation:

Total RNA was extracted 8 h after immunization from frozen beetles and larvae using TriReagent (Molecular Research Centre, Cincinnati, Ohio, USA) and purified using the RNeasy Micro Kit (Qiagen, Hilden, Germany) in each case following the manufacturers' guidelines. The integrity of the RNA was verified using an Agilent 2100 Bioanalyzer and a RNA 6000 Nano Kit (Agilent Technologies, Palo Alto, Calif., USA). The quantity of RNA was determined using a NANODROP® ND-1000 spectrophotometer. RNA was extracted from each of the adult immune-induced treatment groups, adult control groups, and larval groups individually and equal amounts of total RNA were subsequently combined in one pool per sample (immune-challenged adults, control adults and larvae) for sequencing.

Transcriptome Information:

RNA-Seq data generation and assembly Single-read 100-bp RNA-Seq was carried out separately on 5 μg total RNA isolated from immune-challenged adult beetles, naïve (control) adult beetles and untreated larvae. Sequencing was carried out by Eurofins MWG Operon using the Illumina HiSeq-2000 platform. This yielded 20.8 million reads for the adult control beetle sample, 21.5 million reads for the LPS-challenged adult beetle sample and 25.1 million reads for the larval sample. The pooled reads (67.5 million) were assembled using Velvet/Oases assembler software (M. H. Schulz et al. (2012) Bioinformatics. 28:1086-92; Zerbino & E. Birney (2008) Genome Research. 18:821-9). The transcriptome contained 55648 sequences.

Pollen Beetle Rop Identification:

A tblastn search of the transcriptome was used to identify matching contigs. As a query the peptide sequence of rop from *Tribolium castaneum* was used (GENBANK® NP_001164155.1). Two contigs were identified (RGK_contig6910, RGK_contig46722). The gap between the contigs was completed with unassembled reads using a propriety tool. GAP5 (Bonfield J K & Whitwham (2010). Bioinformatics 26: 1699-1703) was used for verification of sequences.

Example 17

Mortality of Pollen Beetle (*Meligethes aeneus*) following treatment with rop RNAi Gene-specific primers including the T7 polymerase promoter sequence at the 5' end were used to create PCR products of approximate 500 bp by PCR (SEQ ID NOs:129-130). PCR fragments were cloned in the pGEM T easy vector according to the manufacturer's protocol and sent to a sequencing company to verify the sequence. The dsRNA was then produced by the T7 RNA polymerase (MEGAscript® RNAi Kit, Applied Biosystems) from a PCR construct generated from the sequenced plasmid according to the manufacturer's protocol.

Injection of ~100 nl dsRNA (1 ug/ul) into larvae and adult beetles was performed with a micromanipulator under a dissecting stereomicroscope (n=10, 3 biological replications) Animals were anaesthetized on ice before they were affixed to double-stick tape. Controls received the same volume of water. A negative control dsRNA of IMPI (insect metalloproteinase inhibitor gene of the lepidopteran *Galleria mellonella*) were conducted. All controls in all stages could not be tested due to a lack of animals.

Pollen beetles were maintained in Petri dishes with dried pollen and a wet tissue. The larvae were reared in plastic boxes on inflorescence of canola in an agar/water media.

TABLE 14

Results of adult pollen beetle injection bioassay.

| Treatment | % Survival Mean ± SD* | | | | |
|---|---|---|---|---|---|
| | Day 0 | Day 2 | Day 4 | Day 6 | Day 8 |
| rop | 100 ± 0 | 90 ± 10 | 87 ± 15 | 87 ± 15 | 80 ± 10 |
| water | 100 ± 0 | 100 ± 0 | 100 ± 0 | 100 ± 0 | 100 ± 0 |
| | Day 10 | Day 12 | Day 14 | Day 16 | |
| rop | 73 ± 6 | 67 ± 6 | 63 ± 12 | 53 ± 6 | |
| water | 93 ± 12 | 90 ± 10 | 87 ± 12 | 80 ± 10 | |

*Standard deviation

TABLE 15

| Results of larval pollen beetle injection bioassay. | | | | |
|---|---|---|---|---|
| | % Survival Mean ± SD* | | | |
| Treatment | Day 0 | Day 2 | Day 4 | Day 6 |
| rop | 100 ± 0 | 77 ± 21 | 73 ± 15 | 43 ± 6 |
| Negative control | 100 ± 0 | 100 ± 0 | 97 ± 6 | 73 ± 21 |

*Standard deviation

Controls were performed on a different date due to the limited availability of insects.

Feeding Bioassay: Beetles were kept without access to water in empty falcon tubes 24 h before treatment. A droplet of dsRNA (~5 μl) was placed in a small Petri dish and 5 to 8 beetles were added to the Petri dish. Animals were observed under a stereomicroscope and those that ingested dsRNA containing diet solution were selected for the bioassay. Beetles were transferred into petri dishes with dried pollen and a wet tissue. Controls received the same volume of water. A negative control dsRNA of IMPI (insect metalloproteinase inhibitor gene of the lepidopteran *Galleria mellonella*) was conducted. All controls in all stages could not be tested due to a lack of animals.

TABLE 16

| Results of adult feeding bioassay. | | | | | |
|---|---|---|---|---|---|
| Treatment | % Survival Mean ± SD* | | | | |
| | Day 0 | Day 2 | Day 4 | Day 6 | Day 8 |
| rop | 100 ± 0 | 89 ± 10 | 78 ± 10 | 76 ± 14 | 60 ± 18 |
| Negative control | 100 ± 0 | 93 ± 5.8 | 90 ± 10 | 87 ± 5.8 | 83 ± 5.8 |
| water | 100 ± 0 | 100 ± 0 | 100 ± 0 | 93 ± 3.8 | 93 ± 3.8 |
| | Day 10 | Day 12 | Day 14 | Day 16 | |
| rop | 51 ± 14 | 44 ± 10 | 38 ± 14 | 38 ± 14 | |
| Negative control | 80 ± 10 | 80 ± 10 | 80 ± 10 | 77 ± 12 | |
| water | 93 ± 3.8 | 87 ± 10 | 80 ± 13 | 80 ± 13 | |

*Standard deviation

Controls were performed on a different date due to the limited availability of insects.

Example 18

*Agrobacterium*-mediated transformation of Canola (*Brassica napus*) hypocotyls

*Agrobacterium* Preparation

The *Agrobacterium* strain containing a binary plasmid is streaked out on YEP media (Bacto Peptone™ 20.0 gm/L and Yeast Extract 10.0 gm/L) plates containing streptomycin (100 mg/ml) and spectinomycin (50 mg/mL) and incubated for 2 days at 28° C. The propagated *Agrobacterium* strain containing the binary plasmid is scraped from the 2-day streak plate using a sterile inoculation loop. The scraped *Agrobacterium* strain containing the binary plasmid is then inoculated into 150 mL modified YEP liquid with streptomycin (100 mg/ml) and spectinomycin (50 mg/ml) into sterile 500 mL baffled flask(s) and shaken at 200 rpm at 28° C. The cultures are centrifuged and resuspended in M-medium (LS salts, 3% glucose, modified B5 vitamins, 1 μM kinetin, 1 μM 2,4-D, pH 5.8) and diluted to the appropriate density (50 Klett Units as measured using a spectrophotometer) prior to transformation of canola hypocotyls.

Canola Transformation

Seed Germination:

Canola seeds (var. NEXERA 710™) are surface-sterilized in 10% Clorox™ for 10 minutes and rinsed three times with sterile distilled water (seeds are contained in steel strainers during this process). Seeds are planted for germination on ½ MS Canola medium (½ MS, 2% sucrose, 0.8% agar) contained in Phytatrays™ (25 seeds per Phytatray™) and placed in a Percival™ growth chamber with growth regime set at 25° C., photoperiod of 16 hours light and 8 hours dark for 5 days of germination.

Pre-Treatment:

On day 5, hypocotyl segments of about 3 mm in length are aseptically excised, the remaining root and shoot sections are discarded (drying of hypocotyl segments is prevented by immersing the hypocotyls segments into 10 mL of sterile milliQ™ water during the excision process). Hypocotyl segments are placed horizontally on sterile filter paper on callus induction medium, MSK1D1 (MS, 1 mg/L kinetin, 1 mg/L 2,4-D, 3.0% sucrose, 0.7% phytagar) for 3 days pre-treatment in a Percival™ growth chamber with growth regime of 22-23° C., and a photoperiod of 16 hours light, 8 hours dark.

Co-Cultivation with *Agrobacterium:*

The day before *Agrobacterium* co-cultivation, flasks of YEP medium containing the appropriate antibiotics, are inoculated with the *Agrobacterium* strain containing the binary plasmid. Hypocotyl segments are transferred from filter paper callus induction medium, MSK1D1 to an empty 100×25 mm Petri™ dishes containing 10 mL of liquid M-medium to prevent the hypocotyl segments from drying. A spatula is used at this stage to scoop the segments and transfer the segments to new medium. The liquid M-medium is removed with a pipette and 40 mL of *Agrobacterium* suspension is added to the Petri™ dish (500 segments with 40 mL of *Agrobacterium* solution). The hypocotyl segments are treated for 30 minutes with periodic swirling of the Petri™ dish so that the hypocotyl segments remain immersed in the *Agrobacterium* solution. At the end of the treatment period, the *Agrobacterium* solution is pipetted into a waste beaker; autoclaved and discarded (the *Agrobacterium* solution is completely removed to prevent *Agrobacterium* overgrowth). The treated hypocotyls are transferred with forceps back to the original plates containing MSK1D1 media overlaid with filter paper (care is taken to ensure that the segments did not dry). The transformed hypocotyl segments and non-transformed control hypocotyl segments are returned to the Percival™ growth chamber under reduced light intensity (by covering the plates with aluminum foil), and the treated hypocotyl segments are co-cultivated with *Agrobacterium* for 3 days.

Callus Induction on Selection Medium:

After 3 days of co-cultivation, the hypocotyl segments are individually transferred with forceps onto callus induction medium, MSK1D1H1 (MS, 1 mg/L kinetin, 1 mg/L 2,4-D, 0.5 gm/L MES, 5 mg/L $AgNO_3$, 300 mg/L Timentin™, 200 mg/L carbenicillin, 1 mg/L Herbiace™, 3% sucrose, 0.7% phytagar) with growth regime set at 22-26° C. The hypocotyl segments are anchored on the medium but are not deeply embedded into the medium.

Selection and Shoot Regeneration:

After 7 days on callus induction medium, the callusing hypocotyl segments are transferred to Shoot Regeneration Medium 1 with selection, MSB3Z1H1 (MS, 3 mg/L BAP, 1 mg/L zeatin, 0.5 gm/L MES, 5 mg/L $AgNO_3$, 300 mg/L Timentin™, 200 mg/L carbenicillin, 1 mg/L Herbiace™, 3% sucrose, 0.7% phytagar). After 14 days, the hypocotyl segments which develop shoots are transferred to Regeneration Medium 2 with increased selection, MSB3Z1H3 (MS, 3 mg/L BAP, 1 mg/L Zeatin, 0.5 gm/L MES, 5 mg/L $AgNO_3$, 300 mg/l Timentin™, 200 mg/L carbenicillin, 3 mg/L Herbiace™, 3% sucrose, 0.7% phytagar) with growth regime set at 22-26° C.

Shoot Elongation:

After 14 days, the hypocotyl segments that develop shoots are transferred from Regeneration Medium 2 to shoot elongation medium, MSMESH5 (MS, 300 mg/L Timentin™, 5 mg/l Herbiace™, 2% sucrose, 0.7% TC Agar) with growth regime set at 22-26° C. Shoots that are already elongated were isolated from the hypocotyl segments and transferred to MSMESH5. After 14 days the remaining shoots which have not elongated in the first round of culturing on shoot elongation medium are transferred to fresh shoot elongation medium, MSMESH5. At this stage all remaining hypocotyl segments which do not produce shoots are discarded.

Root Induction:

After 14 days of culturing on the shoot elongation medium, the isolated shoots are transferred to MSMEST medium (MS, 0.5 g/L MES, 300 mg/L Timentin™, 2% sucrose, 0.7% TC Agar) for root induction at 22-26° C. Any shoots which do not produce roots after incubation in the first transfer to MSMEST medium are transferred for a second or third round of incubation on MSMEST medium until the shoots develop roots.

PCR Analysis:

Transformed canola hypocotyl segments which regenerated into shoots comprising roots are further analyzed via a PCR molecular confirmation assay. Leaf tissue is obtained from the green shoots and tested via PCR for the presence of the pat selectable marker gene. Any chlorotic shoots are discarded and not subjected to PCR analysis. Samples that are identified as positive for the presence of the pat selectable marker gene are kept and cultured on MSMEST medium to continue development and elongation of the shoots and roots. The samples that are identified as not containing the pat selectable marker gene negative according to PCR analysis are discarded.

The transformed canola plants comprising shoots and roots that are PCR-positive for the presence of the pat selectable marker gene are transplanted into soil in a greenhouse. After establishment of the canola plants within soil, the canola plants are further analyzed to quantitate the copy number of the pat gene expression cassette via an Invader™ quantitative PCR assay and Southern blotting. Transgenic $T_0$ canola plants which are confirmed to contain at least one copy of the pat gene expression cassette are advanced for further analysis of the seed. The seeds obtained from theses transgenic $T_0$ canola plants, i.e., $T_1$ canola seeds, are analyzed to detect the presences of the target gene.

While the present disclosure may be susceptible to various modifications and alternative forms, specific embodiments have been described by way of example in detail herein. However, it should be understood that the present disclosure is not intended to be limited to the particular forms disclosed. Rather, the present disclosure is to cover all modifications, equivalents, and alternatives falling within the scope of the present disclosure as defined by the following appended claims and their legal equivalents.

What is claimed is:

1. A double-stranded ribonucleic acid (dsRNA) molecule comprising a first polyribonucleotide consisting of at least 23 contiguous nucleotides of the polyribonucleotide encoded by a polynucleotide selected from the group consisting of SEQ ID NO:1, SEQ ID NO:115, SEQ ID NO:120, SEQ NO:122, SEQ ID NO:124, SEQ ID NO:126, SEQ ID NO:131, and SEQ ID NO:133, wherein the first polyribonucleotide is hybridized in the dsRNA molecule to a second polyribonucleotide that is the complement or reverse complement of the first polyribonucleotide, and wherein delivery of the dsRNA molecule inhibits the expression of a target gene in a coleopteran or hemipteran insect selected from the group consisting of *Diabrotica virgifera, Euschistus heros*, and *Meligethes aeneus*.

2. The dsRNA molecule of claim 1, wherein the second polyribonucleotide is the reverse complement of the first polyribonucleotide, and wherein the dsRNA molecule comprises a third polyribonucleotide separating the first and second polyribonucleotides in a single transcript.

3. The dsRNA molecule of claim 2, where the dsRNA has a hairpin structure comprising a stem and a loop, wherein the hybridized first and second polyribonucleotides form the stein and the third polyribonucleotide forms the loop in the dsRNA molecule.

4. The dsRNA molecule of claim 1, wherein the dsRNA is a siRNA, shRNA, miRNA, or hpRNA.

5. The dsRNA molecule of claim 1, wherein the RNA molecule comprises a nucleic acid analogue.

6. The dsRNA molecule of claim 1, wherein the first polyribonucleotide is encoded by a polynucleotide selected from the group of SEQ ID NO:3, SEQ ID NO:4, SEQ ID NO:114, SEQ ID NO:119, and SEQ ID NO:128.

7. A plant cell comprising the dsRNA molecule of claim 1.

8. The plant cell of claim 7, wherein the plant is selected from the group consisting of corn, maize, soybean, and plants of the family Poaceae.

9. A nucleic acid molecule encoding the dsRNA molecule of claim 1, comprising a polynucleotide encoding the first polyribonucleotide, wherein the polynucleotide is operably linked to a heterologous promoter.

10. The nucleic acid molecule of claim 9, wherein the molecule is a vector.

11. A method of controlling a population of coleopteran or hemipteran pests selected from the group consisting of *Diabrotica virgifera, Euschistus heros*, and *Meligethes aeneus*, the method comprising:

feeding the dsRNA molecule of claim 1 to insects of the population.

12. A food source for an insect pest comprising the dsRNA molecule of claim 1.

13. The method according to claim 11 wherein feeding the dsRNA molecule to insects of the population comprises feeding the insects with an artificial diet food source comprising the dsRNA molecule.

14. The method according to claim 11, wherein feeding the dsRNA molecule to insects of the population comprises spraying a plant infested with the insects with a formulation comprising the dsRNA molecule.

15. The dsRNA molecule of claim 2, wherein the dsRNA molecule is encoded by a polynucleotide selected from the group consisting of SEQ ID NOs:13-15.

16. A nucleic acid molecule encoding the dsRNA molecule of claim 2, comprising a polynucleotide encoding the dsRNA, wherein the polynucleotide is operably linked to a promoter.

17. The nucleic acid molecule of claim 16, wherein the molecule is a plant transformation vector.

18. The nucleic acid molecule of claim 16, wherein the polynucleotide is selected from the group consisting of SEQ ID NOs:13-15.

19. A plant cell comprising the nucleic acid molecule of claim 16.

20. The plant cell of claim 19, wherein the plant is selected from the group consisting of corn, maize, soybean, and plants of the family Poaceae.

21. The plant cell of claim 19, wherein the nucleic acid molecule is integrated into the genome of the plant cell.

22. A plant comprising the plant cell of claim 21.

23. A method of controlling a population of coleopteran or hemipteran pests selected from the group consisting of *Diabrotica virgifera, Euschistus heros*, and *Meligethes aeneus*, the method comprising:

feeding the plant cell of claim 19 to insects of the population.

24. The method according to claim 23, wherein the plant cell is present in a plant material or whole plant.

25. The method according to claim 23, wherein the plant cell is of a plant selected from the group consisting of corn, maize, soybean, and plants of the family Poaceae.

* * * * *